United States Patent
Lawrence et al.

(10) Patent No.: US 8,673,910 B2
(45) Date of Patent: Mar. 18, 2014

(54) PROTEASOME INHIBITORS FOR SELECTIVELY INDUCING APOPTOSIS IN CANCER CELLS

(75) Inventors: Harshani Lawrence, Tampa, FL (US); Yiyu Ge, Tampa, FL (US); Said M. Sebti, Tampa, FL (US); Wayne Guida, St. Petersburg, FL (US)

(73) Assignees: H. Lee Moffitt Cancer Center and Research Institute, Tampa, FL (US); University of South Florida, Tampa, FL (US)

( * ) Notice: Subject to any disclaimer, the term of this patent is extended or adjusted under 35 U.S.C. 154(b) by 0 days.

(21) Appl. No.: 12/997,192

(22) PCT Filed: Jun. 30, 2009

(86) PCT No.: PCT/US2009/003926
§ 371 (c)(1),
(2), (4) Date: Apr. 14, 2011

(87) PCT Pub. No.: WO2010/005534
PCT Pub. Date: Jan. 14, 2010

(65) Prior Publication Data
US 2011/0201609 A1     Aug. 18, 2011

Related U.S. Application Data

(60) Provisional application No. 61/158,016, filed on Mar. 6, 2009, provisional application No. 61/076,835, filed on Jun. 30, 2008.

(51) Int. Cl.
| | | |
|---|---|---|
| A61K 31/5377 | (2006.01) |
| A61K 31/4402 | (2006.01) |
| A61K 31/415 | (2006.01) |
| A61K 31/18 | (2006.01) |
| A61K 31/42 | (2006.01) |
| A61K 31/505 | (2006.01) |
| A61K 31/433 | (2006.01) |
| A61K 31/496 | (2006.01) |
| A61K 31/4196 | (2006.01) |
| A61K 31/381 | (2006.01) |
| A61K 31/216 | (2006.01) |
| A61K 31/41 | (2006.01) |
| A61K 31/196 | (2006.01) |

(52) U.S. Cl.
USPC ........ 514/235.5; 514/352; 514/404; 514/603; 514/380; 514/272; 514/363; 514/275; 514/274; 514/253.01; 514/384; 514/445; 514/510; 514/382; 514/569

(58) Field of Classification Search
USPC .............. 514/235.5, 352, 404, 603, 380, 272, 514/363, 275, 274, 253.01, 384, 445, 510, 514/382, 569
See application file for complete search history.

(56) References Cited

U.S. PATENT DOCUMENTS

| | | |
|---|---|---|
| 4,559,157 A | 12/1985 | Smith et al. |
| 4,608,392 A | 8/1986 | Jacquet et al. |
| 4,820,508 A | 4/1989 | Wortzman |
| 4,938,949 A | 7/1990 | Borch et al. |
| 4,992,478 A | 2/1991 | Geria |
| 5,167,649 A | 12/1992 | Zook |
| 6,902,721 B1 | 6/2005 | Mundy et al. |
| 6,960,648 B2 | 11/2005 | Bonny |
| 2002/0035243 A1 | 3/2002 | Imfeld et al. |
| 2002/0120100 A1 | 8/2002 | Bonny |

(Continued)

FOREIGN PATENT DOCUMENTS

WO    WO 00/61167    10/2000

OTHER PUBLICATIONS

Cancer [online], [retrieved on Jul. 6, 2007] Retrieved from the Internet, URL: http://www.nlm.nih.gov/medlineplus/cancer.html.*

(Continued)

Primary Examiner — Kristin Vajda
(74) Attorney, Agent, or Firm — Saliwanchik, Lloyd & Eisenschenk

(57) ABSTRACT

The subject invention concerns compounds having activity as inhibitors of proteasomes and methods of using the subject compounds. In one embodiment, a compound of the invention has the chemical structure shown in formula I:

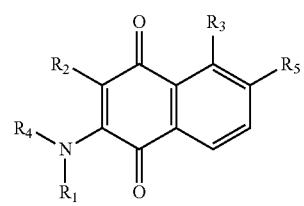

or a pharmaceutically acceptable salt or hydrate thereof.
In another embodiment, a compound of the invention has the chemical structure shown in formula II:

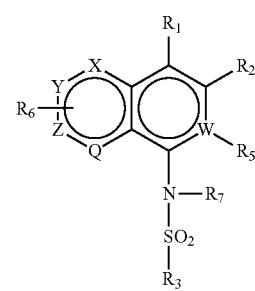

or a pharmaceutically acceptable salt or hydrate thereof.

21 Claims, 12 Drawing Sheets

(56) References Cited

U.S. PATENT DOCUMENTS

| | | | |
|---|---|---|---|
| 2003/0032594 | A1 | 2/2003 | Bonny |
| 2004/0167189 | A1 | 8/2004 | Bulavin et al. |
| 2005/0282818 | A1 | 12/2005 | Ramesh et al. |
| 2007/0203236 | A1 | 8/2007 | Smith et al. |

OTHER PUBLICATIONS

Lala et al., Role of nitric oxide in tumor progression: Lessons from experimental tumors, Cancer and Metastasis Reviews (1998), 17, 91-106.*
Golub et al., Molecular Classification of Cancer: Class Discovery and Class Prediction by Gene Expression Monitoring, Science (1999), vol. 286, 531-537.*
Vippagunta et al., Crystalline solids, 2001, Advanced Drug Delivery Reviews, 48, pp. 3 and 18.*
Adams J. and Kauffman M. Development of the proteasome inhibitor Velcade (Bortezomib). *Cancer Invest* 2004;22:304-11.
Adams J. et al. Proteasome Inhibitors: A Novel Class of Potent and Effective Antitumor Agents. *Cancer Res* 1999;59:2615-22.
Adams J. The development of proteasome inhibitors as anticancer drugs. *Cancer Cell* 2003;5:417-21.
Adams J. The proteasome: A suitable antineoplastic target. *Nat Rev Cancer* 2004;4:349-60.
Aghajanian C. et al. A phase I trial of the novel proteasome inhibitor PS341 in advanced solid tumor malignancies. *Clin Cancer Res* 2002;8:2505-11.
Arrigo A-P. et al. Identity of the 19S 'prosome' particle with the large multifunctional protease complex of mammalian cells (the proteasome). *Nature* 1988;331:192-4.
Bang S-M. et al. A multicenter retrospective analysis of adverse events in Korean patients using bortezomib for multiple myeloma. *Int J Hematol* 2006;83:309-13.
Bazzaro M. et al. Ubiquitin-proteasome system stress sensitizes ovarian cancer to proteasome inhibitor-induced apoptosis. *Cancer Res* 2006;66:3754-63.
Bold RJ. et al. Chemosensitization of Pancreatic Cancer by Inhibition of the 26S Proteasome. *J Surg Res* 2001;100:11-7.
Burger AM. and Seth AK. The ubiquitin-mediated protein degradation pathway in cancer: therapeutic implications. *Eur J Cancer* 2004;40:2217-29.
Ciechanover A. The ubiquitin-proteasome proteolytic pathway. *Cell* 1994;79:13-21.
Codony-Servat J. et al. Differential cellular and molecular effects of bortezomib, a proteasome inhibitor, in human breast cancer cells. *Mol Cancer Ther* 2006;5:665-75.
Coux O. Structure and functions of the 20S and 26S proteasomes. *Annu Rev Biochem* 1996;65:801-47.
Davies AM. et al. Phase I study of two different schedules of bortezomib and pemetrexed in advanced solid tumors with emphasis on non-small cell lung cancer. *J Thorac Oncol* 2007;2:1112-6.
Davis NB. et al. Phase II trial of PS-341 in patients with renal cell cancer: A University of Chicago phase II consortium study. *J Clin Oncol* 2004;22:115-9.
Downward J. Targeting ras signalling pathways in cancer therapy. *Nat Rev Cancer* 2003;3:11-22.
Groll M. et al. Crystal structure of the 20S proteasome:TMC-95A complex: A non-covalent proteasome inhibitor. *J Mol Biol* 2001;311:543-8.
Groll M. et al. Crystal structure of the boronic acid-based proteasome inhibitor bortezomib in complex with the yeast 20S proteasome. *Structure* 2006;14:451-6.
Groll M. et al. Structure of the 20S proteasome from yeast at 2.4Å resolution. *Nature* 1997;386:463-71.
Hahn WC. and Weinberg R. Modelling the molecular circuitry of cancer. *Nat Rev Cancer* 2002;2:331-41.
Hershko A. et al. Components of the ubiquitin-protein ligase system. *J Biol Chem* 1983;258:8206-14.

Hideshima T. et al. The proteasome inhibitor PS-341 inhibits growth, induces apoptosis, and overcomes drug resistance in human multiple myeloma cells. *Cancer Res* 2001;61:3071-6.
Hochstrasser M. Ubiquitin, proteasomes, and the regulation of intracellular protein degradation. *Curr Opin Cell Biol* 1995;7:215-23.
Ikezoe T. et al. Proteasome inhibitor PS-341 downregulates prostate-specific antigen (PSA) and induces growth arrest and apoptosis of androgen-dependent human prostate cancer LNCaP cells. *Cancer Sci* 2004;95:271-5.
Jagannath S. et al. Bortezomib therapy alone and in combination with dexamethasone for previously untreated symptomatic multiple myeloma. *Br J Haematol* 2005;129:776-83.
Kazi A. et al. Structure-activity relationships of synthetic analogs of (−)-epigallocatechin-3-gallate as proteasome inhibitors. *Anticancer Res* 2004;24:943-54.
Kisselev AF. and Goldberg A. Proteasome inhibitors: from research tools to drug candidates. *Chem & Biol* 2001;8:739-58.
Kondagunta GV. et al. Phase II trial of bortezomib for patients with advanced renal cell carcinoma. *J Clin Oncol* 2004;22:3720-5.
Ling Y-H. etal. Reactive Oxygen Species Generation and Mitochondrial Dysfunction in the Apoptotic Response to Bortezomib, a Novel Proteasome Inhibitor, in Human H460 Non-small Cell Lung Cancer Cells. *J Biol Chem* 2003;278:33714-33723.
Liu J. et al. A genetically defined model for human ovarian cancer. *Cancer Res* 2004;64:1655-63.
Mani A. and Gelmann E. The ubiquitin-proteasome pathway and its role in cancer. *J Clin Oncol* 2005;23:4776-89.
Mortenson MM. et al. Effects of the proteasome inhibitor bortezomib alone and in combination with chemotherapy in the A549 non-small-cell lung cancer cell line. *Cancer Chemother Pharmacol* 2004;54:343-53.
Nalepa G. et al. Drug discovery in the ubiquitin-proteasome system. *Nat Rev Drug Disc* 2006;5:596-613.
Oakervee HE. et al. PAD combination therapy (PS-341/bortezomib, doxorubicin and dexamethasone) for previously untreated patients with multiple myeloma. *Br J Haematol* 2005;129:755-62.
Papandreou CN. and Legothetis CJ. Bortezomib as a potential treatment for prostate cancer. *Cancer Res* 2004;64:5036-43.
Papandreou CN. et al. Phase I trial of the proteasome inhibitor bortezomib in patients with advanced solid tumors with observations in androgen-independent prostate cancer. *J Clin Oncol* 2004;22:2108-21.
Prescott B. Potential antimalarial agents. Derivatives of 2-chloro-1,4-naphthoquinone. *J Med Chem* 1969;12:181-2.
Qian J. et al. In vitro modeling of human pancreatic duct epithelial cell transformation defines gene expression changes induced by K-ras oncogenic activation in pancreatic carcinogenesis. *Cancer Res* 2005;65:5045-53.
Raff MC. Social controls on cell survivial and cell death. *Nature* 1992;356:397-400.
Rangarajan A. et al. Species- and cell type-specific requirements for cellular transformation. *Cancer Cell* 2004;6:171-83.
Richardson PG. et al. Bortezomib (PS-341): a novel, first-in-class proteasome inhibitor for the treatment of multiple myeloma and other cancers. *Cancer Control* 2003;10:361-9.
Richardson PG. et al. Proteasome inhibition in the treatment of cancer. *Cell Cycle* 2005;4:290-6.
Scagliotti G. Proteasome inhibitors in lung cancer. *Crit Rev Oncol Hematol* 2006;58:177-89.
Sunwoo JB. et al. Novel proteasome inhibitor PS-341 inhibits activation of nuclear factor-kappa B, cell survival, tumor growth, and angiogenesis in squamous cell carcinoma. *Clin Cancer Res* 2001;7:1419-28.
Voges D. et al. The 26S proteasome: a molecular machine designed for controlled proteolysis. *Annu Rev Biochem* 1999;68:1015-68.
Williams S. et al. Differential effects of the proteasome inhibitor bortezomib on apoptosis and angiogenesis in human prostate tumor xenografts *Mol Cancer Ther* 2003;2:835-43.
Belova G. Chemical inhibition of Wip1 phosphatase contributes to suppression of tumorigenesis. *Cancer Biol & Ther* 2005;4:1154-1158.

\* cited by examiner

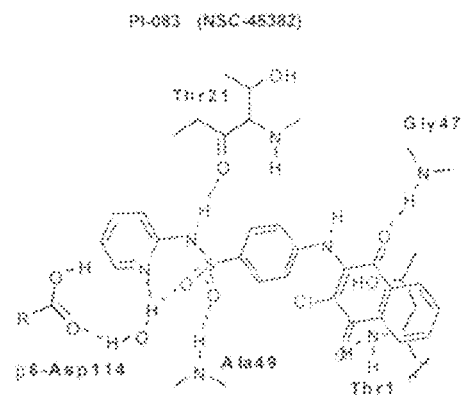 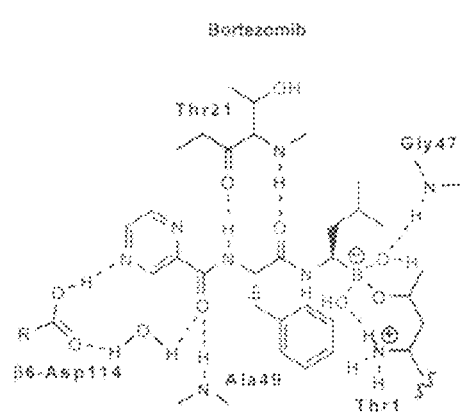
FIG. 1A  FIG. 1B
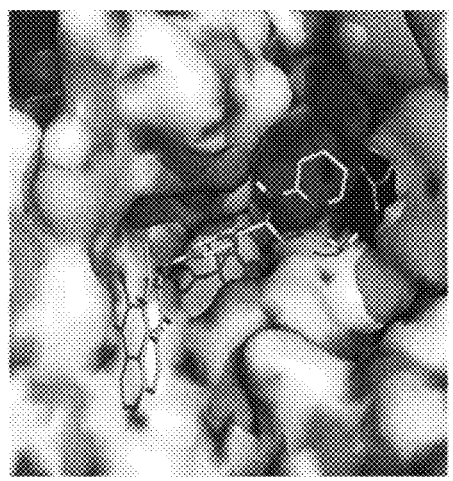 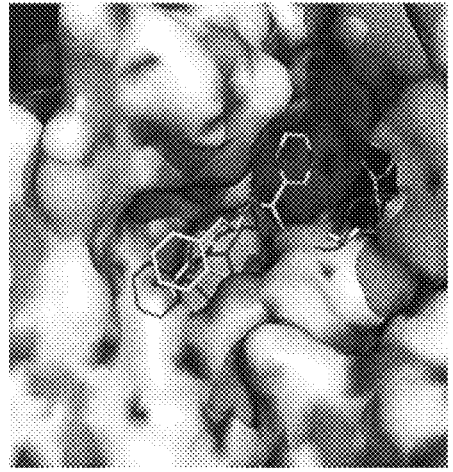
FIG. 1C  FIG. 1D

PI-083 (μM)

Bortezomib (nM)

PI-083 (µM)

Bortezomib (nM)

PI-083 (µM)

Bortezomib (nM)

FIG. 7

Naphthoquinone Pharmacophore

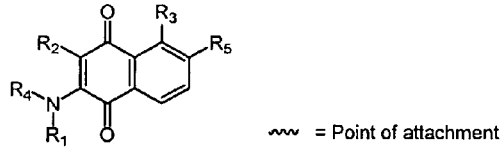

ᨐᨐ = Point of attachment $R_1$ = Commercially available and in-house synthesized sulfonamide-aniline building blocks

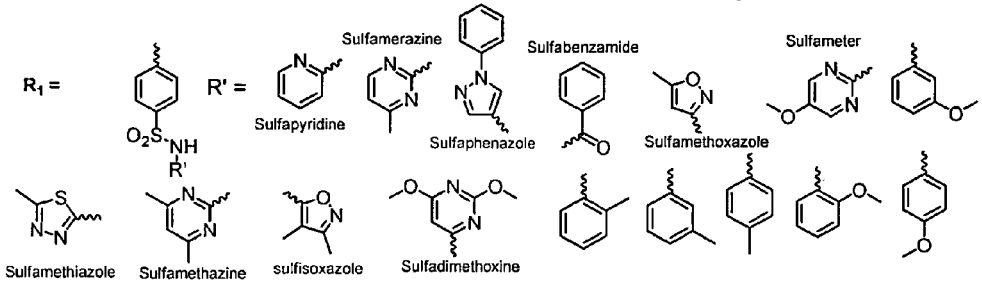

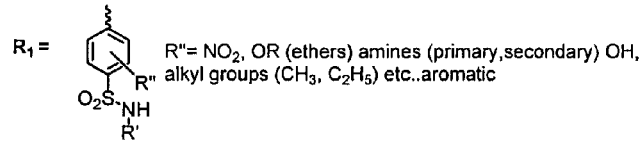

R" = NO$_2$, OR (ethers) amines (primary, secondary) OH, alkyl groups (CH$_3$, C$_2$H$_5$) etc..aromatic

R' = Aromatic, hetero-aromatic 5 & 6 member rings (see above), substituted aromatic rings (see above), alkyl groups (e.g. Methyl, Ethyl, Cyclopropyl, Isopropyl), acyl groups (e.g. CO-CH$_3$, CO-aromatic, CO-CF$_3$, CO-ethyl, CO-pyridyl)

R" = NO$_2$, Hydroxy, Ethers (O-alkyl, O-aromatic), Amines (primary, secondary or tertiary), alkyl groups (Methyl, Cyclopropyl, Ethyl etc.) and aromatic groups.

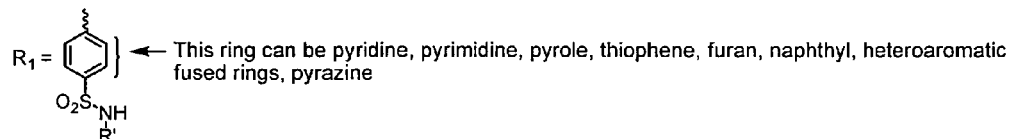

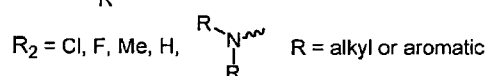 R = alkyl or aromatic

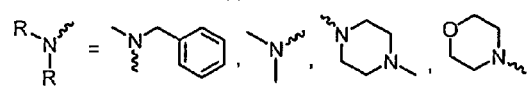

ᨐᨐ = Point of attachment $R_3$ = NO$_2$, NH$_2$ and substituted amines, OH, O-alkyl, Alkyl, Aromatic, Halogens
$R_4$ = H, Et, Me, Butyl, Me, CH$_2$-Phenyl, CH$_2$-Nathyl, CH$_2$-4-nitrophenyl, CH$_2$-4-methylphenyl, CH$_2$-4-trifluoromethylphenyl
$R_5$ = NO$_2$, NH$_2$ and substituted amines, OH, O-alkyl, O-aromatic, alkyl, aromatic, Halogens

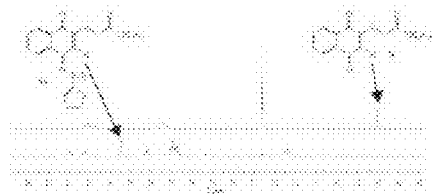 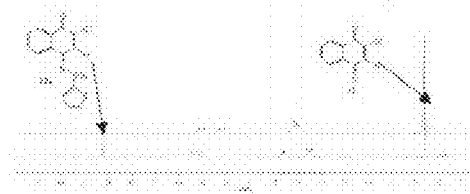
FIG. 12A  FIG. 12B
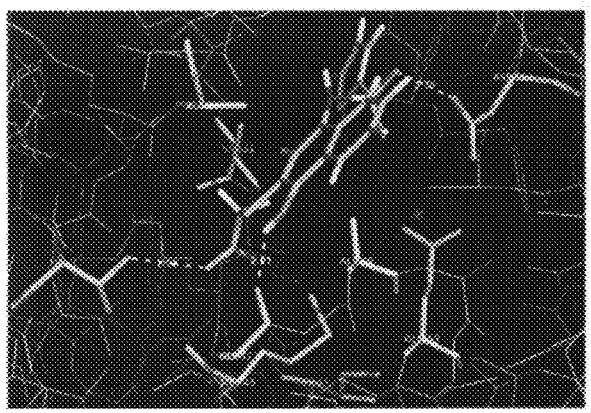 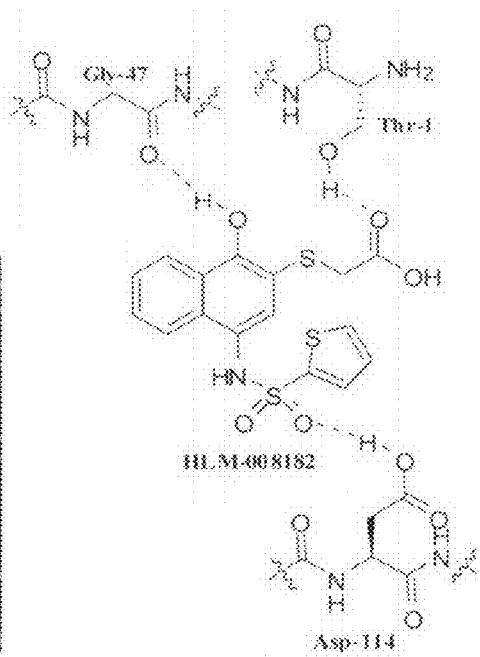
FIG. 13

PROTEASOME INHIBITORS FOR SELECTIVELY INDUCING APOPTOSIS IN CANCER CELLS

CROSS-REFERENCE TO RELATED APPLICATIONS

The present application is the National Stage of International Application Number PCT/US2009/003926, filed Jun. 30, 2009, which claims the benefit of U.S. Provisional Application Ser. Nos. 61/158,016, filed Mar. 6, 2009, and 61/076,835, filed Jun. 30, 2008, each of which is hereby incorporated by reference herein in its entirety, including any figures, tables, nucleic acid sequences, amino acid sequences, and drawings.

GOVERNMENT SUPPORT

This invention was made with government support under grant number CA118210 awarded by the Nation Institutes of Health/National Cancer Institute. The government has certain rights in the invention.

BACKGROUND OF THE INVENTION

Cancer is associated with increased proliferation and/or decreased apoptosis. Both of these processes are regulated by a complex interplay of transcription, protein synthesis, protein-protein interactions, protein phosphorylation and protein degradation. More than 80% of cellular proteins are degraded by the ubiquitin/proteasome system (UPS) (Adams, 2004a). Deregulation of various components of the UPS resulting in increased degradation of cell cycle inhibitors or pro-apoptotic proteins (e.g. $p21^{Cip1}$, $p27^{Kip1}$, p53, Bax, IκBα) or decreased degradation of cell cycle stimulators or anti-apoptotic proteins (e.g. cyclins, Bcl-2) can contribute to the transformed phenotype (Adams, 2004a; Mani and Gelmann, 2005; and Nalepa et al., 2006). The UPS has two distinct steps: recognition/ubiquitination and degradation (reviewed in Ciechanover, 1994; Hochstrasser, 1995). The ubiquitin-protein ligase system was discovered in 1983 and involves three enzymes and results in the transfer of multiple ubiquitin molecules, polypeptides of 76 amino acids, to the target protein (Hershko et al., 1983). Polyubiquitin-flagged proteins are then recognized by the proteasome, a large multi-subunit complex found in the cytoplasm and nuclei of all eukaryotic cells, which was first described in 1988 (Arrigo et al., 1988). Degradation of proteins is mediated by the 20S catalytic complex (Coux et al., 1996; Voges et al., 1999), containing three proteolytic enzymes, namely peptidylglutamyl peptide hydrolyzing (PGPH), trypsin-like (T-L), and chymotrypsin-like (CT-L) activities, residing in the β1, β2, and β5 catalytic subunits, respectively (Mani and Gelmann, 2005; Adams, 2004b).

In contrast to normal cells, which just require a low level of survival signals to stay alive (Raff, 1992), cancer cells typically have acquired a series of mutations that render them dependent on strong activation of one or a few survival pathways (Downward, 2003). One of these is the degradation of cellular proteins by the UPS, which drive cell cycle progression and/or survival. Therefore, the UPS has become a promising target for anti-cancer strategies (reviewed in Adams, 2004b; Mani and Gelmann, 2005; Nalepa et al., 2006; Burger and Seth, 2004).

One proteasome inhibitor that has been studied extensively is the dipeptide boronic acid analog PS-341 (bortezomib, VELCADE) (for reviews, see Adams, 2004a; Richardson et al., 2005). Preclinical studies have shown that VELCADE induces apoptosis in cancer cell lines derived from multiple myeloma (MM) (Hideshima et al., 2001), lung (Ling et al., 2003; Mortenson et al., 2004) and prostate cancer (Williams et al., 2003; Ikezoe et al., 2004). Likewise, in xenografts implanted in nude mice, VELCADE inhibits the growth of human prostate cancer (Williams et al., 2003; Adams et al., 1999), squamous cell carcinoma (Sunwoo et al., 2001), and ovarian cancer (Bazzaro et al., 2006). However, in other tumors such as human A549 lung tumors (Mortenson et al., 2004) or MIA-PaCa2 pancreatic tumors (Bold et al., 2001), even when administered in combination with other agents, VELCADE has only marginal effects. Currently, VELCADE has been approved by the Food and Drug Administration (FDA) for treatment of relapsed/refractory MM (Richardson et al., 2003; Adams and Kauffman, 2004), as a single agent or in combination with conventional therapies (Jagannath et al., 2005; Oakervee et al., 2005), and is being investigated for solid tumors (Aghajanian et al., 2002), including non-small cell lung cancer (Davies et al., 2004), renal cell cancer (Davies et al., (2004), Kondagunta et al., (2004)) and prostate cancer (reviewed in Scagliotti, 2006; Papandreou and Logothetis, 2004).

However, VELCADE is associated with undesired side effects in MM patients (Bang et al., 2006) and does not display substantial antitumor activity in other cancers (Scagliotti, 2006; Papandreou and Logothetis, 2004).

Thus, there remains a need in the art for proteasome inhibitors having better antitumor activity profile and less toxicity.

BRIEF SUMMARY OF THE INVENTION

The subject invention concerns compounds having activity as inhibitors of proteasomes and methods of using the subject compounds. In one embodiment, a compound of the invention has the chemical structure shown in formula I:

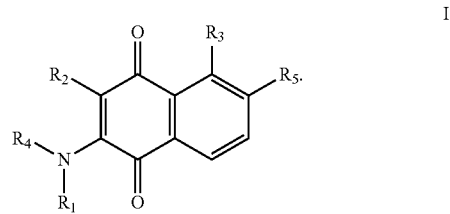

wherein
$R_1$ is an organic cyclic ring structure bonded to a sulfonamide structure;
$R_2$ is H, halogen, alkyl, —$NR_6R_7$, or heteroalkyl;
$R_3$ is H, halogen, —OH, —O-alkyl, alkyl, cycloalkyl, heterocycloalkyl, aryl, heteroaryl, —$NO_2$, —$NH_2$ or substituted amines;
$R_4$ is H, alkyl, heteroalkyl, aryl, or heteroaryl, any of which can be optionally substituted with one or more of —$NO_2$, alkyl, heteroalkyl, aryl, or heteroaryl, or halogen;
$R_5$ is H, —OH, halogen, alkyl, aryl, heteroaryl, cycloalkyl, heterocycloalkyl, —O-alkyl, -D-aryl, heteroalkyl, —$NO_2$, —$NH_2$, or substituted amine; and
$R_6$ and $R_7$ are independently H, O, alkyl, aryl, heterocycloalkyl, or heteroaryl, or together can form a heterocycloalkyl or a heteroaryl, any of which can be optionally substituted with one or more of —$NO_2$, alkyl, heteroalkyl, aryl, or halogen;
or a pharmaceutically acceptable salt or hydrate thereof.

In an exemplified embodiment, a compound of the invention (designated as PI-083) has the chemical structure:

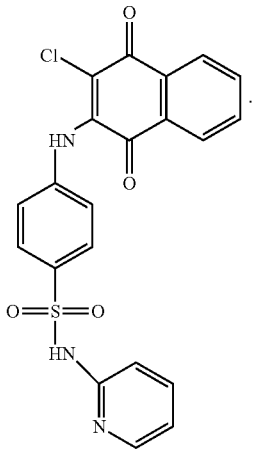

PI-083

In another embodiment, a compound of the invention has the chemical structure shown in formula II:

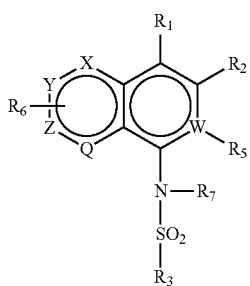

II wherein

Q, W, X, Y, Z are each independently carbon, oxygen, or nitrogen;

$R_1$ is H, or $X_1R_8$;

$R_2$ is heteroalkyl, which can be optionally substituted with one or more of —OH, halogen, —C(O)OR$_4$, alkyl, heteroalkyl, heterocycloalkyl, or heteroaryl;

$R_3$ is heterocycloalkyl, aryl, heteroaryl, any of which can be optionally substituted with one or more of a halogen or —OH; and $R_4$ is H or alkyl;

$R_5$ is halogen, alkyl or nitro;

$R_6$ is nitro, $X_2R_9$ or a halogen;

$R_7$ is H or alkyl;

$R_8$ is H, alkyl, aryl, CH$_2$-alkyl-aryl, -alkyl-C(O)OH, or alkyl-tetrazole (aromatic and aliphatic heterocyclic groups);

$R_9$ is H or alkyl;

$X_1$ is oxygen, nitrogen, or sulfur;

$X_2$ is oxygen, nitrogen, or sulfur;

or a pharmaceutically acceptable salt or hydrate thereof.

The subject invention also concerns methods for treating oncological disorders in a patient. In one embodiment, an effective amount of a compound of the present invention is administered to a patient having an oncological disorder and who is in need of treatment thereof.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIGS. 1A-1D show molecular modeling of PI-083 (NSC-45382), a novel proteasome inhibitor. Chemical structures of PI-083 (NSC-45382) (FIG. 1A), and VELCADE (FIG. 1B) are shown in red. The hydrogen bonds formed between PI-083 or VELCADE and the protein, via Thr1, Thr21, Ala49, Gly47, and Asp114 (from the β6 subunit) are shown schematically but not to scale. FIG. 1C shows protein surface rendering of the chymotrypsin-like subunits β5 (left) and β6 (right) of the 20S proteasome with PI-083 docked. The surface is colored according to atomic charge. Positively charged areas are colored in blue and negatively charged areas are colored in red. For PI-083, carbon atoms are colored in cyan, oxygen in red, nitrogen in blue, hydrogen in white, and sulfur in dark yellow. Asp114 from the β6 subunit is also shown (carbon atoms in gray) along with a crystallographically located water molecule that is H-bonded to Asp114. FIG. 1D shows protein surface rendering of the chymotrypsin-like subunits β5 (left) and β6 (right) of the 20S proteasome with VELCADE bound (from the X-ray structure). Asp114 from the β6 subunit is also shown (carbon atoms colored in gray) along with the crystallographically located water molecule. Note that the pyrazine ring of VELCADE is within H-bond distance from Asp114. Since the pK$_a$ of pyrazine is approximately 1.0, Asp114 is most likely protonated (not shown).

FIGS. 2A and 2D show MCF-7 breast cancer and MCF-10A breast epithelial cells. FIGS. 2B and 2E show T80-H ovarian cancer and T80 ovarian epithelial cells. FIGS. 2C and 2F show HPDE6-C7-Kras pancreatic cancer and HPDE6-C7 pancreatic epithelial cells. The graphs represent the means±standard deviation of at least 3 independent experiments. Asterisks indicate statistical significance ($p<0.05$).

FIGS. 3A and 3D show MCF-7 breast cancer and MCF-10A breast epithelial cells. FIGS. 3B and 3E show T80-H ovarian cancer and T80 ovarian epithelial cells. FIGS. 3C and 3F show HPDE6-C7-Kras pancreatic cancer and HPDE6-C7 pancreatic epithelial cells. The graphs represent the means±standard deviation of at least 3 independent experiments. Asterisks indicate statistical significance ($p<0.05$).

FIGS. 4A and 4D show MCF-7 breast cancer and MCF-10A breast epithelial cells. FIGS. 4B and 4E show T80-H ovarian cancer and T80 ovarian epithelial cells. FIGS. 4C and 4F show HPDE6-C7-Kras pancreatic cancer and HPDE6-C7 pancreatic epithelial cells. The graphs represent the means±standard deviation of at least 3 independent experiments. Asterisks indicate statistical significance (p<0.05).

FIGS. 5A-4F show the effects of PI-083 and VELCADE on apoptosis in cancer and normal/immortalized cells from the same tissue. Exponentially growing cancer cells (|) and normal cells (□) were treated with indicated concentrations of PI-083 (FIGS. 5A-5C) or VELCADE (FIGS. 5D-5F) for 24 h, followed by determination of degree of apoptosis. FIGS. 5A and 5D show MCF-7 breast cancer and MCF-10A breast epithelial cells.

In FIG. 6D, A549 lung cancer cells were treated with 0.1% DMSO (lane 1) or water (lane 5) or the indicated drug concentrations for 48 h. Cell lysates were then subjected to Western blot analyses with antibodies to p27$^{Kip1}$ and β-actin as a loading control. In FIG. 6F, p27$^{Kip1}$ levels were determined in lysates prepared from vehicle- or drug-treated A549-tumors by Western blots, with β-actin serving as a loading control.

FIG. 7 shows SAR summary of the NSC 45382 library. $R_1$=commercially available and in-house synthesized sulfonamide-aniline building blocks; $R_2$=Cl, Me, H; $R_3$=NO$_2$, NH$_2$; $R_4$=H, Et, Butyl, Me, CH$_2$-phenyl, CH$_2$-naphthyl, CH$_2$-4-Nitro-Phenyl, CH$_2$-4-Methyl-Phenyl, CH$_2$-4-trifluoromethyl-Phenyl; and $R_5$=NO$_2$.

FIG. 12: A, chemical shift (in CDCl$_3$, 400 Hz) of 3-H in compound 7a (upper) and 8a (lower); B, chemical shift of 3-H in compound 11 (upper) and 12a (lower).

FIG. 13: H-bonding interaction between HLM-008182 and chymotrypsin-like catalytic site of 20S proteasome predicted by molecular modeling.

DETAILED DESCRIPTION OF THE INVENTION

Figure 2A:
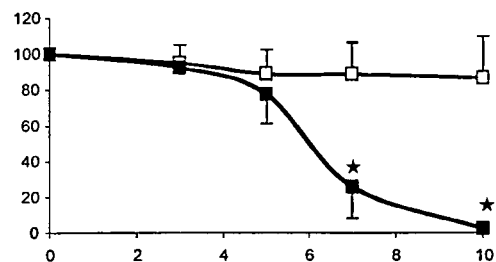
FIGS. 2A-2F show the effects of PI-083 and VELCADE on proteasomal CT-L activities in cancer and normal/immortalized cells from the same tissue. Exponentially growing cancer cells (|) and normal cells (□) were treated with indicated concentrations of PI-083 (FIGS. 2A-2C) or VELCADE (FIGS. 2D-2F) for 24 h, followed by measurement of CT-L activity in whole cell extracts.

The subject invention concerns compounds having activity as inhibitors of proteasomes and methods of using the subject compounds. In one embodiment, a compound of the invention has the chemical structure shown in formula I:

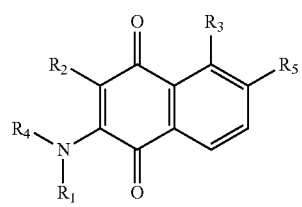

wherein $R_1$ is an organic cyclic ring structure bonded to a sulfonamide structure;

$R_2$ is H, halogen, alkyl, —NR$_6$R$_7$, or heteroalkyl;

$R_3$ is H, halogen, —OH, —O-alkyl, alkyl, cycloalkyl, heterocycloalkyl, aryl, heteroaryl, —NO$_2$, —NH$_2$ or substituted amines;

$R_4$ is H, alkyl, heteroalkyl, aryl, or heteroaryl, any of which can be optionally substituted with one or more of —NO$_2$, alkyl, heteroalkyl, aryl, or heteroaryl, or halogen;

$R_5$ is H, —OH, halogen, alkyl, aryl, heteroaryl, cycloalkyl, heterocycloalkyl, —O-alkyl, —O-aryl, heteroalkyl, —NO$_2$, —NH$_2$, or substituted amine; and $R_6$ and $R_7$ are independently H, O, alkyl, aryl, heterocycloalkyl, or heteroaryl, or together can form a heterocycloalkyl or a heteroaryl, any of which can be optionally substituted with one or more of —NO$_2$, alkyl, heteroalkyl, aryl, or halogen;

or a pharmaceutically acceptable salt or hydrate thereof.

In one embodiment, $R_2$ is Cl or F.

In another embodiment, $R_2$ is —CH$_3$.

In one embodiment, $R_2$ is NR$_6$R$_7$ and has a structure selected from:

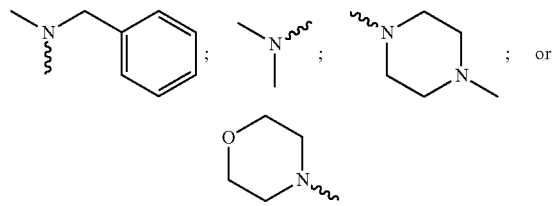

wherein ⌇ indicates the point of attachment.

In one embodiment, $R_4$ is ethyl, methyl, butyl, —CH$_2$-phenyl, —CH$_2$-naphthyl, —CH$_2$-4-nitro-phenyl, —CH$_2$-4-methyl-phenyl, or —CH$_2$-4-trifluoromethyl-phenyl.

In an exemplified embodiment, a compound of the invention (designated as PI-083) has the chemical structure:
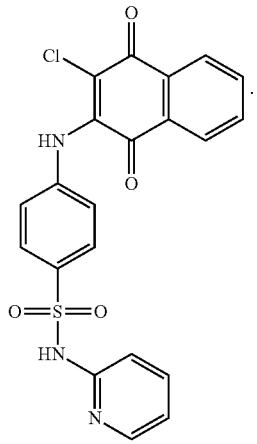
PI-083
Other exemplified embodiments of compounds of the invention include:
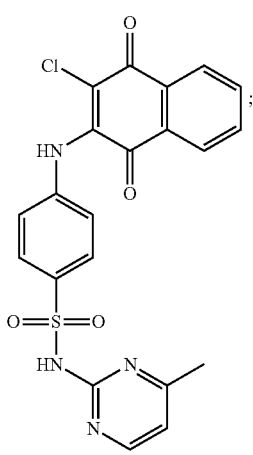
1
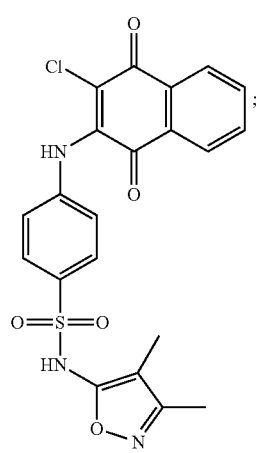
2
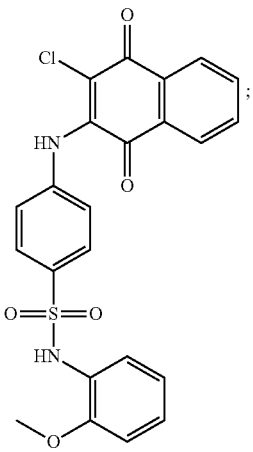
3
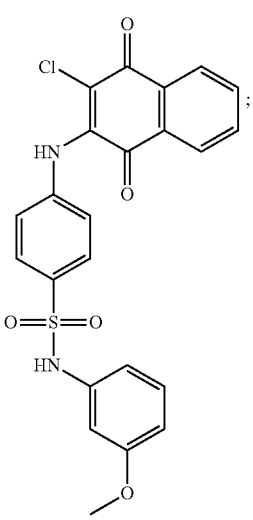
4
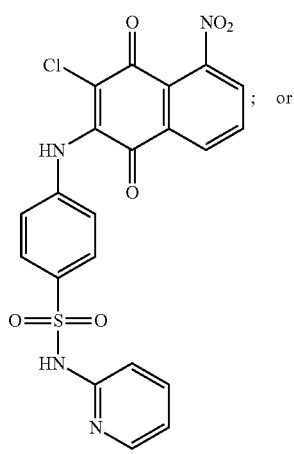
5
; or -continued

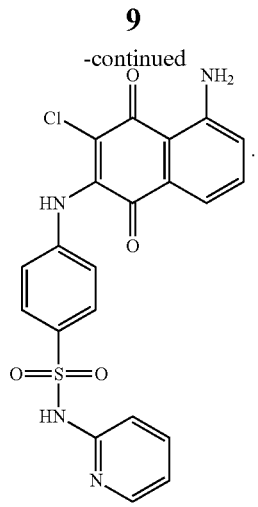

In one embodiment, R$_1$ has the chemical structure:

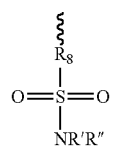

wherein R$_8$ is cycloalkyl, aryl, heterocycloalkyl, or heteroaryl, wherein R$_8$ can be substituted at any position with R'''; 
wherein R' and R'' are independently selected from H, alkyl, aryl, heterocycloalkyl, heteroaryl, alkylcarbonyl, heterocycloalkylcarbonyl, arylcarbonyl or heteroarylcarbonyl, any of which can optionally be substituted with one or more halogen, alkyl, or alkoxy; and
R''' is —NO$_2$, —OH, alkyl, cycloalkyl, heterocycloalkyl, aryl, heteroaryl, —O-alkyl, —O-aryl, —O-heteroaryl, —O-heterocycloalkyl, or an amine (primary, secondary, or tertiary).

In one embodiment, R$_8$ is a pyridine, pyrimidine, pyrole, thiophene, furan, naphthyl, heteroaromatic fused rings, or pyrazine ring structure.

In a specific embodiment, R$_1$ has the chemical structure:

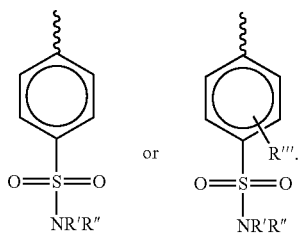

In one embodiment, R' and R'' are independently selected from H and the following:

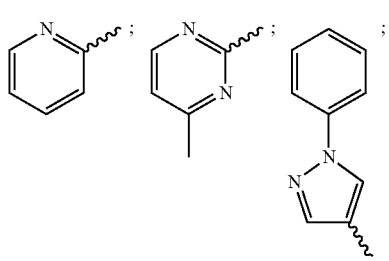

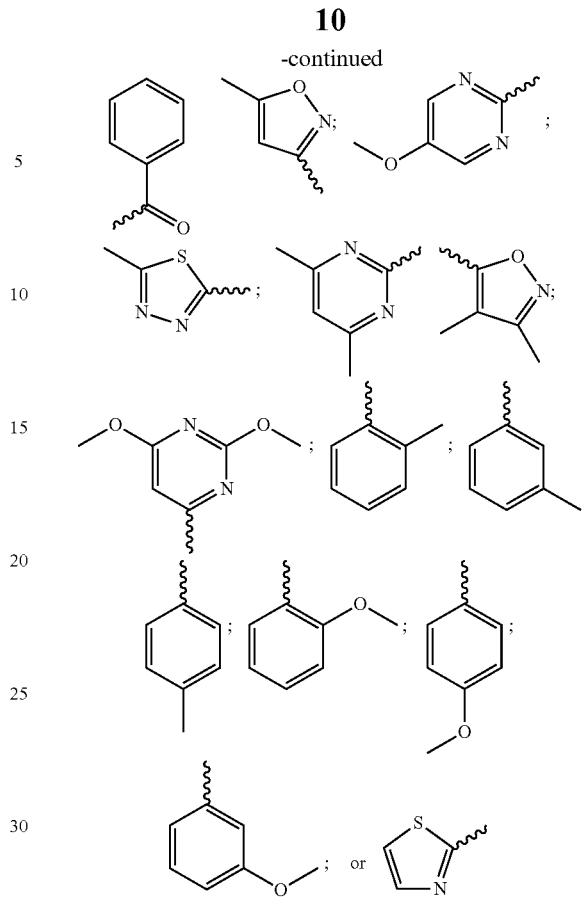

wherein § indicates the point of attachment.

In one embodiment, R' and R'' are both H.

In another embodiment, a compound of the invention has the chemical structure shown in formula II:

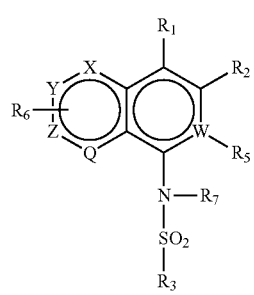

II wherein
Q, W, X, Y, Z are each independently carbon, oxygen, or nitrogen;
R$_1$ is H, or X$_1$R$_8$;
R$_2$ is heteroalkyl, which can be optionally substituted with one or more of —OH, halogen, —C(O)OR$_4$, alkyl, heteroalkyl, heterocycloalkyl, or heteroaryl;
R$_3$ is heterocycloalkyl, aryl, heteroaryl, any of which can be optionally substituted with one or more of a halogen or —OH; and
R$_4$ is H or alkyl;
R$_5$ is halogen, alkyl or nitro;
R$_6$ is nitro, X$_2$R$_9$ or a halogen;
R$_7$ is H or alkyl;

R$_8$ is H, alkyl, aryl, CH$_2$-alkyl-aryl, -alkyl-C(O)OH, or alkyl-tetrazole (aromatic and aliphatic heterocyclic groups);

R$_9$ is H or alkyl;

X$_1$ is oxygen, nitrogen, or sulfur;

X$_2$ is oxygen, nitrogen, or sulfur;

or a pharmaceutically acceptable salt or hydrate thereof.

In one embodiment, R$_1$ is —OH.

In one embodiment, X$_1$ and/or X$_2$ is SO$_2$.

In one embodiment, X$_1$ and/or X$_2$ is —NH.

In another embodiment, R$_2$ is —S-alkyl-C(O)OR$_4$, —SO$_2$-alkyl-C(O)OR$_4$, or —O-alkyl-C(O)OR$_4$.

In a specific embodiment, R$_2$ is —S-alkyl-C(O)OH, —SO$_2$-alkyl-C(O)OH, or —O-alkyl-C(O)OH.

In another specific embodiment, R$_2$ is

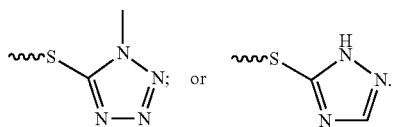

In one embodiment, R$_3$ is

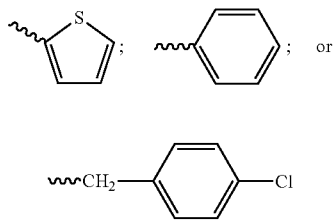

wherein either of which can be optionally substituted at any position with one or more halogen and § indicates the point of attachment.

In a specific embodiment, R$_3$ is

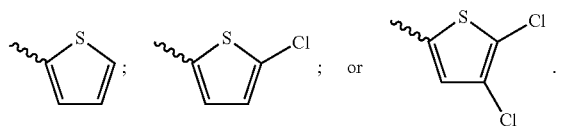

In another specific embodiment, R$_3$ is

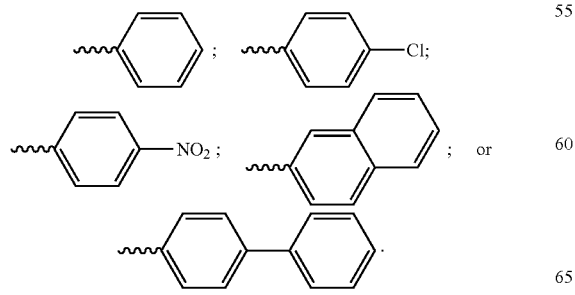

Exemplified embodiments of compounds of formula II are shown below:

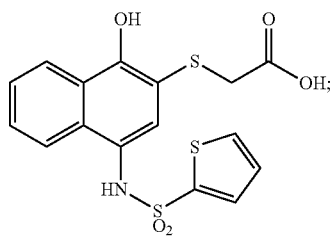
(HLM-008182)

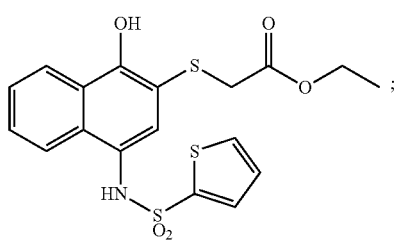
(9a)

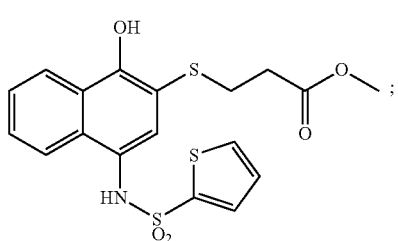
(9b)

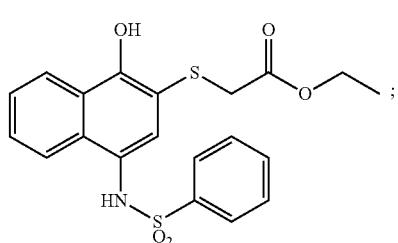
(9c)

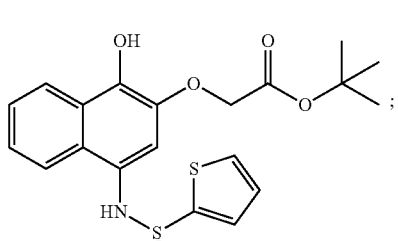
(9d)

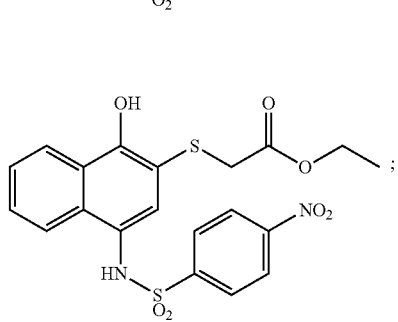
(9e)

-continued
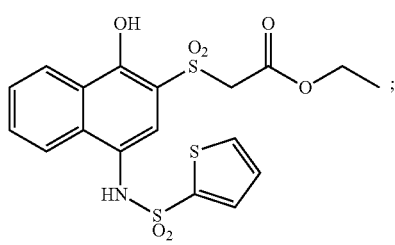
(9f)
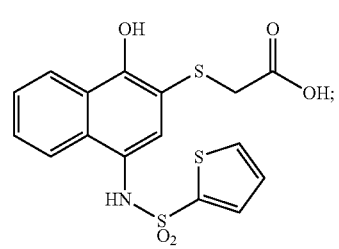
(10a)
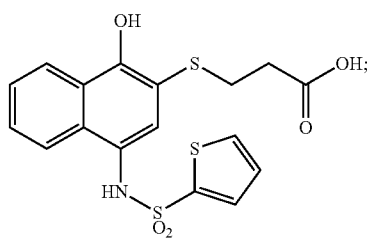
(10b)
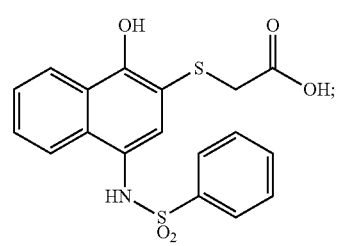
(10c)
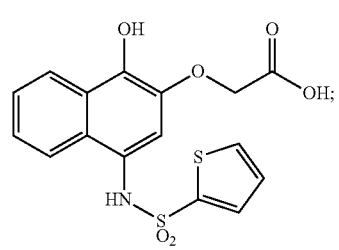
(10d)
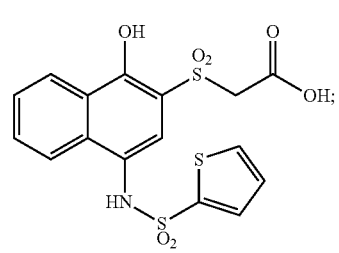
(10f)
-continued
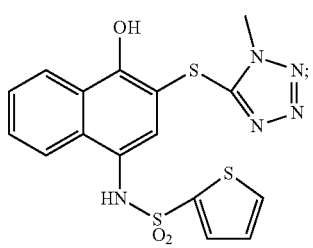
(14d)
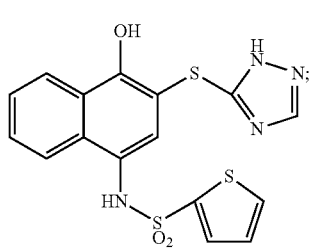
(14e)
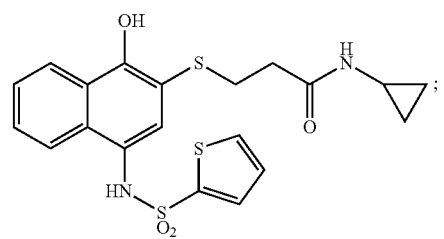
(14h)
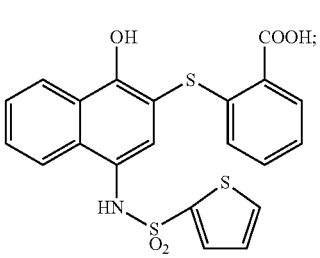
(14l)
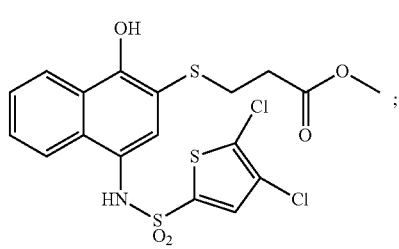
(14m)
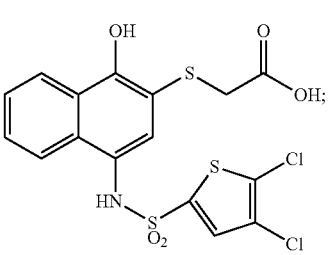
(14n)

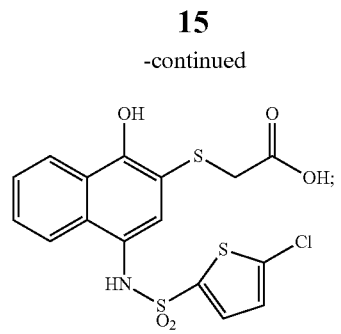
(14o)

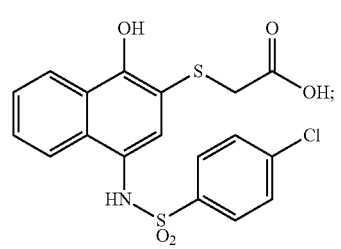
(14p)

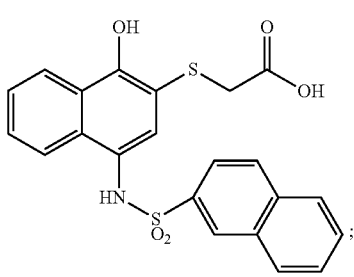
(14q)

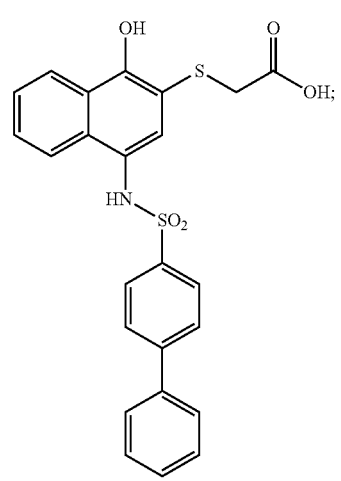
(14s)

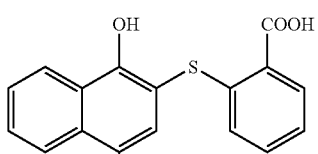
(14t)

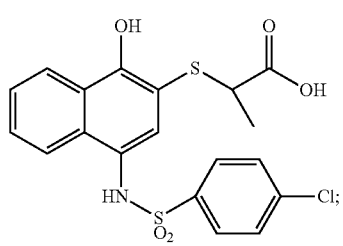
(14u)

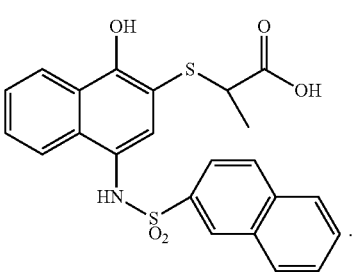
(14v)

The subject invention also concerns methods for treating a person or animal having a disorder or condition associated with aberrant or excessive CT-L activity in a cell or decreased apoptosis of a cell, or a disorder or condition associated with inhibition or downregulation of apoptosis of a cell. In one embodiment, the disorder or condition is an oncological disorder or condition. In one embodiment, a person or animal is administered an effective amount of one or more proteasome inhibitor compounds or compositions of this invention. In a specific embodiment, the compound is the compound designated herein as PI-083. In another embodiment, the compound is the compound designated herein as HLM-008182.

The subject invention also concerns methods of inducing apoptosis in a cell. In one embodiment, a cell is contacted with an effective amount of one or more proteasome inhibitor compounds or compositions of this invention. In a specific embodiment, the compound is the compound designated herein as PI-083. In another embodiment, the compound is the compound designated herein as HLM-008182. Cells can be any mammalian cell, such as a human cell, canine cell, feline cell, or equine cell. In one embodiment the cell is a tumor cell, a cancer cell or a transformed cell.

The subject invention also concerns methods for inhibiting CT-L enzymatic activity in a cell. In one embodiment, a cell is contacted with an effective amount of one or more proteasome inhibitor compounds or compositions of this invention.

In a specific embodiment, the compound is the compound designated herein as PI-083. In another embodiment, the compound is the compound designated herein as HLM-008182. Cells can be any mammalian cell, such as a human cell, canine cell, feline cell, or equine cell. In one embodiment the cell is a tumor cell, a cancer cell or a transformed cell.

The subject invention also concerns a packaged dosage formulation comprising in one or more containers at least one proteasome inhibitor compound or composition of the invention. In one embodiment, a packaged dosage formulation comprises a compound designated herein as PI-083. In another embodiment, the compound is the compound designated herein as HLM-008182. A packaged dosage formulation can optionally comprise in one or more containers a pharmaceutically acceptable carrier or diluent.

As used herein, alkyl means straight or branched chain, saturated or mono- or polyunsaturated hydrocarbon groups having from 1 to 20 carbon atoms and $C_{1-X}$ alkyl means straight or branched chain alkyl groups containing from one up to X carbon atoms. For example, $C_{1-6}$ alkyl means straight or branched chain alkyl groups containing from one up to 6 carbon atoms. Alkoxy means an alkyl-O— group in which the alkyl group is as previously described. Cycloalkyl includes a nonaromatic monocyclic or multicyclic ring system, including fused and spiro rings, of from about three to about 10 carbon atoms. A cyclic alkyl may optionally be partially unsaturated. Cycloalkoxy means a cycloalkyl-O-group in which cycloalkyl is as defined herein. Aryl means an aromatic monocyclic or multicyclic carbocyclic ring system, including fused and spiro rings, containing from about six to about 14 carbon atoms. Aryloxy means an aryl-O— group in which the aryl group is as described herein. Alkylcarbonyl means a RC(O)— group where R is an alkyl group as previously described. Alkoxycarbonyl means an ROC(O)— group where R is an alkyl group as previously described. Cycloalkylcarbonyl means an RC(O)— group where R is a cycloalkyl group as previously described. Cycloalkoxycarbonyl means an ROC(O)— group where R is a cycloalkyl group as previously described.

Heteroalkyl means a straight or branched-chain having from one to 20 carbon atoms and one or more heteroatoms selected from nitrogen, oxygen, or sulphur, wherein the nitrogen and sulphur atoms may optionally be oxidized, i.e., in the form of an N-oxide or an S-oxide. Heterocycloalkyl means a monocyclic or multicyclic ring system (which may be saturated or partially unsaturated), including fused and spiro rings, of about five to about 10 elements wherein one or more of the elements in the ring system is an element other than carbon and is selected from nitrogen, oxygen, silicon, or sulphur atoms. Heteroaryl means a five to about a 14-membered aromatic monocyclic or multicyclic hydrocarbon ring system, including fused and spiro rings, in which one or more of the elements in the ring system is an element other than carbon and is selected from nitrogen, oxygen, silicon, or sulphur and wherein an N atom may be in the form of an N-oxide. Arylcarbonyl means an aryl-CO— group in which the aryl group is as described herein. Heteroarylcarbonyl means a heteroaryl-CO— group in which the heteroaryl group is as described herein and heterocycloalkylcarbonyl means a heterocycloalkyl-CO— group in which the heterocycloalkyl group is as described herein. Aryloxycarbonyl means an ROC(O)— group where R is an aryl group as previously described. Heteroaryloxycarbonyl means an ROC(O)— group where R is a heteroaryl group as previously described. Heteroaryloxy means a heteroaryl-O— group in which the heteroaryl group is as previously described. Heterocycloalkoxy means a heterocycloalkyl-O— group in which the heterocycloalkyl group is as previously described. Heterocycloalkoxycarbonyl means an ROC(O)— group where R is a heterocycloalkyl group as previously described.

Examples of saturated alkyl groups include, but are not limited to, methyl, ethyl, N-propyl, isopropyl, N-butyl, tert-butyl, isobutyl, sec-butyl, N-pentyl, N-hexyl, N-heptyl, and N-octyl. An unsaturated alkyl group is one having one or more double or triple bonds. Unsaturated alkyl groups include, for example, ethenyl, propenyl, butenyl, hexenyl, vinyl, 2-propynyl, 2-isopentenyl, 2-butadienyl, ethynyl, 1-propynyl, 3-propynyl, and 3-butynyl. Cycloalkyl groups include, for example, cyclopentyl, cyclohexyl, 1-cyclohexenyl, 3-cyclohexenyl, and cycloheptyl. Heterocycloalkyl groups include, for example, 1-piperidinyl, 2-piperidinyl, 3-piperidinyl, 3-morpholinyl, 4-morpholinyl, tetrahydrofuran-2-yl, tetrahydrofuran-3-yl, tetrahydrothien-2-yl, tetrahydrothien-3-yl, 1-piperazinyl, 2-piperazinyl, and 1,4-diazabicyclooctane. Aryl groups include, for example, phenyl, indenyl, biphenyl, 1-naphthyl, 2-naphthyl, anthracenyl, and phenanthracenyl. Heteroaryl groups include, for example, 1-pyrrolyl, 2-pyrrolyl, 3-pyrrolyl, furyl, thienyl, imidazolyl, oxazolyl, thiazolyl, pyrazolyl, pyridyl, indolyl, quinolinyl, isoquinolinyl, benzoquinolinyl, carbazolyl, and diazaphenanthrenyl.

As used herein, halogen means the elements fluorine (F), chlorine (Cl), Bromine (Br), and iodine (I).

Compounds of the subject invention also include physiologically-acceptable salts and hydrates of the subject compounds. Physiologically-acceptable salts include salts of the compounds of the invention which are prepared with acids or bases, depending on the particular substituents found on the subject complexes described herein. Examples of physiologically-acceptable base addition salts include sodium, potassium, calcium, ammonium, or magnesium salt. Examples of physiologically-acceptable acid addition salts include hydrochloric, hydrobromic, nitric, phosphoric, carbonic, sulphuric, and organic acids like acetic, propionic, benzoic, succinic, fumaric, mandelic, oxalic, citric, tartaric, maleic, and the like. Physiologically-acceptable salts of compounds of the invention can be prepared using conventional techniques.

It will be appreciated by those skilled in the art that certain of the compounds of the invention may contain one or more asymmetrically substituted carbon atoms which can give rise to stereoisomers. It is understood that the invention extends to all such stereoisomers, including enantiomers, and diastereoisomers and mixtures, including racemic mixtures thereof.

In vivo application of the subject compounds, and compositions containing them, can be accomplished by any suitable method and technique presently or prospectively known to those skilled in the art. The subject compounds can be formulated in a physiologically- or pharmaceutically-acceptable form and administered by any suitable route known in the art including, for example, oral, nasal, rectal, and parenteral routes of administration. As used herein, the term parenteral includes subcutaneous, intradermal, intravenous, intramuscular, intraperitoneal, and intrasternal administration, such as by injection. Administration of the subject compounds of the invention can be a single administration, or at continuous or distinct intervals as can be readily determined by a person skilled in the art.

The compounds of the subject invention, and compositions comprising them, can also be administered utilizing liposome technology, slow release capsules, implantable pumps, and biodegradable containers. These delivery methods can, advantageously, provide a uniform dosage over an extended period of time. The compounds of the invention can also be administered in their salt derivative forms or crystalline forms.

Compounds of the subject invention can be formulated according to known methods for preparing physiologically acceptable compositions. Formulations are described in detail in a number of sources which are well known and readily available to those skilled in the art. For example, Remington's Pharmaceutical Science by E. W. Martin describes formulations which can be used in connection with the subject invention. In general, the compositions of the subject invention will be formulated such that an effective amount of the compound is combined with a suitable carrier in order to facilitate effective administration of the composition. The compositions used in the present methods can also be in a variety of forms. These include, for example, solid, semi-solid, and liquid dosage forms, such as tablets, pills, powders, liquid solutions or suspension, suppositories, injectable and infusible solutions, and sprays. The preferred form depends on the intended mode of administration and therapeutic application. The compositions also preferably include conventional physiologically-acceptable carriers and diluents which are known to those skilled in the art. Examples of carriers or diluents for use with the subject compounds include ethanol, dimethyl sulfoxide, glycerol, alumina, starch, saline, and equivalent carriers and diluents. To provide for the administration of such dosages for the desired therapeutic treatment, compositions of the invention will advantageously comprise between about 0.1% and 99%, and especially, 1 and 15% by weight of the total of one or more of the subject compounds based on the weight of the total composition including carrier or diluent.

Compounds of the invention, and compositions comprising them, can be delivered to a cell either through direct contact with the cell or via a carrier means. Carrier means for delivering compounds and compositions to cells are known in the art and include, for example, encapsulating the composition in a liposome moiety. Another means for delivery of compounds and compositions of the invention to a cell comprises attaching the compounds to a protein or nucleic acid that is targeted for delivery to the target cell. U.S. Pat. No. 6,960,648 and Published U.S. Patent Application Nos. 20030032594 and 20020120100 disclose amino acid sequences that can be coupled to another composition and that allows the composition to be translocated across biological membranes. Published U.S. Patent Application No. 20020035243 also describes compositions for transporting biological moieties across cell membranes for intracellular delivery. Compounds can also be incorporated into polymers, examples of which include poly(D-L lactide-co-glycolide) polymer for intracranial tumors; poly[bis(p-carboxyphenoxy) propane:sebacic acid] in a 20:80 molar ratio (as used in GLIADEL); chondroitin; chitin; and chitosan.

The subject invention also concerns methods for treating oncological disorders in a patient. In one embodiment, an effective amount of one or more compounds or compositions of the present invention is administered to a patient having an oncological disorder and who is in need of treatment thereof. Methods of the invention can optionally include identifying a patient who is or may be in need of treatment of an oncological disorder. The patient can be a human or other mammal, such as a primate (monkey, chimpanzee, ape, etc.), dog, cat, cow, pig, or horse, or other animals having an oncological disorder. Means for administering and formulating compounds for administration to a patient are known in the art, examples of which are described herein. Oncological disorders within the scope of the invention include, but are not limited to, cancer and/or tumors of the anus, bile duct, bladder, bone, bone marrow, bowel (including colon and rectum), breast, eye, gall bladder, kidney, mouth, larynx, esophagus, stomach, testis, cervix, head, neck, ovary, lung, mesothelioma, neuroendocrine, penis, skin, spinal cord, thyroid, vagina, vulva, uterus, liver, muscle, pancreas, prostate, blood cells (including lymphocytes and other immune system cells), and brain. Specific cancers contemplated for treatment with the present invention include carcinomas, Karposi's sarcoma, melanoma, mesothelioma, soft tissue sarcoma, pancreatic cancer, lung cancer, leukemia (acute lymphoblastic, acute myeloid, chronic lymphocytic, chronic myeloid, and other), and lymphoma (Hodgkin's and non-Hodgkin's), and multiple myeloma.

Examples of cancers that can be treated according to the present invention are listed in Table 1.

TABLE 1

| Examples of Cancer Types | |
|---|---|
| Acute Lymphoblastic Leukemia, Adult | Hairy Cell Leukemia |
| Acute Lymphoblastic Leukemia, Childhood | Head and Neck Cancer |
| Acute Myeloid Leukemia, Adult | Hepatocellular (Liver) Cancer, Adult |
| Acute Myeloid Leukemia, Childhood | (Primary) |
| Adrenocortical Carcinoma | Hepatocellular (Liver) Cancer, Childhood |
| Adrenocortical Carcinoma, Childhood | (Primary) |
| AIDS-Related Cancers | Hodgkin's Lymphoma, Adult |
| AIDS-Related Lymphoma | Hodgkin's Lymphoma, Childhood |
| Anal Cancer | Hodgkin's Lymphoma During Pregnancy |
| Astrocytoma, Childhood Cerebellar | Hypopharyngeal Cancer |
| Astrocytoma, Childhood Cerebral | Hypothalamic and Visual Pathway Glioma, |
| Basal Cell Carcinoma | Childhood |
| Bile Duct Cancer, Extrahepatic | Intraocular Melanoma |
| Bladder Cancer | Islet Cell Carcinoma (Endocrine Pancreas) |
| Bladder Cancer, Childhood | Kaposi's Sarcoma |
| Bone Cancer, Osteosarcoma/Malignant | Kidney (Renal Cell) Cancer |
| Fibrous Histiocytoma | Kidney Cancer, Childhood |
| Brain Stem Glioma, Childhood | Laryngeal Cancer |
| Brain Tumor, Adult | Laryngeal Cancer, Childhood |
| Brain Tumor, Brain Stem Glioma, Childhood | Leukemia, Acute Lymphoblastic, Adult |
| | Leukemia, Acute Lymphoblastic, Childhood |
| Brain Tumor, Cerebellar Astrocytoma, Childhood | Leukemia, Acute Myeloid, Adult |
| | Leukemia, Acute Myeloid, Childhood |
| Brain Tumor, Cerebral Astrocytoma/Malignant Glioma, | Leukemia, Chronic Lymphocytic |
| | Leukemia, Chronic Myelogenous |

TABLE 1-continued

Examples of Cancer Types

Childhood
Brain Tumor, Ependymoma, Childhood
Brain Tumor, Medulloblastoma, Childhood
Brain Tumor, Supratentorial Primitive Neuroectodermal Tumors, Childhood
Brain Tumor, Visual Pathway and Hypothalamic Glioma, Childhood
Brain Tumor, Childhood
Breast Cancer
Breast Cancer, Childhood
Breast Cancer, Male
Bronchial Adenomas/Carcinoids, Childhood
Burkitt's Lymphoma
Carcinoid Tumor, Childhood
Carcinoid Tumor, Gastrointestinal
Carcinoma of Unknown Primary
Central Nervous System Lymphoma, Primary
Cerebellar Astrocytoma, Childhood
Cerebral Astrocytoma/Malignant Glioma, Childhood
Cervical Cancer
Childhood Cancers
Chronic Lymphocytic Leukemia
Chronic Myelogenous Leukemia
Chronic Myeloproliferative Disorders
Colon Cancer
Colorectal Cancer, Childhood
Cutaneous T-Cell Lymphoma, see Mycosis Fungoides and Sézary Syndrome
Endometrial Cancer
Ependymoma, Childhood
Esophageal Cancer
Esophageal Cancer, Childhood
Ewing's Family of Tumors
Extracranial Germ Cell Tumor, Childhood
Extragonadal Germ Cell Tumor
Extrahepatic Bile Duct Cancer
Eye Cancer, Intraocular Melanoma
Eye Cancer, Retinoblastoma
Gallbladder Cancer
Gastric (Stomach) Cancer
Gastric (Stomach) Cancer, Childhood
Gastrointestinal Carcinoid Tumor
Germ Cell Tumor, Extracranial, Childhood
Germ Cell Tumor, Extragonadal
Germ Cell Tumor, Ovarian
Gestational Trophoblastic Tumor
Glioma, Adult
Glioma, Childhood Brain Stem
Glioma, Childhood Cerebral Astrocytoma
Glioma, Childhood Visual Pathway and Hypothalamic
Skin Cancer (Melanoma)
Skin Carcinoma, Merkel Cell
Small Cell Lung Cancer
Small Intestine Cancer
Soft Tissue Sarcoma, Adult
Soft Tissue Sarcoma, Childhood
Squamous Cell Carcinoma, see Skin Cancer (non-Melanoma)
Squamous Neck Cancer with Occult Primary, Metastatic
Stomach (Gastric) Cancer
Stomach (Gastric) Cancer, Childhood
Supratentorial Primitive Neuroectodermal Tumors, Childhood
T-Cell Lymphoma, Cutaneous, see Mycosis Fungoides and Sézary Syndrome
Testicular Cancer
Thymoma, Childhood
Leukemia, Hairy Cell
Lip and Oral Cavity Cancer
Liver Cancer, Adult (Primary)
Liver Cancer, Childhood (Primary)
Lung Cancer, Non-Small Cell
Lung Cancer, Small Cell
Lymphoma, AIDS-Related
Lymphoma, Burkitt's
Lymphoma, Cutaneous T-Cell, see Mycosis Fungoides and Sézary Syndrome
Lymphoma, Hodgkin's, Adult
Lymphoma, Hodgkin's, Childhood
Lymphoma, Hodgkin's During Pregnancy
Lymphoma, Non-Hodgkin's, Adult
Lymphoma, Non-Hodgkin's, Childhood
Lymphoma, Non-Hodgkin's During Pregnancy
Lymphoma, Primary Central Nervous System
Macroglobulinemia, Waldenström's
Malignant Fibrous Histiocytoma of Bone/Osteosarcoma
Medulloblastoma, Childhood
Melanoma
Melanoma, Intraocular (Eye)
Merkel Cell Carcinoma
Mesothelioma, Adult Malignant
Mesothelioma, Childhood
Metastatic Squamous Neck Cancer with Occult Primary
Multiple Endocrine Neoplasia Syndrome, Childhood
Multiple Myeloma/Plasma Cell Neoplasm
Mycosis Fungoides
Myelodysplastic Syndromes
Myelodysplastic/Myeloproliferative Diseases
Myelogenous Leukemia, Chronic
Myeloid Leukemia, Adult Acute
Myeloid Leukemia, Childhood Acute
Myeloma, Multiple
Myeloproliferative Disorders, Chronic
Nasal Cavity and Paranasal Sinus Cancer
Nasopharyngeal Cancer
Nasopharyngeal Cancer, Childhood
Neuroblastoma
Non-Hodgkin's Lymphoma, Adult
Non-Hodgkin's Lymphoma, Childhood
Non-Hodgkin's Lymphoma During Pregnancy
Non-Small Cell Lung Cancer
Oral Cancer, Childhood
Oral Cavity Cancer, Lip and
Oropharyngeal Cancer
Osteosarcoma/Malignant Fibrous Histiocytoma of Bone
Ovarian Cancer, Childhood
Ovarian Epithelial Cancer
Ovarian Germ Cell Tumor
Ovarian Low Malignant Potential Tumor
Pancreatic Cancer
Pancreatic Cancer, Childhood
Pancreatic Cancer, Islet Cell
Paranasal Sinus and Nasal Cavity Cancer
Parathyroid Cancer
Penile Cancer
Pheochromocytoma
Pineoblastoma and Supratentorial Primitive Neuroectodermal Tumors, Childhood
Pituitary Tumor
Plasma Cell Neoplasm/Multiple Myeloma
Pleuropulmonary Blastoma
Pregnancy and Breast Cancer
Pregnancy and Hodgkin's Lymphoma
Pregnancy and Non-Hodgkin's Lymphoma
Primary Central Nervous System Lymphoma
Prostate Cancer
Rectal Cancer
Renal Cell (Kidney) Cancer
Renal Cell (Kidney) Cancer, Childhood
Renal Pelvis and Ureter, Transitional Cell

TABLE 1-continued

Examples of Cancer Types

| | |
|---|---|
| Thymoma and Thymic Carcinoma | Cancer |
| Thyroid Cancer | Retinoblastoma |
| Thyroid Cancer, Childhood | Rhabdomyosarcoma, Childhood |
| Transitional Cell Cancer of the Renal Pelvis and Ureter | Salivary Gland Cancer |
| | Salivary Gland Cancer, Childhood |
| Trophoblastic Tumor, Gestational | Sarcoma, Ewing's Family of Tumors |
| Unknown Primary Site, Carcinoma of, Adult | Sarcoma, Kaposi's |
| | Sarcoma, Soft Tissue, Adult |
| Unknown Primary Site, Cancer of, Childhood | Sarcoma, Soft Tissue, Childhood |
| | Sarcoma, Uterine |
| Unusual Cancers of Childhood | Sezary Syndrome |
| Ureter and Renal Pelvis, Transitional Cell Cancer | Skin Cancer (non-Melanoma) |
| | Skin Cancer, Childhood |
| Urethral Cancer | |
| Uterine Cancer, Endometrial | |
| Uterine Sarcoma | |
| Vaginal Cancer | |
| Visual Pathway and Hypothalamic Glioma, Childhood | |
| Vulvar Cancer | |
| Waldenström's Macroglobulinemia | |
| Wilms' Tumor | |

In a specific embodiment, the oncological disorder is multiple myeloma.

For the treatment of oncological disorders, the compounds of this invention can be administered to a patient in need of treatment in combination with other antitumor or anticancer substances and/or with radiation and/or photodynamic therapy and/or with surgical treatment to remove a tumor. These other substances or treatments may be given at the same as or at different times from the compounds of this invention. For example, the compounds of the present invention can be used in combination with mitotic inhibitors such as taxol or vinblastine, alkylating agents such as cyclophosamide or ifosfamide, antimetabolites such as 5-fluorouracil or hydroxyurea, DNA intercalators such as adriamycin or bleomycin, topoisomerase inhibitors such as etoposide or camptothecin, antiangiogenic agents such as angiostatin, antiestrogens such as tamoxifen, and/or other anti-cancer drugs or antibodies, such as, for example, GLEEVEC (Novartis Pharmaceuticals Corporation) and HERCEPTIN (Genentech, Inc.), respectively. In one embodiment, compounds and compositions of the invention can be used in combination with other proteasome inhibitors, including, but not limited to, Bortezomib, Carfilzomib, and Salinosporamide A.

Many tumors and cancers have viral genome present in the tumor or cancer cells. For example, Epstein-Barr Virus (EBV) is associated with a number of mammalian malignancies. The compounds of the subject invention can also be used alone or in combination with anticancer or antiviral agents, such as ganciclovir, azidothymidine (AZT), lamivudine (3TC), etc., to treat patients infected with a virus that can cause cellular transformation and/or to treat patients having a tumor or cancer that is associated with the presence of viral genome in the cells. The compounds of the subject invention can also be used in combination with viral based treatments of oncologic disease. For example, compounds of the invention can be used with mutant herpes simplex virus in the treatment of non-small cell lung cancer (Toyoizumi et al., 1999).

The methods of the present invention can be used with humans and other animals. The other animals contemplated within the scope of the invention include domesticated, agricultural, or zoo- or circus-maintained animals. Domesticated animals include, for example, dogs, cats, rabbits, ferrets, guinea pigs, hamsters, pigs, monkeys or other primates, and gerbils. Agricultural animals include, for example, horses, mules, donkeys, burros, cattle, cows, pigs, sheep, and alligators. Zoo- or circus-maintained animals include, for example, lions, tigers, bears, camels, giraffes, hippopotamuses, and rhinoceroses.

While inhibitor compounds or agents of the invention can be administered as isolated compounds or agents, these compounds can also be administered as part of a pharmaceutical composition. The subject invention thus further provides compositions comprising one or more compounds or agents in association with at least one pharmaceutically acceptable carrier. The pharmaceutical composition can be adapted for various routes of administration, such as enteral, parenteral, intravenous, intramuscular, topical, subcutaneous, and so forth. Administration can be continuous or at distinct intervals, as can be determined by a person of ordinary skill in the art.

The inhibitor compounds or agents of the invention can be formulated according to known methods for preparing pharmaceutically useful compositions. Formulations are described in a number of sources which are well known and readily available to those skilled in the art. For example, *Remington's Pharmaceutical Science* (Martin 1995) describes formulations which can be used in connection with the subject invention. Formulations suitable for administration include, for example, aqueous sterile injection solutions, which may contain antioxidants, buffers, bacteriostats, and solutes that render the formulation isotonic with the blood of the intended recipient; and aqueous and nonaqueous sterile suspensions which may include suspending agents and thickening agents. The formulations may be presented in unit-dose or multi-dose containers, for example sealed ampoules and vials, and may be stored in a freeze dried (lyophilized) condition requiring only the condition of the sterile liquid carrier, for example, water for injections, prior to use. Extemporaneous injection solutions and suspensions may be prepared from sterile powder, granules, tablets, etc. It should be understood that in addition to the ingredients particularly mentioned above, the compositions of the subject invention can include other agents conventional in the art having regard to the type of formulation in question.

The compounds and agents of the present invention include all hydrates and salts that can be prepared by those of skill in the art. Under conditions where the compounds and agents of the present invention are sufficiently basic or acidic to form stable nontoxic acid or base salts, administration of the compounds as salts may be appropriate. Examples of pharmaceutically acceptable salts are organic acid addition salts formed with acids that form a physiological acceptable anion, for example, tosylate, methanesulfonate, acetate, citrate, malonate, tartarate, succinate, benzoate, ascorbate, alpha-ketoglutarate, and alpha-glycerophosphate. Suitable inorganic salts may also be formed, including hydrochloride, sulfate, nitrate, bicarbonate, and carbonate salts.

Pharmaceutically acceptable salts of a compound or agent may be obtained using standard procedures well known in the art, for example, by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

Therapeutic application of compounds and/or agents and compositions containing them can be accomplished by any suitable therapeutic method and technique presently or prospectively known to those skilled in the art. Further, compounds and agents of the invention have use as starting materials or intermediates for the preparation of other useful compounds and compositions.

Compounds and agents of the invention, and compositions thereof, may be locally administered at one or more anatomical sites, such as sites of unwanted cell growth (such as a tumor site or benign skin growth, e.g., injected or topically applied to the tumor or skin growth) or sites of fungal infection, optionally in combination with a pharmaceutically acceptable carrier such as an inert diluent. Compounds and agents of the invention, and compositions thereof, may be systemically administered, such as intravenously or orally, optionally in combination with a pharmaceutically acceptable carrier such as an inert diluent, or an assimilable edible carrier for oral delivery. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, aerosol sprays, and the like.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac, or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

Compounds and agents and compositions of the invention, including pharmaceutically acceptable salts or analogs thereof, can be administered intravenously, intramuscularly, or intraperitoneally by infusion or injection. Solutions of the active agent or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations can contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. The ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. Optionally, the prevention of the action of microorganisms can be brought about by various other antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the inclusion of agents that delay absorption, for example, aluminum monostearate and gelatin.

Sterile injectable solutions are prepared by incorporating a compound and/or agent of the invention in the required amount in the appropriate solvent with various other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, compounds and agents of the invention may be applied in as a liquid or solid. However, it will generally be desirable to administer them topically to the skin as compositions, in combination with a dermatologically acceptable carrier, which may be a solid or a liquid. Compounds and agents and compositions of the subject invention can be applied topically to a subject's skin to reduce the size (and may include complete removal) of malignant or benign growths, or to treat an infection site. Compounds and agents of the invention can be applied directly to the growth or infection site. Preferably, the compounds and agents are applied to the growth or infection site in a formulation such as an ointment, cream, lotion, solution, tincture, or the like. Drug delivery systems for delivery of pharmacological substances to dermal lesions can also be used, such as that described in U.S. Pat. No. 5,167,649.

Useful solid carriers include finely divided solids such as talc, clay, microcrystalline cellulose, silica, alumina and the like. Useful liquid carriers include water, alcohols or glycols or water-alcohol/glycol blends, in which the compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers, for example.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user. Examples of useful dermatological compositions which can be used to deliver a compound to the skin are disclosed in U.S. Pat. No. 4,608,392; U.S. Pat. No. 4,992,478; U.S. Pat. No. 4,559,157; and U.S. Pat. No. 4,820,508.

Useful dosages of the compounds and agents and pharmaceutical compositions of the present invention can be determined by comparing their in vitro activity, and in vivo activity in animal models. Methods for the extrapolation of effective dosages in mice, and other animals, to humans are known to the art; for example, see U.S. Pat. No. 4,938,949.

The present invention also concerns pharmaceutical compositions comprising a compound and/or agent of the invention in combination with a pharmaceutically acceptable carrier. Pharmaceutical compositions adapted for oral, topical or parenteral administration, comprising an amount of a compound constitute a preferred embodiment of the invention. The dose administered to a patient, particularly a human, in the context of the present invention should be sufficient to achieve a therapeutic response in the patient over a reasonable time frame, without lethal toxicity, and preferably causing no more than an acceptable level of side effects or morbidity. One skilled in the art will recognize that dosage will depend upon a variety of factors including the condition (health) of the subject, the body weight of the subject, kind of concurrent treatment, if any, frequency of treatment, therapeutic ratio, as well as the severity and stage of the pathological condition.

For the treatment of oncological disorders, compounds and agents and compositions contemplated by the present invention can be administered to a patient in need of treatment prior to, subsequent to, or in combination with other antitumor or anticancer agents or substances (e.g., chemotherapeutic agents, immunotherapeutic agents, radiotherapeutic agents, cytotoxic agents, etc.) and/or with radiation therapy and/or with surgical treatment to remove a tumor. For example, compounds and agents and compositions of the present invention can be used in methods of treating cancer wherein the patient is to be treated or is or has been treated with mitotic inhibitors such as taxol or vinblastine, alkylating agents such as cyclophosamide or ifosfamide, antimetabolites such as 5-fluorouracil or hydroxyurea, DNA intercalators such as adriamycin or bleomycin, topoisomerase inhibitors such as etoposide or camptothecin, antiangiogenic agents such as angiostatin, antiestrogens such as tamoxifen, and/or other anti-cancer drugs or antibodies, such as, for example, GLEEVEC (Novartis Pharmaceuticals Corporation) and HERCEPTIN (Genentech, Inc.), respectively. These other substances or radiation treatments may be given at the same as or at different times from the compounds of this invention. Examples of other chemotherapeutic agents contemplated within the scope of the invention include, but are not limited to, altretamine, bleomycin, bortezomib (VELCADE), busulphan, calcium folinate, capecitabine, carboplatin, carmustine, chlorambucil, cisplatin, cladribine, crisantaspase, cyclophosphamide, cytarabine, dacarbazine, dactinomycin, daunorubicin, docetaxel, doxorubicin, epirubicin, etoposide, fludarabine, fluorouracil, gefitinib (IRESSA), gemcitabine, hydroxyurea, idarubicin, ifosfamide, imatinib (GLEEVEC), irinotecan, liposomal doxorubicin, lomustine, melphalan, mercaptopurine, methotrexate, mitomycin, mitoxantrone, oxaliplatin, paclitaxel, pentostatin, procarbazine, raltitrexed, streptozocin, tegafur-uracil, temozolomide, thiotepa, tioguanine/thioguanine, topotecan, treosulfan, vinblastine, vincristine, vindesine, vinorelbine. In an exemplified embodiment, the chemotherapeutic agent is melphalan. Examples of immunotherapeutic agents contemplated within the scope of the invention include, but are not limited to, alemtuzumab, cetuximab (ERBITUX), gemtuzumab, iodine 131 tositumomab, rituximab, trastuzumab (HERCEPTIN). Cytotoxic agents include, for example, radioactive isotopes (e.g., $I^{131}$, $I^{125}$, $Y^{90}$, $P^{32}$, etc.), and toxins of bacterial, fungal, plant, or animal origin (e.g., ricin, botulinum toxin, anthrax toxin, aflatoxin, jellyfish venoms (e.g., box jellyfish), etc.) The subject invention also concerns methods for treating an oncological disorder comprising administering an effective amount of a compound and/or agent of the invention prior to, subsequent to, and/or in combination with administration of a chemotherapeutic agent, an immunotherapeutic agent, a radiotherapeutic agent, or radiotherapy.

Examples of some chemotherapeutic agents that can be used according to the present invention are listed in Table 2.

TABLE 2

| Examples of Chemotherapeutic Agents | |
|---|---|
| 13-cis-Retinoic Acid | Mylocel |
| 2-Amino-6- | Letrozole |
| Mercaptopurine | Neosar |
| 2-CdA | Neulasta |
| 2-Chlorodeoxyadenosine | Neumega |
| 5-fluorouracil | Neupogen |
| 5-FU | Nilandron |
| 6-TG | Nilutamide |
| 6-Thioguanine | Nitrogen Mustard |
| 6-Mercaptopurine | Novaldex |
| 6-MP | Novantrone |
| Accutane | Octreotide |
| Actinomycin-D | Octreotide acetate |
| Adriamycin | Oncospar |
| Adrucil | Oncovin |
| Agrylin | Ontak |
| Ala-Cort | Onxal |
| Aldesleukin | Oprevelkin |
| Alemtuzumab | Orapred |
| Alitretinoin | Orasone |
| Alkaban-AQ | Oxaliplatin |
| Alkeran | Paclitaxel |
| All-transretinoic acid | Pamidronate |
| Alpha interferon | Panretin |
| Altretamine | Paraplatin |
| Amethopterin | Pediapred |
| Amifostine | PEG Interferon |
| Aminoglutethimide | Pegaspargase |
| Anagrelide | Pegfilgrastim |
| Anandron | PEG-INTRON |
| Anastrozole | PEG-L-asparaginase |
| Arabinosylcytosine | Phenylalanine Mustard |
| Ara-C | Platinol |
| Aranesp | Platinol-AQ |
| Aredia | Prednisolone |
| Arimidex | Prednisone |
| Aromasin | Prelone |
| Arsenic trioxide | Procarbazine |
| Asparaginase | PROCRIT |
| ATRA | Proleukin |
| Avastin | Prolifeprospan 20 with Carmustine implant |
| BCG | Purinethol |
| BCNU | Raloxifene |
| Bevacizumab | Rheumatrex |
| Bexarotene | Rituxan |
| Bicalutamide | Rituximab |
| BiCNU | Roveron-A (interferon alfa-2a) |
| Blenoxane | Rubex |
| Bleomycin | Rubidomycin hydrochloride |
| Bortezomib | Sandostatin |
| Busulfan | Sandostatin LAR |
| Busulfex | Sargramostim |

TABLE 2-continued

Examples of Chemotherapeutic Agents

| | |
|---|---|
| C225 | Solu-Cortef |
| Calcium Leucovorin | Solu-Medrol |
| Campath | STI-571 |
| Camptosar | Streptozocin |
| Camptothecin-11 | Tamoxifen |
| Capecitabine | Targretin |
| Carac | Taxol |
| Carboplatin | Taxotere |
| Carmustine | Temodar |
| Carmustine wafer | Temozolomide |
| Casodex | Teniposide |
| CCNU | TESPA |
| CDDP | Thalidomide |
| CeeNU | Thalomid |
| Cerubidine | TheraCys |
| cetuximab | Thioguanine |
| Chlorambucil | Thioguanine Tabloid |
| Cisplatin | Thiophosphoamide |
| Citrovorum Factor | Thioplex |
| Cladribine | Thiotepa |
| Cortisone | TICE |
| Cosmegen | Toposar |
| CPT-11 | Topotecan |
| Cyclophosphamide | Toremifene |
| Cytadren | Trastuzumab |
| Cytarabine | Tretinoin |
| Cytarabine liposomal | Trexall |
| Cytosar-U | Trisenox |
| Cytoxan | TSPA |
| Dacarbazine | VCR |
| Dactinomycin | Velban |
| Darbepoetin alfa | Velcade |
| Daunomycin | VePesid |
| Daunorubicin | Vesanoid |
| Daunorubicin hydrochloride | Viadur |
| | Vinblastine |
| Daunorubicin liposomal | Vinblastine Sulfate |
| DaunoXome | Vincasar Pfs |
| Decadron | Vincristine |
| Delta-Cortef | Vinorelbine |
| Deltasone | Vinorelbine tartrate |
| Denileukin diftitox | VLB |
| DepoCyt | VP-16 |
| Dexamethasone | Vumon |
| Dexamethasone acetate | Xeloda |
| dexamethasone sodium phosphate | Zanosar |
| | Zevalin |
| Dexasone | Zinecard |
| Dexrazoxane | Zoladex |
| DHAD | Zoledronic acid |
| DIC | Zometa |
| Diodex | Gliadel wafer |
| Docetaxel | Glivec |
| Doxil | GM-CSF |
| Doxorubicin | Goserelin |
| Doxorubicin liposomal | granulocyte-colony stimulating factor |
| Droxia | Granulocyte macrophage colony stimulating factor |
| DTIC | |
| DTIC-Dome | Halotestin |
| Duralone | Herceptin |
| Efudex | Hexadrol |
| Eligard | Hexalen |
| Ellence | Hexamethylmelamine |
| Eloxatin | HMM |
| Elspar | Hycamtin |
| Emcyt | Hydrea |
| Epirubicin | Hydrocort Acetate |
| Epoetin alfa | Hydrocortisone |
| Erbitux | Hydrocortisone sodium phosphate |
| Erwinia L-asparaginase | Hydrocortisone sodium succinate |
| Estramustine | Hydrocortone phosphate |
| Ethyol | Hydroxyurea |
| Etopophos | Ibritumomab |
| Etoposide | Ibritumomab Tiuxetan |
| Etoposide phosphate | Idamycin |
| Eulexin | Idarubicin |
| Evista | Ifex |
| Exemestane | IFN-alpha |

TABLE 2-continued

Examples of Chemotherapeutic Agents

| | |
|---|---|
| Fareston | Ifosfamide |
| Faslodex | IL-2 |
| Femara | IL-11 |
| Filgrastim | Imatinib mesylate |
| Floxuridine | Imidazole Carboxamide |
| Fludara | Interferon alfa |
| Fludarabine | Interferon Alfa-2b (PEG conjugate) |
| Fluoroplex | Interleukin-2 |
| Fluorouracil | Interleukin-11 |
| Fluorouracil (cream) | Intron A (interferon alfa-2b) |
| Fluoxymesterone | Leucovorin |
| Flutamide | Leukeran |
| Folinic Acid | Leukine |
| FUDR | Leuprolide |
| Fulvestrant | Leurocristine |
| G-CSF | Leustatin |
| Gefitinib | Liposomal Ara-C |
| Gemcitabine | Liquid Pred |
| Gemtuzumab ozogamicin | Lomustine |
| Gemzar | L-PAM |
| Gleevec | L-Sarcolysin |
| Lupron | Meticorten |
| Lupron Depot | Mitomycin |
| Matulane | Mitomycin-C |
| Maxidex | Mitoxantrone |
| Mechlorethamine | M-Prednisol |
| Mechlorethamine Hydrochlorine | MTC |
| | MTX |
| Medralone | Mustargen |
| Medrol | Mustine |
| Megace | Mutamycin |
| Megestrol | Myleran |
| Megestrol Acetate | Iressa |
| Melphalan | Irinotecan |
| Mercaptopurine | Isotretinoin |
| Mesna | Kidrolase |
| Mesnex | Lanacort |
| Methotrexate | L-asparaginase |
| Methotrexate Sodium | LCR |
| Methylprednisolone | |

The subject invention also concerns methods for inhibiting proteasome function in a cell by contacting the cell with an effective amount of a compound, agent, or composition of the invention. In one embodiment, the cell is a human or mammalian cell, and can be a cancer or tumor cell or other cell that exhibits abnormal proliferation, survival, migration or differentiation. In one embodiment, the cell constitutively expresses or expresses elevated or abnormal levels of a 20S proteasome.

The subject invention also concerns methods for treating a person or animal having a disorder associated with constitutive, abnormal, or elevated expression of a proteasome in a cell, wherein a therapeutically effective amount of a compound, agent, or composition of the invention is administered to the person or animal. The disorder can be one characterized, for example, by abnormal cell proliferation, cell survival, cell migration, and/or cell differentiation.

Depending upon the disorder or disease condition to be treated, a suitable dose(s) may be that amount that will reduce proliferation or growth of the target cell(s). In the context of cancer, a suitable dose(s) is that which will result in a concentration of the active agent in cancer tissue, such as a malignant tumor, which is known to achieve the desired response. The preferred dosage is the amount which results in maximum inhibition of cancer cell growth, without unmanageable side effects. Administration of a compound and/or agent can be continuous or at distinct intervals, as can be determined by a person of ordinary skill in the art.

To provide for the administration of such dosages for the desired therapeutic treatment, in some embodiments, pharmaceutical compositions of the invention can comprise between about 0.1% and 45%, and especially, 1 and 15%, by weight of the total of one or more of the compounds based on the weight of the total composition including carrier or diluents. Illustratively, dosage levels of the administered active ingredients can be: intravenous, 0.01 to about 20 mg/kg; intraperitoneal, 0.01 to about 100 mg/kg; subcutaneous, 0.01 to about 100 mg/kg; intramuscular, 0.01 to about 100 mg/kg; orally 0.01 to about 200 mg/kg, and preferably about 1 to 100 mg/kg; intranasal instillation, 0.01 to about 20 mg/kg; and aerosol, 0.01 to about 20 mg/kg of animal (body) weight.

The subject invention also concerns kits comprising a composition comprising an inhibitor compound and/or agent of the invention in one or more containers. Kits of the invention can optionally include pharmaceutically acceptable carriers and/or diluents. In one embodiment, a kit of the invention includes one or more other components, adjuncts, or adjuvants as described herein. In another embodiment, a kit includes one or more anti-cancer agents, such as those agents described herein. In one embodiment, a kit of the invention includes instructions or packaging materials that describe how to administer a compound or composition of the kit. Containers of the kit can be of any suitable material, e.g., glass, plastic, metal, etc., and of any suitable size, shape, or configuration. In one embodiment, a compound and/or agent of the invention is provided in the kit as a solid, such as a tablet, pill, or powder form. In another embodiment, a compound and/or agent of the invention is provided in the kit as a liquid or solution. In one embodiment, the kit comprises an ampoule or syringe containing a compound and/or agent of the invention in liquid or solution form.

Mammalian species which benefit from the disclosed methods include, but are not limited to, primates, such as apes, chimpanzees, orangutans, humans, monkeys; domesticated animals (e.g., pets) such as dogs, cats, guinea pigs, hamsters, Vietnamese pot-bellied pigs, rabbits, and ferrets; domesticated farm animals such as cows, buffalo, bison, horses, donkey, swine, sheep, and goats; exotic animals typically found in zoos, such as bear, lions, tigers, panthers, elephants, hippopotamus, rhinoceros, giraffes, antelopes, sloth, gazelles, zebras, wildebeests, prairie dogs, koala bears, kangaroo, opossums, raccoons, pandas, hyena, seals, sea lions, elephant seals, otters, porpoises, dolphins, and whales. Other species that may benefit from the disclosed methods include fish, amphibians, avians, and reptiles. As used herein, the terms "patient" and "subject" are used interchangeably and are intended to include such human and non-human species. Likewise, in vitro methods of the present invention can be carried out on cells of such human and non-human species.

The inventors screened compounds from the NCI chemical libraries for inhibitors against the chymotrypsin-like (CT-L) activity of the proteasome and identified PI-083, which was synthesized in-house and compared with bortezomib. Unlike bortezomib, PI-083 inhibits CT-L activity and proliferation, and induces apoptosis selectively in cancer cells as compared to their normal/immortalized counterparts. In addition, in all cancer cells tested, including MM, breast, pancreatic, ovarian, lung, prostate cancer cells as well as fresh MM cells from patients, PI-083 required less time than bortezomib to induce its antitumor effects. Furthermore, in nude mouse xenografts in vivo, PI-083, but not bortezomib, suppressed the growth of human breast and lung tumors. Finally, following in vivo treatment of mice, PI-083 inhibited tumor, but not hepatic liver CT-L activity, whereas bortezomib inhibited both tumor and liver CT-L activities. These results suggest that PI-083 may be more selective and may have broader antitumor activity than bortezomib and therefore warrants further advanced preclinical studies.

The invention includes proteasome inhibitor compounds and associated methods of using a proteasome inhibitor, such as PI-083, that have several advantages over the only FDA-approved proteasome inhibitor, bortezomib (originally PS-341 and marketed as VELCADE by Millennium Pharmaceuticals, Inc.). The proteasome inhibitor compounds of the invention, but not bortezomib, selectively inhibit the growth and induce apoptosis of cancer cells over their non-transformed "normal" counterparts. Furthermore, in animal models compounds of the invention, but not bortezomib, inhibited tumor growth in vivo of human lung and breast tumors. Surprisingly, despite these important differences, docking studies (based on the actual X-ray-determined structure of bortezomib complexed to the $\beta5/\beta6$ subunit of the proteasome) suggest remarkable similarities between the binding modes of the subject compounds and bortezomib to the active site of the CT-L enzyme within the proteasome.

Indeed, although the proteasome inhibitor of the invention designated as PI-083 and bortezomib are structurally distinct, molecular modeling suggests that they engage identical amino acids to bind CT-L. For example, Asp114 binds to PI-083 through its pyridine nitrogen and to bortezomib through its pyrazine nitrogen. In the case of PI-083 this hydrogen bond is apparently mediated by an intervening water molecule, whereas with bortezomib there is a direct hydrogen bond between one of its pyrazine nitrogen atoms and protonated Asp114. Note that the $pK_a$ of protonated pyrazine is <1 and thus presumably Asp114 is protonated since in the X-ray structure the O—N distance is 2.9 Å, indicative of a strong hydrogen bond. The intervening water molecule is also hydrogen-bonded to one of the sulfonamide oxygen atoms in PI-083, and in bortezomib it is hydrogen bonded to the oxygen atom of the carbonyl group attached to the pyrazine ring. Similarly, Ala49 and Thr21 of CT-L form hydrogen bonds with PI-083 through its sulfonamide group and to bortezomib through its two amide groups. Furthermore, Gly47 and Thr1 of CT-L are hydrogen bonded to bortezomib through its boronate hydroxyls whereas PI-083 is hydrogen-bonded through one of the carbonyl groups of its naphthoquinone ring to Gly47. This carbonyl group is also possibly hydrogen-bonded to Thr1, but the distance between the Thr1 hydroxyl oxygen and the carbonyl oxygen is 3.4 Å in our computer model, which is a bit long for a strong hydrogen bond. The 100-fold difference in potency between bortezomib and PI-083 is undoubtedly due to the fact that bortezomib forms a covalent bond to the 135 subunit through formation of a boronate complex with Thr1 that is further stabilized by hydrogen bonding between Thr1 and Gly47 with the boronate hydroxyl groups. In fact, bortezomib is a potent inhibitor in spite of the fact that the P2 phenylalanine side chain does not make any appreciable interactions with the protein and, in fact, is observed to be oriented toward the solvent interface in the X-ray structure. It is worth noting that we cannot completely rule out covalent bond formation between Thr1 and PI-083 that could conceivably occur via displacement of the chloro substituent in PI-083 by the Thr1 hydroxyl group to form an ether. In our computer model, though, the distance between the threonine hydroxyl oxygen atom and carbon atom to which the chloro group is attached is 5.9 Å which would mean that a rather significant conformational change in the protein and/or repositioning of the ligand would be required for the obligatory nucleophilic addition/elimination reaction to take place.

One of the most striking and critical differences between PI-083 and bortezomib is the ability of the former, but not the latter, to selectively inhibit the CT-L enzymatic activity in cancer cells over non-transformed "normal" cells. This was seen in both cultured cells (MCF-7/MCF-10A, C7Kras/C7, and T80 Hras/T80) as well as in vivo (tumors vs. livers). Although the reason(s) for this selectivity is not known, a plausible explanation could be that normal cells metabolically inactivate PI-083, but not bortezomib. Regardless of the mechanism of selectivity, the fact that PI-083, but not bortezomib, inhibits the CT-L activity selectively in tumor cells but not normal cells is most likely the reason why PI-083 inhibits the growth and induces apoptosis selectively in cancer cells as compared to bortezomib. This selectivity for cancer over "normal" cells is an unexpected advantage of PI-083 over bortezomib.

In addition to its selectivity for cancer over "normal" cells, another advantage of Proteasome inhibitors of the invention, such as PI-083, over bortezomib is the rapid action. For example, although both PI-083 and bortezomib inhibit the CT-L activity of the proteasome within 24 hours, PI-083, but not bortezomib, inhibits growth and induces tumor cell death within 24 hours in a wide variety of human cancer cells lines as well as fresh biopsies from MM patients. The fact that bortezomib requires 48 to 72 hours may necessitate its presence in the patient's blood for long periods of time, and this, coupled to its ability to inhibit CT-L equally in tumor and normal cells may contribute to its known toxicities in patients. In contrast, the rapid action and selectivity towards cancer cells of protaesome inhibitors of the invention provides for less toxicity.

In addition to reduced toxicity of the compounds of the invention, they also have a broader spectrum of anti-tumor activity. Indeed, in two animal xenograft models of solid tumors, MCF-7 human breast tumors and A-549 non-small cell lung tumors were sensitive to PI-083, but not bortezomib. The fact that bortezomib is ineffective against MCF-7-derived tumors is consistent with the work of others (Codony-Servat et al., 2006). The resistance of A-549 tumors to bortezomib is also consistent with the work of others showing that even in combination with other agents, bortezomib's antitumor activity against A-549 tumors is marginal (Mortenson et al., 2004). Although both PI-083 and bortezomib inhibited the CT-L enzymatic activity and accumulated p27$^{kip1}$, a proteasomal substrate, only PI-083 inhibited tumor growth in vivo. Thus, the ability of bortezomib to inhibit the proteasome is not sufficient to inhibit tumor growth, at least in the tumors studied. This also suggests that in addition to inhibiting CT-L, PI-083 most likely modulated the function of other target(s) yet to be identified. The fact that both p53 and Bax, two substrates of the CT-L enzyme were not required for PI-083 and bortezomib to inhibit tumor growth at least in cultured cancer cells also begs the question of whether proteasome inhibitors' antitumor activity is only due to their ability to inhibit CT-L activity. Linking PI-083 and bortezomib to affinity columns to identify additional potential targets will assist in answering this important question.

Compounds of the present invention, such as PI-083, present major advantages over bortezomib, namely selectivity for cancer over "normal" cells and broader spectrum of antitumor activity.

Materials and Methods

Reagents.

DMEM, RPMI-1640, DMEM/Ham's F12, horse serum donor herd, Keratinocyte-SFM penicillin and streptomycin were purchased from Invitrogen (Carlsbad, Calif.). Fetal bovine serum was from Atlanta Biologicals (Atlanta, Ga.). Purified 20S proteasome (rabbit), fluorogenic peptide substrates Suc-Leu-Leu-Val-Tyr-AMC (for the proteasomal CT-L activity), benzyloxy-carbonyl (Z-Leu-Leu-Glu-AMC (for the proteasomal PGPH activity) were purchased from Boston Biochem (Cambridge, Mass.). Fluorogenic peptide substrates Bz-Val-Gly-Arg-AMC (for the proteasomal T-L activity) were obtained from Biomol International (Plymouth Meeting, Pa.). Antibodies were obtained from the following suppliers: p27$^{Kip1}$ (BD Biosciences, San Jose, Calif.), and β-actin (Sigma-Aldrich, St. Louis, Mo.). The APO-Direct Kit was from BD Biosciences (San Jose, Calif.). The proteasome inhibitor NSC-45382 (PI-083) was synthesized in-house as reported previously (Prescott, 1969). All other reagents were from Sigma-Aldrich unless otherwise noted.

Determination of Proteolytic Activity.

In the high-throughput screen, the inventors used fluorogenic peptides as substrates to assay 3,229 compounds of the NCI Diversity, Natural Product, Challenge and Mechanistic Sets for inhibitory activity against the proteolytic activities of the purified 20S proteasome, resulting in the identification of PI-083. Briefly, 70 ng of purified 20S rabbit proteasome was incubated with 20 μM Suc-Leu-Leu-Val-Tyr-AMC for the CT-L activity, Bz-Val-Gly-Arg-AMC for the T-L activity, and benzyloxycarbonyl Z-Leu-Leu-Glu-AMC for the PGPH activity for 1 hours at 37° C. in 100 μl of assay buffer (50 mM Tris-HCl, pH 7.6) with or without PI-083 and bortezomib. After incubation, production of hydrolyzed 7-amido-4-methyl-coumarin (AMC) groups was measured using a WAL-LAC Victor$^2$ 1420 Multilabel Counter with an excitation filter of 355 nm and an emission filter of 460 nm (Perkin Elmer Life Sciences, Turku, Finland).

To determine proteasome activity in whole cell extracts from cultured cells (5 μg) or tumor and liver tissue extracts (30 μg) from nude mice, the same assay was used except that the buffer was changed to 20 mM HEPES, 0.5 mM EDTA, pH 8.0.

Cell Culture and Extract Preparation.

Human MCF-7 breast cancer and DU-145 prostate cancer cells were cultured in DMEM, and LNCaP prostate cancer as well as U266 and RPMI-8226 mM cells were cultured in RPMI-1640 medium containing 10% fetal calf serum (FCS). Normal immortalized MCF-10A breast cells were cultured in DMEM/Ham's F-12 containing 5% horse serum donor herd, 20 ng/ml epidermal growth factor (EGF), 100 ng/ml cholera toxin, 500 ng/ml hydrocortisone and 0.01 mg/ml insulin. Human lung carcinoma cell lines A549 and CaLu-1 were cultured in F-12 Kaighn's and McCoy's 5A medium, respectively, with 10% FCS. T80H cells (an Hras-V12-transformed human ovarian epithelial cell line) and their normal/immortalized counterpart T80 cells (a generous gift from J. Liu and R. Bast (Liu et al., 2004)) were cultured in Medium 199/MCDB 105 with 10% fetal calf serum. Normal/immortalized pancreatic duct epithelial cells HPDE6-C7 and their mutated K-ras derivatives HPDE6-C7K-ras (kindly provided by M. S. Tsao (Qian et al., 2005)) were cultured in Keratinocyte-SFM supplemented with EGF 1-53 and bovine pituitary extract. All media were supplemented with 100 units/ml of penicillin and 100 μg/ml of streptomycin. All cells were maintained at 37° C. in a humidified incubator in an atmosphere of 5% $CO_2$.

Whole cell extracts were prepared as follows: Cells were harvested, washed with PBS twice, and homogenized in a lysis buffer (50 mM Tris-HCl, pH 8.0, 5 mM EDTA, 150 mM NaCl, 0.5% NP-40) for 30 min at 4° C. Cell extracts from tumors and livers of nude mice were prepared in 50 mM HEPES, 0.5 mM EDTA, pH 8.0. Cell lysates were centrifuged at 12,000 g for 15 min, and the supernatants were collected as whole cell extracts.

Preparation of Bone Marrow Samples from MM Patients.

MM patients' bone marrow samples were collected from Liquid Tissue Bank facility. Freshly isolated bone marrow samples were fractionated by Ficoll-Paque (Pharmacia Biotech, Piscataway, N.J.) sedimentation. The mononuclear cellular layer was then resuspended in RPMI-1640 containing 10% heat-inactivated fetal bovine serum, 10 mM HEPES (pH 7.4), sodium pyruvate, L-glutamine, and 1% penicillin-streptomycin. The mononuclear cells were then treated with different concentrations of PI-083 or bortezomib for indicated periods.

Trypan Blue Exclusion Assay.

Adherent cells were harvested using trypsinization and pooled with suspension cells from media supernatant by pelleting at 300 g for 5 min at 4° C. The cells were then resuspended in an appropriate volume of media by pipetting gently up and down. Two 20 µl aliquots were removed and combined with an equal volume of 0.4% Trypan blue and allowed to mix for 1 minute. A 10 µl volume was loaded onto a hemacytometer and cells were scored as live or dead based on Trypan blue dye exclusion and the percentage of dead cell number to total cell number was calculated. To calculate the percentage of proliferation, the number of live cells in the treated samples was divided by the number of live cells in the untreated vehicle control.

MTT (3-(4,5-dimethylthiazol-2-yl)-2,5-diphenyltetrazolium bromide) metabolism assay.

Cells were plated in 96-well plates in 100 µl medium and allowed to attach overnight. Cells were then incubated for 24 or 72 hours with varying concentrations of PI-083, bortezomib or appropriate control. Media was aspirated after 24 or 72 hours and replaced with 100 µl complete media containing 1 mg/ml MTT and incubated for three hours at 37° C. in 5% $CO_2$ humidified incubator. Media was then aspirated and DMSO was added. Cells were incubated for 10 min at room temperature while shaking, and the absorbance was determined at 540 nm using a µQuant spectrophotometric plate reader (Bio-TEK, Winooski, Vt.).

TUNEL Assay.

Terminal deoxynucleotidyl transferase-mediated nick-end labeling (TUNEL) was used to determine the extent of DNA strand breaks (Kazi et al., 2004). The assay was performed with the APO-Direct Kit following the manufacturer's instructions. In brief, the harvested cells were fixed in 1% paraformaldehyde for 45 minutes on ice, washed twice with PBS, and then fixed again in 70% ethanol at −20° C. overnight. The cells were then incubated in DNA labeling solution (containing terminal deoxynucleotidyl transferase (TdT) enzyme, fluorescence-conjugated dUTP and reaction buffer) for 60 minutes at 37° C. After rinsing the cells to remove the DNA labeling solution, the cells were incubated with the propidium iodide/RNase A solution, incubated for 30 minutes at room temperature in the dark, and analyzed by flow cytometry within 3 hours of staining.

Antitumor Studies of Human Tumor Xenografts in Nude Mice.

Nude mice (Charles River Laboratories, Wilmington, Mass.) were maintained and treated in accordance with the Institutional Animal Care and Use Committee procedures and guidelines. Seven days before inoculation with MCF-7 cells, the animals were fully anesthetized for subcutaneous implantation of estradiol pellets (0.25 mg per pellet, 60-day release; Innovative Research of America, Sarasota, Fla.) on the dorsal surface of mice. Exponentially growing MCF-7 and A549 cells were harvested via trypsinization, pelleted at 300 g for 5 minutes, resuspended in sterile PBS (Invitrogen) at $10^7$ cells per 100 µl, and injected into each flank of mice. The tumor xenografts were monitored with an electronic caliper every other day for 16 days. Tumor volume was calculated using the formula $V=W^2L$, where width is the largest diameter and length is the smallest diameter. When the tumors reached ~200 mm³, the animals were randomized and treatment schedules were implemented. Treatments consisted of intraperitoneal (i.p.) injections of PI-083 or bortezomib at 1.0 mpk (twice per week) or vehicle control (100% DMSO). 2 hours after the last injections animals were sacrificed via $CO_2$ inhalation, and then tumors and livers were harvested and snap frozen in liquid $N_2$.

Western Blot Analysis.

Cell lysates (50 µg) were separated by SDS-PAGE and transferred to a nitrocellulose membrane, probed with $p27^{Kip1}$ and β-actin antibodies, and signals were visualized by enhanced chemoluminescence (ECL, Amersham, Piscataway, N.J.) according to the manufacturer's protocol.

All patents, patent applications, provisional applications, and publications referred to or cited herein are incorporated by reference in their entirety, including all figures and tables, to the extent they are not inconsistent with the explicit teachings of this specification.

Following are examples that illustrate procedures for practicing the invention. These examples should not be construed as limiting. All percentages are by weight and all solvent mixture proportions are by volume unless otherwise noted.

Example 1

Proteasome Inhibitors Exhibit Broad Antitumor Activity and Limited Toxicity

The only FDA-approved proteasome inhibitor bortezomib exhibits both toxicity and a limited anti-tumor activity spectrum. Accordingly, proteasome inhibitors with a broader anti-tumor activity spectrum and less toxicity are required. To this end, both experimental and virtual HTS was used to screen chemical libraries from the NCI. For the experimental portion, the NCI Diversity Set (1,990 compounds), the Natural Product Set (235 compounds), and the Challenge and Mechanistic Sets (1,004 compounds) were screened against the CT-L activity of the proteasome. Eight compounds with $IC_{50}$ values<10 µM were identified. The most potent of these, PI-083 ($IC_{50}=1$ µM), was confirmed with in-house synthesized material and is shown along with the structure of bortezomib in FIGS. 1A and B.

In order to determine the utility of virtual screening to potentially identify additional lead compounds from other NCI libraries like the Plated Set or from commercial sources, virtual screening on the NCI Diversity Set was performed for comparison with the experimental results. For this purpose, the GLIDE computer program, version 3.0 (Schrödinger, LLC, New York, N.Y.), using default options and parameters for grid generation and docking, was employed to screen the NCI-3D Diversity Set database that had been processed with LigPrep (Schrödinger, LLC). Processing of the 3D structures with LigPrep generates alternative ionization states, tautomers, and ring conformations. Coordinates for the chymotrypsin-like (β5) subunit derived from the X-ray crystal structure of the yeast 20S proteasome determined at 3.0 Å resolution (PDB ID: 1JD2) were employed for the automated docking studies (Groll et al., 2001). The β6 subunit, which is in contact with the β5 subunit and contributes to the S3 binding pocket, was not included in initial docking simulations.

Structurally, the yeast 20S proteasome is similar to the mammalian 20S proteasome, and the catalytic site in the β5 subunit is highly conserved between the two species (Groll et al., 1997; Kisselev and Goldberg, 2001). Of the 8 above-mentioned compounds with experimental IC$_{50}$ values of less than 10 μM, 5 were from the NCI Diversity Set and 4 of these ranked within the top 125 compounds with the best docking scores using GLIDE in extra precision mode. Subsequent to initial docking studies, the X-ray structure of the yeast 20S proteasome complexed to bortezomib became available (Groll et al., 2006). This structure revealed that the pyrazine ring in bortezomib interacts via a direct hydrogen bond with Asp114 from the β6 subunit of the proteasome. Since PI-083 contains a pyridine ring it has re-docked to a new model that was derived from the bortezomib-proteasome complex that included both the β5 and β6 subunits (PDB ID: 2F16). The structure of lead compound, PI-083, as it appears when docked to the CT-L subunit of the proteasome using this new model, is shown in FIG. 1C. Similar to the X-ray structure of bortezomib (FIG. 1D), the computer model of PI-083 docked to the proteasome suggests key hydrogen-bonding interactions between the napthoquinone ring and Gly47 and between the sulfonamide and Thr21 and Ala49 (FIG. 1A). Moreover, the modeling suggests that the pyridine ring of PI-083 is hydrogen-bonded to Asp114 via an intervening water molecule located crystallographically in the bortezomib structure and included in model.

The above virtual and experimental HTS as well as molecular modeling suggests that PI-083 is a CT-L inhibitor with similar binding interactions to bortezomib. The potency and selectivity of PI-083 was compared to bortezomib to inhibit CT-L, T-L and PGPH activities of the proteasome as described under Material and Methods.

PI-083 inhibited CT-L, T-L and PGPH with IC$_{50}$ values of 1, 4.48 and 4.52 μM, respectively. Bortezomib inhibited these activities with IC$_{50}$ values of 0.009, 7.02 and 0.475 μM, respectively. Therefore, while bortezomib was highly potent and selective for CT-L over T-L (700-fold) and PGPH (50-fold), PI-083 was less potent and less selective (only 4-fold selectivity for CT-L over both T-L and PGPH).

Example 2

Figure 2D:
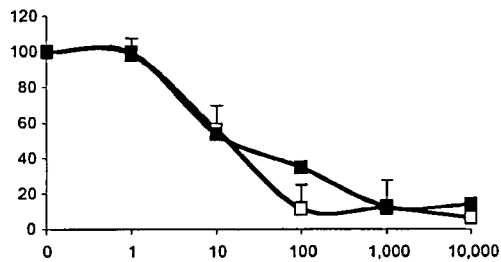
Figure 2B:
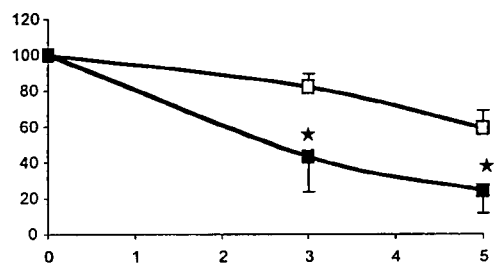
Figure 2E:
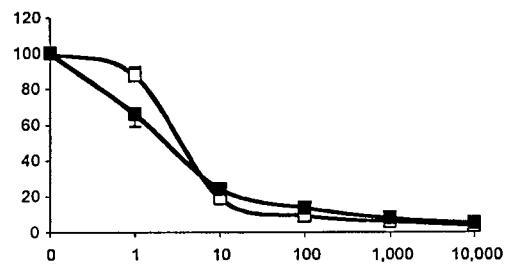
Figure 2C:
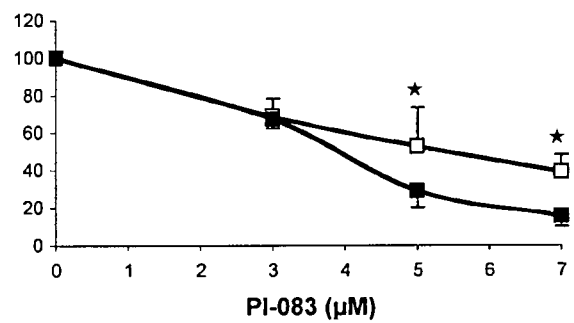
Figure 2F:
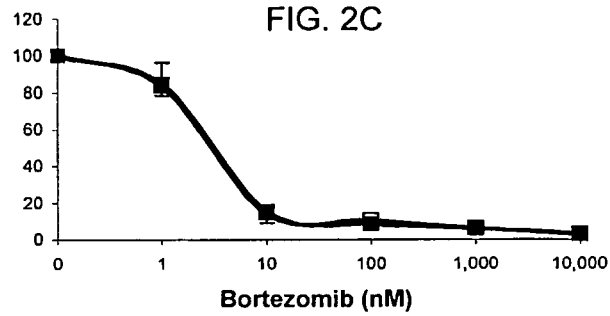

PI-083 Inhibits CT-L and Cell Proliferation Selectively in Cancer Cells Over Their Non-Transformed Counterparts Taken together, FIGS. 1A-1D and the IC$_{50}$ values indicated above indicate that although PI-083 and bortezomib appear to bind similarly to the CT-L activity of the proteasome, their potency and selectivity towards the 3 proteolytic activities of the proteasome are different. The ability of these two proteasome inhibitors to inhibit growth and induce apoptosis in tumor compared to non-transformed cells was determined. To this end, 3 pairs of cell lines from breast, ovarian and pancreatic origin were used. The first pair consists of MCF-7 (a human breast cancer cell line) and MCF-10A (an immortalized non-transformed breast cell line). The second consists of T-80 normal human ovarian cells immortalized with Large T-antigen (inactivates both p53 and pRb) and hTERT (human telomerase) based on the original Weinberg model (Hahn and Weinberg, 2002; Rangarajan et al., 2004) and T-80-Hras (T-80 cells expressing oncogenic human V12-Hras) (Liu et al., 2004). The third pair of cell lines consists of C7 and C7-Kras (generated in a similar fashion to the T-80/T-80-Hras pair except that this pair originated from normal pancreatic duct epithelial cells and the oncogene is C7-Kras and not V12-Hras; Qian et al., 2005). First, the ability of PI-083 and bortezomib to inhibit CT-L in the 3 pairs of tumor/non-transformed cell lines as described under Material and Methods was compared. FIGS. 2A-2C show that PI-083 inhibited more selectively the CT-L activity in tumor over non-transformed cells in the 3 pairs of cell lines. The selectivity was statistically significant (p<0.05) and was more pronounced in the breast cell lines. In contrast, though bortezomib was more potent as anticipated from the in vitro data, it was non-selective and inhibited CT-L activity equally well in both cancer and non-transformed cells (FIGS. 2D-2F).

Figure 3A:
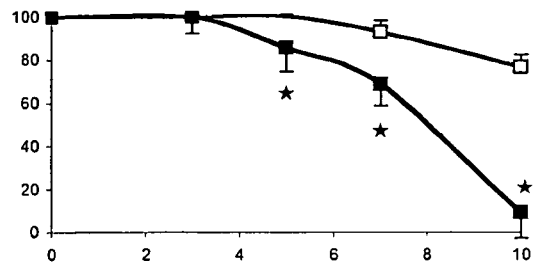
FIGS. 3A-3F show the effects of PI-083 and VELCADE on proliferation in cancer and normal/immortalized cells from the same tissue. Exponentially growing cancer cells (|) and normal cells (□) were treated with indicated concentrations of PI-083 (FIGS. 3A-3C) or VELCADE (FIGS. 3D-3F) for 24 h, followed by determination of viable cells.
Figure 3D:
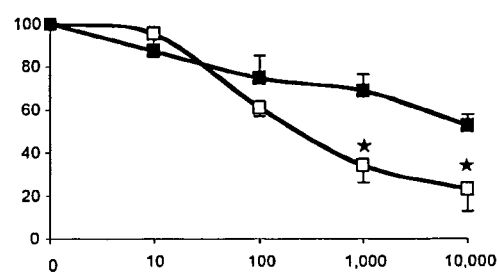
Figure 3B:
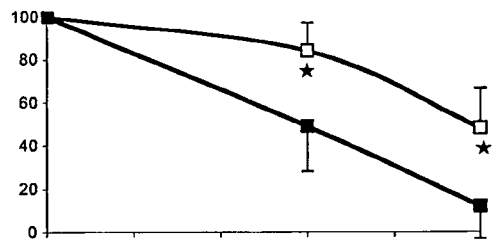
Figure 3E:
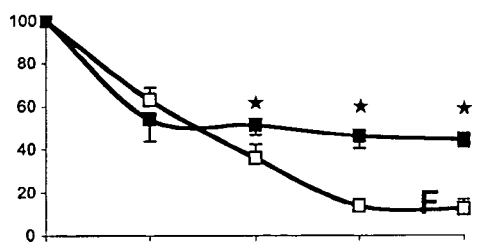
Figure 3C:
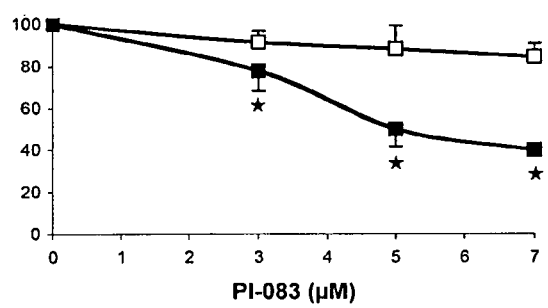
Figure 3F:
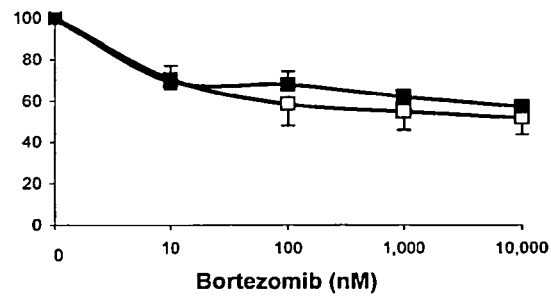
Figure 4A:
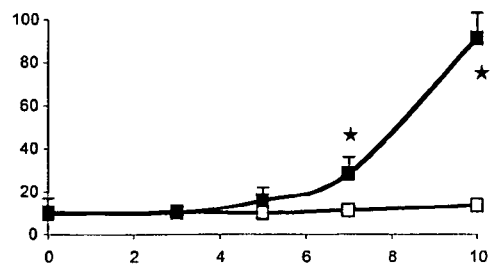
FIGS. 4A-4F show the effects of PI-083 and VELCADE on cell death in cancer and normal/immortalized cells from the same tissue. Exponentially growing cancer cells (|) and normal cells (□) were treated with indicated concentrations of PI-083 (FIGS. 4A-4C) or VELCADE (FIGS. 4D-4F) for 24 h, followed by determination of dying/dead cells.
Figure 4D:
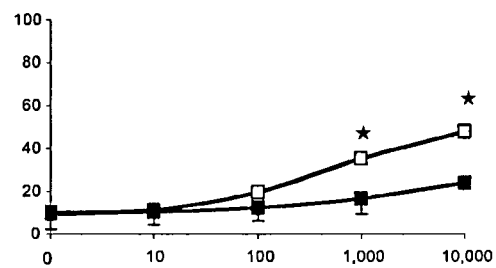
Figure 4B:
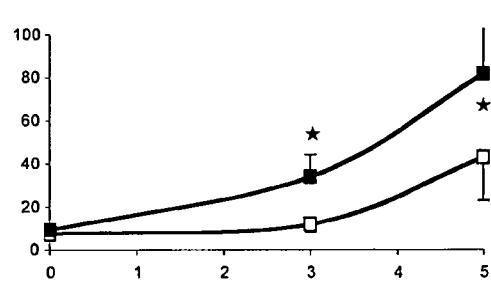
Figure 4E:
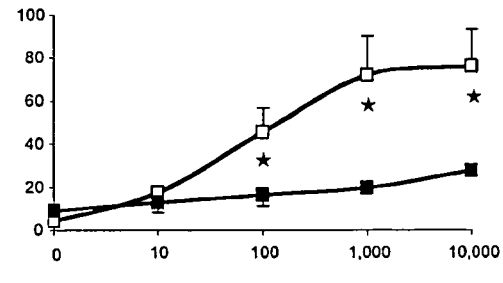
Figure 4C:
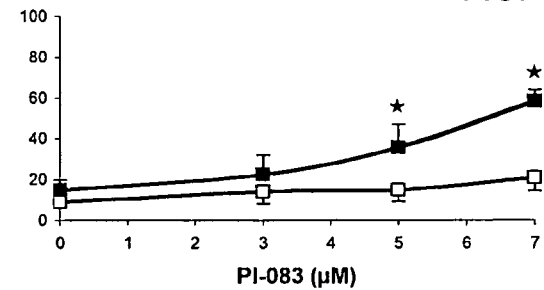
Figure 4F:
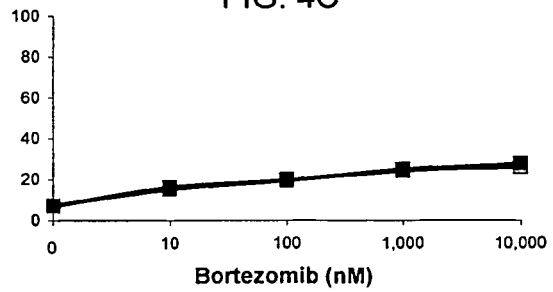

Next, the ability of PI-083 and bortezomib to inhibit cell proliferation of the above 3 pairs of cell lines was determined. To this end, cells were treated with various concentrations of either PI-083 or bortezomib for 24 hours and processed for Trypan blue cell counting as described under Materials and Methods. FIGS. 3A-3C show that PI-083 inhibited the proliferation of all three cancer cell lines (MCF-7, T-80-Hras and C7-Kras) more potently than their non-transformed "normal" counterparts (MCF-10A, T-80 and C7). This selectivity was statistically significant in all 3 pairs of cell lines (p<0.05). In contrast, bortezomib was either more potent towards normal over tumor cells (breast and ovarian, FIGS. 3D and 3E) or equally potent (pancreatic, FIG. 3F). To confirm these results, the 3 pairs of cell lines (breast, ovarian and pancreatic) as well as multiple myeloma, human prostate cancer and lung cancer cell lines were treated with either PI-083 or bortezomib for 24 or 72 hours and determined their effects on proliferation by MTT assays as described under Materials and Methods.

At the 24-hour time point, as with the Trypan blue results of FIGS. 2A-2C, PI-083 was more selective at inhibiting proliferation of cancer cells as compared to non-transformed cells. The difference in IC$_{50}$ values between the cancer cells and their non-transformed counterparts was statistically significant for breast (p<0.0001), pancreatic (p<0.0013) and ovarian (p<0.017) cells. In contrast, at 24 hours, bortezomib IC$_{50}$ values were over 30 μM for all cancer and non-transformed cell lines except for the RPMI-8226 cell line. Furthermore, after 72 hours of treatment, PI-083 continued to be more selective for inhibiting the proliferation of cancer over non-transformed cells. In contrast, bortezomib was more selective for non-transformed over cancer cells (breast) and equally potent (ovarian and pancreatic).

After both 24 and 72 hours, PI-083 inhibited the proliferation of human prostate cancer cells DU-145 (Bax-negative) and LNCaP (Bax-positive) as well as that of lung cancer cells CaLu-1 (p53-negative) and A549 (p53-positive), suggesting that PI-083 does not require the two proteasome substrates Bax or p53 for inhibiting cancer cell proliferation. Similar results were obtained with bortezomib except that, as seen with the other cell lines, PI-083 was more potent after 24 hours whereas bortezomib was more potent after 72 hours of treatment. Finally, both PI-083 and bortezomib inhibited proliferation in MM cells, with RPMI-8226 being much more sensitive especially to bortezomib after 24 hours of treatment.

Example 3

PI-083 Selectively Induces Apoptosis in Cancer Cells Over Non-Transformed Cells

Figure 5A:
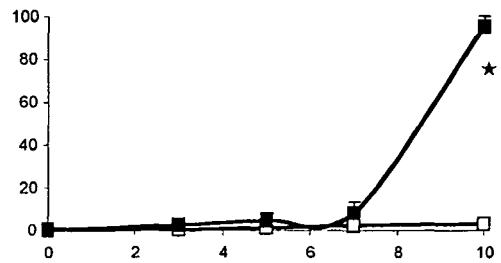
Figure 5D:
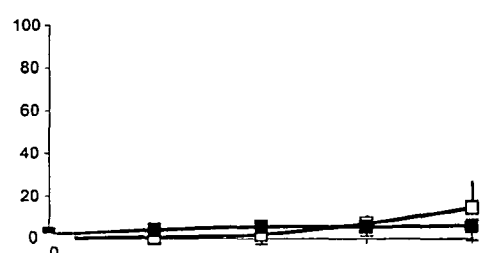
Figure 5B:
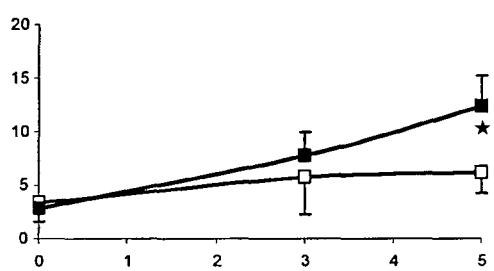
FIGS. 5B and 5E show T80-H ovarian cancer and T80 ovarian epithelial cells.
Figure 5E:
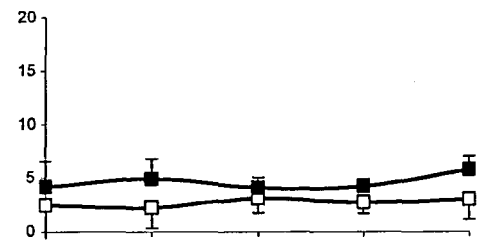
Figure 5C:
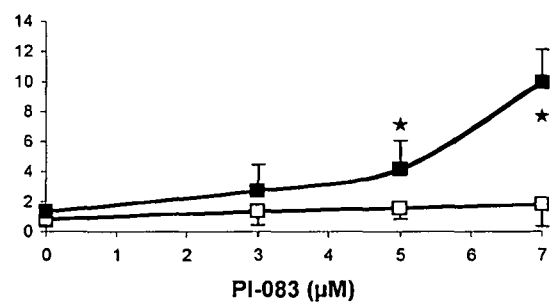
FIGS. 5C and 5F show HPDE6-C7-Kras pancreatic cancer and HPDE6-C7 pancreatic epithelial cells. The graphs represent the means±standard deviation of at least 3 independent experiments. Asterisks indicate statistical significance (p<0.05).
Figure 5F:
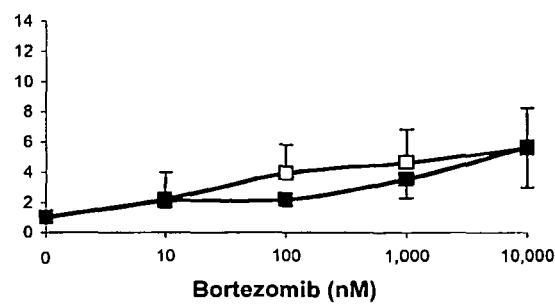

FIGS. 3A-3F and Table 3 show major differences between PI-083 and bortezomib, with PI-083, but not bortezomib, being more selective towards inhibiting the proliferation of cancer over non-transformed cells. The ability of PI-083 and bortezomib to induce cell death (Trypan Blue) and apoptosis (TUNEL) in the above 3 pairs of cancer/non-transformed cell lines was determined as described under Materials and Methods. As seen with proliferation assays, PI-083 was much more effective in increasing cell death in all 3 cancer cell lines over their non-transformed counterparts, whereas bortezomib was not (FIGS. 4A-4F). These results were confirmed by TUNEL assay: FIGS. 5A-5C show that PI-083 induced apoptosis in all 3 cancer cell lines MCF-7, T-80-Hras and C7-Kras, with MCF-7 being the most sensitive. In contrast, PI-083 did not induce apoptosis in non-transformed MCF-10A and C7 and induced very little apoptosis in T-80 cells. On the other hand, in contrast to PI-083, bortezomib induced little apoptosis in any of the cell lines (FIGS. 5D-5F). Taken together, Tables 3 and 4 and FIGS. 2-5 show that after 24 hours of treatment, PI-083 inhibited proliferation and induced cell death and apoptosis with $IC_{50}$ values similar to those that inhibited the CT-L activity of the proteasome. In contrast, bortezomib after 24 hours of treatment inhibited potently the CT-L activity with very little effect on proliferation, cell death and apoptosis. However, after 72 hours of treatment, both PI-083 and bortezomib inhibited proliferation at concentrations that inhibited the CT-L activity.

Example 4

Effects of PI-083 and Bortezomib on Bone Marrow Cells Isolated from Multiple Myeloma Patients The ability of PI-083 and bortezomib to inhibit proliferation and induce cell death in bone marrow cells from MM patients was compared. Table 5 shows that treatment of the cells from 10 patients with either PI-083 or bortezomib for 24 hours resulted in inhibition of the CT-L activity of the proteasome with $IC_{50}$ values of 1.27±0.19 or 0.012±0.006 μM, respectively. With PI-083, this 24 hours treatment resulted in inhibition of proliferation and induction of cell death with $IC_{50}$ values of 3.72±0.86 and 4.03±0.82 μM, respectively. In contrast, although bortezomib was more potent than PI-083 at inhibiting CT-L activity, it was less potent at inhibiting proliferation and at inducing cell death after 24 hours of treat-

TABLE 3

IC50 values (μM) of PI-083 and bortezomib for cell viability measured by MTT assay in different cancer and normal cell lines

| Cancer | Cell line | 24 h | | 72 h | |
|---|---|---|---|---|---|
| | | PI-083 | Bortezomib | PI-083 | Bortezomib |
| Breast cancer | MCF-7 | 4.5 ± 0.82* (0.0001) | >30 | 2.2 ± 1.1* (0.04) | 8.6 ± 1.41 |
| | MCF-10A | 17 ± 0.86 | >30 | 4.2 ± 2.1 | 0.15 ± 0.074* (0.0015) |
| Pancreas | C7-Kras | 2.4 ± 0.23* (0.0013) | >30 | 1.9 ± 0.2* (0.007) | 0.028 ± 0.006 (0.51) |
| | C7 | 5.1 ± 0.53 | >30 | 4.2 ± 1.6 | 0.032 ± 0.001 |
| Ovary | T80-Hras | 1.5 ± 0.57* (0.017) | >30 | 2.1 ± 0.4 | 0.024 ± 0.01 |
| | T80 | 2.7 ± 0.53 | >30 | 1.7 ± 0.39 (0.15) | 0.014 ± 0.001 (0.29) |
| Prostate | DU-145 | 8.6 ± 0.63 | >30 | 5.0 ± 0.72 | 0.025 ± 0.002 |
| Prostate | LNCaP | 14 ± 2.8 | >30 | 5.2 ± 1.1 | 0.057 ± 0.004 |
| Lung | CaLu-1 | 7.3 ± 0.43 | >30 | 4.9 ± 1.2 | 0.022 ± 0.002 |
| Lung | A549 | 41 ± 17 | >30 | 11 ± 6.7 | 0.41 ± 0.07 |
| Multiple Myeloma | U266 | 23 ± 1.7 | >30 | 7.0 ± 1.5 | 0.012 ± 0.003 |
| Multiple Myeloma | RPMI-8226 | 7.4 ± 0.38 | 0.049 ± 0.025 | 10 ± 4.0 | 0.026 ± 0.003 |

The values given are the means of 3 to 5 experiments ± standard deviation. Statistically significant differences between cancer and non-transformed cells were established by performing a t-test (*p < 0.05).

TABLE 4

$IC_{50}$ values (μM) of PI-083 and bortezomib for CT-L, T-L and PGPH-like activities in vitro

| Compound | CT-L | T-L | PGPH |
|---|---|---|---|
| PI-083 | 1.0 ± 0.63 | 4.5 ± 1.4 | 4.5 ± 1.2 |
| Bortezomib | 0.009 ± 0.006 | 7.0 ± 0.24 | 0.48 ± 0.021 |

The values given are the means of 3 experiments ± standard error.

ment ($IC_{50}$ values over 10 μM for all 10 patients). However, the MM cells became more sensitive to bortezomib with increasing length of time of treatment with $IC_{50}$ values to inhibit cell viability (MTT assay) of >10, 0.14±0.08 and 0.046±0.008 μM after 24, 48, and 72 hours, respectively. In contrast, the ability of PI-083 to inhibit viability was rapid and improved only slightly over time with $IC_{50}$ values of 2.15±0.27, 1.79±0.43, and 1.60±0.32 μM, after 24, 48, and 72 hours of PI-083 treatment.

TABLE 5

Effects of PI-083 and bortezomib on primary multiple myeloma cells isolated from patients' bone marrow ($IC_{50}$ values, μM)

| | CT-L activity | | Proliferation | | Cell death | | Viability | | | | | |
|---|---|---|---|---|---|---|---|---|---|---|---|---|
| | 24 h | | 24 h | | 24 h | | 24 h | | 48 h | | | |
| Patient No. | PI-083 | Bortezomib | PI-083 | Bortezomib | PI-083 | Bortezomib | PI-083 | Bortezomib | PI-083 | Bortezomib | PI-083 | 72 h Bortezomib |
| 1 | 2.1 | 0.0054 | 5 | >10 | 7.3 | >10 | ND | ND | ND | ND | ND | ND |
| 2 | 1.5 | 0.062 | 2.9 | >10 | 3.2 | >10 | >10 | >10 | ND | ND | ND | ND |
| 3 | 1.4 | 0.0015 | 6.6 | >10 | 6.2 | >10 | >10 | >10 | ND | ND | ND | ND |
| 4 | 0.68 | 0.0031 | 1.3 | >10 | 2.7 | >10 | 2.2 | >10 | 2.6 | 0.45 | 2.2 | 0.052 |
| 5 | 0.57 | 0.0046 | 2.2 | >10 | 1.1 | >10 | 3.4 | >10 | 3.6 | 0.079 | 2.6 | 0.074 |

TABLE 5-continued

Effects of PI-083 and bortezomib on primary multiple myeloma cells isolated from patients' bone marrow ($IC_{50}$ values, μM)

| | CT-L activity 24 h | | Proliferation 24 h | | Cell death 24 h | | Viability 24 h | | 48 h | | 72 h | |
|---|---|---|---|---|---|---|---|---|---|---|---|---|
| Patient No. | PI-083 | Bortezomib | PI-083 | Bortezomib | PI-083 | Bortezomib | PI-083 | Bortezomib | PI-083 | Bortezomib | PI-083 | Bortezomib |
| 6 | 1.2 | 0.015 | 2.2 | >10 | 2.7 | >10 | 2.1 | >10 | 0.9 | 0.055 | 1.4 | 0.054 |
| 7 | 0.57 | 0.0034 | 2.6 | >10 | 2.4 | >10 | 1.8 | >10 | 1.4 | >10 | 1.3 | 0.023 |
| 8 | 2.1 | 0.004 | 1.7 | >10 | 1.7 | >10 | 2 | 0.19 | 1.5 | 0.064 | 1.8 | 0.052 |
| 9 | 1.8 | 0.0028 | 2.8 | >10 | 4.1 | >10 | 1.4 | 0.28 | 0.89 | 0.032 | 0.35 | 0.02 |
| 10 | 0.78 | 0.017 | 10 | >10 | 9 | >10 | >10 | >10 | ND | ND | ND | ND |

Example 5

PI-083 Inhibits the Growth of Human Breast and Lung Tumors In Vivo

Figure 6A:
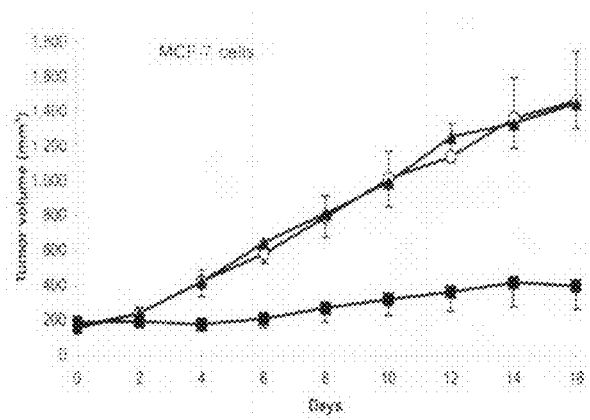
FIGS. 6A-6F show the effect of PI-083 and VELCADE on tumor growth and the proteasomal substrate p27 in vivo. The growth of human tumors following the injection of MCF-7 breast cancer (FIG. 6A) and A549 lung cancer (FIG. 6B) cells into nude mice was determined as described in Materials and Methods. Mice were treated with DMSO (○), 1 mpk VELCADE (▲) or 1 mpk PI-083 (|). Data represent the means±standard error of one of three independent experiments with 4 to 6 animals in each group. Asterisks indicate statistical significance (p<0.05). Proteasomal activities in tumor cell lysates (FIG. 6C) or liver cell lysates (FIG. 6E) following treatment with DMSO (n=5, white), PI-083 (n=4, gray) or VELCADE (n=4, black). The asterisks indicate p values=0.006 for a comparison of experimental and DMSO-treated mice.
Figure 6B:
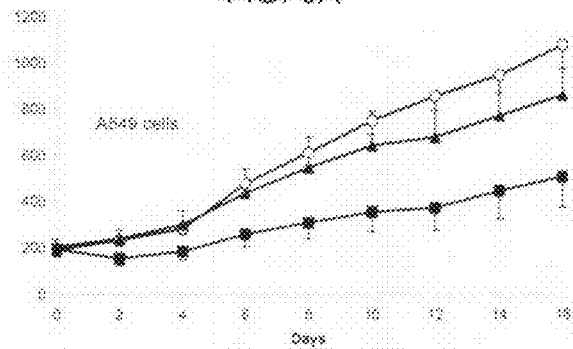

The anti-tumor activities of PI-083 and bortezomib was evaluated in a nude mouse xenograft model. To this end, MCF-7 and A549 cells was implanted s.c. in nude mice, and when tumors reached an average size of 200 mm³, the mice were treated 2× weekly either with vehicle, 1 mpk bortezomib or 1 mpk PI-083. MCF-7 derived xenografts from control and bortezomib-treated animals grew to an average size of 1,465±285, and 1,448±145 mm³, respectively. In contrast, tumors from PI-083-treated animals grew to an average size of about 396±137 mm³. Thus, while bortezomib appeared to be ineffective in the nude mouse model, treatment with PI-083 resulted in a significant tumor growth inhibition of 84% (FIG. 6A). Similar results were obtained with A549 xenografts. FIG. 6B shows that A549-derived xenografts from control and bortezomib-treated animals grew to an average size of 1,081±103, and 864±207 mm³, respectively. Tumors from PI-083-treated animals grew to an average size of about 511±134 mm³, which corresponds to a tumor growth inhibition of 54%. Using the Wilcoxon Signed Rank Test, it was determined that the PI-083-treated, but not the bortezomib-treated tumors were significantly different ($p<0.008$) from the controls.

Figure 6C:
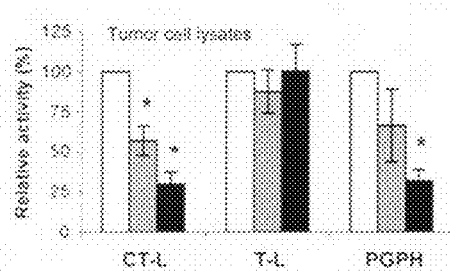

It was next determined whether PI-083 and bortezomib inhibited the proteasome activity in tumors and livers of mice that were injected i.p. with either PI-083 or bortezomib. To this end, A549 tumors and livers were extracted 2 hours after the last drug injection, and the lysates processed for CT-L, T-L and PGPH activities of the proteasome as described under Materials and Methods. FIG. 6C shows that PI-083 treatment resulted in 43%, 12%, and 34% inhibition of tumor CT-L, T-L and PGPH activities, respectively, compared to those of tumors from DMSO-treated controls. On the other hand, bortezomib treatment resulted in 70%, 0%, and 68% inhibition of CT-L, T-L, and PGPH activities, respectively, compared to DMSO-treated controls.

Figure 6D:
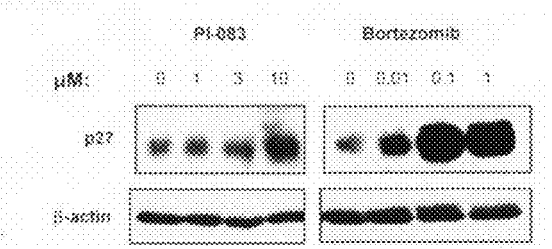
Figure 6E:
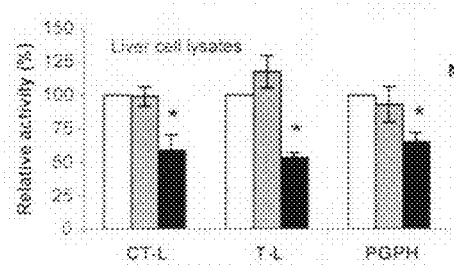

It was next determined the effects of PI-083 and bortezomib on proteasome activities in livers of tumor-bearing mice. PI-083 did not inhibit liver proteasome activities, whereas bortezomib significantly inhibited hepatic CT-L, T-L, and PGPH activities following in vivo treatments (FIG. 6E). These results are consistent with cell culture data where PI-083 inhibited the proteasome activity more potently in tumor cells compared to non-transformed "normal" cells.

Example 6

Figure 6F:
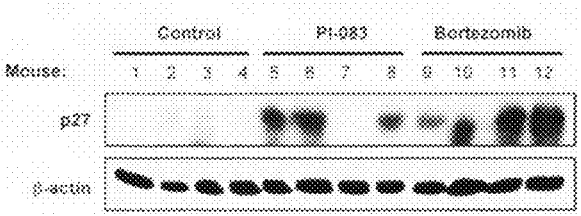
Figure 8:
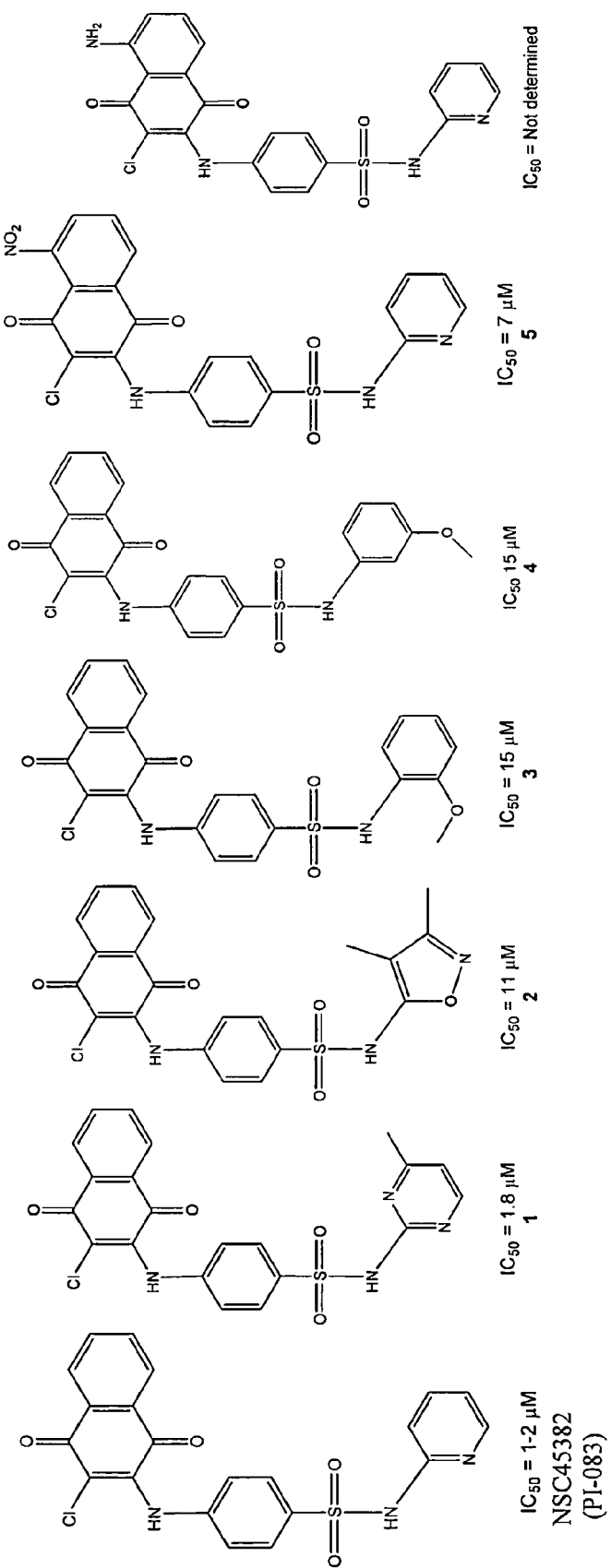
FIG. 8 shows SAR summary of the Naphthoquinone Library; Compounds with activity. When $R_1$=Sulfonamide anilines with heterocyclic units, moderate chymotrypsin-like activities are shown (IC 50=1.8-15 μM). Pyridine and Pyrimidine showed best activity. Units with H-bond acceptor properties desired. When $R_2$=Me or H loss of activity is observed, Cl is the best; when $R_3$=NH$_2$, or NO$_2$, moderate activity; $R_4$ substitution show loss of activity; $R_5$=NO$_2$ show moderate activity.

Both PI-083 and Bortezomib Accumulate the Proteasomal Substrate $p27^{Kip1}$ The ability of PI-083 and bortezomib to inhibit CT-L activity in tumors following i.p. treatments of mice suggests that these drugs may be able to accumulate proteasomal substrates. Therefore, the levels of $p27^{Kip1}$ were examined in cultured A549 lung cancer cells exposed to PI-083 and bortezomib. As shown in FIG. 6D, both of these drugs triggered a marked increase in $p27^{Kip1}$ levels, although the increase produced by bortezomib was much more pronounced than PI-083. Furthermore, the levels of $p27^{Kip1}$ were examined in tumor lysates derived from A549-bearing nude mice treated with PI-083 or bortezomib as described in FIG. 6B. As shown in FIG. 6F, 3 out of 4 PI-083-treated tumors, and 4 out of 4 bortezomib-treated tumors demonstrated a dramatic upregulation of $p27^{Kip1}$ protein.

Example 7

Cell Culture and Cell Lysate Preparation

Human MCF-7 breast cancer cells were cultured in DMEM medium containing 10% fetal calf serum (FCS) and 100 units/ml of penicillin and 100 μg/ml of streptomycin. Cells were maintained at 37° C. in a humidified incubator in an atmosphere of 5% $CO_2$. Cells were treated with different concentrations of PI-083, YG1-080, YG1-075, HL2-090-2, HL2-090-4, HL2-090-6, and HL2-090-9 or vehicle control (DMSO) for 16 h. Cells were then harvested, washed with PBS twice, and homogenized in a lysis buffer (50 mM Tris-HCl, pH 8.0, 5 mM EDTA, 150 mM NaCl, 0.5% NP-40) for 30 mM at 4° C. Cell lysates were centrifuged at 12,000 g for 15 min, and the supernatants were collected as cell lysates.

Determination of Proteolytic Activity in Cell Lysates.

Intact cells were treated with compounds and lysates prepared as described above. Cell lysates (5 μg) was incubated with 20 μM Suc-Leu-Leu-Val-Tyr-AMC for the CT-L activity for 1 h at 37° C. in 100 μl of assay buffer (50 mM Tris-HCl, pH 7.6). After incubation, production of hydrolyzed 7-amido-4-methyl-coumarin (AMC) groups was measured using a WALLAC Victor² 1420 Multilabel Counter with an excitation filter of 355 nm and an emission filter of 460 nm (Perkin Elmer Life Sciences, Turku, Finland).

MTT (3-(4,5-dimethylthiazol-2-yl)-2,5-diphenyltetrazolium bromide) metabolism assay.

Cells were plated in 96-well plates in 100 µl medium and allowed to attach overnight. Cells were then incubated for 72 h with varying concentrations of PI-083, YG1-080, YG1-075, HL2-090-2, HL2-090-4, HL2-090-6, and HL2-090-9 or vehicle control (DMSO). Media was aspirated and replaced with 100 µl complete media containing 1 mg/ml MTT and incubated for three hours at 37° C. in 5% $CO_2$ humidified incubator. Media was then aspirated and DMSO was added. Cells were incubated for 10 min at room temperature while shaking, and the absorbance was determined at 540 nm using a µQuant spectrophotometric plate reader (Bio-TEK, Winooski, Vt.).

Dialysis Using Purified Rabbit 20S Proteasome.

To measure the effect of dialysis on CT-L activity, compounds (10 µM) or vehicle (0.1% DMSO) were added to rabbit 20S proteasome (225 ng) (Boston Biochem) in proteasome assay buffer (50 mM Tris-HCl, pH 7.6) and incubated at 37° C. for 30 min. After 30 min of incubation, proteasome-compound mixtures were added to 10,000 MWCO Thermo Scientific Slide-A-Lyzer Dialysis Cassette (Rockford, Ill.) and dialyzed against proteasome assay buffer. Immediately (t=0) and 0.5 h, 1 h, 2 h, 4 h, and 18 h of dialysis at 4° C., samples were removed from the dialysis cassette and the CT-L 20S proteasome activity was determined. Proteasome activity was normalized against proteasome activity of DMSO control.

Inhibition of Cellular Proteasome Activity and Cell Growth by PI-083 and its Analogue.

Previously we have shown that PI-083 inhibits proteasome activity in vitro and in vivo (Ref). In this study we have shown that YG1-080, an analogue of PI-083 can also inhibit cellular proteasome activity and inhibit cell growth with similar potency. Table 6 shows that treatment of MCF-7 cells with either PI-083 or its analogue YG1-080, but not HL2-090-2,4,6, and 9 or YG1-075 resulted in inhibition of the CT-L activity of the proteasome with $IC_{50}$ values of 6.2 or 5.6 µM, and 5.1 or 4.7 µM, respectively. Like PI-083, YG1-080 also inhibited cell viability equally with $IC_{50}$ values 2.31±0.10 and 2.41±0.19 µM, respectively (Table 6).

PI-083 Reversibly Inhibits the Chymotrypsin-Like Activity of Purified 20S Proteasome.

Figure 9:
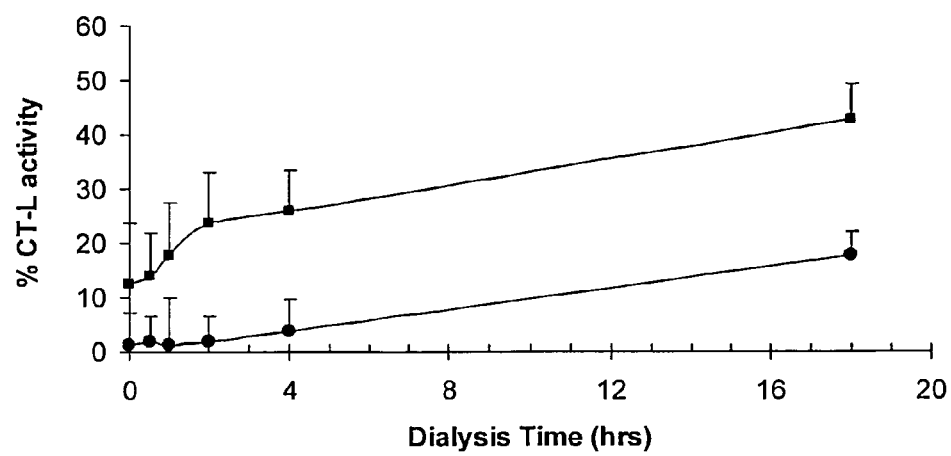
FIG. 9 shows recovery of CT-L activity upon dialysis of the 20S proteasome-compound complexes after pre-incubation with PI-083 (■) and Bortezomib (●).

To investigate the nature of PI-083-mediated proteasome inhibition, we performed a dialysis experiment. Bortezomib, a reversible proteasome inhibitor was used as an internal control for the experiment. FIG. 9, shows that in the absence of dialysis PI-083 and Bortezomib were able to inhibit the CT-L activity of the 20S proteasome by 88 and 99%, respectively. CT-L activity started to recover as early as 30 min and improved over time of dialysis with PI-083. In contrast, in Bortezomib treated samples, CT-L activity recovery did not begin until 4 hrs. The recovery rate of CT-L activity was more than 2-fold (43 vs. 18) by PI-083 than Bortezomib at 18 h. However, proteasome activity was not fully recovered after 18 h of dialysis. This result suggests that PI-083 is a reversible proteasome inhibitor.

TABLE 6

$IC_{50}$ values (µM) of PI-083 and its analogues for CT-L activity and cell viability measured by MTT assay in MCF-7 human breast cancer cells.

| Compounds | CT-L | MTT |
| --- | --- | --- |
| PI-083 | 6.2, 5.6 | 2.31 ± 0.10 |
| 2t | 5.1, 4.7 | 2.41 ± 0.19 |
| 2s | >10 | NT |
| 2b | >10 | NT |
| 2d | >10 | NT |
| 2f | >10 | NT |
| 2h | >10 | NT |
| HLM-008182 | NT | 7.67 ± 1.61 |
| 10a (in-house compound of HLM-008182) | NT | 10.87 ± 2.77 |

Example 8

Figure 11:
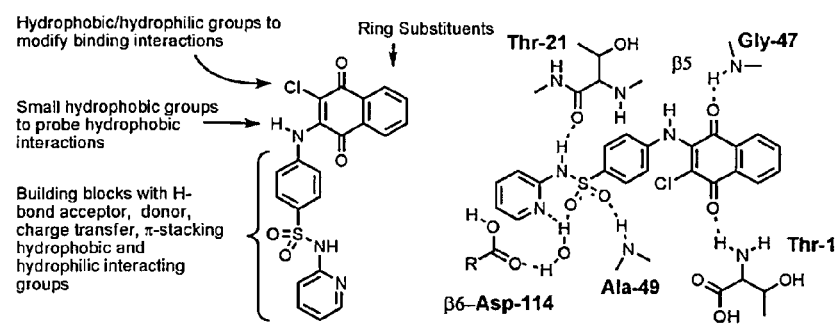
FIG. 11 shows modifications around PI-083 for library synthesis. Predicted binding interactions of PI-083 in the β5 and β6 subunits of the 20S proteasome.

The synthesis of the initial PI-083 compound library involved modification of the aniline-sulfonamide moiety where functionality is present for rapid modifications and analog synthesis. Commercially available 'sulfapyridine'-like building blocks with diverse electronic properties, for example hydrogen-bond donor/acceptor, charge-transfer, dipolar interactions and steric properties, were employed to explore the chymotrypsin-like inhibitory activities (FIG. 11). The predicted binding interactions of PI-083 in the β5 and β6 subunits of the proteasome (FIG. 11) suggest favorable interactions with Thr-21, Asp-114, Ala-49, Gly-47 and Thr-1. We were able to introduce two points of molecular diversity to target compounds 3 and 6 (Schemes 1 and 2 respectively) that exploit these interactions via replacement of the chloride and alkylation of the secondary amine (FIG. 11). Further diversity may be introduced via naphthoquinone ring substituents.

First, in-house synthesis of PI-083 (NSC-45382) was carried out using a literature protocol (Calandra et al., 1950) to provide material with >95% purity (as determined by HPLC) to confirm the inhibitory activity ($IC_{50}$=1.2±1.0 µM) and the structure shown in FIG. 2. The confirmation of the PI-083 structure was obtained using $^1H$ & $^{13}C$ NMR and high resolution mass spectrometry. Library 2 was synthesized from commercially available aniline building blocks and 2,3-dichloro-1,4-naphthoquinone, 1,4-naphthoquinone or 2-methyl-1,4-naphthoquinone using the protocol employed for PI-083 (Scheme 1). The synthetic protocol for compounds 2k-2o (Scheme 1) was validated using commercially available building blocks with 2-methyl-1,4-naphthoquinone and ytterbium trifluoromethanesulfonate in anhydrous dioxane under reflux. The crude reaction mixtures were purified by $SiO_2$ chromatography to obtain the desired compounds with low to moderate yields. To study the effects of hydrophobic and hydrophilic substitutions at the 2-position of the naphthoquinone ring in PI-083, a set of analogs of 3 (Scheme 1) was generated via a two-step synthesis. The targeted compounds with amine groups at the 2 position ($R^4$, Scheme 1) were prepared in moderate yields by the microwave-assisted reaction of PI-083 with various secondary amines.

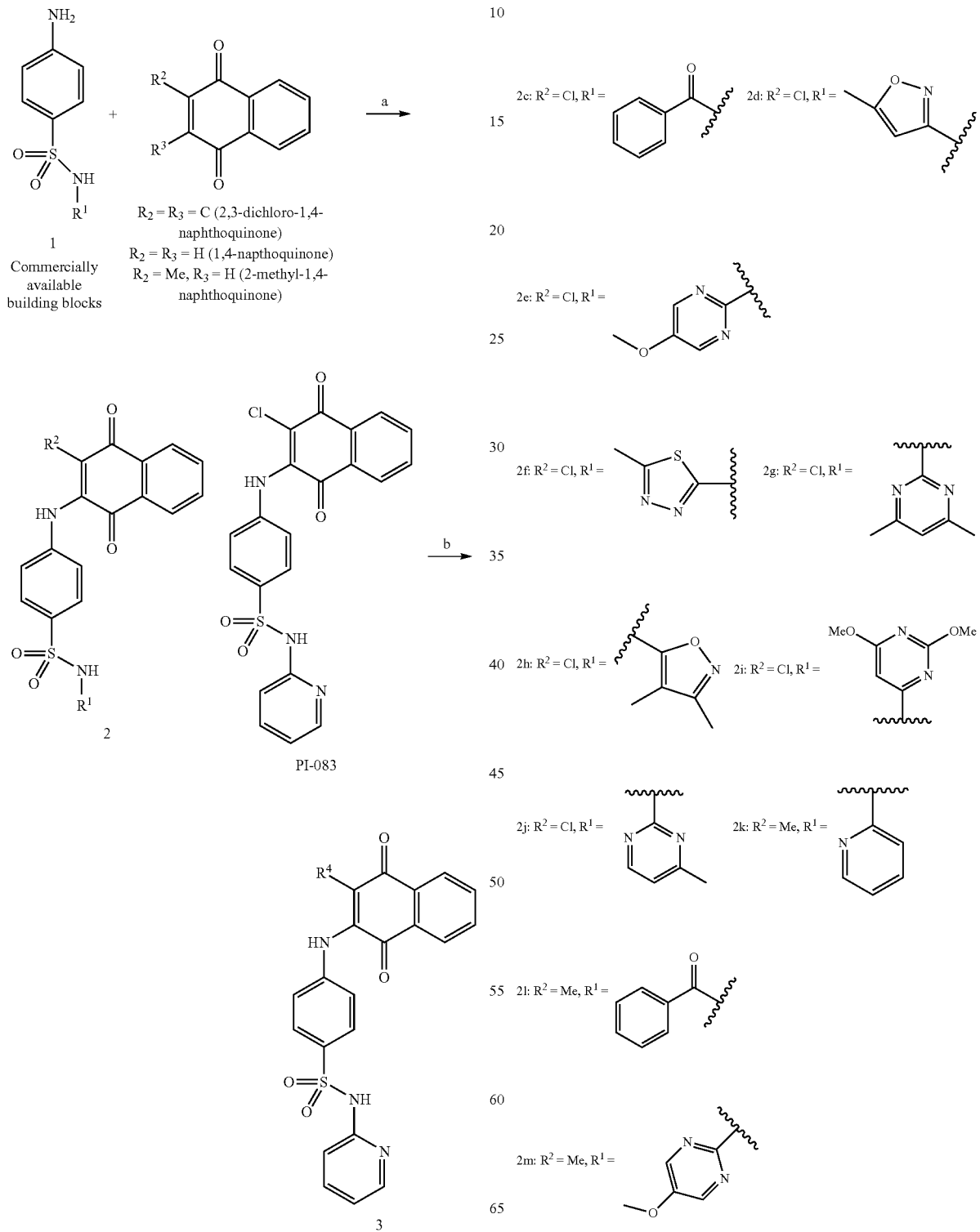

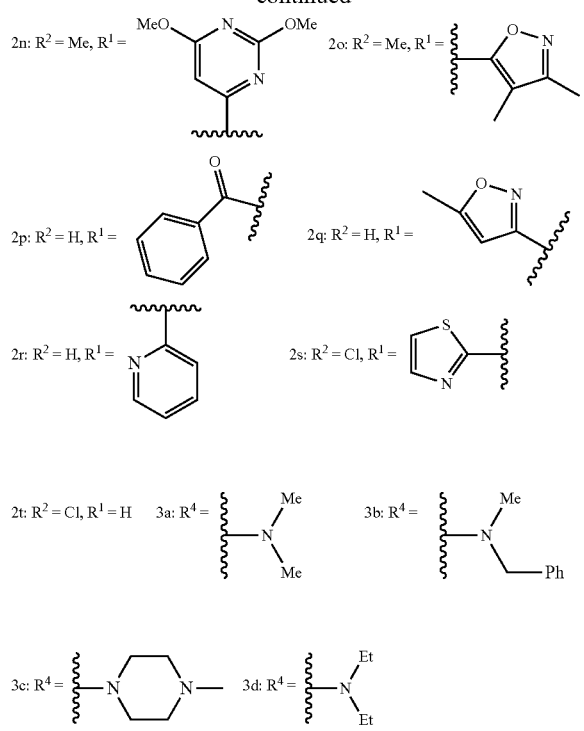

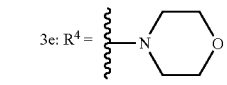

Modifications of the secondary amine group of PI-083 (R in library 6) were carried out as shown in Scheme 2 to provide a set of analogs using standard methods. Intermediates 5 were generated via reductive amination of the commercially available sulfapyridine (4) with requisite aldehydes, then coupled with commercially available 2,3-dichloronaphthoquinone to obtain 6 in good yields. In an alternative approach, PI-083 was reacted with an alkyl bromide or alkyl iodide in DMF, either at room temperature or with microwave heating, to obtain the alkylated analogs 6 in good yield. Most of the compounds 6 described in Scheme 2 were generated by way of PI-083. Library 6 was purified using flash chromatography to obtain the desired compounds with greater than 95% purity as assessed by $^1$H NMR analysis. Intermediates 7a and 7b were synthesized in good yields via coupling commercially available 5- and 6-nitro-2,3-dichloro-1,4-naphthoquinone, respectively, with the sulfapyridine 4 in refluxing ethanol. Compound 7a and 7b were obtained as a mixture of regioisomers in a 1:3 ratio by $^1$H NMR. The 5-nitro-2,3-dichloronaphthoquinone is reported to be more reactive towards amines affording regioisomeric mixtures of mono-substituted products (Blackburn, 2005). Attempts to separate these isomers by $SiO_2$ chromatography were unsuccessful. Reduced products 8a and 8b (mixture of regioisomers) were obtained from 7a and 7b using the hydrogenation conditions described in the Scheme 2.

Scheme 2.
Reagents and conditions: a NaBH$_3$CN, AcOH, MeOH, 0° C.- rt; b 95% EtOH, seal tube, reflux, 115° C., 3 days. c (i) RBr, (or RI), DIPEA, μw 160° C., 15 min or (ii) RI, DIPEA, DMF, Ar, rt d DMF/MeOH, H-cube H$_2$, 10% Pd/C., 40 bar, rt.

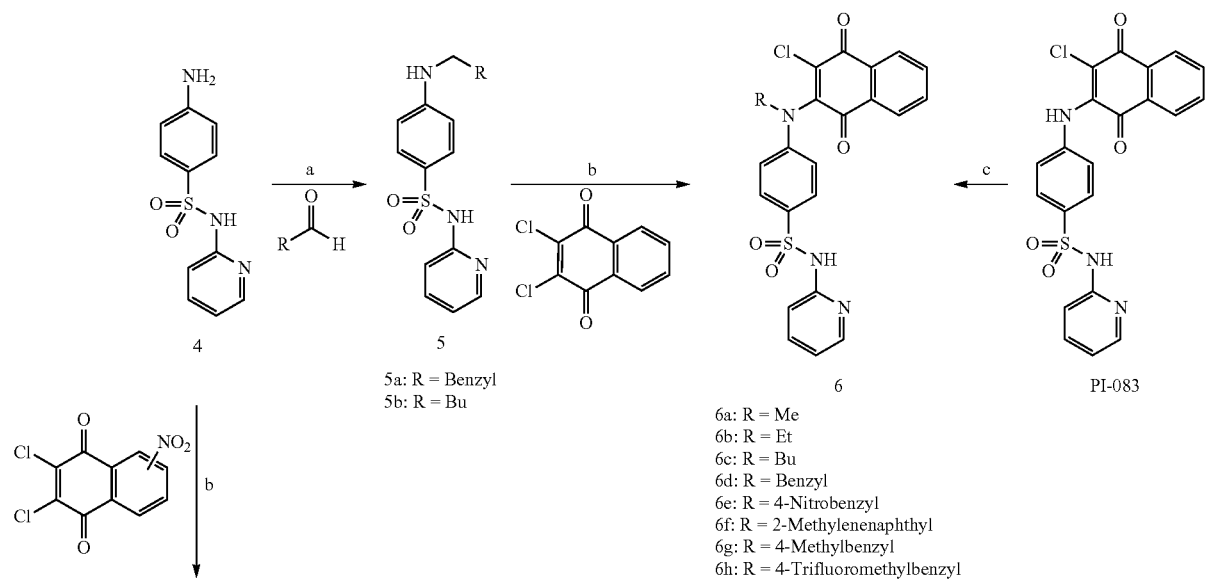

-continued

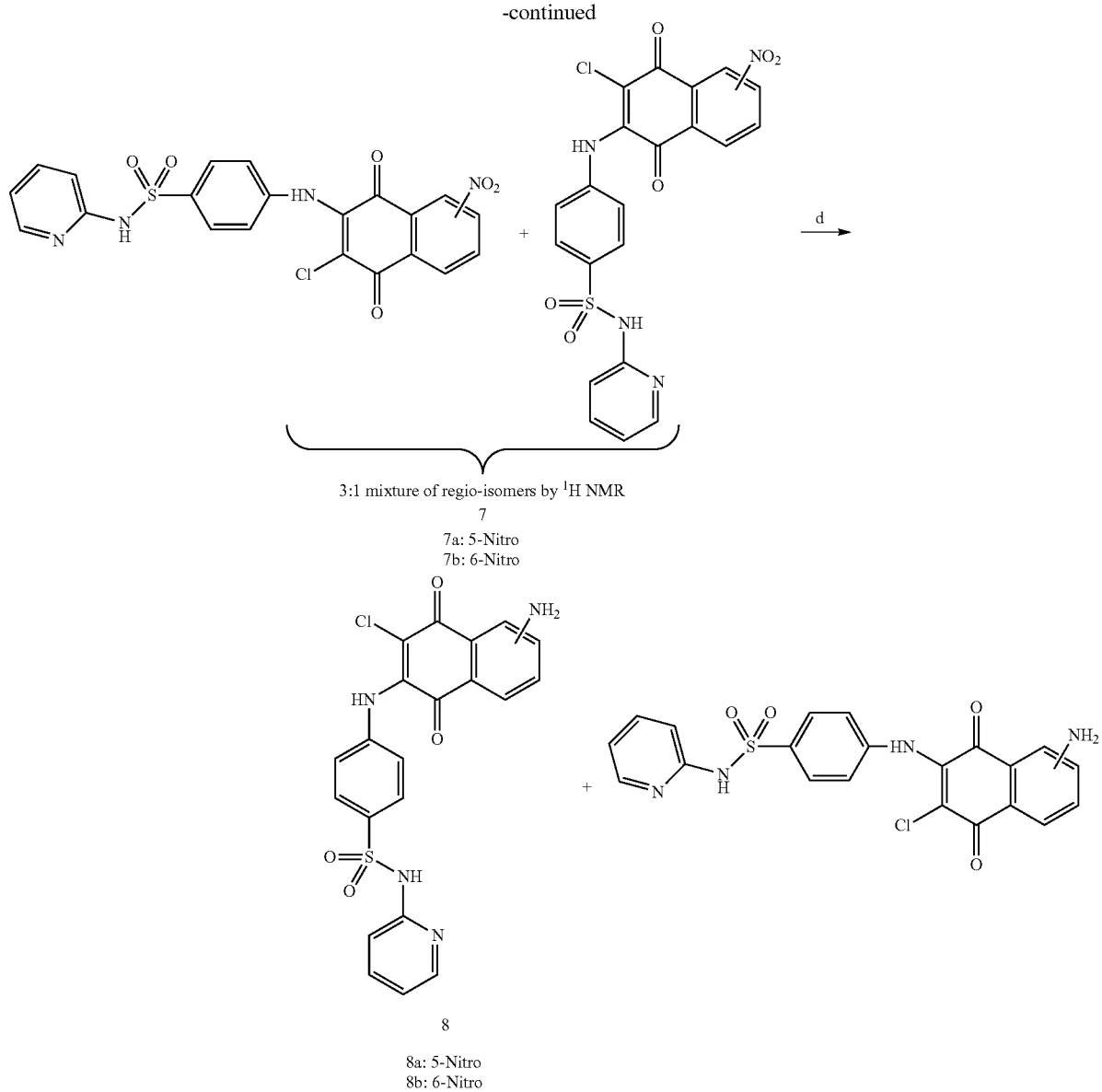

3:1 mixture of regio-isomers by ¹H NMR
7
7a: 5-Nitro
7b: 6-Nitro 8
8a: 5-Nitro
8b: 6-Nitro The possible binding interactions of the pyridylsulfonamide moiety of PI-083 with the proteasome were further investigated via the synthetic modifications outlined in Scheme 3. A series of nitrosulfonamide building blocks (11) were generated in good yield by microwave-assisted coupling of commercially available sulfonylchlorides and anilines. The corresponding amine intermediates (12) were obtained in good yields via NiCl$_2$/NaBH$_4$ mediated reduction (Walz and Sundberg, 2000). The final library (13) was prepared as described previously by reaction of the anilines with 2,3-dichloronaphthoquinone with >95% purity. Starting from 4-nitrobenzenesulfonyl chloride and 5-aminotetrazole at room temperature and using sodium carbonate as a base, compound 13i was obtained using a similar procedure as described in Scheme 3; modifying the reaction in this way produced 4-nitrobenzenesulfonylguanyl azide as an intermediate (Nagy et al., 1960). The synthesis and the purity of library 13 that was tested in the in-vitro proteasome assay was confirmed by ¹H NMR and LCMS analysis. The inhibitory activities of libraries 2, 3, 6 and 3 are summarized in Table 7.

Scheme 3.
Reagents and conditions: a Pyridine, DCE, μw 150° C., 10 min.;
b NiCl$_2$•6H$_2$O, MeOH/THF 1:1, NaBH$_4$, 0° C.;
c 95% EtOH, sealed tube, reflux, 115° C., 3 days.

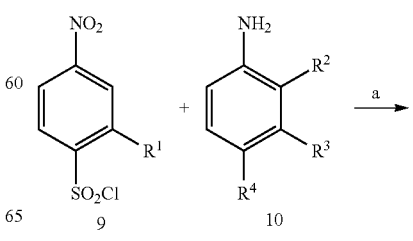

9     10

-continued

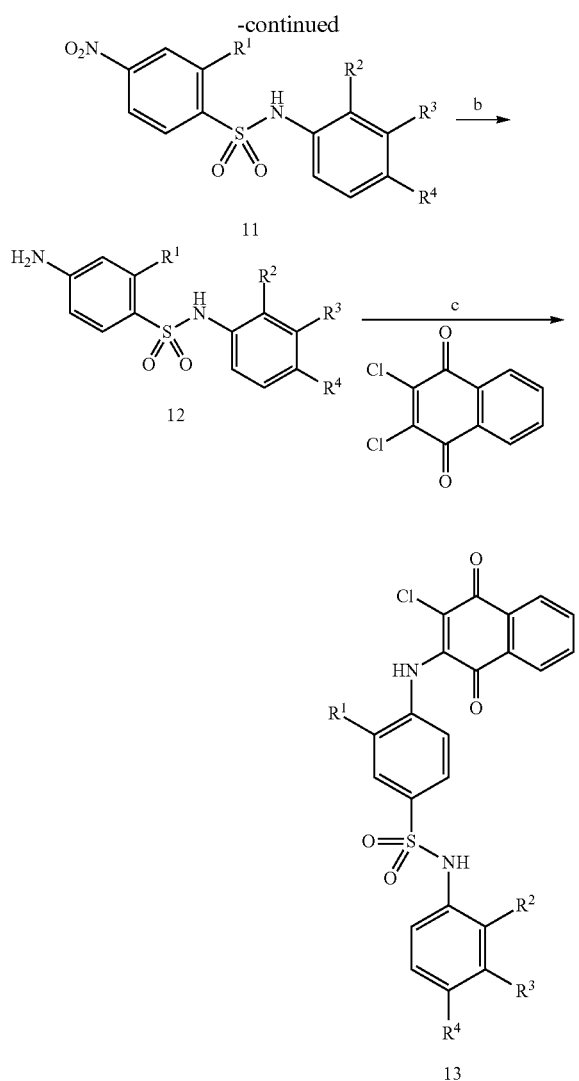

11a: $R^1=H, R^2=Me, R^3=R^4=H$
11b: $R^1=H, R^2=R^3=R^4=H$
11c: $R^1=H, R^2=H, R^3=Me, R^4=H$
11d: $R^1=H, R^2=R^3=H, R^4=Me$
11e: $R^1=H, R^2=OMe, R^3=R^4=H$
11f: $R^1=H, R^2=H, R^3=OMe, R^4=H$
11g: $R^1=H, R^2=R^3=H, Cl;=OMe$
11h: $R^1=OMe, R^2=Me, R^3=H, R^4=H$
11i: $R^1=OMe, R^2=H, R^3=Me, R^4=H$
11j: $R^1=OMe, R^2=R^3=H, R^4=Me$
11k: $R^1=OMe, R^2=R^3=H, R^4=OMe$

12a: $R^1=H, R^2=Me, R^3=R^4=H$
12b: $R^1=H, R^2=R^3=R^4=H$
12c: $R^1=H, R^2=H, R^3=Me, R^4=H$
12d: $R^1=H, R^2=R^3=H, R^4=Me$
12e: $R^1=H, R^2=OMe, R^3=R^4=H$
12f: $R^1=H, R^2=H, R^3=OMe, R^4=H$
12g: $R^1=H, R^2=R^3=H, R^4=OMe$
12h: $R^1=OMe, R^2=Me, R^3=H, R^4=H$
12i: $R^1=OMe, R^2=H, R^3=Me, R^4=H$
12j: $R^1=OMe, R^2=R^3=H, R^4=Me$
12k: $R^1=OMe, R^2=R^3=H, R^4=OMe$

13a: $R^1=H, R^2=Me, R^3=R^4=H$
13b: $R^1=H, R^2=R^3=R^4=H$
13c: $R^1=H, R^2=H, R^3=Me, R^4=H$
13d: $R^1=H, R^2=R^3=H, R^4=Me$
13e: $R^1=H, R^2=OMe, R^3=R^4=H$
13f: $R^1=H, R^2=H, R^3=OMe, R^4=H$
13g: $R^1=H, R^2=R^3=H, R^4=OMe$
13h: $R^1=OMe, R^2=Me, R^3=H, R^4=H$
13i: $R^1=OMe, R^2=H, R^3=Me, R^4=H$
13j: $R^1=OMe, R^2=R^3=H, R^4=Me$
13k: $R^1=OMe, R^2=R^3=H, R^4=OMe$

TABLE 7

PI-083 derivatives with moderate activities.

| Compound | $R^1$ | $IC_{50}$ (μM) Chymotrypsin-like activity |
|---|---|---|
| 2b | 1-phenyl-pyrazol-4-yl | 7.4 |
| 2d | 5-methylisoxazol-3-yl | 5.9 |
| 2h | 3,4-dimethylisoxazol-5-yl | 6.4 |
| 2f | 5-methyl-1,3,4-thiadiazol-2-yl | 3.9 |
| 2s | thiazol-2-yl | 3.3 |
| 2t | H | 1.1 |
| PI-083 | 2-Pyridyl | 1.2 ± 1.0 μM |

To assess the ability of the synthesized compounds to inhibit the chymotrypsin-like (CL-like) proteolytic activity of purified rabbit 20S proteasome, a fluorometric assay was utilized (70 ng of purified 20S proteasome was incubated with 20 μM Suc-Leu-Leu-Val-Tyr-AMC for the chymotrypsin-like activity for 1 hour at 37° C. in 100 μl of assay buffer (50 mM Tris-HCl, pH 7.6) with or without inhibitors. After incubation, production of hydrolyzed 7-amido-4-methyl-coumarin (AMC) was measured using a WALLAC Victor2 1420 Multilabel Counter with an excitation filter of 355 nm and an emission filter of 460 nm (Perkin Elmer Life Sciences, Turku, Finland). The inhibitory activity of the compounds was calculated based on vehicle control). This technique monitors the hydrolytic release of a coumarin species from a synthetic peptide substrate. The most promising compounds (i.e. those exhibiting single-digit micromolar inhibitory activities) are shown in the Table 7 along with their respective $IC_{50}$ values. The replacement of the pyridine unit in PI-083 with aryl groups bearing largely hydrophobic substituents in series 13 all showed inhibitory activity with $IC_{50}$>10 μM. In our focused library synthesis, the rationale for replacement of the pyridine sulfonamide moiety with basic units (Scheme 4) was to probe interactions with Asp-114 in the β6 subunit (FIG. 11). Pyrimidine moieties did not lead to compounds with appreciable activity. It is possible the compounds possessing weakly basic moieties bind in a region where hydrogen bonding (possibly via Asp-114 and a water molecule) is important. It is interesting to observe that the primary sulfonamide 2t is equally as active as PI-083, despite significantly different steric and electronic properties of the $R_1$ groups. This may indicate that 2t inhibits the CL-like activity via a unique binding mode, distinct from the method suggested in FIG. 2. In addition, the chloride at the 2-position of the naphthoquinone is important for activity. We found replacement of the chlorine by other groups such as methyl (2k-2o), hydrogen (2p-2r), and amines (3a-3e) is detrimental to the proteasome inhibitory activity. It is conceivable that PI-083 undergoes Michael type nucleophilic addition with residues such as Thr-1 in the β5-subunit of the proteasome and inhibits the chymotryptic site. Our in-vitro data suggested PI-083 binds to purified 20s proteasome in an irreversible manner. Compounds 6, derived from alkylation of the secondary amine moiety, (Scheme 5) lacked inhibitory activities.

We found PI-083 inhibits the chymotrypsin-like activity of purified 20S proteasome, inhibits proliferation and induces cell death in three different human tumor cell lines (breast, pancreatic and ovarian), but not in their normal/immortalized counterparts. Our studies indicated (not reported here) that PI-083 induces apoptosis in cancer cell lines derived from prostate, lung and multiple myeloma, in addition to the human tumor cells lines mentioned above. Furthermore, PI-083 suppresses the growth of human breast and lung tumors implanted as xenografts into nude mice, and is efficient in inhibiting proliferation and survival of primary cells derived from patients with multiple myeloma. This data will be published elsewhere in due course. In conclusion, initial SAR indicates that the activity appears very sensitive to changes around the molecule. The chlorine and N-aryl NH groups of PI-083 appear essential for activity. The pyridyl group can be replaced with N-heterocycles without significant reduction of activity.

Altogether our data suggest PI-083 has potential for further development as an anti-cancer agent.

General Procedure for Synthesis of Library 2:

The starting material 2,3-dichloronathoquinone (700 mg, 3.08 mmol) and appropriate commercially available sulfonamide aniline (0.5 equivalents) were suspended in 95% ethanol and heated at 115° C. for 3 days to obtain mixtures of red/orange precipitates. The reaction mixtures were cooled to room temperature and the resultant precipitates were filtered and washed with hot ethanol (5 times). Most compounds were rinsed with EtOAc, DCM, MeOH in order to remove the aniline starting materials (impurities) and quick acetone rinse was able to remove the starting materials. The required products in the library 2 were obtained as red or orange solids with 30-60% yield.

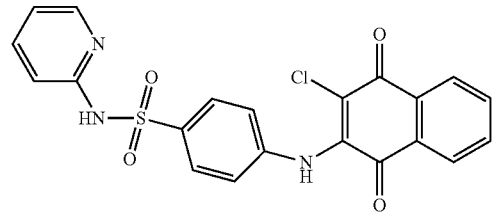
HL1-083

4-(3-chloro-1,4-dioxo-1,4-dihydronaphthalen-2-ylamino)-N-(pyridin-2-yl)benzenesulfonamide (2a). Mp=273-275° C.; $^1$H NMR (400 MHz, DMSO-d$_6$) δ 9.48 (s, 1H), 8.04-7.99 (m, 3H), 7.84 (dt, J=7.6, 1.6 Hz, 1H), 7.80 (dt, J=7.6, 1.2 Hz, 1H), 7.74 (d, J=8.4 Hz, 2H), 7.69 (dt, J=8.8, 1.6 Hz, 1H), 7.17-7.12 (m, 3H), 6.86 (bs, 1H); ESI-HRMS m/z calculated for $C_{21}H_{15}ClN_3O_4S$ (M+H)$^+$ 440.0466, found 440.0470; HPLC 99% ($R_t$=1.80, 10% water in acetonitrile).

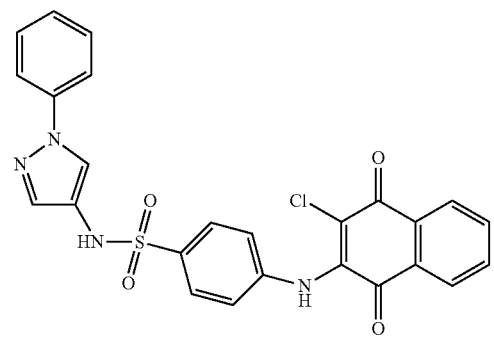
HL2-090-2

4-(3-chloro-1,4-dioxo-1,4-dihydronaphthalen-2-ylamino)-N-(1-phenyl-1H-pyrazol-4-yl)benzenesulfonamide (2b). Mp=230-231° C. $^1$H NMR (400 MHz, DMSO-d$_6$) δ 10.31 (s, 1H), 9.60 (s, 1H), 8.06 (d, J=8.0 Hz, 2H), 7.88 (dt, J=7.6, 1.6 Hz, 1H), 7.83 (dt, J=7.6, 1.6 Hz, 1H), 7.60-7.56 (m, 3H), 7.50-7.37 (m, 5H), 7.19 (d, J=8.8 Hz, 2H), 5.79 (d, J=1.6 Hz, 1H), ESI-HRMS m/z calculated for $C_{25}H_{18}ClN_4O_4S$ 505.0732, found 505.0736.

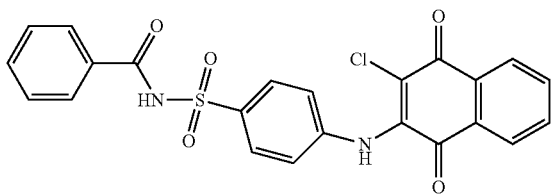
HL2-090-3

N-(4-(3-chloro-1,4-dioxo-1,4-dihydronaphthalen-2-ylamino)phenylsulfonyl)benzamide (2c). Mp=216-217° C.; $^1$H NMR (400 MHz, DMSO-d$_6$) δ 12.45 (s, 1H), 9.61 (s, 1H), 8.06-8.03 (m, 2H), 7.88-7.81 (m, 6H), 7.61 (t, J=7.2 Hz, 1H), 7.48 (t, J=8.0 Hz, 2H), 7.24 (d, J=8.4 Hz, 2H); ESI-HRMS m/z calculated for C₂₃H₁₆ClN₂O₅S 467.0463, found 467.0468.

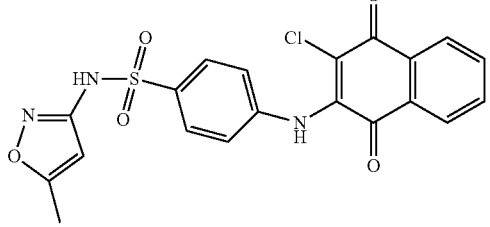

4-(3-chloro-1,4-dioxo-1,4-dihydronaphthalen-2-ylamino)-N-(5-methylisoxazol-3-yl)benzenesulfonamide (2d). Mp=215-217° C.; ¹H NMR (400 MHz, DMSO-d₆) δ 11.32 (s, 1H), 9.55 (s, 1H), 8.05-8.02 (m, 2H), 7.89-7.80 (m, 2H), 7.71 (d, J=8.8 Hz, 2H), 7.20 (d, J=8.8 Hz, 2H), 6.14 (s, 1H), 2.28 (s, 3H); ESI-HRMS m/z calculated for C₂₀H₁₅ClN₃O₅S 444.0416, found 444.0418.

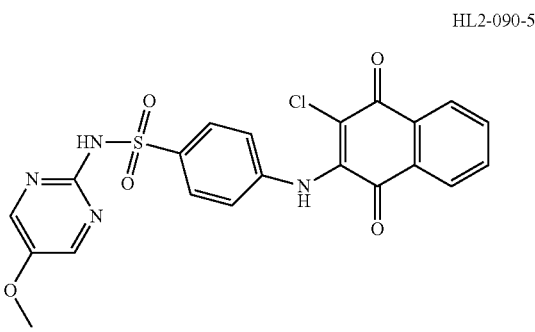 [SMILES: COc1cnc(NS(=O)(=O)c2ccc(NC3=C(Cl)C(=O)c4ccccc4C3=O)cc2)nc1]

4-(3-chloro-1,4-dioxo-1,4-dihydronaphthalen-2-ylamino)-N-(5-methoxypyrimidin-2-yl)benzenesulfonamide (2e). Mp=269-271° C.; ¹H NMR (400 MHz, DMSO-d₆) δ 11.38 (s, 1H), 9.52 (s, 1H), 8.28 (s, 2H), 8.03 (t, J=5.6 Hz, 2H), 7.89-7.82 (m, 4H), 7.18 (d, J=8.4 Hz, 2H), 3.78 (s, 3H); ESI-HRMS m/z calculated for C₂₁H₁₆ClN₄O₅S 471.0524, found 471.0527.

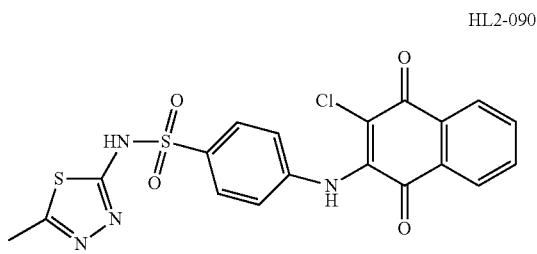

4-(3-chloro-1,4-dioxo-1,4-dihydronaphthalen-2-ylamino)-N-(5-methyl-1,3,4-thiadiazol-2-yl)benzene-sulfonamide (2f). Mp=220° C. decomposed; ¹H NMR (400 MHz, DMSO-d₆) δ 13.92 (s, 1H), 9.53 (s, 1H), 8.03 (d, J=8.0 Hz, 2H), 7.91-7.80 (m, 2H), 7.66 (d, J=8.8 Hz, 2H), 7.18 (d, J=8.8 Hz, 2H), 4.35 (bs, 1H), 2.45 (s, 3H); ESI-HRMS m/z calculated for C₁₉H₁₄ClN₄O₄S₂ 461.0140, found 461.0131.

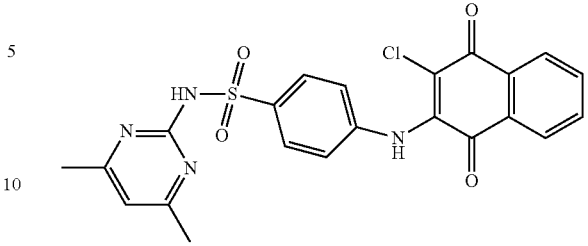

4-(3-chloro-1,4-dioxo-1,4-dihydronaphthalen-2-ylamino)-N-(4,6-dimethylpyrimidin-2-yl)benzenesulfonamide (2g). Mp=210° C. decomposed; ¹H NMR (400 MHz, DMSO-d₆) δ 9.52 (s, 1H), 8.04 (m, 2H), 7.89-7.80 (m, 4H), 7.71 (d, J=12 Hz, 1H), 7.29 (s, 1H), 7.21 (d, J=8.0 Hz, 2H), 2.31 (s, 6H); ESI-HRMS m/z calculated for C₂₂H₁₈ClN₄O₄S 469.0732, found 469.0734. (Note: base line impurities present between 8.10 to 7.80 ppm).

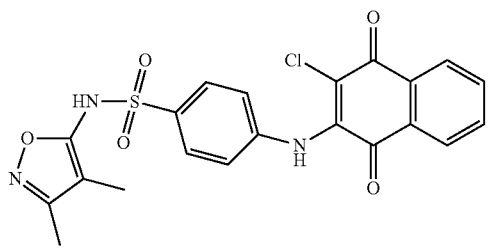

4-(3-chloro-1,4-dioxo-1,4-dihydronaphthalen-2-ylamino)-N-(3,4-dimethylisoxazol-yl)-benzenesulfonamide (2h). Mp=208-210° C.; ¹H NMR (400 MHz, DMSO-d₆) δ 10.92 (bs, 1H), 9.61 (s, 1H), 8.04 (d, J=7.6 Hz, 2H), 7.91-7.81 (m, 2H), 7.62 (d, J=8.8 Hz, 2H), 7.21 (d, J=8.8 Hz, 2H), 2.07 (s, 3H), 1.60 (s, 3H); ESI-HRMS m/z calculated for C₂₁H₁₇ClN₃O₅S 458.0572, found 458.0579.

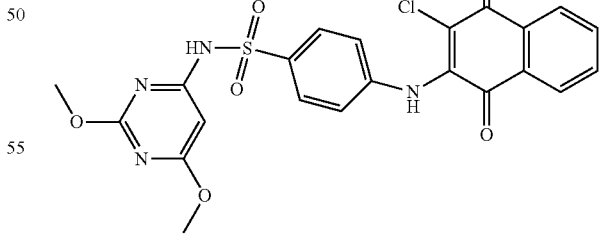

4-(3-chloro-1,4-dioxo-1,4-dihydronaphthalen-2-ylamino)-N-(2,6-dimethoxypyrimidin-4-yl)-benzene-sulfonamide (2i). Mp=220-222° C.; ¹H NMR (400 MHz, DMSO-d₆) δ 11.48 (bs, 1H), 9.56 (s, 1H), 8.03 (dt, J=8.0, 1.6 Hz, 2H), 7.91-7.80 (m, 4H), 7.21 (d, J=8.8 Hz, 2H), 5.93 (s, 1H), 3.78 (s, 3H), 3.74 (s, 3H); ESI-HRMS m/z calculated for C₂₂H₁₈ClN₄O₆S 501.0630, found 501.0648.

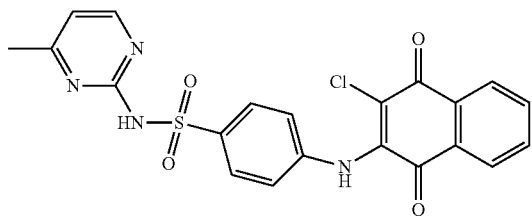

HL2-090-1

4-(3-chloro-1,4-dioxo-1,4-dihydronaphthalen-2-ylamino)-N-(4-methylpyrimidin-2-yl)-benzenesulfonamide (2j). Mp=246-248° C.; $^1$H NMR (400 MHz, DMSO-d$_6$) δ 9.53 (s, 1H), 8.31 (d, J=4.4 Hz, 1H), 8.04-8.02 (m, 2H), 7.87-7.81 (m, 4H), 7.18 (d, J=8.0 Hz, 2H), 6.90 (s, 1H), 2.30 (s, 3H); ESI-HRMS m/z calculated for $C_{21}H_{16}ClN_4O_4S$ 455.0575, found 455.0581.

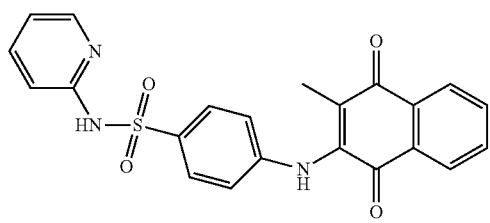

HL3-001

4-(3-methyl-1,4-dioxo-1,4-dihydronaphthalen-2-ylamino)-N-(pyridin-2-yl)benzenesulfonamide (2k). Mp=220-222° C.; $^1$H NMR (400 MHz, DMSO-d$_6$) δ 8.94 (s, 1H), 7.98 (d, J=7.6 Hz, 2H), 7.84-7.65 (m, 6H), 7.09 (d, J=8.4 Hz, 1H), 6.99 (d, J=8.8 Hz, 2H), 6.85 (br s, 1H), 1.70 (s, 3H); ESI-HRMS m/z calculated for $C_{22}H_{18}N_3O_4S$ 420.1013, found 420.1018.

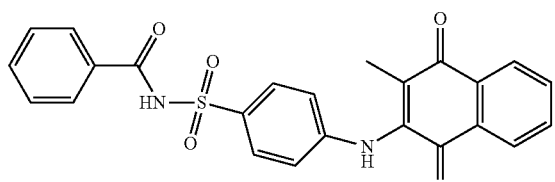

HL3-006-1

N-(4-(3-methyl-1,4-dioxo-1,4-dihydronaphthalen-2-ylamino)phenylsulfonyl)benzamide (2l). Mp=235-237° C.; $^1$H NMR (400 MHz, DMSO-d$_6$) δ 12.35 (br s, 1H), 9.06 (s, 1H), 8.00 (d, J=6.8 Hz, 2H), 7.83-7.68 (m, 6H), 7.59 (t, J=8.0 Hz, 1H), 7.46 (t, J=7.6 Hz, 2H), 7.05 (d, J=8.8 Hz, 2H), 1.78 (s, 3H); ESI-HRMS m/z calculated for $C_{24}H_{19}N_2O_5S$ 447.1009, found 447.1014.

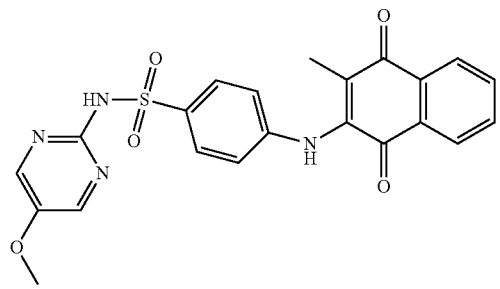

HL3-006-2

N-(5-methoxypyrimidin-2-yl)-4-(3-methyl-1,4-dioxo-1,4-dihydronaphthalen-2-ylamino)-benzenesulfonamide (2m). Mp=215-217° C.; $^1$H NMR (400 MHz, DMSO-d$_6$) δ 8.95 (s, 1H), 8.24 (s, 2H), 8.00-7.98 (m, 2H), 7.83 (dt, J=7.6, 1.6 Hz, 1H), 7.80-7.77 (m, 3H), 7.00 (d, J=8.8 Hz, 2H), 3.78 (s, 3H), 1.70 (s, 3H); ESI-HRMS m/z calculated for $C_{22}H_{19}N_4O_5S$ 451.1071, found 451.1076.

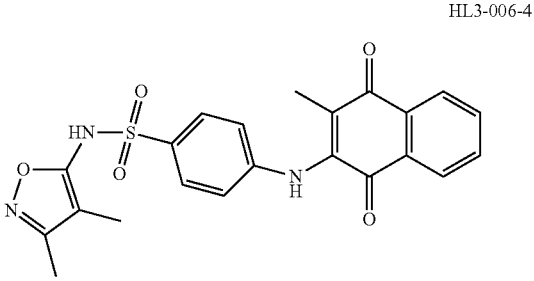 [SMILES: CC1=C(Nc2ccc(S(=O)(=O)Nc3onc(C)c3C)cc2)C(=O)c2ccccc2C1=O]

HL3-006-3

N-(2,6-dimethoxypyrimidin-4-yl)-4-(3-methyl-1,4-dioxo-1,4-dihydronaphthalen-2-ylamino)-benzenesulfonamide (2n). Mp=255-257° C.; ESI-HRMS m/z calculated for $C_{23}H_{21}N_4O_6S$ 481.1176, found 481.1182.

HL3-006-4

N-(3,4-dimethylisoxazol-5-yl)-4-(3-methyl-1,4-dioxo-1,4-dihydronaphthalen-2-ylamino)-benzenesulfonamide (2o). Mp=not determined; $^1$H NMR (400 MHz, DMSO-d$_6$) δ 10.84 (bs, 1H), 9.07 (s, 1H), 8.00 (d, J=7.6 Hz, 2H), 7.86-7.77 (m, 2H), 7.57 (d, J=8.8 Hz, 2H), 7.04 (d, J=8.8 Hz, 2H), 2.06 (s, 3H), 1.73 (s, 3H), 1.59 (s, 3H).

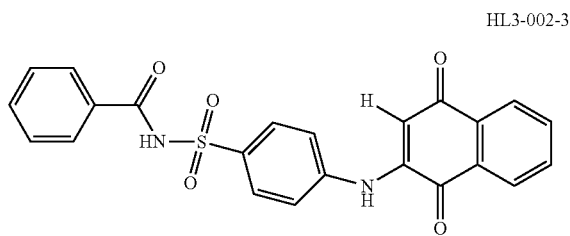 [SMILES: O=C(NS(=O)(=O)c1ccc(NC2=CC(=O)c3ccccc3C2=O)cc1)c1ccccc1]

HL3-002-3

N-(4-(1,4-dioxo-1,4-dihydronaphthalen-2-ylamino)phenylsulfonyl)benzamide (2p). Mp=294-296° C.; $^1$H NMR (400 MHz, DMSO-d$_6$) δ 12.57 (br s, 1H), 9.52 (s, 1H), 8.06 (d, J=7.6 Hz, 1H), 7.99 (d, J=8.4 Hz, 2H), 7.95 (d, J=7.2 Hz, 1H), 7.86-7.78 (m, 4H), 7.66-7.59 (m, 3H), 7.47 (t, J=7.2 Hz, 2H), 6.41 (s, 1H); ESI-HRMS m/z calculated for C$_{23}$H$_{17}$N$_2$O$_5$S 433.0853, found 433.0857.

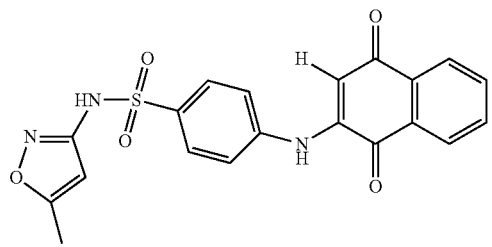

HL3-002-4

4-(1,4-dioxo-1,4-dihydronaphthalen-2-ylamino)-N-(5-methylisoxazol-3-yl)benzenesulfonamide (2q). Mp=290-192° C.; $^1$H NMR (400 MHz, DMSO-d$_6$) δ 11.43 (br s, 1H), 9.47 (s, 1H), 8.06 (d, J=6.4 Hz, 1H), 7.94 (d, J=7.6 Hz, 1H), 7.88-7.77 (m, 4H), 7.60 (d, J=8.8 Hz, 2H), 6.37 (s, 1H), 6.14 (s, 1H), 2.28 (s, 3H); ESI-HRMS m/z calculated for C$_{20}$H$_{16}$N$_3$O$_5$S 410.0805, found 410.0812.

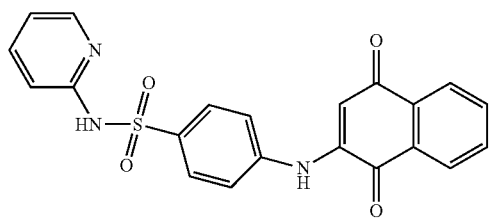

HL2-075

4-(1,4-dioxo-1,4-dihydronaphthalen-2-ylamino)-N-(pyridin-2-yl)benzenesulfonamide (2r). Mp=286° C. decomposed; $^1$H NMR (400 MHz, DMSO-d$_6$) δ 9.41 (s, 1H), 8.05 (d, J=7.6 Hz, 1H), 7.99-7.94 (m, 2H), 7.90-7.87 (m, 3H), 7.79 (t, J=7.6 Hz, 1H), 7.72 (t, J=7.6 Hz, 1H), 7.53 (d, J=8.4 Hz, 2H), 7.15 (d, J=8.4 Hz, 1H), 6.86 (br s, 1H), 6.30 (s, 1H); ESI-HRMS m/z calculated for C$_{21}$H$_{16}$N$_3$O$_4$S (M+H)$^+$ 406.0856, found 406.0860.

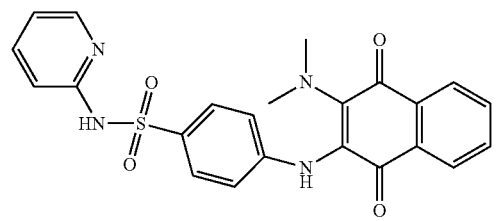

HL2-034

4-(3-(dimethylamino)-1,4-dioxo-1,4-dihydronaphthalen-2-ylamino)-N-(pyridin-2-yl)-benzenesulfonamide (3a). Mp=118-120° C.; $^1$H NMR (400 MHz, DMSO-d$_6$) δ 8.42 (s, 1H), 8.03 (br s, 1H), 7.94-7.89 (m, 2H), 7.76-7.71 (m, 2H), 7.66-7.59 (m, 3H), 7.06 (d, J=8.4 Hz, 1H), 6.88-6.83 (m, 3H), 2.66 (s, 6H); ESI-HRMS m/z calculated for C$_{23}$H$_{21}$N$_4$O$_4$S (M+H)$^+$449.1278, found 449.1279.

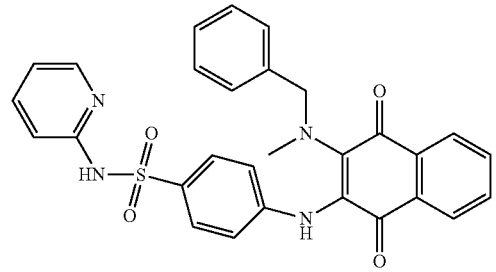

HL2-044-3

4-(3-(benzyl(methyl)amino)-1,4-dioxo-1,4-dihydronaphthalen-2-ylamino)-N-(pyridin-2-yl)-benzenesulfonamide (3b). Mp=135-140° C.; $^1$H NMR (400 MHz, DMSO-d$_6$) δ 8.58 (s, NH, 1H, disappeared in D$_2$O shake), 8.03 (d, J=4.0 Hz, 1H), 7.93-7.90 (m, 2H), 7.78-7.72 (m, 2H), 7.67-7.62 (m, 3H), 7.31 (d, J=4.4 Hz, 1H), 7.22-7.13 (m, 3H), 7.08 (d, J=8.8 Hz, 1H), 7.03 (d, J=6.8 Hz, 2H), 6.96 (d, J=8.8 Hz, 2H), 6.85 (t, J=6.0 Hz, 1H), 3.85 (s, 2H), 2.75 (s, 3H); ESI-HRMS m/z calculated for C$_{29}$H$_{25}$N$_4$O$_4$S (M+H)$^+$525.1591, found 525.1588.

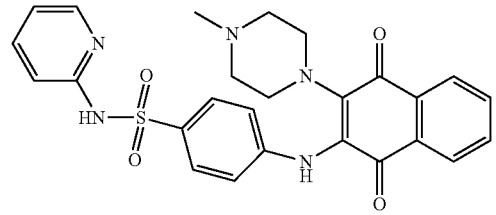

HL2-044-4

4-(3-(4-methylpiperazin-1-yl)-1,4-dioxo-1,4-dihydronaphthalen-2-ylamino)-N-(pyridin-2-yl)-benzenesulfonamide (3c). Mp=222-224° C.; $^1$H NMR (400 MHz, DMSO-d$_6$) δ 8.48 (s, 1H), 8.02 (d, J=4.0 Hz, 1H), 7.93-7.90 (m, 2H), 7.78-7.71 (m, 2H), 7.66-7.62 (m, 3H), 7.07 (d, J=8.4 Hz, 1H), 6.91 (m, 2H), 6.85 (t, J=6.0 Hz, 1H), 3.09 (br t, 4H), 1.98-1.97 (br t, 4H), 1.87 (s, 3H); ESI-HRMS m/z calculated for C$_{26}$H$_{26}$N$_5$O$_4$S (M+H)$^+$504.1700, found 504.1713.

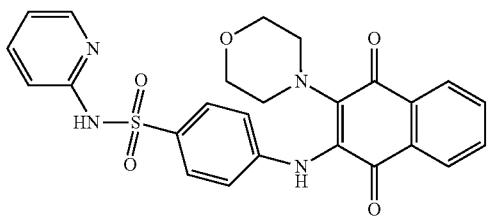

HL2-044-6

4-(3-morpholino-1,4-dioxo-1,4-dihydronaphthalen-2-ylamino)-N-(pyridin-2-yl)benzenesulfonamide (3e). Mp=220-222° C.; $^1$H NMR (400 MHz, DMSO-d$_6$) δ 8.57 (s, 1H), 8.00 (br s, 1H), 7.96-7.91 (m, 2H), 7.67-7.61 (m, 3H), 7.06 (d, J=8.4 Hz, 1H), 6.95 (d, J=8.8 Hz, 2H), 6.84 (br s, 1H), 3.14 (d, J=4.0 Hz, 4H), 3.06 (d, J=4.0 Hz, 4H); HRMS (ESI+ve) m/z calculated for C$_{25}$H$_{23}$N$_4$O$_5$S (M+H)$^+$491.1384, found 491.1386.

General Procedure for Synthesis of Sulfanilamide Derivatives (5a, 5b) (YL1-003-1 and YL1-003-2)[1]. Sodium cyanoborohydride (0.36 g, 5.65 mmol) was added to a mixture of benzyaldehyde (0.45 g, 4.25 mmol), sulfapyridine (1.00 g, 4.01 mmol), and acetic acid (0.67 g, 11.23 mmol) in methanol (13 ml) at 0° C. The crude reaction mixture was warmed to r.t., stirred for 1 h. The reaction was quenched with KHSO$_4$ (5% aqueous solution, 10 ml), and extracted with ethyl acetate (3×20 ml). The organic phase was washed with sat. NaHCO$_3$, brine, dried (Na$_2$SO$_4$), and concentrated. The crude product was purified by flash chromatography (SiO$_2$ MeOH in DCM gradient elution).

YL1-003-1

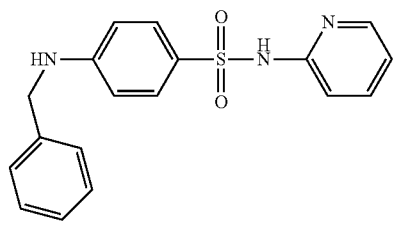

4-(benzylamino)-N-(pyridin-2-yl)benzenesulfonamide (5a) (YL1-003-1). White solid (246 mg, 17%). Mp=163-165° C.; $^1$H NMR (400 MHz, Acetone-d$_6$) δ 9.99 (br s, 1H disappeared on D$_2$O shake), 8.22-8.20 (m, 1H), 7.67-7.60 (m, 3H), 7.32-7.24 (m, 5H), 7.19 (t, J=7.2), 6.93 (ddd, J=7.2, 4.8, 0.8, 1H), 6.64 (d, J=9.2, 2H), 6.33 (ap t, J=5.6 Hz, 1H disappeared on D$_2$O shake), 4.35 (d, J=5.6 Hz, 2H, CH$_2$, singlet on D$_2$O shake); ESI-LRMS m/z 340.1 (M+H)$^+$ found; ESI-HRMS m/z calculated C$_{18}$H$_{18}$N$_3$O$_2$S (M+H)$^+$ 340.1114, found 340.1131.

YL1-003-2

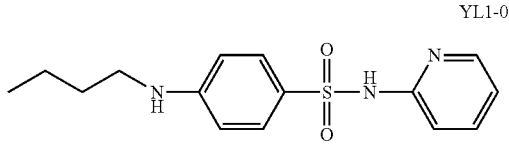

4-(butylamino)-N-(pyridin-2-yl)benzenesulfonamide (5b) (YL1-003-2). White solid, (235 mg, 54%). Mp=128-130° C.;
$^1$H NMR (400 MHz, CDCl$_3$), 13.15 (br s), 8.40 (dd, J=5.6, 0.8 Hz, 1H), 7.62-7.54 (m, 3H), 7.35 (dd, J=8.8, Hz, 1H), 6.75 (t, J=6.4 Hz, 1H), 6.47 (d, J=8.8 Hz, 2H), 3.04 (br t, 2H), 1.56-1.49 (m, 2H), 1.39-1.29 (m, 2H), 0.88 (t, J=7.2 Hz, 3H); ESI-LRMS m/z 306.1 (M+H)$^+$; ESI-HRMS m/z calculated for C$_{15}$H$_{20}$N$_3$O$_2$S (M+H)$^+$ 306.1271, found: 306.1311.

Sulfapyridine Naphthoquinone Derivatives (6a, 6b, 6c). (YL1-018-1, YL1-018-2, YL1-018-9). DIPEA (52.9 mg, 0.41 mmol) was added to solution of 4-(3-Chloro-1,4-dioxo-1,4-dihydro-naphthalen-2-ylamino-N-pyridin-2-yl-benzenesulfonamide (150 mg, 0.34 mmol) in anhydrous DMF (3 ml) under inert conditions. Methyl iodide (58 mg, 0.41 mmol) was added to the reaction mixture after 5 min. and the reaction was stirred at r.t. for two days. The reaction mixture was dried under reduced pressure and purified by flash chromatography (SiO$_2$, EtOAC in Hexane, gradient elution).

YL1-018-1

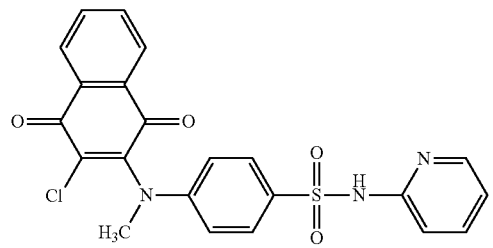

4-((3-chloro-1,4-dioxo-1,4-dihydronaphthalen-2-yl)(methyl)amino)-N-(pyridin-2-yl)benzenesulfonamide (6a) (YL1-018-1). Orange solid, (13 mg, 25%). Mp=152-154° C.; $^1$H NMR (400 MHz, CDCl$_3$) δ 8.28-8.27 J=7.6 (m, 1H), 8.19 (dd, J=7.6, 1.2 Hz, 1H), 8.13 (dd, J=7.6, 1.2 Hz, 1H), 7.79 (dt, J=7.6, 1.6 Hz, 1H), 7.75-7.66 (m, 4H), 7.52 (d, J=8.8 Hz, 2H), 7.13 (ddd, J=6.8, 4.8, 1.2 Hz, 1H), 7.00 (d, J=8.8 Hz, 2H), 3.28 (s, 3H); ESI-LRMS m/z 455.0 (M+H)$^+$; ESI-HRMS m/z calculated for C$_{22}$H$_{17}$ClN$_3$O$_4$S (M+H)$^+$ 454.0623, found 454.0638.

YL1-018-2

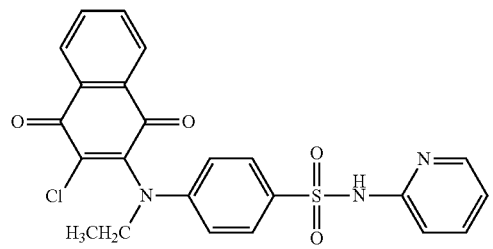

4-((3-chloro-1,4-dioxo-1,4-dihydronaphthalen-2-yl)(ethyl)amino)-N-(pyridin-2-yl)benzenesulfonamide (6b) (YL1-018-2) Orange solid, (60 mg, 38%). Mp=180-182° C.; $^1$H NMR (400 MHz, CDCl$_3$) δ 8.33-8.32 (m, 1H), 8.20 (dd, J=7.6, 1.2 Hz, 1H), 8.13 (dd, J=7.6, 1.2 Hz, 1H), 7.80 (dt, J=7.6, 1.2 Hz, 1H), 7.73 (dt, J=7.6, 1.2 Hz, 2H), 7.67 (br s, 1H), 7.59-7.55 (m, 3H), 7.16 (ddd, J=7.2, 4.8, 1.6 Hz, 1H), 7.01 (d, J=8.4 Hz, 2H), 3.84 (q, J=7.2 Hz, 2H), 1.12 (t, J=7.2 Hz, 3H). ESI-LRMS m/z 469.0 (M+H)$^+$; ESI-HRMS m/z calculated for C$_{23}$H$_{19}$ClN$_3$O$_4$S (M+H)$^+$ 468.0779, found 468.0800.

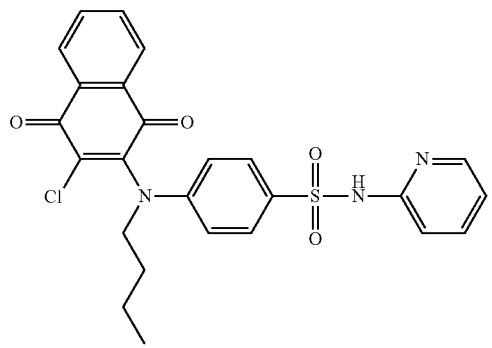

YL1-018-9

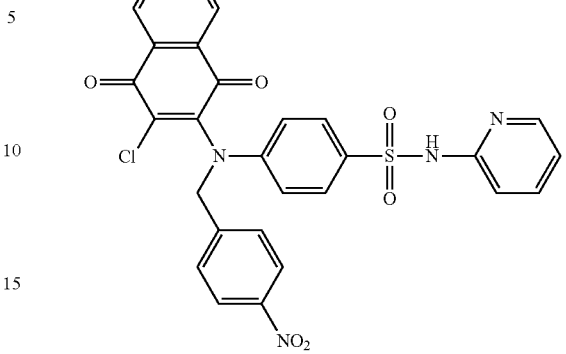

YL1-018-6

4-(butyl(3-chloro-1,4-dioxo-1,4-dihydronaphthalen-2-yl) amino)-N-(pyridin-2-yl)benzenesulfonamide (6c) (YL1-018-9). Orange solid, (52 mg, 46%). Mp=181-183° C.; $^1$H NMR (400 MHz, CDCl$_3$) δ 8.36-8.34 (m, 1H), 8.13 (dt, J=7.6, 1.2 Hz, 2H), 7.75-7.54 (m, 6H), 7.30 (d, J=8.8 Hz, 2H), 7.19 (ddd, J=7.6, 4.8, 1.2 Hz, 1H), 3.75 (t, J=7.2 Hz, 2H), 1.46-1.40 (m, 2H), 1.36-1.30 (m, 2H), 0.86 (t, J=7.2 Hz, 3H); ESI-LRMS 497.0 (M+H)$^+$; ESI-HRMS m/z calculated for $C_{25}H_{23}ClN_3O_4S$ (M+H)$^+$ 496.1092, found 496.1104.

General procedure for synthesis of sulfapyridine naphthoquinone derivatives (6d, 6e, 6f, 6g, 6h) (YL1-018-5, YL1-018-6, YL1-018-11, YL1-018-12, YL1-018-13). 4-(3-Chloro-1,4-dioxo-1,4-dihydro-naphthalen-2-ylamino-N-pyridin-2-yl-benzenesulfonamide (100 mg, 0.23 mmol), Benzylbromide (47 mg, 0.27 mmol) and Hunig's base (35 mg, 0.27 mmol) were mixed in anhydrous DMF (2 ml). The reaction mixture was reacted at 160° C. for 15 min. in a microwave reactor. (For 6f, 6g, the reactions were heated for 30 min. at same temperature.) The mixture was dried under reduced pressure. The product was purified using flash chromatography (SiO$_2$, EtOAC in Hexane gradient elution).

4-((3-chloro-1,4-dioxo-1,4-dihydronaphthalen-2-yl)(4-nitrobenzyl)amino)-N-(pyridin-2-yl)benzenesulfonamide (6e) (YL1-018-6). Orange solid (75 mg, 58%). Mp=80-82° C.; $^1$H NMR (400 MHz, CDCl$_3$) δ 8.24-8.23 (m, 1H), 8.20 (dd, J=7.6, 0.8 Hz, 1H), 8.14 (dd, J=7.6, 1.2 Hz, 1H), 8.09 (dd, J=8.8, 2.0 Hz, 2H), 7.81 (dt, J=7.2, 1.2 Hz, 1H), 7.76-7.56 (m, 5H), 7.51 (d, J=8.8 Hz, 2H), 7.10 (ddd, J=7.2, 4.8, 1.2 Hz, 1H), 7.03 (d, J=8.4 Hz, 2H), 5.11 (s, 2H); ESI-LRMS m/z 576.0 (M+H)$^+$; ESI-HRMS m/z calculated for $C_{28}H_{20}ClN_4O_6S$ (M+H)$^+$ 575.0787, found 575.0795.

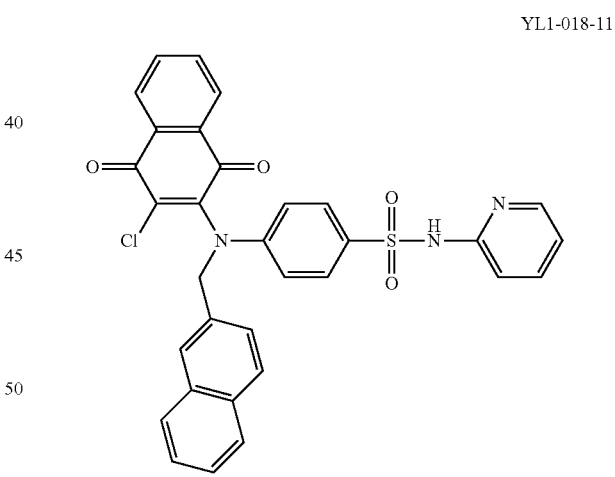

YL1-018-11

YL1-018-5

4-(benzyl(3-chloro-1,4-dioxo-1,4-dihydronaphthalen-2-yl)amino)-N-(pyridin-2-yl)benzenesulfonamide (6d) (YL1-018-5). Orange solid (56 mg, 47%). Mp=78-80° C.; $^1$H NMR (400 MHz, CDCl$_3$) δ 8.28-8.26 (m, 1H), 8.20 (dd, J=7.6, 1.2 Hz, 1H), 8.14 (td, J=7.6, 1.6 Hz, 1H), 7.8-7.59 (m, 7H), 7.48 (d, J=8.0 Hz, 1H), 7.30 (d, J=7.2 Hz, 2H), 7.24-7.15 (m, 3H), 7.09-7.03 (m, 3H), 5.01 (s, 2H); ESI-LRMS m/z 531.0 (M+H)$^+$; ESI-HRMS m/z calculated for $C_{28}H_{21}ClN_3O_4S$ (M+H)$^+$ 530.0936, found 530.0936.

4-((3-chloro-1,4-dioxo-1,4-dihydronaphthalen-2-yl) (naphthalen-2-ylmethyl)amino)-N-(pyridin-2-yl)benzenesulfonamide (6f) (YL1-018-11). Orange solid (60 mg, 46%). Mp=165-167° C.; $^1$H NMR (400 MHz, CDCl$_3$) δ 8.28-8.26 (m, 1H), 8.20 (dd, J=7.6, 1.2 Hz, 1H), 8.13 (dd, J=7.6, 1.2 Hz, 1H), 7.82-7.70 (m, 7H), 7.64-7.56 (m, 3H), 7.51-7.49 (m, 2H), 7.42-7.39 (m, 2H), 7.08-7.03 (m, 2H), 5.15 (s, 2H); ESI-LRMS m/z 580.0 (M+H)$^+$; ESI-HRMS m/z calculated for $C_{32}H_{22}ClN_3O_4S$ M$^+$ 579.1014, found 579.1034.

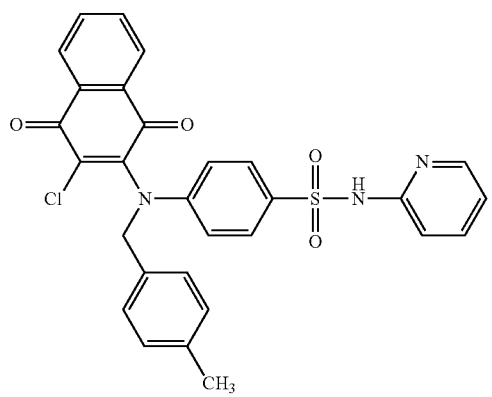

YL1-018-12

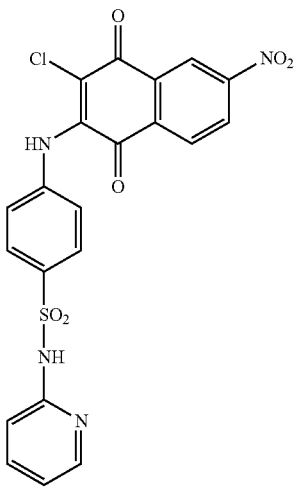

YL1-104-2

4-((3-chloro-1,4-dioxo-1,4-dihydronaphthalen-2-yl)(4-methylbenzyl)amino)-N-(pyridin-2-yl)benzenesulfonamide (6g) (YL1-018-12). Orange solid (50 mg, 40%). Mp=99-101° C.; $^1$H NMR (400 MHz, CDCl$_3$) δ 8.28-8.26 (m, 1H), 8.21 (dd, J=7.6, 1.2 Hz, 1H), 8.15 (dd, J=7.6, 1.2 Hz, 1H), 7.80 (dt, J=7.6, 1.2 Hz, 1H), 7.74 (dt, J=7.6, 1.2 Hz, 1H), 7.61 (bs, 1H disappeared on D$_2$O shake), 7.64-7.60 (m, 2H), 7.56 (d, J=8.4 Hz, 2H), 7.18 (d, J=8.0 Hz, 2H), 7.09-7.01 (m, 5H), 4.96 (s, 2H), 2.25 (s, 3H); ESI-LRMS m/z 545.1 (M+H)$^+$; ESI-HRMS m/z calculated for C$_{29}$H$_{23}$ClN$_3$O$_4$S (M+H)$^+$ 544.1092, found 544.1101.

Mixture of regio-isomers of 4-(3-chloro-6-nitro-1,4-dioxo-1,4-dihydronaphthalen-2-ylamino)-N-(pyridin-2-yl)benzenesulfonamide and 4-(3-chloro-7-nitro-1,4-dioxo-1,4-dihydronaphthalen-2-ylamino)-N-(pyridin-2-yl)benzenesulfonamide (7a) (YL-104-2). A well-stirred suspension of sulfapyridine (0.229 g, 0.919 mmol) and 2,3-dichloro-6-nitronaphthalene-1,4-dione (0.5 g, 1.84 mmol) in 10.0 mL of 95% EtOH/5% water cosolvent was refluxed at 115° C. for three days in a sealed tube. The resultant orange precipitate was filtered and washed with hot ethanol (5×5 ml), acetone (3×5 ml), and dried under reduced pressure to afford the title compound as an orange solid (0.393 g, 88%). $^1$H NMR (400 MHz, DMSO-d$_6$) δ 9.76, (9.72 for isomer) (s, 1H), 8.64-8.56 (m, 2H), 8.26 (8.25 for isomer) (d, J=8.4 Hz, 1H), 8.02 (br s, 1H), 7.78 (d, J=8.4 Hz, 2H), 7.71 (t, J=7.2 Hz, 1H), 7.22 (d, J=8.4 Hz, 2H), 7.15 (d, J=8.0 Hz, 1H), 6.88 (br t, J=6.4 Hz, 1H); ESI-LRMS m/z 485.0 (M+H)$^+$; ESI-HRMS m/z calculated for C$_{21}$H$_{14}$ClN$_4$O$_6$S (M+H)$^+$ 485.0317, found 485.0330.

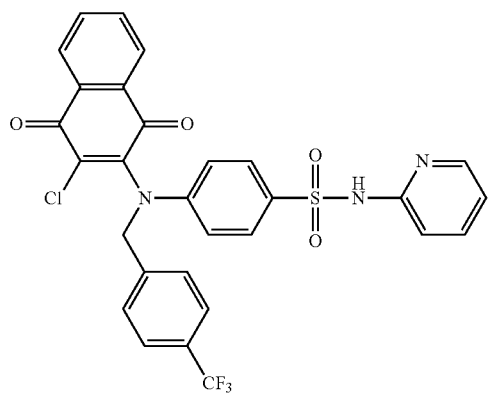

YL1-018-13

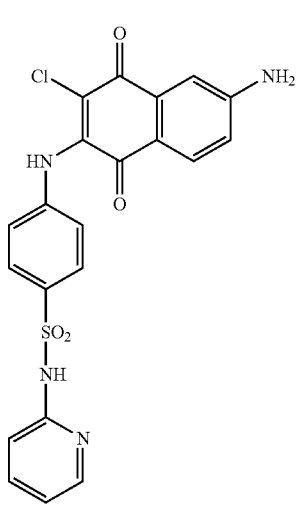

YL1-109

4-((3-chloro-1,4-dioxo-1,4-dihydronaphthalen-2-yl)(4-(trifluoromethyl)benzyl)amino)-N-(pyridin-2-yl)benzenesulfonamide (6h) (YL1-018-13). Orange solid (62 mg 46%). Mp=157-159° C.; $^1$H NMR (400 MHz, CDCl$_3$) δ 8.25 (d, J=4.8 Hz, 1H), 8.21 (d, J=7.6 Hz, 1H), 8.14 (d, J=7.6, 1H), 7.83-7.64 (m, 4H), 7.59-7.55 (m, 3H), 7.46 (dd, J=15.2, 8.0 Hz, 4H), 7.11-7.03 (m, 2H), 5.01 (s, 2H); $^{19}$F NMR: δ −62.93 (s); ESI-LRMS m/z 599.1 (M+H)$^+$; ESI-HRMS m/z calculated for C$_{29}$H$_{20}$ClF$_3$N$_3$O$_4$S (M+H)$^+$ 598.0810, found 598.0816.

Mixture of regio-isomers of 4-(6-amino-3-chloro-1,4-dioxo-1,4-dihydronaphthalen-2-ylamino)-N-(pyridin-2-yl)benzenesulfonamide and 4-(7-amino-3-chloro-1,4-dioxo-1,4-dihydronaphthalen-2-ylamino)-N-(pyridin-2-yl)benzenesulfonamide (8) (YL1-109). Compound 7a (0.213 g, 0.44 mmol) was dissolved in mixed solvent of DMF:MeOH (4:1) and passed through H-cube apparatus (40 bar pressure and 10% Pd/C as catalyst under room temperature). The resultant solution was evaporated and dried under reduced pressure to give red color solid. This product was purified with SiO$_2$ flash chromatography, gradient MeOH/DCM 5%-10% to obtain required product as a red solid (50 mg, 25%). $^1$H NMR (400 MHz, DMSO-d$_6$) δ 9.17 (9.40 for isomer) (s, 1H), 8.03 (s, 1H), 7.74 (dd, J=16.0, 7.2 Hz, 4H), 7.17-7.15 (m, 2H), 7.06 (d, J=8.8 Hz, 2H), 6.86-6.77 (m, 2H), 6.54 (s, 2H disappear on D$_2$O shake); ESI-HRMS m/z calculated for C$_{21}$H$_{16}$ClN$_4$O$_4$S (M+H)$^+$ 455.0575, found 455.0588.

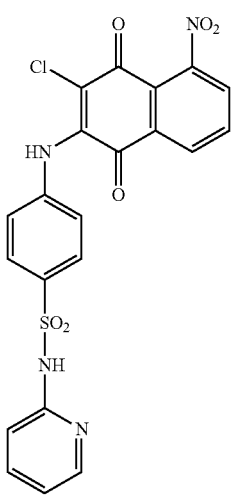

YL1-112

Mixture of regio-isomers of 4-(3-chloro-5-nitro-1,4-dioxo-1,4-dihydronaphthalen-2-ylamino)-N-(pyridin-2-yl)benzenesulfonamide and 4-(3-chloro-8-nitro-1,4-dioxo-1,4-dihydronaphthalen-2-ylamino)-N-(pyridin-2-yl)benzenesulfonamide (7b) (YL1-112). This compound was prepared according to the procedure for 7a except using 2,3-dichloro-5-nitronaphthalene-1,4-dione to obtain 7b as an orange solid (0.178 g, 92%); $^1$H NMR (400 MHz, DMSO-d$_6$) δ 9.73 (9.67 for isomer) (s, 1H), 8.25 (8.23 for isomer) (dd, J=7.6, 1.2 Hz, 1H), 8.13 (d, J=8.4 Hz, 1H), 8.07-7.97 (m, 2H), 7.77 (dd, J=8.4, 3.2 Hz, 2H), 7.72 (t, J=8.4 Hz, 1H), 7.23-7.15 (m, 2H), 6.88 (br t, J=5.6 Hz, 1H); ESI-HRMS m/z calculated for C$_{21}$H$_{14}$ClN$_4$O$_6$S (M+H)$^+$ 485.0317, found 485.0327.

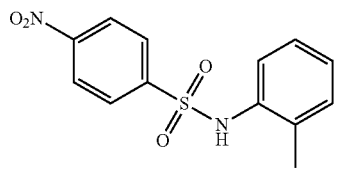

4-Nitro-N-o-tolyl-benzenesulfonamide (11a). (RK1-1-22) I A solution of 4-nitrobenzenesulfonyl chloride (200 mg, 0.90 mmol), o-toluidine (106 mg, 0.99 mmol), and pyridine (79 mg, 0.08 ml, 0.993 mmol) in 5.0 mL 1,2-dichloroethane was heated to 150° C. for 10 minutes in the microwave. A 1M HCl solution was added until the pH of the mixture indicated pH=2, and the acidified aqueous layer was separated and extracted with CH$_2$Cl$_2$ (3×10 mL). The combined organic fractions were washed successively with brine and water then dried over Na$_2$SO$_4$ and evaporated to dryness to afford the title compound as a peach solid (127 mg, 47%). Mp=139-142° C. (lit. 157-159° C., Tetrahedron 62(25), 6100-6106; 2006); $^1$H NMR (400 MHz, CDCl$_3$) δ 8.28 (d, J=9.0 Hz, 2H), 7.89 (d, J=9.0 Hz, 2H), 7.28-7.27 (m, 1H), 7.20-7.12 (m, 3H), 6.30 (br s, 1H), 2.01 (s, 3H).

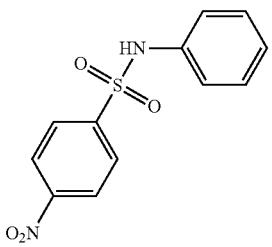 [SMILES: O=[N+]([O-])c1ccc(S(=O)(=O)Nc2ccccc2)cc1]

4-Nitro-N-phenyl-benzenesulfonamide (11b). (RK1-1-27A) I This compound was prepared according to the procedure described for compound 11a except using aniline to obtain required product as an off-white solid, (222 mg, 87%). Mp=154-156° C. (lit 174-176° C. (Tetrahedron 62(25), 6100-6106; 2006)); $^1$H NMR (400 MHz, CDCl$_3$) δ 8.28 (d, J=9.2 Hz, 2H), 7.93 (d, J=9.2 Hz, 2H), 7.31-7.26 (m, 2H), 7.22-7.18 (m, 1H), 7.08 (d, J=8.4 Hz, 2H), 6.73 (br s, 1H).

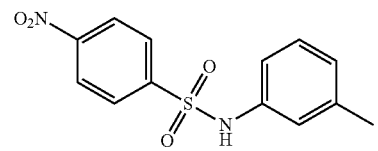

4-Nitro-N-m-tolyl-benzenesulfonamide (11c). (RK1-1-27B) I This compound was prepared according to the procedure described for compound 11a except using m-toluidine to obtain required product as a light tan solid, (264 mg, 100%). Mp=121-124° C. (lit 138-139° C. Tetrahedron 62(25), 6100-6106; 2006); $^1$H NMR (400 MHz, CDCl$_3$) δ 8.28 (d, J=8.8 Hz, 2H), 7.91 (d, J=8.8 Hz, 2H), 7.15 (t, J=7.8 Hz, 1H), 7.00 (d, J=7.6 Hz, 1H), 6.90 (br s, 1H), 6.85 (d, J=8.0 Hz, 1H), 6.56 (br s, 1H).

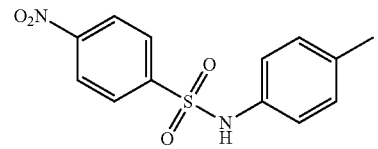 [SMILES: Cc1ccc(NS(=O)(=O)c2ccc([N+](=O)[O-])cc2)cc1]

4-Nitro-N-p-tolyl-benzenesulfonamide (11d). (RK1-1-29)I This compound was prepared according to the procedure described for compound 11a except using p-toluidine to obtain required product as a yellow solid, (256 mg, 97%). Mp=170-172° C. (lit 184-184.5° C. Bioorganic and Medicinal Chemistry 15(2), 1014-1021; 2007); $^1$H NMR (400 MHz, CDCl$_3$) δ 8.27 (d, J=9.0 Hz, 2H), 7.88 (d, J=9.0 Hz, 2H), 7.08 (d, J=8.2 Hz, 2H), 6.94 (d, J=8.2 Hz, 2H), 6.41 (bs, 1H), 2.30 (s, 3H).

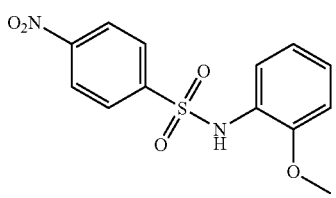 [SMILES: COc1ccccc1NS(=O)(=O)c1ccc([N+](=O)[O-])cc1]

N-(2-methoxy-phenyl)-4-nitro-benzenesulfonamide (11e). (RK1-1-27C) I This compound was prepared according to the procedure described for compound 11a except using o-anisidine. Recrystallization from DCM/Hexanes obtained the required product as white crystals, (164 mg, 59%). Mp=141-143° C.; $^1$H NMR (400 MHz, CDCl$_3$) δ 8.24 (d, J=8.8 Hz, 2H), 7.91 (d, J=8.8 Hz, 2H), 7.56 (dd, J=8.0, 1.6 Hz, 1H), 7.11 (td, J=7.9, 1.5 Hz, 1H), 7.02 (br s, 1H), 6.94 (td, J=7.6, 1.2 Hz, 1H), 6.74 (dd, J=8.0, 1.2 Hz, 1H), 3.62 (s, 3H).

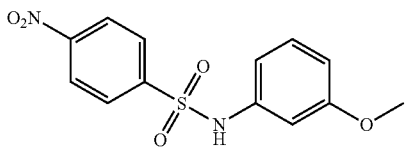 [SMILES: COc1cccc(NS(=O)(=O)c2ccc([N+](=O)[O-])cc2)c1]

N-(3-methoxy-phenyl)-4-nitro-benzenesulfonamide (RK1-1-27D) I This compound was prepared according to the procedure described for compound 11a except using m-anisidine. Recrystallization from DCM/Hexanes obtained the required product as brown-yellow needles (202 mg, 73%). Mp=96-98° C.; $^1$H NMR (400 MHz, CDCl$_3$) δ 8.29 (d, J=9.0 Hz, 2H), 7.94 (d, J=9.0 Hz, 2H), 7.16 (t, J=8.0 Hz, 1H), 6.73-6.70 (m, 2H), 6.60-6.58 (m, 2H), 3.76 (s, 3H).

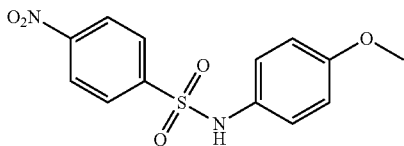 [SMILES: COc1ccc(NS(=O)(=O)c2ccc([N+](=O)[O-])cc2)cc1]

N-(4-methoxy-phenyl)-4-nitro-benzenesulfonamide (11g). (RK1-1-27E) I This compound was prepared according to the procedure described for compound 11a except using p-anisidine to obtain the required product as a light brown solid. (278 mg, 100%) Mp=173-175° C. (lit 187-189° C., *Tetrahedron* 62(25), 6100-6106; 2006); $^1$H NMR (400 MHz, CDCl$_3$) δ 8.28 (d, J=8.8 Hz, 2H), 7.85 (d, J=8.8 Hz, 2H), 6.97 (d, J=9.0 Hz, 2H), 6.80 (d, J=9.0 Hz, 2H), 6.36 (br s, 1H), 3.78 (s, 3H).

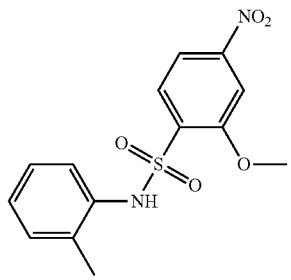 [SMILES: COc1cc([N+](=O)[O-])ccc1S(=O)(=O)Nc1ccccc1C]

2-Methoxy-4-nitro-N-o-tolyl-benzenesulfonamide (11h). (RK2-063-03)I This compound was prepared according to the procedure for compound 11a except using 2-methoxy-4-nitrobenzenesulfonyl chloride. Recrystallization from DCM/Hexanes obtained the required product as brown crystals (202 mg, 79%). Mp=127-129° C.; $^1$H NMR (400 MHz, CDCl$_3$) δ 8.03 (d, J=8.8 Hz, 1H), 7.85-7.88 (m, 2H), 7.14-7.11 (m, 2H), 7.06-7.04 (m, 2H), 6.76 (br s, 1H), 4.13 (s, 3H), 2.26 (s, 3H).

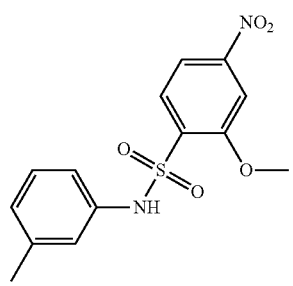 [SMILES: COc1cc([N+](=O)[O-])ccc1S(=O)(=O)Nc1cccc(C)c1]

2-Methoxy-4-nitro-N-m-tolyl-benzenesulfonamide (11i). (RK2-063-02)I This compound was prepared according to the procedure described for compound 11a except using 2-methoxy-4-nitrobenzenesulfonyl and m-toluidine as starting materials. Recrystallization from DCM/Hexanes obtained the required product as gold-brown needles (236 mg, 92%). Mp=142-145° C.; $^1$H NMR (400 MHz, CDCl$_3$) δ 8.03 (d, J=9.2 Hz, 1H), 7.84-7.81 (m, 2H), 7.28 (br s, 1H), 7.07 (t, J=7.6, 1H), 6.90-6.83 (m, 3H), 4.16 (s, 3H), 2.25 (s, 3H).

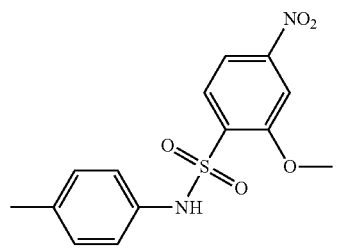

2-Methoxy-4-nitro-N-p-tolyl-benzenesulfonamide (11j). (RK2-063-04)I This compound was prepared according to the procedure described for compound 11a except using 2-methoxy-4-nitrobenzenesulfonyl and p-toluidine as starting materials. Recrystallization from DCM/Hexanes obtained the required product as yellow-brown needles (199 mg, 78%). Mp=126-129° C.; $^1$H NMR (400 MHz, CDCl$_3$) δ 7.97 (d, J=8.4 Hz, 1H), 7.85-7.81 (m, 2H), 7.01 (d, J=8.2 Hz, 2H), 6.93 (d, J=8.2 Hz, 2H), 6.85 (br s, 1H), 4.17 (s, 3H), 2.23 (s, 3H).

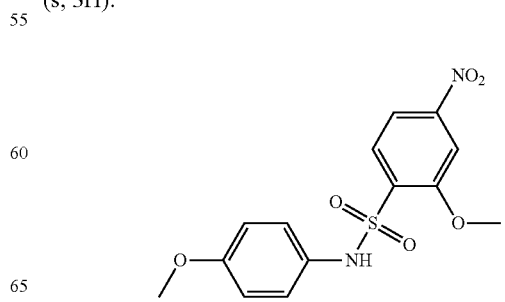

2-Methoxy-N-(4-methoxy-phenyl)-4-nitro-benzene-sulfonamide (11k). (RK2-063-01)I This compound was prepared according to the procedure described for compound 11a except using 2-methoxy-4-nitrobenzenesulfonyl and p-anisidine as starting materials. Recrystallization from DCM/Hexanes obtained the required product as gold-brown needles (213 mg, 79%). Mp=117-119° C.; $^1$H NMR (400 MHz, CDCl$_3$) δ 7.93 (d, J=8.4 Hz, 1H), 7.88 (d, J=2.0 Hz, 1H), 7.82 (dd, J=8.4, 2.0 Hz, 1H), 6.97 (d, J=9.2 Hz, 2H), 6.78 (br s, 1H), 6.73 (d, J=9.2 Hz, 2H), 4.19 (s, 3H), 3.72 (s, 3H).

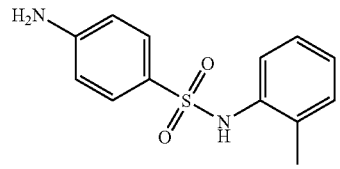

4-Amino-N-o-tolyl-benzenesulfonamide (12a) (RK1-1-24) I To a solution of 4-Nitro-N-o-tolyl-benzenesulfonamide (11a) in 4.0 mL of a 1:1 MeOH/THF mixture, was added nickel chloride hexahydrate (163 mg, 0.68 mmol) at 0° C. under constant stirring. Sodium borohydrate (52 mg, 1.37 mmol) was added portion wise and the progress of the reaction monitored by TLC (60% hexanes/40% ethylacetate). The solvent was removed in vacuo and the remaining black solid was re-suspended in EtOAc and filtered using a pad of celite and washed with EtOAc until the filtrate, when visualized under UV light, showed no product. The solvent was removed under vacuum affording the title compound as an off-white solid (0.045 g, 100%). $^1$H NMR (400 MHz, CDCl$_3$) δ 7.41 (d, J=8.8 Hz, 2H), 7.24 (d, J=8.0 Hz, 1H), 7.05 (td, J=2.0, 2.4, 2.4 Hz, 1H), 7.01-6.95 (m, 2H), 6.50 (d, J=8.8 Hz, 2H), 6.35 (br s, 1H), 4.05 (br s, 2H), 1.95 (s, 3H).

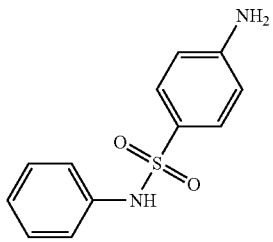 [SMILES: Nc1ccc(S(=O)(=O)Nc2ccccc2)cc1]

4-Amino-N-phenyl-benzenesulfonamide (12b) (RK1-1-27AII)I This compound was prepared according to the procedure described for compound 12a except using 11b to obtain required product as pale yellow solid (109 mg, 70%). Mp=180-182° C. (lit 260.5-261.5° C. (*Bioorganic and Medicinal Chemistry* 15(2), 1014-1021; 2007)); $^1$H NMR (400 MHz, CDCl$_3$) δ 7.52 (d, J=8.8 Hz, 2H), 7.24-7.21 (m, 2H), 7.12-7.08 (m, 1H), 7.06-7.03 (m, 2H), 6.58 (d, J=8.8 Hz, 2H), 6.32 (br s, 1H), 4.08 (br s, 2H).

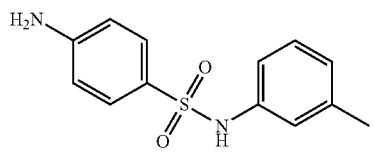 [SMILES: Cc1cccc(NS(=O)(=O)c2ccc(N)cc2)c1]

4-Amino-N-m-tolyl-benzenesulfonamide (12c) (RK1-1-27B II)I This compound was prepared according to the procedure described for compound 12a except using 11c to obtain the required product as a light yellow solid (160 mg, 74%). Mp=117-120° C. (lit. 132.5-133° C. (*Bioorganic and Medicinal Chemistry* 15(2), 1014-1021; 2007); $^1$H NMR (400 MHz, CDCl$_3$) δ 7.47 (d, J=8.6 Hz, 2H), 7.03 (t, J=7.8 Hz, 1H), 6.84-6.81 (m, 2H), 6.76 (br d, J=8.0 Hz, 1H), 6.52 (d, J=8.6 Hz, 2H), 6.26 (br s, 1H), 4.01 (br s, 2H), 2.203 (s, 3H).

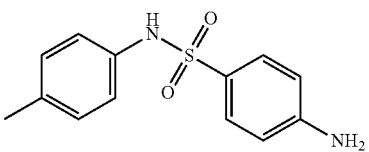 [SMILES: Cc1ccc(NS(=O)(=O)c2ccc(N)cc2)cc1]

4-Amino-N-p-tolyl-benzenesulfonamide (12d). (RK1-1-30)I This compound was prepared according to the procedure for compound 12a except using 11d to obtain the required product as an off-white solid (225 mg, 99%). Mp=174-176° C. (lit 190-190.5° C., *Bioorganic and Medicinal Chemistry* 15(2), 1014-1021; 2007); $^1$H NMR (400 MHz, CDCl$_3$) δ 7.43 (d, J=8.8 Hz, 2H), 6.96 (d, J=8.4 Hz, 2H), 6.86 (d, J=8.4 Hz, 2H), 6.52 (d, J=8.8 Hz, 2H), 6.14 (br s, 1H), 4.00 (br s, 2H), 2.20 (s, 3H).

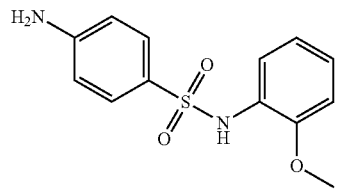

4-Amino-N-(2-methoxy-phenyl)-benzenesulfonamide (12e). (RK1-1-27C II) I This compound was prepared according to the procedure described for compound 12a except using 11e to obtain required the product as a white solid (85 mg, 57%). Mp not determined; $^1$H NMR (400 MHz, CDCl$_3$) δ 7.47 (d, J=8.6 Hz, 2H), 7.42 (dd, J=7.8, 1.1 Hz, 1H), 7.19 (br s, 1H), 6.96-6.89 (m, 2H), 6.81 (td, J=7.8, 1.1 Hz, 1H), 6.67 (dd, J=8.2, 1.1 Hz, 1H), 6.49 (d, J=8.6 Hz, 2H), 3.60 (s, 3H).

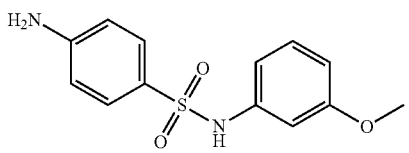

4-Amino-N-(3-methoxy-phenyl)-benzenesulfonamide (12l). (RK1-1-27D II) I This compound was prepared according to the procedure described for compound 12a except using 11f to obtain required product as a pale yellow solid (151 mg, 83%). Mp=142-145° C.; $^1$H NMR (400 MHz, CDCl$_3$) δ 7.49 (d, J=8.8 Hz, 2H), 7.05 (t, J=8.0 Hz, 1H), 6.61-6.50 (m, 5H), 6.32 (br s, 1H), 3.679 (s, 3H).

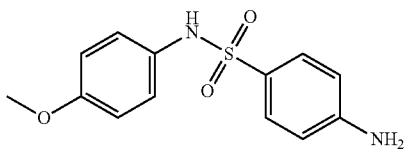 [SMILES: COc1ccc(NS(=O)(=O)c2ccc(N)cc2)cc1]

4-Amino-N-(4-methoxy-phenyl)-benzenesulfonamide (12g). (RK1-1-27E II) I This compound was prepared according to the procedure described for compound 12a except using 11g to obtain the required product as a light yellow solid, (197 mg, 79%). Mp: not determined; ¹H NMR. (400 MHz, CDCl₃) δ 7.45 (d, J=9.0 Hz, 2H), 6.96 (d, J=8.8 Hz, 2H), 6.76 (d, J=9.0 Hz, 2H), 6.58 (d, J=8.8 Hz, 2H), 6.09 (br s, 1H), 4.07 (br s, 2H), 3.76 (s, 3H).

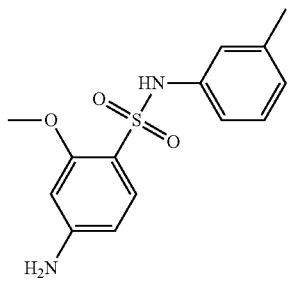

4-amino-2-methoxy-N-m-tolyl-benzenesulfonamide (12h). (RK1-1-39) I This compound was prepared according to the procedure described for compound 12a except using 11h to obtain the required product as an orange-brown solid in (169 mg, 66%). Mp: not determined; ¹H NMR (400 MHz, CDCl₃) δ 7.50 (d, J=8.4 Hz, 1H), 6.99 (t, J=7.8 Hz, 1H), 6.82 (br s, 1H), 6.79-6.73 (m, 2H), 6.65 (br s, 1H), 6.11 (d, J=2.0 Hz, 1H), 6.09 (s, 1H), 3.99 (br s, 2H), 3.86 (s, 3H), 2.18 (s, 3H).

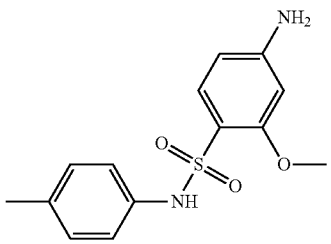

4-amino-2-methoxy-N-p-tolyl-benzenesulfonamide (12i). (RK1-1-42) I This compound was prepared according to the procedure described for compound 12a except using 11i to obtain the required product as a light yellow solid (130 mg, 93%). Mp=158-160° C.; ¹H NMR (400 MHz, CDCl₃) δ 7.52 (d, J=8.8 Hz, 1H), 6.98 (d, J=8.2 Hz, 2H), 6.93 (d, J=8.2 Hz, 2H) 6.70 (br s, 1H), 6.16 (s, 1H), 6.14 (app d, J=2.0 Hz, 1H), 4.05 (br s, 2H), 3.95 (s, 3H), 2.23 (s, 3H).

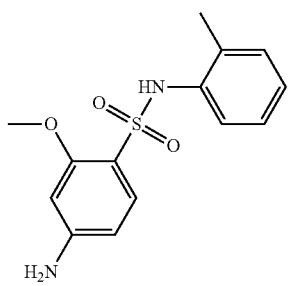 [SMILES: COc1cc(N)ccc1S(=O)(=O)Nc1ccccc1C]

4-amino-2-methoxy-N-o-tolyl-benzenesulfonamide (12j). (RK2-065-01) I This compound was prepared according to the procedure described for compound 12a except using 11j to obtain the required product as a yellow solid (63 mg, 93%). Mp=189-191° C.; ¹H NMR (400 MHz, CD₃OD) δ 7.30 (d, J=8.8 Hz, 1H), 7.10-7.06 (m, 2H), 7.01-6.97 (m, 2H), 6.31 (d, J=1.6 Hz, 1H), 6.12 (dd, J=8.8, 2.0 Hz, 1H), 3.30 (s, 3H), 2.22 (s, 3H).

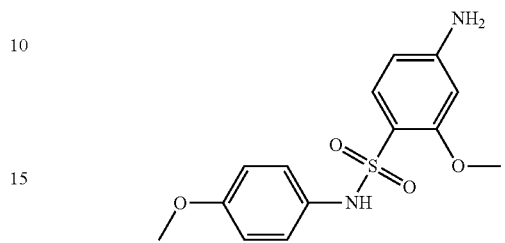

4-amino-2-methoxy-N-(4-methoxy-phenyl)-benzenesulfonamide (12k). (RK1-1-45) I This compound was prepared according to the procedure described for compound 12a except using 11k to obtain the required product as a yellow solid (141 mg, 77%). Mp=51-54° C.; ¹H NMR (400 MHz, CDCl₃) δ 7.44 (d, J=8.4 Hz, 1H), 6.97 (d, J=8.8 Hz, 2H), 6.72 (d, J=8.8 Hz, 2H), 6.61 (br s, 1H), 6.19 (d, J=2.0 Hz, 1H), 6.14 (dd, J=8.6, 2.2 Hz, 1H), 4.06 (br s, 2H), 3.98 (s, 3H), 3.72 (s, 3H).

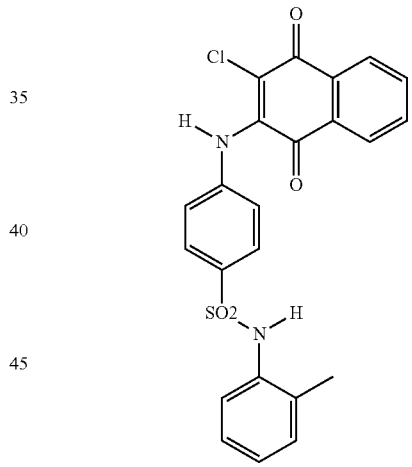

RK1-1-25

4-(3-chloro-1,4-dioxo-1,4-dihydro-naphthalen-2-ylamino)-N-o-tolyl-benzenesulfonamide (13a) (RK1-1-25). A well-stirred suspension of 4-Amino-N-o-tolyl-benzenesulfonamide 12a (47 mg, 179 mmol) and 2,3-dichloro-1,4-naphthoquinone (41 mg, 179 mmol) in 10.0 mL of 95% EtOH/ 5% water solution mixture was refluxed at 115° C. for three days. The orange precipitate obtained was filtered and washed with hot ethanol (5×5 mL), dried under reduced pressure to afford the title compound (23 mg, 28%). Mp=265-266° C.; ¹H NMR (400 MHz, DMSO-d₆) δ 9.55 (br s, 1H), 9.45 (br s, 1H), 8.04 (d, J=7.2 Hz, 2H), 7.89-7.80 (m, 2H), 7.49 (d, J=8.4 Hz, 2H), 7.17-7.07 (m, 5H), 6.98-6.96 (m, 1H), 1.97 (s, 3H); ESI-LRMS m/z 453.0 (M+³⁵Cl+H)⁺, 455.0 (M+³⁷Cl+H)⁺; ESI-HRMS m/z calculated for C₂₃H₈ClN₂O₄S (M+H)⁺ 453.0670, found 453.0665.

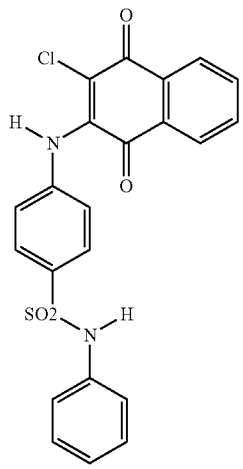

RK1-1-27A III 4-(3-chloro-1,4-dioxo-1,4-dihydro-naphthalen-2-ylamino)-N-phenyl-benzenesulfonamide (13b) (RK1-1-27A III). This compound was prepared according to the procedure described for compound 13a except using 12b to obtain required product as an orange-red solid (79 mg, 41%). Mp=220-223° C.; $^1$H NMR (400 MHz, DMSO-$d_6$) δ 10.14 (br s, 1H), 9.50 (br s, 1H), 8.03-8.01 (m, 2H), 7.88-7.79 (m, 2H), 7.61 (d, J=8.8 Hz, 2H), 7.20 (t, J=7.8 Hz, 2H), 7.14 (d, J=8.8 Hz, 2H), 7.06 (d, J=8.0 Hz, 2H), 7.00 (t, J=7.4 Hz, 1H); ESI-LRMS m/z 438.9 (M+$^{35}$Cl+H)$^+$, 441.0 (M+$^{37}$Cl+H)$^+$; ESI-HRMS m/z calculated for $C_{22}H_6ClN_2O_4S$ (M+H)$^+$ 439.0514, found 439.0508.

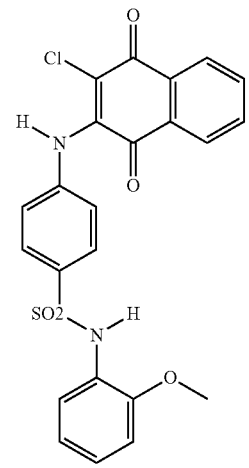

RK1-1-27C III 4-(3-chloro-1,4-dioxo-1,4-dihydro-naphthalen-2-ylamino)-N-(2-methoxy-phenyl)-benzenesulfonamide (13d). (RK1-1-27C III) This compound was prepared according to the procedure described for compound 13a except using 12d to obtain the required product as an orange solid (41 mg, 28%). Mp=198-201° C.; $^1$H NMR (400 MHz, DMSO-$d_6$) δ 9.51 (br s, 1H), 9.34 (br s, 1H), 8.04-8.02 (m, 2H), 7.92-7.79 (m, 2H), 7.55 (d, J=8.8 Hz, 2H), 7.20 (d, J=7.6 Hz, 1H), 7.14-7.08 (m, 3H), 6.90-6.83 (m, 2H), 3.52 (s, 3H). ESI-LRMS m/z 469.0 (M+$^{35}$Cl+H)$^+$, 471.0 (M+$^{37}$Cl+H)$^+$; ESI-HRMS m/z calculated for $C_{23}H_{18}ClN_2O_5S$ (M+H)$^+$ 469.0620, found 469.0609.

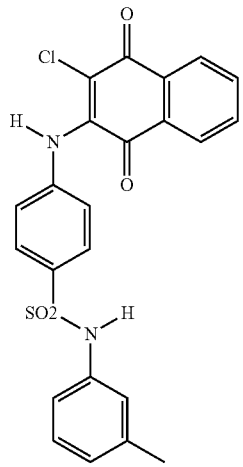

RK1-1-27B III 4-(3-chloro-1,4-dioxo-1,4-dihydro-naphthalen-2-ylamino)-N-m-tolyl-benzenesulfonamide (13c). (RK1-1-27B III). This compound was prepared according to the procedure described for compound 13a except using 12c to obtain required product as an orange-red solid (139 mg, 56%). Mp=234-237° C.; $^1$H NMR (400 MHz, DMSO-$d_6$) δ 10.07 (br s, 1H), 9.50 (br s, 1H), 8.04-8.01 (m, 2H), 7.88-7.79 (m, 2H), 7.61 (d, J=8.6 Hz, 2H), 7.15 (d, J=8.6 Hz, 2H), 7.10 (t, J=7.4 Hz, 1H), 6.88-6.81 (m, 3H), 2.17 (s, 3H); ESI-LRMS m/z for 453.0 (M+$^{35}$Cl+H)$^+$, 455.0 (M+$^{37}$Cl+H)$^+$; ESI-HRMS m/z calculated for $C_{23}H_{18}ClN_2O_4S$ (M+H)$^+$ 453.0670, found 453.0662.

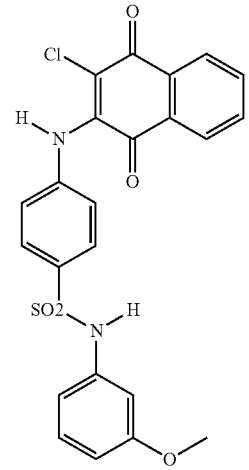

RK1-1-27D III 4-(3-chloro-1,4-dioxo-1,4-dihydro-naphthalen-2-ylamino)-N-(3-methoxy-phenyl)-benzenesulfonamide (13e). (RK1-1-27D III) This compound was prepared according to the procedure described for compound 13a except using 12e to obtain the required product as an orange solid, (135 mg, 53%). Mp=213-216° C.; $^1$H NMR (400 MHz, DMSO-$d_6$) δ 10.16 (br s, 1H), 9.51 (br s, 1H), 8.04-8.01 (m, 2H), 7.91-7.78 (m, 2H), 7.63 (d, J=8.6 Hz, 2H), 7.15 (d, J=8.6 Hz, 2H), 7.11 (t, J=8.0 Hz, 1H), 6.66-6.63 (m, 2H), 6.59-6.56 (m, 1H), 3.64 (s, 3H). ESI-LRMS m/z 469.0 (M+$^{35}$Cl+H)$^+$, 471.0 (M $^{37}$Cl+H)$^+$; ESI-HRMS m/z calculated for $C_{23}H_{18}ClN_2O_5S$ (M+H)$^+$ 469.0620, found 469.0611.

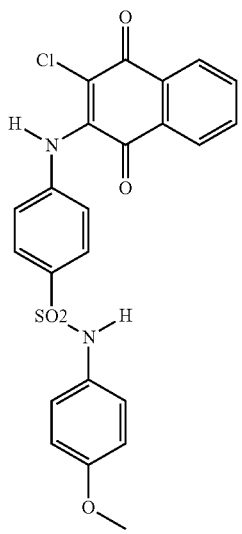

RK1-1-27E III 4-(3-chloro-1,4-dioxo-1,4-dihydro-naphthalen-2-ylamino)-N-(4-methoxy-phenyl)-benzenesulfonamide (13f). (RK1-1-27E III) This compound was prepared according to the procedure described for compound 13a except using 12f to obtain the required product as a yellow-orange (295 mg, 78%). Mp=233-234° C.; $^1$H NMR (400 MHz, DMSO-$d_6$) δ 9.76 (br s, 1H), 9.50 (br s, 1H), 8.03 (d, J=7.6 Hz, 2H), 7.88-7.79 (m, 2H), 7.53 (d, J=8.4 Hz, 2H), 7.13 (d, J=8.8 Hz, 2H), 6.94 (d, J=8.8 Hz, 2H), 6.78 (d, J=9.2 Hz, 2H), 3.65 (s, 3H); ESI-LRMS m/z 469.0 (M $^{35}$Cl+H)$^+$, 471.0 (M $^{37}$Cl+H)$^+$; ESI-HRMS m/z calculated for $C_{23}H_{18}ClN_2O_5S$ (M+H)$^+$ 469.0620, found 469.0612.

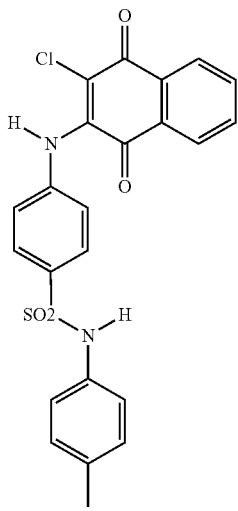

RK1-1-31

4-(3-chloro-1,4-dioxo-1,4-dihydro-naphthalen-2-ylamino)-N-p-tolyl-benzenesulfonamide (13g). (RK1-1-31) This compound was prepared according to the procedure described for compound 13a except using 12g to obtain the required product as a yellow-orange solid (245 mg, 63%). Mp=257-260° C.; $^1$H NMR (400 MHz, DMSO-$d_6$) δ 9.96 (br s, 1H), 9.49 (br s, 1H), 8.04-8.01 (m, 2H), 7.88-7.79 (m, 2H), 7.58 (d, J=8.8 Hz, 2H), 7.13 (d, J=8.8 Hz, 2H), 7.00 (d, J=8.4 Hz, 2H), 6.94 (d, J=8.4 Hz, 2H), 2.17 (s, 3H); ESI-LRMS m/z 453.0 (M+$^{35}$Cl+H)$^+$, 455.0 (M+$^{37}$Cl+H)$^+$; ESI-HRMS m/z calculated for $C_{23}H_{18}ClN_2O_4S$ (M+H)$^+$ 453.0670, found 453.0661.

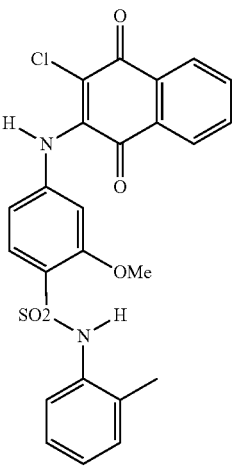

RK1-1-36

4-(3-chloro-1,4-dioxo-1,4-dihydro-naphthalen-2-ylamino)-2-methoxy-N-o-tolyl-benzenesulfonamide (13h). (RK1-1-36) This compound was prepared according to the procedure described for compound 13a except using 12h to obtain the required product as an orange-red solid, (55 mg, 35%). Mp=197-200° C.; $^1$H NMR (400 MHz, DMSO-$d_6$) δ 9.46 (br s, 1H), 9.15 (br s, 1H), 8.04 (dd, J=7.6, 1.2 Hz, 2H), 7.91-7.80 (m, 2H), 7.43 (d, J=8.4 Hz, 1H), 7.12-7.09 (m, 1H), 7.04-6.97 (m, 3H), 6.89 (d, J=1.6 Hz, 1H), 6.65 (dd, J=8.4, 1.6, Hz, 1H), 3.78 (s, 3H), 2.14 (s, 3H); ESI-LRMS m/z 483.1 (M $^{35}$Cl+H)$^+$, 485.0 (M $^{37}$Cl+H)$^+$; ESI-HRMS m/z calculated for (M+H)$^+$ $C_{24}H_{20}ClN_2O_5S$ 483.0776, found 483.0771.

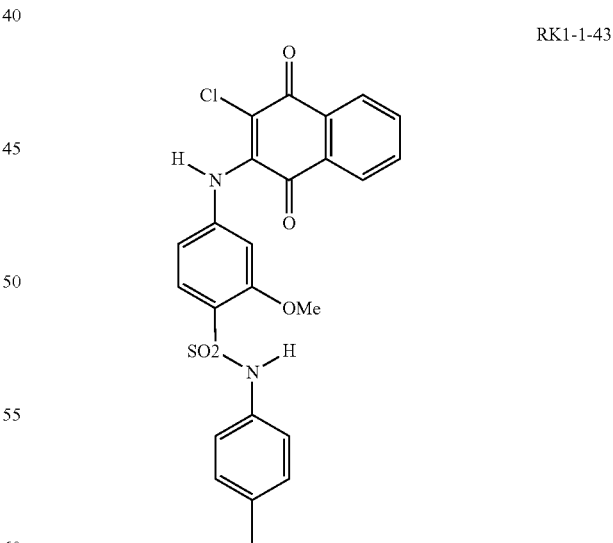

RK1-1-43

4-(3-chloro-1,4-dioxo-1,4-dihydro-naphthalen-2-ylamino)-2-methoxy-N-p-tolyl-benzenesulfonamide (13i). (RK1-1-43) This compound was prepared according to the procedure described for compound 13a except using 12i to obtain the required product as a red solid (80 mg, 38%). Mp=186-189° C.; NMR (400 MHz, DMSO-$d_6$) δ 9.69 (br s, 1H), 9.40 (br s, 1H), 8.04-8.01 (m, 2H), 7.91-7.79 (m, 2H), 7.55 (d, J=8.4 Hz, 1H), 6.92-6.97 (m, 4H), 6.80 (d, J=1.6 Hz, 1H), 6.65 (dd, J=8.6, 1.8 Hz, 1H), 3.79 (s, 3H), 2.14 (s, 3H); ESI-LRMS m/z 483.0 (M $^{35}$Cl+H)$^+$, 485.0 (M $^{37}$Cl+H)$^+$; ESI-HRMS m/z calculated for $C_{24}H_{20}ClN_2O_6S$ (M+H)$^+$ 483.0776, found 483.0769.

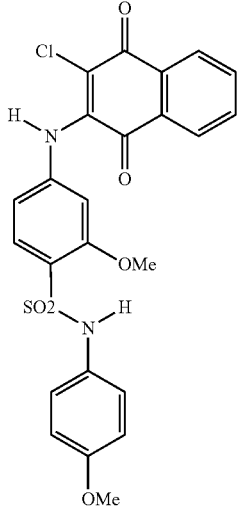

RK1-1-46

4-(3-chloro-1,4-dioxo-1,4-dihydro-naphthalen-2-ylamino)-2-methoxy-N-(4-methoxy-phenyl)-benzene-sulfonamide (13j). (RK1-1-46) This compound was prepared according to the procedure described for compound 13a except using 12j to obtain the required product as a red solid (118 mg, 54%). Mp=165-167° C.; $^1$H NMR (400 MHz, DMSO-d$_6$) δ 9.50 (br s, 1H), 9.40 (br s, 1H), 8.04-8.01 (m, 2H), 7.91-7.79 (m, 2H), 7.48 (d, J=8.8 Hz, 1H), 6.96 (d, J=8.8 Hz, 2H), 6.82 (br s, 1H), 6.74 (d, J=8.8 Hz, 2H), 6.64 (dd, J=8.6, 1.4 Hz, 1H), 3.82 (s, 3H), 3.63 (s, 3H); ESI-LRMS m/z 499.1 (M+$^{35}$Cl+H)$^+$, 501.0 (M+$^{37}$Cl+H)$^+$; ESI-HRMS m/z calculated for $C_{24}H_{20}ClN_2O_6S$ (M+H)$^+$ 499.0725, found 499.0717.

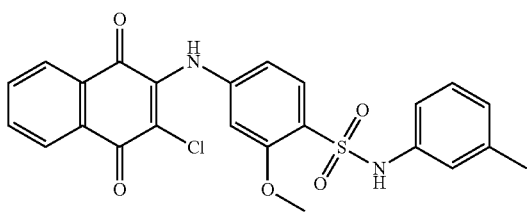

RK1-1-55

4-(3-chloro-1,4-dioxo-1,4-dihydro-naphthalen-2-ylamino)-2-methoxy-N-m-tolyl-benzenesulfonamide (13k). (RK1-1-55) This compound was prepared according to the procedure described for compound 13a except using 12k to obtain the required product as an orange solid, (91 mg 64%). Mp=264-267° C.; $^1$H NMR (400 MHz, DMSO-d$_6$) δ 9.81 (br s, 1H), 9.41 (br s, 1H), 8.04-8.01 (m, 2H), 7.88-7.79 (m, 2H), 7.60 (d, J=8.4 Hz, 1H), 7.03 (t, J=8.2 Hz, 1H), 6.84-6.86 (m, 2H), 6.81 (d, J=2.0 Hz, 1H), 6.76 (d, J=7.6 Hz, 1H), 6.67 (dd, J=8.6, 1.8 Hz, 1H), 3.78 (s, 3H), 2.15 (s, 3H); ESI-LRMS m/z 483.0 (M $^{35}$Cl+H)$^+$, 485.0 (M $^{37}$Cl+H)$^+$; ESI-HRMS m/z calculated for $C_{24}H_{20}ClN_2O_5S$ (M+H)$^+$ 483.0803, found 483.0809.

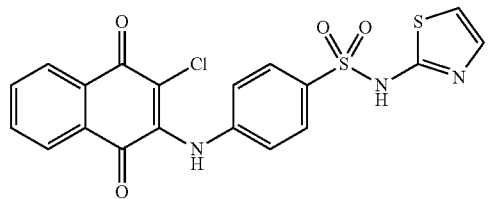 [SMILES: O=C1C(Cl)=C(Nc2ccc(S(=O)(=O)Nc3nccs3)cc2)C(=O)c2ccccc21]

4-(3-chloro-1,4-dioxo-1,4-dihydronaphthalen-2-ylamino)-N-(thiazol-2-yl)benzene-sulfonamide (YG1-075) was prepared according to the procedure for compound 23 (RK1-1-25) except using sulfathiazole (from Aldrich) which afforded the title compound as an orange-red solid (145 mg, 65%). Mp=286-288° C.

$^1$H-NMR (400 MHz, DMSO-d$_6$) δ 12.70 (br, 1H), 9.50 (s, 1H), 8.04 (t, J=1.6 Hz, 1H), 8.02 (t, J=1.6 Hz, 1H), 7.86 (td, J=7.4, 1.5 Hz, 1H), 7.81 (td, J=7.4, 1.5 Hz, 1H), 7.67 (d, J=8.7 Hz, 2H), 7.24 (d, J=4.6 Hz, 1H), 7.17 (d, J=8.7 Hz, 2H), 6.76 (d, J=4.6 Hz, 1H); ESI-HRMS m/z calculated for $C_{19}H_{12}ClN_3O_4S_2$ (M+H)$^+$ 446.0030, found 446.0045.

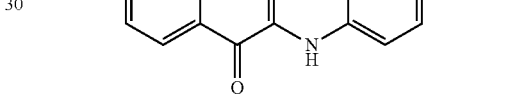

4-(3-chloro-1,4-dioxo-1,4-dihydronaphthalen-2-ylamino) benzenesulfonamide (YG1-080) was prepared according to the procedure for compound 23 (RK1-1-25) except using sulfanilamide (from Aldrich) which afforded the title compound as a wine-red solid, (24 mg, 38.9%). Mp >300° C.; $^1$H-NMR (400 MHz, DMSO-d$_6$) δ 9.52 (br, 1H), 8.04 (d, 7.4 Hz, 1H), 7.87 (t, J=7.5 Hz, 1H), 7.82 (t, J=7.5 Hz, 1H), 7.70 (d, J=8.5 Hz, 2H), 7.28 (br, 2H), 7.21 (d, J=8.5 Hz, 2H); ESI-HRMS m/z calculated for $C_{16}H_{11}ClN_2O_4S$ (M+H)$^+$ 363.0201, found 363.0204.

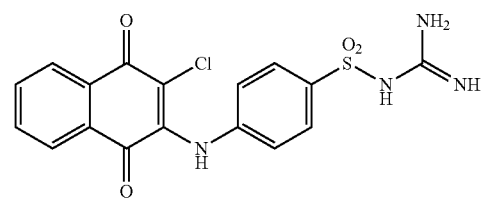 [SMILES: N=C(N)NS(=O)(=O)c1ccc(NC2=C(Cl)C(=O)c3ccccc3C2=O)cc1]

N-carbamimidoyl-4-(3-chloro-1,4-dioxo-1,4-dihydronaphthalen-2-ylamino)benzene-sulfonamide (YG1-084) was prepared according to the procedure for compound 23 (RK1-1-25) except using compound YG1-083 which afforded the title compound as an orange-red solid (35 mg, 54.2%). Mp=294-295° C.; $^1$H-NMR (400 MHz, DMSO-d$_6$) δ 9.46 (s, 1H), 8.03 (d, J=7.5 Hz, 2H), 7.86 (t, J=7.4 Hz, 1H), 7.81 (t, J=7.4 Hz, 1H), 7.63 (d, J=8.5 Hz, 2H), 7.15 (d, J=8.5 Hz, 2H), 6.69 (br, 4H); ESI-HRMS m/z calculated for $C_{17}H_{13}ClN_4O_4S$ (M+H)$^+$ 405.0419, found 405.0422.

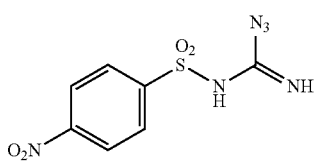

4-nitro-N-(1-azidoformimidoyl)benzenesulfonamide (YG1-074) was prepared according to the procedure for compound 1 except using 2-aminotetrazole, which afforded the title compound as a yellow solid (682 mg, 50.5%). $^1$H NMR (400 MHz, DMSO-$d_6$) δ 9.06 (br, 1H), 8.37 (d, J=8.8 Hz, 2H), 8.13 (d, J=8.8 Hz, 2H), 7.98 (br, 1H). ESI-HRMS m/z calculated for $C_7H_6N_6O_4S$ (M−H)$^+$ 269.0099, found 269.0094.

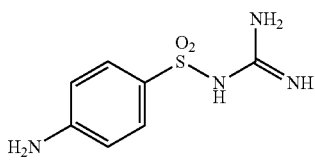 [SMILES: [N-]=[N+]=NC(=N)NS(=O)(=O)c1ccc([N+](=O)[O-])cc1]

4-amino-N-carbamimidoylbenzenesulfonamide (YG1-083) was prepared according to the procedure for compound 12 except using YG1-074 which afforded the title compound as a grey solid (80 mg, 13.2%). M.P=169-171° C.; $^1$H NMR (400 MHz, DMSO-$d_6$) δ 7.36 (d, J=8.3 Hz, 2H), 6.55 (br, 4H), 6.51 (d, J=8.3 Hz, 2H), 5.67 (br, 2H). HRMS (ESI+ve) m/z calculated for $C_7H_{10}N_4O_2S$ (M+H)$^+$ 215.0597, found 215.0595.

Example 9

Synthesis and Assay of Hydronaphthoquinone Derivatives as Proteasome Inhibitors

Figure 10:
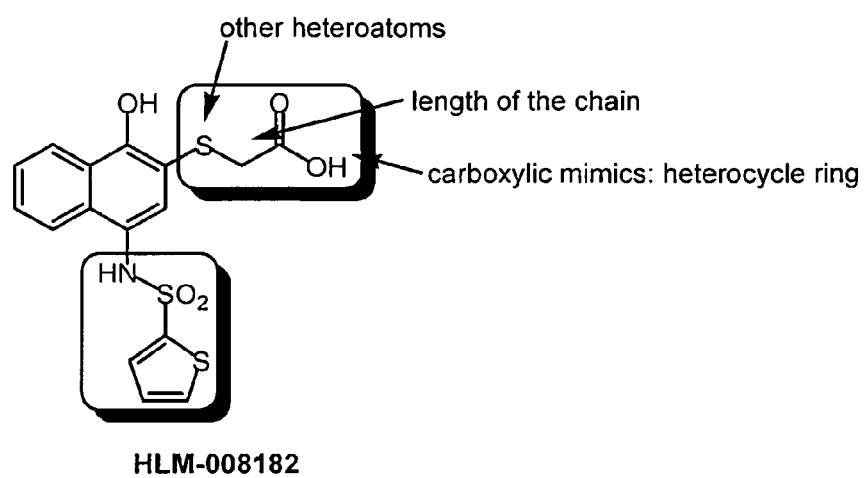
FIG. 10 shows a pharmacophore model of HLM-008182.

Synthesis of HLM-008182 (1) has not yet been reported in the chemical literature. Our current work highlights the synthesis of HLM008182 and modifications around the molecule to obtain a desirable drug-like molecule for proteasome inhibition studies. The hydronaphthoquinone pharmacophore in HLM-008182 (1) has high structural diversity that was exploited for focused library synthesis and HLM-008182 (1) represents an attractive small molecule for medicinal chemistry. The modification was primarily focused on the 2 and 4 positions (FIG. 10) in order to understand how different side chain or functional groups would affect proteasome inhibition potency.

Starting from 4-aminonaphth-1-ol hydrochloride salt 2, compound 4a was synthesized through a one pot oxidation-addition reaction of the intermediate 3 similarly to the reported procedure[27] except in the presence of hydrogen peroxide and 4M HCl dioxane solution. 4b and 4c were synthesized in the presence of bromine or iodine in DMF (Scheme 4) according to the reported method[28] except that the reaction gave the hydronaphthoquinone sulfonamide derivatives (See $^1$H NMR and HRMS of 4b and 4c in the experimental section). Compound 10a~e, 14a~t were synthesized from commercially available 1,4-naphthoquinone (5), 2-hydroxyl-1,4-naphthoquinone (6) or 2-chloro-1,4-naphthoquinone (11) respectively (Scheme 5, 6). As shown in Scheme 5, ethyl mercaptoacetate or methyl 3-mercaptopropionate was added to 2 eq. of the starting material 1,4-naphthoquinone (5) affording precursors 7a~b. The precursor 7c was obtained by nucleophilic substitution of 2-hydroxyl-1,4-naphthoquinone (6) with tertiary butyl bromoacetate using silver oxide as a base[29]. The various sulfonamides ($R^2SO_2NH_2$), ieither commercially available or synthesized according to literature method[30], were regioselectively coupled with the intermediate 7a~c in the presence of titanium (IV) chloride and triethylamine with microwave assisted heating to obtain the library 8. The key intermediates 8 were then reduced by sodium hydrosulfite[31] to hydronaphthoquinone sulfonamide derivatives 9, followed by hydrolysis in a mixture of concentrated HCl and dioxane (1:1) to give the final compounds 10a~d. The compound 10f was obtained by oxidation of compound 9a with oxone[32] followed by acidic hydrolysis. The compound 9e was a 'side product' from coupling 4-nitrobenzene sulfonamide to the intermediate 7a in the presence of titanium (IV) chloride and triethylamine using dichloromethylene as the solvent. The library 14 was synthesized, as shown in Scheme 6, via coupling various sulfonamides to 2-chloro-1,4-naphthoquinone (11) using the same procedure as for the intermediate 8, followed by substitution of 2-chlorine with the various nucleophiles with or without base.

Scheme 4,
reagents and conditions: i) thiophene-2-sulfonyl chloride, Et$_3$N, dichloromethylene; ii) H$_2$O$_2$, HCl, dioxane for 4a; Br$_2$ or I$_2$, TEA, DMF, 0° C. to r.t. for 4b, c.

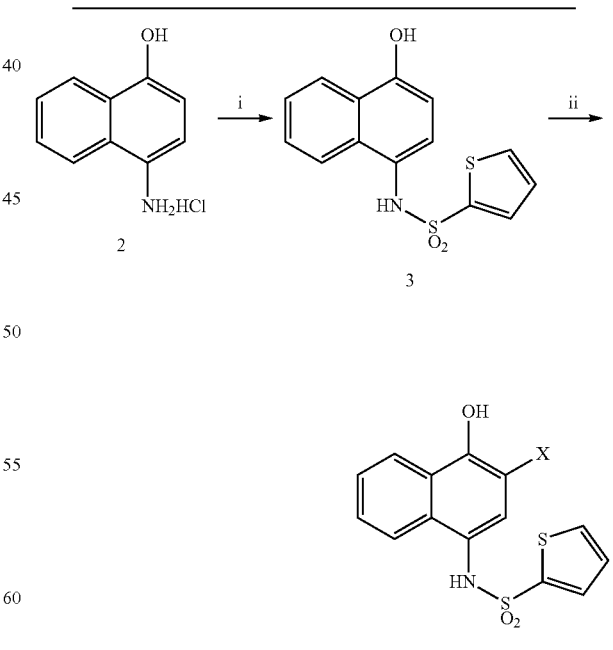

4a X = Cl
4b X = Br
4c X = I

Scheme 5,
reagents and conditions: i) HS(CH$_2$)$_n$COOR$^1$, ethanol, r.t.; ii) BrCH$_2$COOBu-t, Ag$_2$O, CHCl$_3$, cat. KI, reflux, overnight; iii) R$^2$SO$_2$NH$_2$, TiCl$_4$·2THF, Et$_3$N, DCM, or THF, microwave, 60° C.; iv) Na$_2$S$_2$O$_4$, THF or EtOAc, H$_2$O, r.t.; v) conc. HCl, dioxane, r.t or microwave, 100° C.; vi) oxone/H$_2$O/acetone, r.t., overnight.
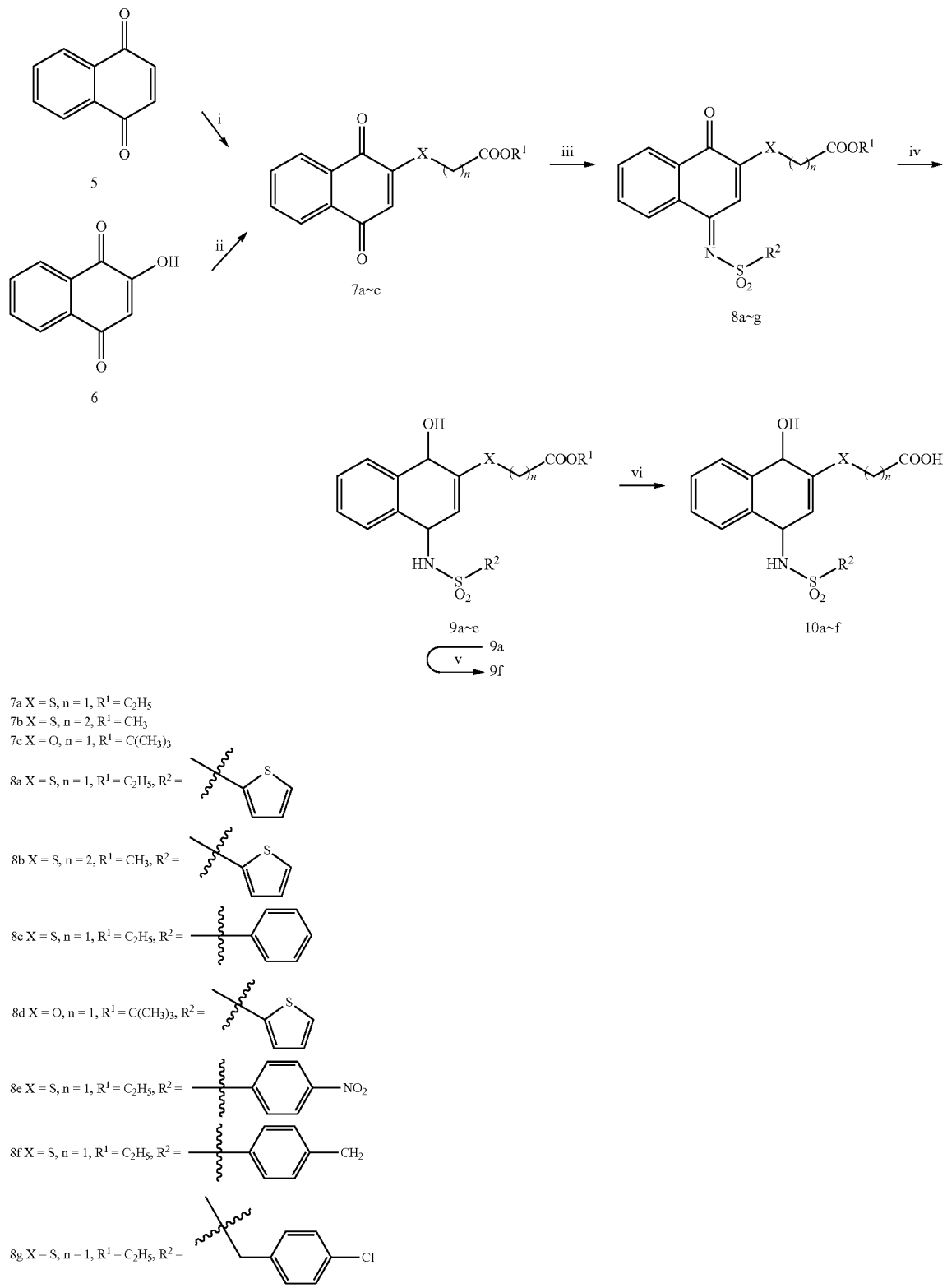

-continued
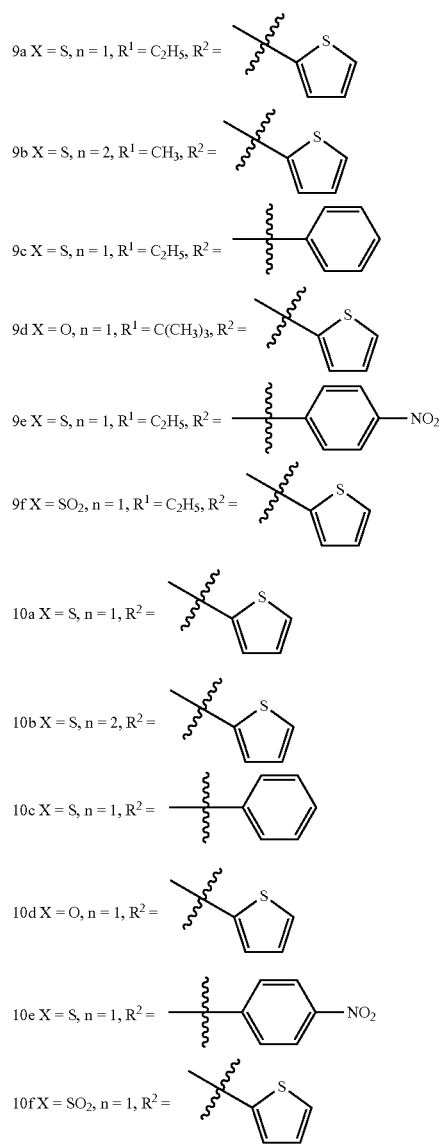
Scheme 6,
reagents and conditions: i) R¹SO₂NH₂, TiCl₄·2THF, Et₃N, THF, microwave, 60° C.; ii) NaOC₂H₅, C₂H₅OH for 13a; NR², THF for 13b~c, 13i; HSR², Py., THF for 13d~h, 13j~k; iii) Na₂S₂O₄, EtOAc and H₂O, shaking in separation funnel; iv) conc. HCl, dioxane, r.t.
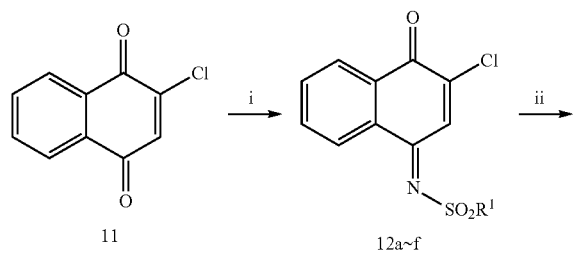
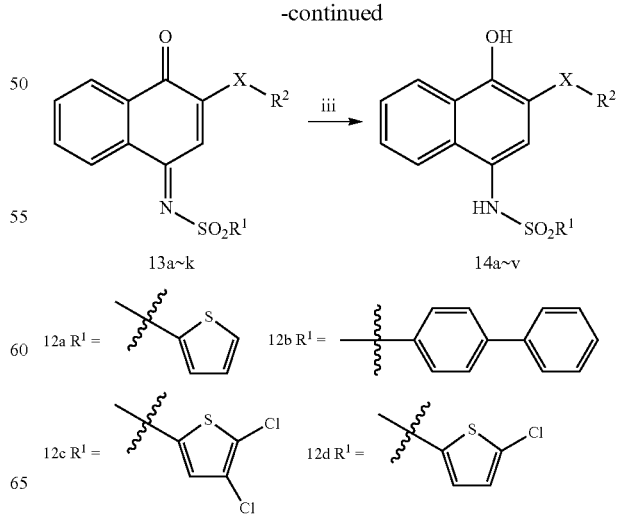

-continued

12e R¹ = 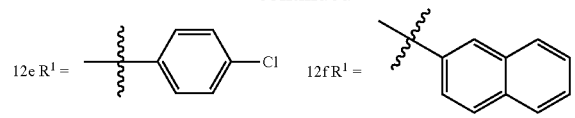 12f R¹ =

13a X = O, R¹ =  R² = C₂H₅

13b X = N, R¹ = R² = (CH₃)₂

13c X = N, R¹ = 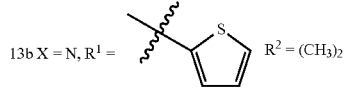 R² = (CH₂CH₂)₂O

13d X = S, R¹ = 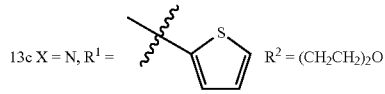 R² =

13e X = S, R¹ = 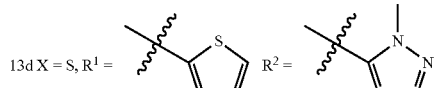 R² =

13f X = S, R¹ = 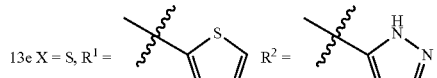 R² = (CH₂)₂CON(CH₃)₂

13g X = S, R¹ = 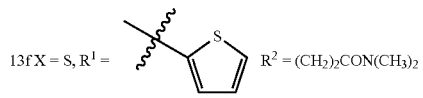 R² = (CH₂)₂CONHCH₃

13h X = S, R¹ = 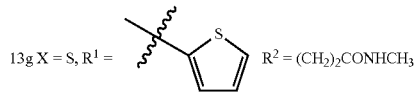 R² = (CH₂)₂CONHCH(CH₂)₂

13i X = NH, R¹ = 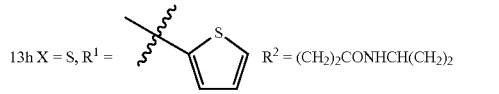 R² =

13j X = S, R¹ = 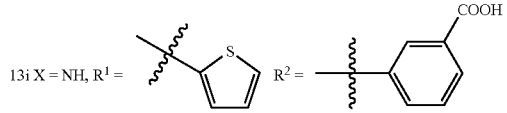 R² = C₂H₅

13k X = S, R¹ = 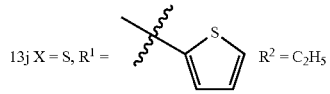 R² = C₂H₄OH

14a X = O, R¹ = 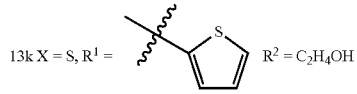 R² = C₂H₅

14b X = N, R¹ = 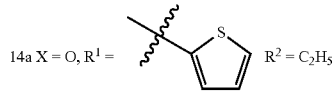 R² = (CH₃)₂

14c X = N, R¹ = 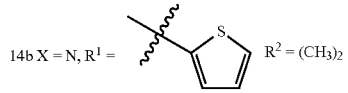 R² = (CH₂CH₂)₂O

14d X = S, R¹ = 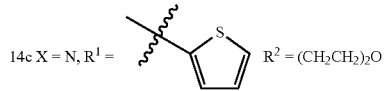 R² =

14e X = S, R¹ = 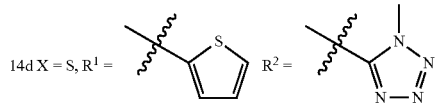 R² =

-continued

14f X = S, R¹ =  R² = (CH₂)₂CON(CH₃)₂

14g X = S, R¹ = 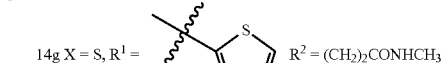 R² = (CH₂)₂CONHCH₃

14h X = S, R¹ = 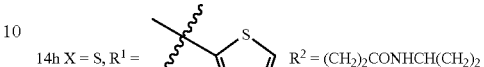 R² = (CH₂)₂CONHCH(CH₂)₂

14i X = NH, R¹ = 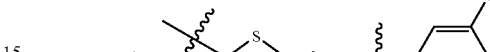 R² =

14j X = S, R¹ =  R² = C₂H₅

14k X = S, R¹ = 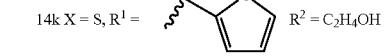 R² = C₂H₄OH

14l X = S, R¹ = 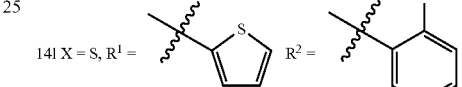 R² =

14m X = S, R¹ = 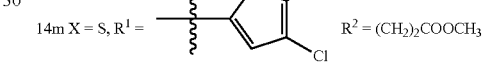 R² = (CH₂)₂COOCH₃

14n X = S, R¹ = 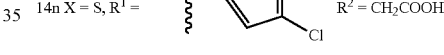 R² = CH₂COOH

14o X = S, R¹ = 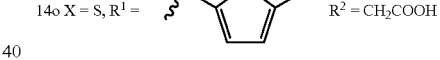 R² = CH₂COOH

14p X = S, R¹ = 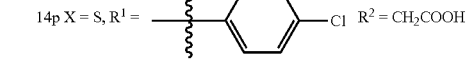 R² = CH₂COOH

14q X = S, R¹ = 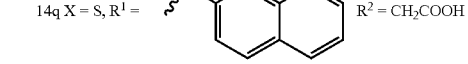 R² = CH₂COOH

14r X = S, R¹ = 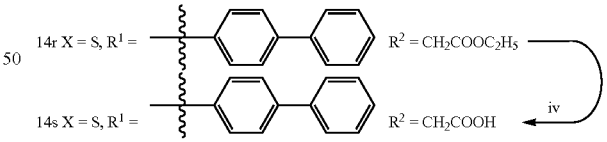 R² = CH₂COOC₂H₅

14s X = S, R¹ = 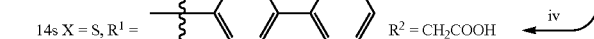 R² = CH₂COOH

14t X = S, R¹ = 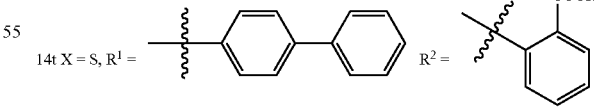 R² =

14u X = S, R¹ = 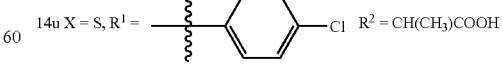 R² = CH(CH₃)COOH

14v X = S, R¹ = 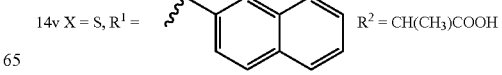 R² = CH(CH₃)COOH

3. Results and Discussion

3.1 Synthesis

3.1.1. Method Development and Optimization

The synthesis of the 'hit' compound HLM-008182 was not reported in the published literatures. Although there were reported protocols for naphthoquinone sulfonimide synthesis[27, 31, 33], these protocols failed to afford HLM-008182 in our lab. We successfully developed in our lab the synthesis of hydronaphthoquinone sulfonamide. Starting from commercially available 1,4-naphthoquinone (5), the hydronaphthoquinone sulfonamide scaffold was built up through addition-oxidation of the starting material 5 with thio-nucleophiles, coupling sulfonamides to the corresponding 1,4-naphthoquinone derivatives, reduction and hydrolysis. The synthesis method was further optimized to a two step protocol. Starting from commercially available 2-chloro-1,4-naphthoquinone (11), the scaffold was formed through coupling sulfonamides to the starting material 11, nucleophilic substitution followed by reduction.

In the protocol using 5 as the starting material (Scheme 5), the key step to afford the intermediates 8 gave several products according to TLC with dichloromethylene as the reaction solvent. In addition to the intermediates 8, the reduced products (see structure of 9) were isolated as well via flash chromatography and identified by $^1$H-NMR and HRMS-(+). In the reaction attempting 8e, only the reduced form 9e was obtained in a low yield. This type of 'side reaction' made the isolation of the intermediates 8 laborious and the library synthesis a time consuming job. The mechanism of the unexpected 'side reaction' remains unknown yet.

The scheme 6 represented an optimized procedure for synthesis of HLM-008182 and its analogues. The key intermediates 12 were purified by either re-crystallization or trituration from appropriate solvents, thus more convenient for library synthesis. The key step for the intermediates 12 was more efficient with microwave assisted heating than conventional heating (Table 8, entry 2 vs 3). The yield of the coupling reaction was significantly improved when dichloromethylene was replaced by THF (Table 8, entry 2 vs 4, entry 5 vs 6). For example, the yields for compound 12e and f (Table 8, entry 7 and 8) were improved to 61.8% and 77.9% respectively when THF was utilized. When aliphatic thiol was used in the subsequent nucleophilic substitution, the products 13, in situ, were partially reduced to the final compounds 14 in the presence of aliphatic thiol giving mixtures of 13 and 14 in a certain ratio. However, we managed to obtain the single component of the final hydronaphthoquinone sulfonamide 14 (Scheme 7) without separation of the mixtures by directly treating the mixtures with sodium hydrosulfite in biphasic solution of ethyl acetate and water. The in situ reduction was not observed with non-reductive nucleophiles such as alcohols (compound 13a) and amines (compound 13b, c, i). However, when we tried to reduce these compounds to hydronaphthoquinone sulfonamide derivatives, we could not get the final products as a single component due to the rapid oxidation of the reduced product when exposed to air. It is notable that compound 10a was oxidized to naphthoquinone sulfonimide derivative when we tried to dissolve it in $CDCl_3$ in a NMR tube by the aid of sonication. The mechanism was not clear although the oxidation could be caused by sonication which facilitated the oxidation in $CDCl_3$.

TABLE 8 optimization of coupling conditions for the key intermediate 12

| Entry | ID | R$^1$ | Conditions | Yield (%)$^a$ |
|---|---|---|---|---|
| 1 | 12a | 2-thienyl | TiCl$_4$$^b$/TEA/DCM M.W., 60°C.$^c$, 10 min | 42.9 |
| 2 | 12a | 2-thienyl | TiCl$_4$$^b$/TEA/DCM M.W., 60°C.$^c$, 15 min | 55.9 |
| 3 | 12a | 2-thienyl | TiCl$_4$$^b$/TEA/DCM conventional, 60°C., 18 hours | 43.1 |
| 4 | 12a | 2-thienyl | TiCl$_4$•2THF/TEA/THF M.W., 60°C.$^c$, 20 min | 77.3 |

TABLE 8-continued optimization of coupling conditions for the key intermediate 12

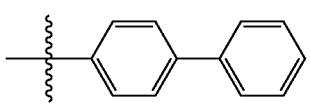 [SMILES: *c1ccc(-c2ccccc2)cc1]

| Entry | ID | R[1] | Conditions | Yield (%)[a] |
|---|---|---|---|---|
| 5 | 12b | 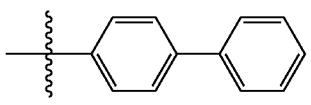 | TiCl$_4$[b]/TEA/DCM/ M.W., 60°C.[c], 15 min | 37.8 |
| 6 | 12b | 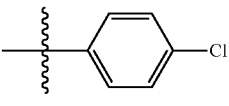 [SMILES: *c1ccc(Cl)cc1] | TiCl$_4$•2THF/TEA/THF M.W., 60°C.[c], 20 min | 72.0 |
| 7 | 12e | 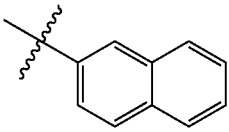 [SMILES: *c1ccc2ccccc2c1] | TiCl$_4$•2THF/TEA/THF M.W., 60°C.[c], 20 min | 61.8 |
| 8 | 12f | 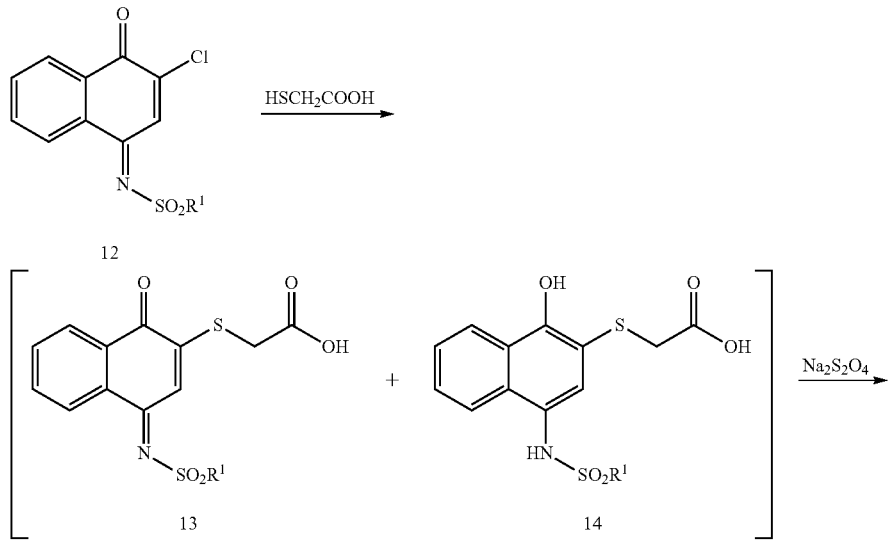 | TiCl$_4$•2THF/TEA/THF M.W., 60°C.[c], 20 min | 77.9 |

Note:
[a]isolated yield;
[b]1M in dichloromethylene solution;
[c]higher temperature gave a complicated mixture.

Scheme 7: in situ reduction of naphthoquinone sulfonimide derivatives 13 to the final hydronaphthoquinone sulfonamide derivatives 14

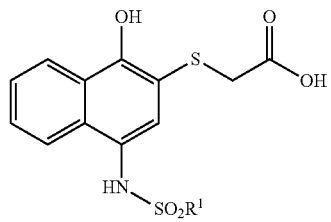

14

3.1.2 Proposed Mechanism for Regioselectivity in Coupling Sulfonamides to 1,4-Naphthoquinone Derivatives Coupling the various sulfonamides to 1,4-naphthoquinone derivatives 7 or 11 in the presence of titanium chloride and triethylamine was the key step to building up naphthoquinone sulfonimide scaffold in our work. TiCl$_4$-Et$_3$N system has been widely used in forming sulfonimides[34, 35] through activation of the reactive ketone by forming a TiCl$_4$-ketone complex. In 1,4-naphthoquinone derivatives 7 or 11, the participation of 2-sulfur, oxygen or chlorine atom facilitated TiCl$_4$ to form the complex with 4-ketone rather than 1-ketone (Scheme 8, 15). The complex was stabilized by the p-π conjugation system formed between the lone pair electrons on 2-sulfur, oxygen or chlorine and the naphthoquinone ring (Scheme 8, 15→16). Therefore in the presence of TiCl$_4$, the sulfonamides were regioselectively coupled to 1,4-naphthoquinone derivatives 7 or 11 at the 4 position. In contrast to TiCl$_4$ assist, the regioselectivity, as reported[36], was reversed to 1-ketone when a coupling occurred under a basic condition because the nucleophilicity of 4-ketone was dramatically decreased by the participation of the 2-oxygen. The coupling procedure was not successful when there was a methyl group at the 3 position due to the steric hindrance effect.

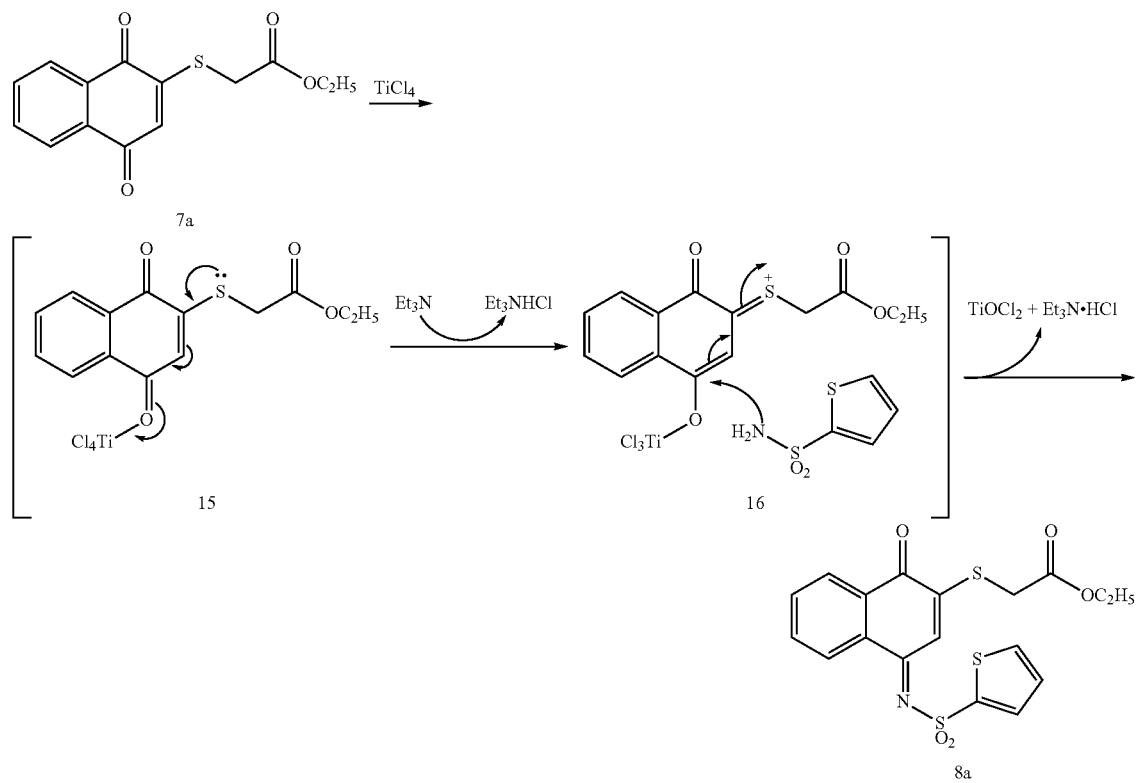

Scheme 8: proposed mechanism for regioselective coupling of sulfonamide to 1,4-naphthoquinone derivative using compound 7a as an example.

The regioselectivity was confirmed by 1H-NMR in that the chemical shift of 3-H significantly shifted down field from 6.70 ppm in 7a to 7.94 ppm in 8a and from 7.24 ppm in 11 to 8.62 ppm in 12a (FIG. 12) due to the effect of the sulfonimide group adjacent to 3-H.

3.2 Proteasome Inhibition Assay

Six distinct catalytic active sites were thought to be responsible for the hydrolysis of polypeptide substrate by proteasome[37], among which chymotrypsin-like (CT-L), tropsin-like (T-L) and polyglutamine peptide hydrolysis (PGPH) activity were most firmly established and characterized[38].

These proteolysis activities are substrate specific. For example, Suc-Leu-Leu-Val-Tyr-AMC has been used for chymotrypsin-like activity substrate, Bz-Val-Gly-Arg-AMC for trypsin-like substrate and benzyloxycarbonyl Z-Leu-Leu-Glu-AMC for PGPH activity substrate. In our work, we used chymotrypsin-like substrate Suc-Leu-Leu-Val-Tyr-AMC to test the proteasome inhibition activity of the synthesized compounds.

3.3 Structure and Activity Relationship by Modifications on 2-Substitution and 4-Sulfonamide Moiety Compound 10a is an in-house synthesis compound of HLM-008182. It exhibits comparable proteasome inhibition activity to the commercial sample HLM-008182 (Table 9, entry 1 and 6). This further confirmed HLM-008182 as a proteasome inhibitor. The interactions between HLM-008182 and chymotrysin-like catalytic site of 20S proteasome was predicted using molecular modeling and suggested that 2-side chain is H-bonding to the residue of Thr-1 through carboxylic acid acceptor (FIG. 13). Replacement of the side chain at the 2 position by small groups, such as hydrogen (compound 3) and halides (compound 4a~c), caused loss of the inhibitory activity. The essentialness of the carboxylic acid moiety to the inhibitory activity was further confirmed by modification of the carboxylic group at the side chain. When the carboxylic acid moiety was replaced by the simple alkyl group (compound 14j) or the hydroxyl group (compound 14k), the inhibitory activity totally lost. The thio-ether side chain at the 2 position was essential to retain the inhibitory activity. For example, replacement of thio-ether side chain by ether or sulfone moiety diminished the inhibitory activity (compound 10d and 10f). Molecular modeling analysis indicated that 1-hydroxyl in the molecule of HLM-008182 played the role as a hydrogen bond donor to Gly47 in the 20S proteasome (FIG. 13). The inhibitory activity could be reduced or lost by formation of an intramolecular hydrogen bond between 1-hydroxyl and other groups in the inhibitor molecules. In compound 10d and 10f, ether and sulfone moiety at the 2 position could play roles as hydrogen bond acceptors from 1-hydroxyl, thus made the loss or reduction of the inhibitory activity.

TABLE 9

Modifications on 2-substitution and 4-sulfonamide

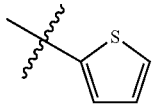 [SMILES: *c1cccs1]

| Entry | Compound | R[1] | R[2] | $IC_{50}^{a}$ (μM) |
|---|---|---|---|---|
| 1 | HLM-008182[b] | CH$_2$COOH | 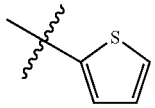 [SMILES: *c1cccs1] | 0.65 ± 0.40 |
| 2 | 9a | CH$_2$COOC$_2$H$_5$ | 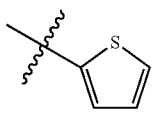 | 7.33 ± 2.82 |
| 3 | 9b | (CH$_2$)$_2$COOCH$_3$ | 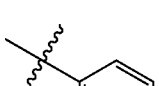 | 4.99 ± 2.08 |
| 4 | 9c | CH$_2$COOC$_2$H$_5$ | 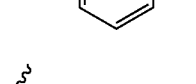 | 5.27 ± 2.23 |
| 5 | 9e | CH$_2$COOC$_2$H$_5$ | 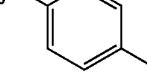 | 3.57 ± 1.53 |
| 6 | 10a[c] | CH$_2$COOH |  | 1.30 ± 0.76 |

TABLE 9-continued
Modifications on 2-substitution and 4-sulfonamide
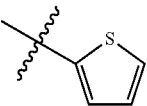
| Entry | Compound | R¹ | R² | IC$_{50}$$^a$ (μM) |
|---|---|---|---|---|
| 7 | 10b | (CH$_2$)$_2$COOH | 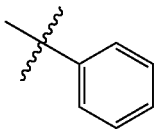 [SMILES: *c1ccccc1] | >10 |
| 8 | 10c | CH$_2$COOH | 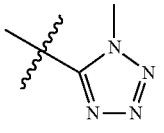 [SMILES: *c1nnnn1C] | 2.08 ± 0.78 |
| 9 | 14d | 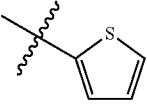 [SMILES: *c1cccs1] | 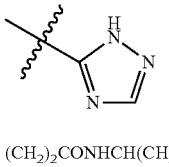 | 4.25 ± 2.13 |
| 10 | 14e | 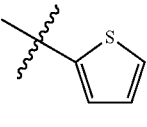 [SMILES: *c1cccs1] | 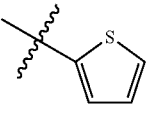 [SMILES: *c1cccs1] | 4.22 ± 2.73 |
| 11 | 14h | (CH$_2$)$_2$CONHCH(CH$_2$)$_2$ | 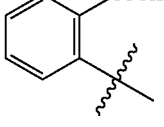 | 7.3 ± 1.30 |
| 12 | 14l | 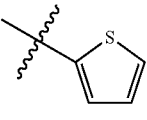 [SMILES: *c1cccs1] | 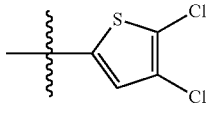 | 4.05 ± 2.64 |
| 13 | 14m | (CH$_2$)$_2$COOCH$_3$ | 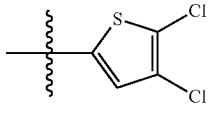 | 1.18 ± 0.30 |
| 14 | 14n | CH$_2$COOH | 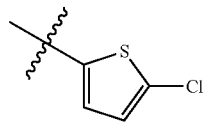 [SMILES: *c1ccc(Cl)s1] | 2.07 ± 0.55 |
| 15 | 14o | CH$_2$COOH |  | 2.07 ± 0.69 |

TABLE 9-continued

Modifications on 2-substitution and 4-sulfonamide

[Structure: 1-hydroxy-naphthalene with 2-S-R¹ and 4-NHSO₂R² substituents]

| Entry | Compound | R¹ | R² | IC$_{50}$$^a$ (μM) |
|---|---|---|---|---|
| 16 | 14p | CH$_2$COOH | 4-chlorophenyl | 3.75 ± 0.30 |
| 17 | 14q | CH$_2$COOH | 2-naphthyl | 4.83 ± 0.79 |
| 18 | 14s | CH$_2$COOH | 4-biphenyl | 1.90 ± 0.60 |
| 19 | 14t | 2-(carboxymethyl)phenyl (CH with COOH-phenyl) | 4-biphenyl | 2.19 ± 0.23 |
| 20 | 14u | CH(CH$_3$)COOH | 4-chlorophenyl | 8.57 ± 0.67 |
| 21 | 14v | CH(CH$_3$)COOH | 2-naphthyl | 9.11 ± 0.47 |

Note:
$^a$inhibition of chymotrypsin-like activity;
$^b$commercial sample;
$^c$from in-house synthesis.

The inhibitory potency of compounds with the ester chain was reduced comparing to acid analogues (Table 9, entry 2, 4, 6 and 8: compound 9a vs 10a, 9c vs 10c). When the length of the 2-side chain was increased by one carbon, the inhibitory activity diminished (Table 9, entry 6 and 7: 10a vs 10b). In series of 2-amide chain inhibitors (compound 14f~h), increasing length of 2-side chain caused the partial or complete loss of the activity. As H-bonding to Thr-1 residue was essential for hydronaphthoquinone sulfonamide inhibitors to inhibit proteasome chymotrypsin-like activity, we also tested compounds with carboxylic acid mimics, such as tetrazole and triazole at the 2 position. The results showed that the compounds bearing these carboxylic acid mimics exhibited comparable inhibition potency against proteasome to the lead compound (Table 9, entry 9 and 10: compound 14d and 14e).

Linear side chain at the 2 position was more favorable for inhibition activity than branched side chain. When the linear chain of acetic acid at the 2 position of compound 14n and 14q was replaced by branched chain of isopropionic acid in compound 14u and 14v, the activity was decreased by ~2 fold (Table 9, entry 16, 17, 20 and 21). The similar results presented when the linear side chain was replaced by an aromatic ring (Table 9, entry 6 and 12: compound 10a vs 14l).

The modification of aromatic sulfonamide at the 4 position retained or slightly decreased the proteasome inhibition activity as compared to the lead compound 10a. For example, the inhibitory activity was tolerated by replacing the thiophene ring by phenyl ring (Table 9, entry 6 and 8: IC$_{50}$=1.47 μM for 10a vs 2.08 μM for 10c) or 4-biphenyl group (Table 9, entry 18: IC$_{50}$=1.90 μM for 14s). Substitution at the para position of 4-benzenesulfonamide by nitro group slightly enhanced the activity (Table 9, entry 4 and 5: compound 9c vs 9e). The decoration of the thiophene ring or phenyl with chlorine also helped to retain the inhibitory activity against proteasome (Table 9, entry 14-16: compound 14n~p). The bulky naphthalene ring slightly decreased the activity by 3 fold (Table 9, entry 17: compound 14q).

It is worthwhile to mention that the intermediates 8a~c, the oxidized form of the hydronaphthoquinone sulfonamides 9, were tested for proteasome inhibition activity as well and showed comparable inhibition potency to their reduced form 9. This indicated that the proteasome inhibition by hydronaphthoquinone sulfonamide derivatives could be mediated by oxidation of the inhibitors. The mechanism of action is not clear yet.

4. Conclusion

In this work, we have confirmed HLM-008182 as a potent proteasome inhibitor via in-house synthesis. A new method was developed for HLM-008182 through a four-step protocol and the method was further optimized to a two step protocol for generating a focused library. The key step of the synthesis in both protocols was regioselective with $TiCl_4$. The reaction was highly efficient with microwave assisted heating and THF as solvent. The modification around the molecule HLM-008182 established primary SAR, indicating that the proteasome inhibition activity was critical to the 2-side chain. Further optimization of the structure is on going.

5. Experimental 5.1 General Procedure:

All reagents were purchased from commercial suppliers and used without further purification. Melting points were determined using a Barnstead international melting point apparatus and remain uncorrected. 1H NMR spectra were recorded on a Varian Mercury 400 MHz spectrometer with $CDCl_3$, $CD_2Cl_2$ or $d^6$-DMSO as the solvents. All coupling constants are measured in hertz (Hz), and the chemical shifts ($\delta$H) are quoted in parts per million (ppm). High resolution mass spectroscopy was carried out on an Agilent 6210 LC/MS (ESI-TOF). Microwave reactions were performed in Biotage initiator 8 machines. Flash chromatograph was done on Flash Master II (Biotage) using a pre-packed silica gel column and gradient elution with Hexane/EtOAc system. Thin layer chromatography was performed using silica gel 60 254 plates (Fisher), with observation under UV when necessary. Anhydrous solvents (ethanol, dichloromethylene, 1,2-dichloroethane, 1,4-dioxane and tetrahydrofuran) were used as purchased from Aldrich. HPLC grade solvents (methanol, acetonitrile, and water) were purchased from Burdick and Jackson for mass analysis.

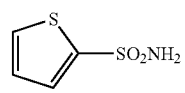

5.2.1 Thiophene-2-sulfonamide: 365.3 mg thiophene-2-sulfonyl chloride was dissolved in 5 ml THF, to which at 0° C. was added 1.7 ml $NH_3$ solution drop wise. The resulting mixture was stirred at r.t. for 2 hrs and acidified with conc. HCl at 0° C. to pH=~2. The organic solvent was removed via rotavap and the aqueous suspension was extracted with ethyl acetate. The extract was combined and washed with saturated $NaHCO_3$ solution, water and brine. Dried over $Na_2SO_4$, the organic phase was filtered and the filtrate was concentrated affording the title compound 212 mg (65%) as a white solid, m.p.: 137-139° C.

$^1$H-NMR, 400 MHz, $CDCl_3$, $\delta$ (ppm): 7.68 (dd, J=1.3 Hz, 3.8 Hz, 1H), 7.60 (dd, J=1.3 Hz, 5.0 Hz, 1H), 7.08 (dd, J=3.8 Hz, 5.0 Hz, 1H), 4.98 (br, 2H).

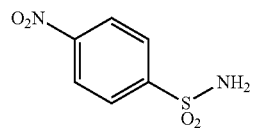

5.2.2 4-nitrobenzenesulfonamide was prepared according to the procedure for thiophene-2-sulfonamide YG1-030 except using 4-nitrobenzenesulfonyl chloride, which afforded the title compound 1.953 g (96.6%) as a pale yellow solid, m.p.: 178-180° C. $^1$H-NMR, 400 MHz, $d^6$-DMSO, $\delta$ (ppm): 8.40 (d, J=8.6 Hz, 2H), 8.04 (d, J=8.6 Hz, 2H), 7.72 (br, 2H).

HRMS (ESI–ve) m/z calculated for $C_6H_6N_2O_4S$ (M–H)_ 200.9976, found 200.9986.

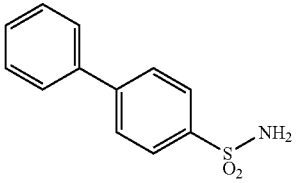 [SMILES: NS(=O)(=O)c1ccc(-c2ccccc2)cc1]

5.2.3 4-biphenylsulfonamide was prepared according to the procedure for thiophene-2-sulfonamide YG1-030 except using 4-biphenylsulfonyl chloride, which afforded the title compound 642.2 mg (90.6%) as a white solid, m.p.: 223-225° C.

$^1$H-NMR, 400 MHz, $d^6$-DMSO, $\delta$ (ppm): 7.88 (d, J=8.0 Hz, 2H), 7.84 (d, J=7.9 Hz, 2H), 7.71 (d, J=7.3 Hz, 2H), 7.49 (t, J=7.1 Hz, 2H), 7.41 (m, 3H).

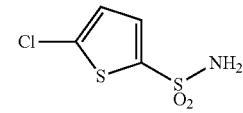

5.2.4 5-chlorothiophene-2-sulfonamide was prepared according to the procedure for thiophene-2-sulfonamide YG1-030 except using 4-biphenylsulfonyl chloride, which afforded the title compound 932.5 mg (94.4%) as a white solid, m.p.: 110-112° C.

$^1$H-NMR, 400 MHz, $CDCl_3$, $\delta$ (ppm): 7.44 (d, J=4.0 Hz, 1H), 7.06 (d, J=4.1 Hz, 1H), 6.01 (br, 2H).

3

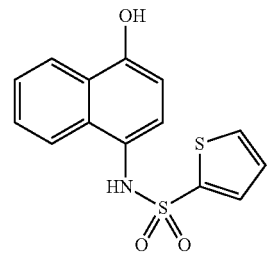

5.2.5 N-(4-hydroxynaphthalen-1-yl)thiophene-2-sulfonamide (3): 1.957 g 4-aminonaphth-1-ol hydrochloride salt was suspended in 80 ml dichloromethylene, to which at 0° C. was added 3.0 ml triethylamine. The suspension became a dark brown solution. To the solution was added 1.827 g thiophene-2-sulfonyl chloride. The mixture was stirred at r.t. overnight. The reaction mixture was diluted with dichloromethylene to 200 ml and washed with 1 N HCl solution (30 ml×3), water (30 ml×3) and brine (30 ml). Dried over MgSO$_4$, the organic phase was filtered and the filtrate was concentrated to dryness. The crude product was suspended in 50% methanol/H$_2$O and filtered. The solid was washed with 50% methanol/H$_2$O affording 2.7 g (90%) brown solid, m.p.: 146-148° C.

$^1$H-NMR, 400 MHz, CD$_2$Cl$_2$, δ (ppm): 7.81 (m, 2H), 7.70 (dd, J=1.4 Hz, 5.0 Hz, 1H), 7.60 (dd, J=1.3 Hz, 3.8 Hz, 1H), 7.46 (m, 2H), 7.07 (d, J=8.2 Hz, 1H), 7.06 (dd, J=3.8 Hz, 5.0 Hz, 1H), 6.66 (d, J=8.2 Hz, 1H), 4.30 (br, 2H).

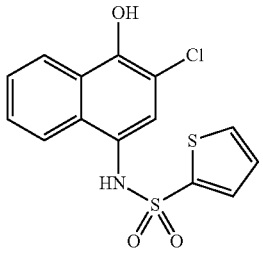

4a 5.2.6 N-(3-chloro-4-hydroxynaphthalen-1-yl)thiophene-2-sulfonamide (4a): 0.987 g N-(4-hydroxynaphthalen-1-yl)thiophene-2-sulfonamide (3) was suspended in 10 ml methanol, to which was added 3 ml hydrogen peroxide solution (35%). The mixture was stirred at r.t. for 2 h. Additional 3 ml hydrogen peroxide solution was added followed by 1 ml HCl solution (4 M in dioxane). The reaction was continued for another 2 h. The organic solvent was removed via rotavap and the residue was redissolved in ethyl acetate (100 ml). Washed with water (20 ml×3) and brine (20 ml×2), the organic phase was dried over Mg$_2$SO$_4$. The organic phase was filtered and concentrated. The crude product was separated via flash chromatography (Hex/EtOAc) affording 244 mg (22.2%) brown solid, m.p.: 113-115° C.

$^1$H-NMR, 400 MHz, CDCl$_3$, δ (ppm): 7.79 (d, J=8.4 Hz, 1H), 7.70 (d, J=8.1 Hz, 1H), 7.64 (dd, J=1.1 Hz, 4.9 Hz, 1H), 7.60 (dd, J=1.2 Hz, 3.8 Hz, 1H), 7.40 (m, 2H), 7.19 (s, 1H), 7.02 (dd, J=4.0 Hz, 4.8 Hz, 1H), 4.46 (br, 2H).

HRMS (ESI+ve) m/z calculated for C$_{14}$H$_{10}$ClO$_3$S$_2$ (M+H)$^+$ 339.9863, found 339.9856.

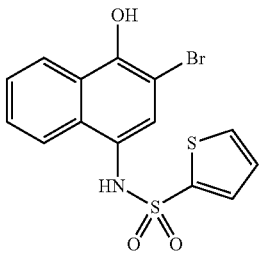

4b 5.2.7 N-(3-bromo-4-hydroxynaphthalen-1-yl)thiophene-2-sulfonamide (4b): 305.7 mg N-(4-hydroxynaphthalen-1-yl)thiophene-2-sulfonamide (3) was dissolved in 1 ml DMF, to which at 0° C. was added 320 mg Br$_2$ in 1 ml dichloromethylene solution. After stirred at r.t. for 1 h, 558 μl TEA was added at 0° C. The reaction was stirred at r.t. overnight and diluted with ethyl acetate to 50 ml. The organic phase was washed with water and brine. Dried over Na$_2$SO$_4$, the organic phase was filtered and concentrated. The crude product was purified via flash chromatography (Hex/EtOAc gradient) affording an orange-red solid 140 mg (36.4%), m.p.: 128-130° C.

$^1$H-NMR, 400 MHz, CDCl$_3$, δ (ppm): 7.81 (m, 1H), 7.75 (m, 1H), 7.66 (dd, J=1.3 Hz, 5.0 Hz, 1H), 7.61 (dd, J=1.3 Hz, 3.8 Hz, 1H), 7.43 (m, 2H), 7.32 (s, 1H), 7.04 (dd, J=3.9 Hz, 5.0 Hz, 1H), 4.75 (br, 2H).

HRMS (ESI+ve) m/z calculated for C$_{14}$H$_{10}$BrO$_3$S$_2$ (M+H)$^+$ 383.9358, found 383.9347.

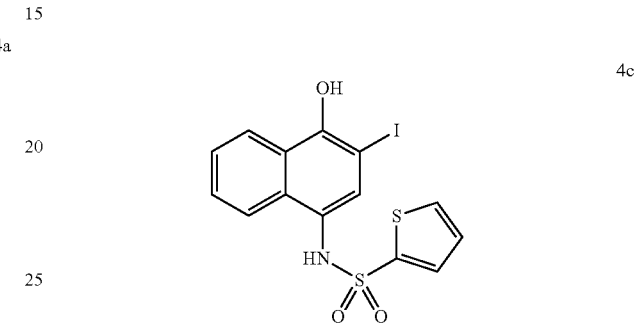

4c 5.2.8 N-(3-iodo-4-hydroxynaphthalen-1-yl)thiophene-2-sulfonamide (4c): was prepared according to the procedure for 4b except using I$_2$ solid. The reaction afforded title compound 129.4 mg (100%) as a brown solid, m.p.: 134-136° C.

$^1$H-NMR, 400 MHz, CDCl$_3$, δ (ppm): 7.82 (d, J=8.0 Hz, 1H), 7.74 (d, J=7.8 Hz, 1H), 7.68 (d, J=5.0 Hz, 1H), 7.62 (d, J=3.8 Hz, 1H), 7.45 (m, 3H), 7.06 (dd, J=3.8 Hz, 5.0 Hz, 1H).

HRMS (ESI+ve) m/z calculated for C$_{14}$H$_{10}$IO$_3$S$_2$ (M+H)$^+$ 431.9220, found 431.9216.

Procedure A for 10a:

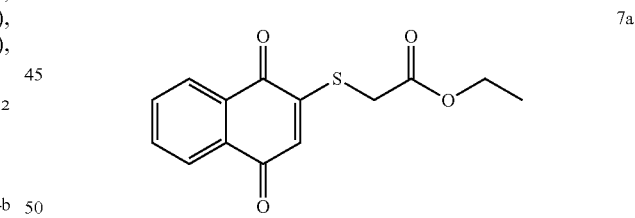

7a 5.2.9 Ethyl 2-(1,4-dioxo-1,4-dihydronaphthalen-2-ylthio)acetate (7a): 790.8 mg 1,4-naphthoquinone was added portion wise to 10 ml ethanol containing 0.5 eq. ethyl mercaptoacetate at room temperature. The mixture was stirred at room temperature for 30 min. The yellow solid was filtered, washed with ethanol and dried over vacuum affording title compound 491 mg (88.9%) as a yellow solid, m.p.: 150-152° C.

$^1$H-NMR, 400 MHz, CDCl$_3$, δ (ppm): 8.12 (d, J=7.4 Hz, 1H), 8.09 (d, J=7.4 Hz, 1H), 7.77 (t, J=7.5 Hz, 1H), 7.72 (t, J=7.5 HZ, 1H), 6.70 (s, 1H), 4.26 (q, J=7.1 Hz, 2H), 3.67 (s, 2H), 1.31 (t, J=7.1 HZ, 3H).

HRMS (ESI+ve) m/z calculated for C$_{14}$H$_{12}$O$_4$S (M+H)$^+$ 277.0529, found 277.0529.

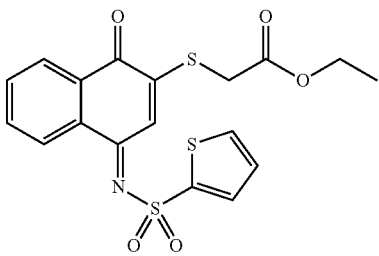

8a

5.2.10 Ethyl 2-(1-oxo-4-(thiophen-2-ylsulfonylimino)-1,4-dihydronaphthalen-2-ylthio)acetate (8a):

63 mg (0.228 mmoles) ethyl 2-(1,4-dioxo-1,4-dihydronaphthalen-2-ylthio)acetate (7a) was mixed with 37 mg (0.228 mmoles) thiophene-2-sulfonamide in 2.5 ml dichloromethylene, to which at 0° C. was added 76 mg $TiCl_4.2THF$ followed by 70 μl triethylamine. The mixture was heated at 60° C. with microwave synthesizer (Initiator 8, Biotage) for 20 min. Diluted with dichloromethylene to 60 ml, the reaction mixture was washed with $H_2O$ and brine and dried over $Na_2SO_4$. After removal of $Na_2SO_4$, the filtrate was concentrated and the residue was purified with flash column (EtOAc/Hexane) affording title compound 58 mg (60.4%) as orange oil which was solidified on standing, m.p.: 110-112° C.

$^1$H-NMR, 400 MHz, $CDCl_3$, δ (ppm): 8.22 (dd, J=3.3 Hz, 5.9 Hz, 1H), 8.15 (dd, J=3.5 Hz, 5.7 HZ, 1H), 7.96 (s, 1H), 7.83 (dd, J=1.3 Hz, 3.8 Hz), 7.70 (m, 3H), 7.15 (dd, J=3.8 Hz, 5.0 Hz, 1H), 4.32 (q, J=7.1 Hz, 2H), 3.80 (s, 2H), 1.35 (t, J=7.1 Hz, 3H).

HRMS (ESI+ve) m/z calculated for $C_{18}H_{15}NO_5S_3$ $(M+H)^+$ 422.0185, found 422.0193.

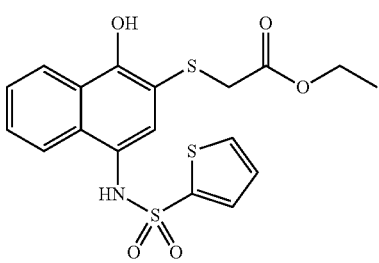

9a

5.2.11 Ethyl 2-(1-hydroxy-4-(thiophene-2-sulfonamido)naphthalen-2-ylthio)acetate (9a):

52 mg (E)-ethyl 2-(1-oxo-4-(thiophen-2-ylsulfonylimino)-1,4-dihydronaphthalen-2-ylthio)acetate (8a) was dissolved in 2 ml THF, to which was added 2 ml aqueous solution containing 107 mg $Na_2S_2O_4$, The resulting biphasic solution was stirred at r.t. for 1 h until it turned pale yellow. The mixture was diluted with ethyl acetate and washed with water and brine. Dried over $Na_2SO_4$, the organic solution was filtered and the filtrate was concentrated. The crude product was purified via flash column (EtOAc/Hexane) yielding 25.2 mg (58.7%) title compound, m.p.: 116-118° C.

$^1$H-NMR, 400 MHz, $CDCl_3$, δ (ppm): 8.42 (s, 1H), 8.29 (dd, J=3.2 Hz, 6.3 Hz, 1H), 7.80 (dd, J=3.1 Hz, 6.3 Hz, 1H), 7.52 (d, J=4.0 Hz, 1H), 7.48 (dd, J=3.2 Hz, 6.4 Hz, 2H), 7.38 (d, J=2.7 Hz, 1H), 7.35 (s, 1H), 6.95 (t, J=4.6 Hz, 1H), 6.77 (s, 1H), 4.18 (q, J=7.1 Hz, 2H), 3.48 (s, 2H), 1.21 (t, J=7.1 Hz, 3H).

HRMS (ESI+ve) m/z calculated for $C_{18}H_{17}NO_5S_3$ $(M+H)^+$ 424.0342, found 424.0335.

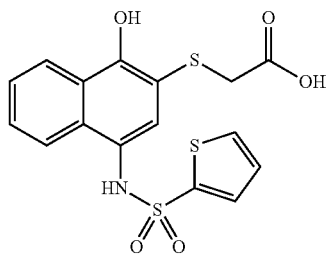

10a

5.2.12 2-(1-hydroxy-4-(thiophene-2-sulfonamido)naphthalen-2-ylthio)acetic acid (10a):

8 mg Ethyl 2-(1-hydroxy-4-(thiophene-2-sulfonamido)naphthalen-2-ylthio)acetate (9a) was dissolved in 0.5 ml dioxane, to which was added 0.5 ml HCl solution (4 N). The reaction mixture was heated at 100° C. with M.W. for 10 min and diluted to 20 ml with ethyl acetate. Washed with water and brine, the organic solution was dried over $Na_2SO_4$ and filtered. The filtrate was concentrated to dryness affording title compound 6 mg (80%) as a pale yellow solid, m.p.: 175-177° C.

$^1$H-NMR, 400 MHz, $d^6$-DMSO, δ (ppm): 10.08 (s, 1H), 8.13 (d, J=8.5 Hz, 1H), 7.85 (s, 1H), 7.84 (d, J=3.6 Hz, 2H), 7.44 (m, 2H), 7.34 (d, J=3.2 Hz, 1H), 7.06 (s, 1H), 7.05 (t, J=4.1 Hz, 1H), 3.52 (s, 2H).

HRMS (ESI–ve) m/z calculated for $C_{16}H_{13}NO_5S_3$ $(M-H)^-$ 393.9883, found 393.9885. Oxidation of 10a: around 1 mg 10a was suspended in 0.6 ml $CDCl_3$ in a NMR tube. The suspension was sonicated with a supersound power of 308 W (50/60 Hz) until a clear bright yellow solution was afforded.

$^1$H-NMR, 400 MHz, $CDCl_3$, δ (ppm): 8.22 (m, 1H), 8.15 (m, 1H), 7.99 (s, 1H), 7.83 (dd, J=1.3 Hz, 3.8 Hz, 1H), 7.71 (m, 3H), 7.15 (dd, J=3.8 Hz, 5.0 Hz, 1H), 3.86 (s, 2H).

Procedure B for 10a:

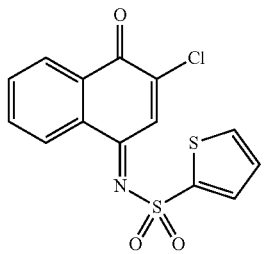

12a

5.2.13 N-(3-chloro-4-oxonaphthalen-1(4H)-ylidene)thiophene-2-sulfonamide (12a):

385.2 mg 2-chloro-1,4-naphthoquinone (11) was mixed with 326.4 mg thiophene-2-sulfonamide in 15 ml dichloromethylene, to which at 0° C. was added 2 ml $TiCl_4$ dichloromethylene solution followed by 613.3 μl. The mixture was heated at 60° C. with M.W. for 15 min and the black mixture was poured into 100 ml ethyl acetate. The insoluble was removed by filtrate through a pad of celite. The filtrate was concentrated and the residue was suspended in dichloromethylene. The brown insoluble stuff was removed by filtration and the filtrate was again concentrated to dryness. The residue was suspended in ethyl acetate/hexane (1:1) and the yellow solid was filtered. The solid was washed with ethyl acetate/hexane (1:1) and dried over vacuum affording title compound 377.7 mg (55.9%) as a yellow solid. When $TiCl_4.2THF$ and THF were used instead, the reaction afforded the title compound 522 mg (77.3%) as a yellow solid, m.p.: 167-169° C.

$^1$H-NMR, 400 MHz, $CDCl_3$, δ (ppm): 8.62 (s, 1H), 8.23 (tt, J=1.5 Hz, 9.2 Hz, 2H), 7.86 (dd, J=1.4 Hz, 3.8 Hz, 1H), 7.75 (m, 3H), 7.18 (dd, J=3.8 Hz, 5.0 Hz, 1H).

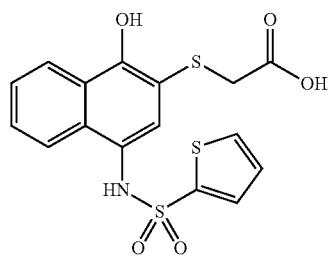

10a 5.2.14 2-(1-hydroxy-4-(thiophene-2-sulfonamido)naphthalen-2-ylthio)acetic acid (10a): 33.8 mg (E)-N-(3-chloro-4-oxonaphthalen-1(4H)-ylidene)thiophene-2-sulfonamide (12a) was dissolved in 2 ml THF, to which was added 0.1 ml THF solution containing 0.1 mmole thioglycolic acid followed by 1 eq. pyridine. The mixture was stirred at r.t. for 10 min and the solvent was removed via votavap. The orange-red residue was redissolved in 50 ml ethyl acetate and 0.5 M $NaHSO_4$ solution and transferred to a separation funnel. The organic layer was separated and washed with 0.5 M $NaHSO_4$ solution. To the ethyl acetate solution, was added 5 eq. sodium hydrosulfite solid, followed by 10 ml water. The mixture was shaken until the organic phase turned colorless. The organic phase was separated and washed with water and brine. Dried over $Na_2SO_4$, the organic phase was filtered and the filtrate was concentrated to dryness. The residual solid was suspended in dichloromethylene/hexane (1:1) and filtered. The solid was washed with dichloromethylene affording title compound 25 mg (63.6%) as an off-white solid.

$^1$H-NMR, 400 MHz, $d^6$-DMSO, δ (ppm): 12.65 (br, 1H), 10.07 (s, 1H), 8.13 (d, J=8.0 Hz, 1H), 7.85 (s, 1H), 7.84 (d, J=3.6 Hz, 1H), 7.44 (m, 2H), 7.34 (d, J=3.7 Hz, 1H), 7.06 (s, 1H), 7.04 (t, J=3.8 Hz, 1H), 3.52 (s, 2H).

HRMS (ESI–ve) m/z calculated for $C_{16}H_{13}NO_5S_3$ (M–H)⁻ 393.9883, found 393.9889.

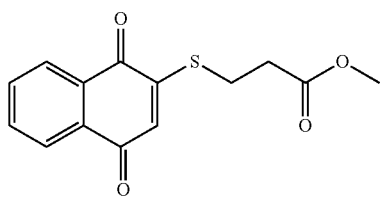

7b 5.2.15 Methyl 3-(1,4-dioxo-1,4-dihydronaphthalen-2-ylthio)propanoate (7b) was prepared according to the procedure for (7a) except using methyl 3-mercaptopropionate. The reaction afforded title compound 1.298 g (93.9%) as a yellow solid, m.p.: 108-110° C.

$^1$H-NMR, 400 MHz, $CDCl_3$, δ (ppm): 8.10 (t, J=7.6 Hz, 2H), 7.76 (t, J=7.5 Hz, 1H), 7.71 (t, J=7.4 Hz, 1H), 6.64 (s, 1H), 3.74 (s, 3H), 3.13 (t, J=7.4 Hz, 2H), 2.78 (t, J=7.3 Hz, 2H).

HRMS (ESI+ve) m/z calculated for $C_{14}H_{12}O_4S$ (M+H)⁺ 277.0529, found 277.0539.

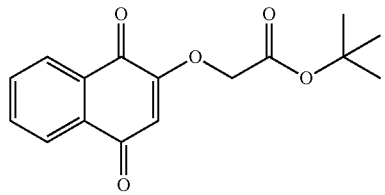

7c 5.2.16 tert-Butyl 2-(1,4-dioxo-1,4-dihydronaphthalen-2-yloxy)acetate (7c): a mixture of 2-hydroxynaphthalene-1,4-dione (6, 0.52 g, 3.0 mmol), tert-butyl 2-bromoacetate (0.78 g, 4.0 mmol), silver oxide (0.93 g, 4.0 mmol) and potassium iodide (0.05 g, 0.3 mmol) were refluxed in 10 ml of chloroform overnight under Ar. The reaction mixture was filtered and washed with DCM (3×20 ml), the filtrate was concentrated and purified with flash chromatography to give compound 7c as a light yellow solid, 13%, m.p.=120-122° C.

$^1$H NMR, 400 MHz, $CDCl_3$, δ (ppm): 8.15 (d, J=7.2 Hz, 1H), 8.08 (d, J=7.2 Hz, 1H), 7.78-7.73 (m, 2H), 6.04 (s, 1H), 4.62 (s, 2H), 1.41 (s, 9H).

HRMS (ESI+ve) m/z calculated for $C_{16}H_{17}O_5$ (M+H)⁺ 289.1071, found 289.1090.

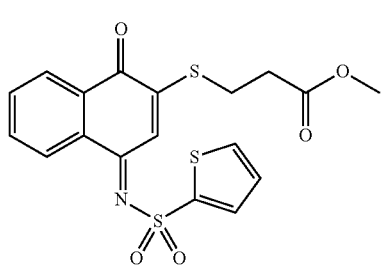

8b 5.2.17 Methyl 3-(1-oxo-4-(thiophen-2-ylsulfonylimino)-1,4-dihydronaphthalen-2-ylthio)propanoate (8b) was prepared according to the procedure for 8a except using 7b, which afforded 74 mg (35.1%) title compound as an orange solid, m.p.: 140-142° C.

$^1$H-NMR, 400 MHz, $CDCl_3$, δ (ppm): 8.22 (m, 1H), 8.12 (m, 1H), 7.90 (s, 1H), 7.82 (dd, J=1.3 Hz, 3.8 Hz, 1H), 7.69 (m, 3H), 7.15 (dd, J=5.0 Hz, 8.8 Hz, 1H), 3.75 (s, 3H), 3.26 (t, J=6.9 Hz, 2H), 2.85 (t, J=6.9 Hz, 2H).

HRMS (ESI+ve) m/z calculated for $C_{18}H_{15}NO_5S_3$ (M+H)⁺ 422.0185, found 422.0185.

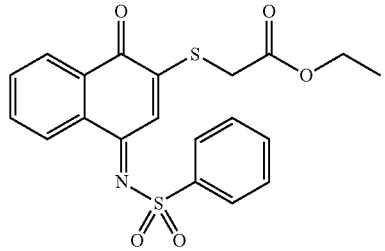

8c 5.2.18 Ethyl 2-(1-oxo-4-(phenylsulfonylimino)-1,4-dihydronaphthalen-2-ylthio)acetate (8c) was prepared according to the procedure for 8a except using benzenesulfonamide, which afforded 131.8 mg (31.7%) title compound as a yellow solid, m.p.: 93-95° C.

$^1$H-NMR, 400 MHz, CDCl$_3$, δ (ppm): 8.11 (dd, J=2.1 Hz, 6.6 Hz, 2H), 8.07 (d, J=7.3 Hz, 2H), 7.99 (s, 1H), 7.64 (m, 3H), 7.85 (t, Hz, 2H), 4.32 (q, J=7.1 Hz, 2H), 3.81 (s, 2H), 1.34 (t, J=7.1 Hz, 3H).

HRMS (ESI+ve) m/z calculated for C$_{20}$H$_{17}$NO$_5$S$_2$ (M+H)$^+$ 416.0621, found 416.0621.

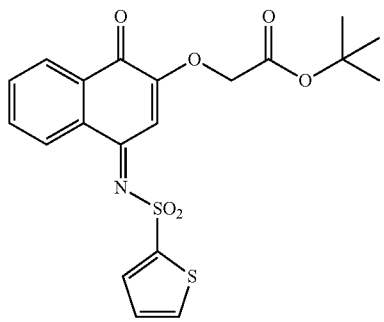

5.2.19 tert-Butyl-2-(1-oxo-4-(thiophen-2-ylsulfonylimino)-1,4-dihydronaphthalen-2-yloxy)acetate (8d): triethyl amine (0.12 ml, 0.88 mmol) was added in the mixture of tert-Butyl 2-(1,4-dioxo-1,4-dihydronaphthalen-2-yloxy)acetate (7c, 0.115 g, 0.4 mmol) and thiophene-2-sulfonamide (0.078 g, 0.48 mmol) in anhydrous DCM (4 ml), followed by adding TiCl$_4$2THF. The reaction mixture was heated with μW at 60° C. for 20 min. and poured into EtOAC, then filtered with celite. The filtrate was concentrated under reduce pressure and purified by flash chromatography to give compound 8d as a yellow solid, 22%, m.p.=153-155° C.

$^1$H NMR, 400 MHz, CDCl$_3$, δ (ppm): 8.07 (d, J=9.0 Hz, 1H), 8.01 (d, J=9.0 Hz, 1H), 7.64 (d, J=3.7 Hz, 1H), 7.55-7.53 (m, 3H), 7.10 (s, 1H), 6.98 (t, J=3.8 Hz, 1H), 4.58 (s, 2H), 1.39 (s, 9H)).

HRMS (ESI+ve) m/z calculated for C$_{16}$H$_{17}$O$_5$ (M+H-tBu-CO$_2$)$^+$334.0208, found 334.0222.

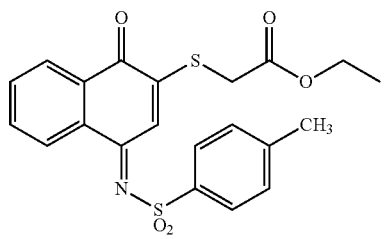

5.2.20 Ethyl 2-(1-oxo-4-(tosylimino)-1,4-dihydronaphthalen-2-ylthio)acetate (8l) was prepared according to the procedure for 8a except using 4-methylbenzenesulfonamide, TiCl$_4$.2THF and THF as solvent. The title compound 100.7 mg (46.9%) was obtained according to the workup procedure for 12a as a yellow solid, m.p.: ° C.

$^1$H-NMR, 400 MHz, CDCl$_3$, δ (ppm): 8.14 (dd, J=1.4 Hz, 7.2 Hz, 2H), 8.03 (s, 1H), 7.95 (d, J=8.2 Hz, 2H), 7.65 (m, 2H), 7.38 (d, J=8.5 Hz, 2H), 4.32 (q, J=7.1 Hz, 2H), 3.81 (s, 2H), 2.47 (s, 3H), 1.35 (t, J=7.1 Hz, 3H).

HRMS (ESI+ve) m/z calculated for C$_{21}$H$_{19}$NO$_5$S$_2$ (M+H)$^+$ 430.0777, found 430.0776.

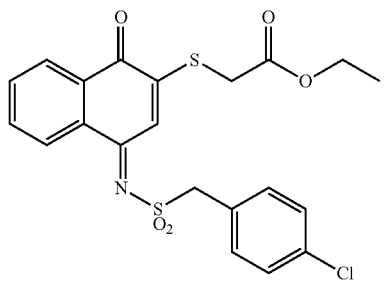

5.2.21 Ethyl 2-(4-(4-chlorobenzylsulfonylimino)-1-oxo-1,4-dihydronaphthalen-2-ylthio)-acetate (8g) was prepared according to the procedure for 8a except using (4-chlorophenyl)methanesulfonamide, TiCl$_4$.2THF and THF as solvent. The title compound 130 mg (56%) was obtained according to the workup procedure for 12a as a yellow solid, m.p.: ° C.

$^1$H-NMR, 400 MHz, CDCl$_3$, δ (ppm): 8.14 (m, 2H), 7.72 (m, 2H), 7.70 (s, 1H), 7.47 (d, J=8.4 Hz, 2H), 7.38 (d, J=8.4 Hz, 2H), 4.55 (s, 2H), 4.26 (q, J=7.1 Hz, 2H), 3.70 (s, 2H), 1.30 (t, J=7.1 Hz, 3H).

HRMS (ESI+ve) m/z calculated for C$_{21}$H$_{18}$ClNO$_5$S$_2$ (M+H)$^+$ 464.0388, found 464.0388.

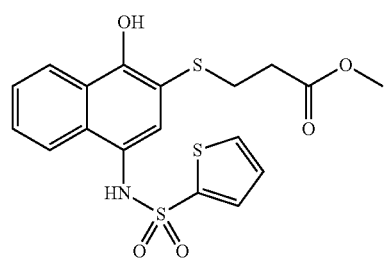

5.2.22 Methyl 3-(1-hydroxy-4-(thiophene-2-sulfonamido) naphthalen-2-ylthio)propanoate (9b) was prepared according to the procedure for 9a except using 8b affording 28 mg (93%) title compound as a pale yellow solid without column purification, m.p.: 117-119° C.

$^1$H-NMR, 400 MHz, CDCl$_3$, δ (ppm): 8.25 (dd, J=3.2 Hz, 6.4 Hz, 1H), 7.87 (dd, J=3.2 Hz, 6.3 Hz, 1H), 7.60 (br, 1H), 7.50 (m, 3H), 7.41 (dd, J=1.3 Hz, 3.7 Hz, 1H), 7.32 (s, 1H), 6.95 (dd, J=3.8 Hz, 5.0 Hz, 1H), 6.91 (br, 1H), 3.70 (s, 3H), 2.93 (t, J=7.1 Hz, 2H), 2.51 (t, J=7.0 Hz, 2H).

HRMS (ESI+ve) m/z calculated for C$_{18}$H$_{17}$NO$_5$S$_3$ (M+Na)$^{+b\ 446.0161}$, found 446.0157.

5.2.23 Ethyl 2-(1-hydroxy-4-(phenylsulfonamido)naphthalen-2-ylthio)acetate (9c) was prepared according to the procedure for 9a affording 68 mg (81.5%) title compound as a pale yellow solid, m.p.: 118-120° C.

$^1$H-NMR, 400 MHz, CD$_2$Cl$_2$, δ (ppm): 8.52 (s, 1H), 8.27 (m, 1H), 7.84 (m, 1H), 7.68 (d, J=8.4 Hz, 2H), 7.57 (t, J=7.5 Hz, 1H), 7.50 (m, 2H), 7.43 (t, J=7.9 Hz, 2H), 7.17 (s, 1H), 6.59 (br, 1H), 4.17 (q, J=7.1 Hz, 2H), 3.44 (s, 2H), 1.21 (t, J=7.2 Hz, 3H).

HRMS (ESI+ve) m/z calculated for C$_{20}$H$_{19}$NO$_5$S$_2$ (M+Na)$^+$440.0597, found 440.0596.

mide, 1,2-dichloroethane as solvent and applying 100° C. to the reaction. The reaction was worked up according to the procedure for 12a and the title compound was isolated from the product mixture by flash chromatography (EtOAc/Hex) affording 48 mg (10.4%) as a brown solid, m.p.: 143-145° C.

$^1$H-NMR, 400 MHz, CD$_3$CN, δ (ppm): 8.49 (s, 1H), 8.25 (d, J=8.9 Hz, 2H), 8.24 (m, 1H), 8.01 (br, 1H), 7.89 (m, 1H), 7.87 (d, J=8.7 Hz, 2H), 7.54 (m, 2H), 7.13 (s, 1H), 4.11 (q, J=7.1 Hz, 2H), 3.47 (s, 2H), 1.16 (t, J=7.1 Hz, 3H).

HRMS (ESI+ve) m/z calculated for C$_{20}$H$_{18}$N$_2$O$_7$S$_2$ (M+Na)$^+$485.0448, found 485.0438.

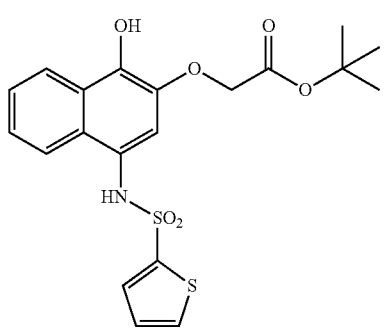

9d

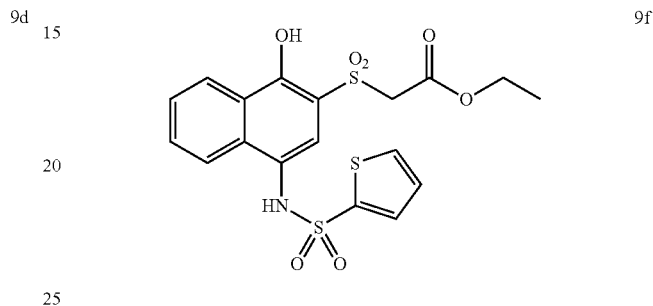

9f 5.2.24 tert-Butyl-2-(1-hydroxy-4-(thiophene-2-sulfonamido)naphthalen-2-yloxy)acetate (9d): tert-Butyl-2-(1-oxo-4-(thiophen-2-ylsulfonylimino)-1,4-dihydronaphthalen-2-yloxy)acetate (8d, 0.07 g, 0.16 mmol) was dissolved in 3 ml of THF and stirred at r.t., Na$_2$SO$_4$ (0.139 g, 0.8 mmol) was added with vigorously stirring. 1 ml of H$_2$O was added to mixture until Na$_2$SO$_4$ was dissolved completely. The reaction mixture was stirred at r.t. for 10 min. The color changed from orange to light yellow. 40 ml of EtOAc was added into the mixture and washed with 40 ml of water, followed by washing with brine, dried with MgSO$_4$ and filtered. The filtrate was concentrated under reduced pressure. The product was obtained by crystallization with EtOAc and hexane as a light yellow solid, 71%, m.p.=155-157° C.

$^1$H NMR, 400 MHz, CDCl$_3$, δ (ppm): 8.55 (broad s, 1H, disappear on D$_2$O shake), 8.25 (d, J=8.0 Hz, 1H), 7.55 (d, J=8.0 Hz, 1H), 7.45 (d, J=4.8 Hz, 1H), 7.45-7.29 (m, 3H), 7.24 (s, 1H), 6.90 (1H, J=4.8 Hz, 1H), 6.71 (s, 1H, disappear on D$_2$O shake), 4.54 (s, 2H), 1.51 (s, 9H).

HRMS (ESI–ve) m/z calculated for C$_{20}$H$_{20}$NO$_6$S$_2$ (M–H)$^-$ 434.0738, found 434.0755.

5.2.26 Ethyl 2-(1-hydroxy-4-(thiophene-2-sulfonamido) naphthalen-2-ylsulfonyl)acetate (9f): 42.4 mg Ethyl 2-(1-hydroxy-4-(thiophene-2-sulfonamido)naphthalen-2-ylthio)acetate (9a) was dissolved in 2 ml acetone, to which was added 2 ml aqueous solution containing 307.4 mg oxone. The resulting mixture was stirred at r.t. overnight. The organic solvent was removed by rotavap and the residue extracted with ethyl acetate. The organic extract was combined and washed with water and brine. Dried over Na$_2$SO$_4$, the organic phase was filtered and the filtrate was concentrated to dryness affording 47 mg (100%) title compound as a pale yellow solid, m.p.: 154-156° C.

$^1$H-NMR, 400 MHz, CDCl$_3$, δ (ppm): 10.02 (s, 1H), 8.43 (d, J=8.4 Hz, 1H), 7.98 (d, J=8.4 Hz, 1H), 7.70 (t, J=8.0 Hz, 1H), 7.62 (t, J=7.9 Hz, 1H), 7.57 (d, J=5.0 Hz, 1H), 7.43 (d, J=3.7 Hz, 1H), 7.29 (s, 1H), 7.00 (dd, J=3.8 Hz, 4.9 Hz, 1H), 6.58 (s, 1H), 4.16 (q, J=7.2 Hz, 2H), 4.12 (s, 2H), 1.15 (t, J=7.2 Hz, 3H).

HRMS (ESI–ve) m/z calculated for C$_{18}$H$_{17}$NO$_7$S$_3$ (M–H)_454.0094, found 454.0112.

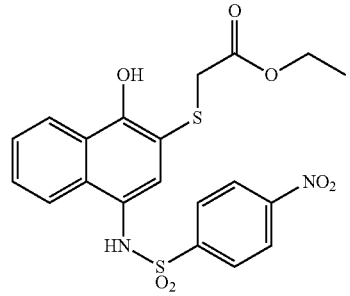

9e

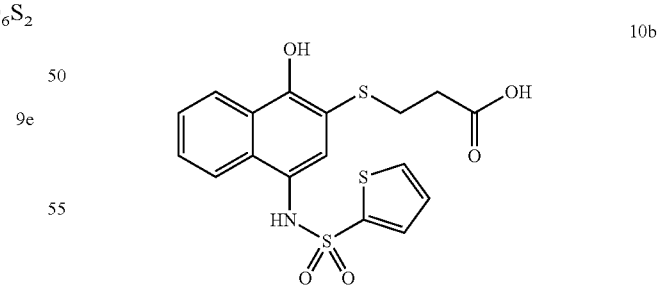

10b 5.2.25 Ethyl 2-(1-hydroxy-4-(4-nitrophenylsulfonamido) naphthalen-2-ylthio)acetate (9e) was prepared according to the procedure for 8a except using 4-nitrobenzenesulfona- 5.2.27 3-(1-hydroxy-4-(thiophene-2-sulfonamido)naphthalen-2-ylthio)propanoic acid (10b) was prepared according to the procedure of procedure A for 10a except applying r.t. to the reaction overnight, which afforded 5.6 mg (13.5%) title compound as a white solid, m.p.: 185° C. (dec.).

$^1$H-NMR, 400 MHz, d$^6$-DMSO, δ (ppm): 12.35 (s, 1H), 10.07 (s, 1H), 9.70 (s, 1H), 8.13 (d, J=7.6 Hz, 1H), 7.91 (d, J=7.8 Hz, 1H), 7.85 (d, J=5.0 Hz, 1H), 7.46 (m, 2H), 7.36 (d, J=3.7 Hz, 1H), 7.07 (t, J=4.9 Hz, 1H), 6.96 (s, 1H), 2.84 (t, J=7.2 Hz, 2H), 2.37 (t, J=7.1 Hz, 2H).

HRMS (ESI−ve) m/z calculated for $C_{17}H_{15}NO_5S_3$ (M−H)⁻ 408.0040, found 408.0054.

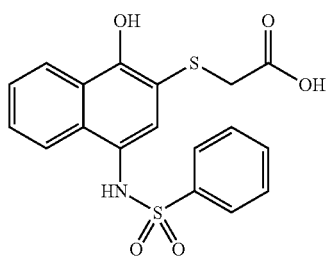
10c 5.2.28  2-(1-hydroxy-4-(phenylsulfonamido)naphthalen-2-ylthio)acetic acid (10c) was prepared according to the procedure of procedure A for 10a except applying r.t. to the reaction overnight, which afforded 20 mg (53.6%) title compound as an off-white solid, m.p.: 100-102° C.

$^1$H-NMR, 400 MHz, d⁶-DMSO, δ (ppm): 12.75 (br, 1H), 9.91 (s, 1H), 9.80 (br, 1H), 8.10 (d, J=8.1 Hz, 1H), 7.83 (d, J=8.3 Hz, 1H), 7.60 (d, J=7.7 Hz, 2H), 7.56 (t, J=7.3 Hz, 1H), 7.46 (t, J=7.6 Hz, 2H), 7.39 (m, 2H), 6.96 (s, 1H), 3.47 (s, 2H).

HRMS (ESI−ve) m/z calculated for $C_{18}H_{15}NO_5S_2$ (M−H)⁻ 388.0319, found 388.0330.

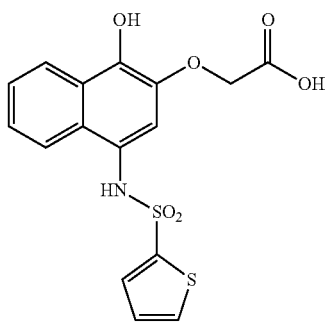
10d 5.2.29  2-(1-hydroxy-4-(thiophene-2-sulfonamido)naphthalen-2-yloxy)acetic acid (10d): tert-Butyl-2-(1-hydroxy-4-(thiophene-2-sulfonamido)naphthalen-2-yloxy)acetate (9d, 0.025 g, 0.057 mmol) was dissolved in 4 ml of 1:1 ratio of dioxane and concentrated hydrochloric acid and stirred at r.t. for 3 h. The mixture solution changed from clear to white cloudy. The solvent was evaporated under reduced pressure. The solid was washed with DCM and hexane separately to get pure product as a gray solid, 97%, m.p.=155-157° C.

$^1$H NMR, 400 MHz, DMSO-d₆, δ (ppm): 10.08 (s, 1H, disappear on D₂O shake), 8.03 (d, J=8.4 Hz, 1H), 7.81 (d, J=4.8 Hz, 1H), 7.77 (d, J=8.4 Hz, 1H), 7.38 (t, J=7.6 Hz, 1H), 7.33 (d, J=2.4 Hz, 1H), 7.27 (t, J=7.6 Hz, 1H), 7.04 (t, J=4.0 Hz, 1H), 6.86 (s, 1H), 4.55 (s, 2H).

HRMS (ESI−ve) m/z calculated for $C_{16}H_{12}NO_6S_2$ (M−H)⁻ 378.0112, found 378.011.

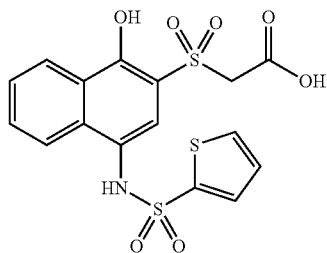
10f 5.2.30  2-(1-hydroxy-4-(thiophene-2-sulfonamido)naphthalen-2-ylsulfonyl)acetic acid (10f): 20 mg Ethyl 2-(1-hydroxy-4-(thiophene-2-sulfonamido)naphthalen-2-ylsulfonyl)-acetate (9f) was dissolved in 2 ml dioxane, to which was added 2 ml conc. HCl. The mixture was stirred at r.t. for 36 h. The solvent was removed by rotavap. The solid residue was washed with dichloromethylene affording title compound 18.3 mg (97.3%) as an off-white solid, m.p.: 210-212° C.

$^1$H-NMR, 400 MHz, d⁶-DMSO, δ (ppm): 10.24 (s, 1H), 8.37 (d, J=8.7 Hz, 1H), 7.97 (d, J=7.8 Hz, 1H), 7.86 (d, J=4.3 Hz, 1H), 7.62 (m, 2H), 7.35 (s, 1H), 7.33 (d, J=3.0 Hz, 1H), 7.05 (dd, J=3.9 Hz, 4.9 Hz, 1H), 4.52 (s, 1H).

HRMS (ESI−ve) m/z calculated for $C_{16}H_{13}NO_7S_3$ (M−H)⁻ 425.9781, found 425.9788.

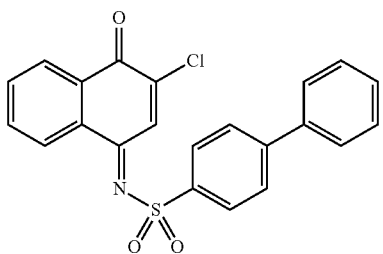
12b 5.2.31  N-(3-chloro-4-oxonaphthalen-1(4H)-ylidene)biphenyl-4-sulfonamide (12b) was prepared according to the procedure for 12a except using 4-biphenylsulfonamide, which afforded the title compound 154 mg (37.8%) as a yellow solid. When TiCl₄.2THF and THF were used instead, the reaction afforded the title compound 586.7 mg (71.9%) as a yellow solid, m.p.: 190-192° C.

$^1$H-NMR, 400 MHz, CDCl₃, δ (ppm): 8.71 (s, 1H), 8.21 (t, J=7.7 Hz, 2H), 8.14 (d, J=8.6 Hz, 2H), 7.81 (d, J=8.6 Hz, 2H), 7.74 (t, J=7.5 Hz, 1H), 7.70 (t, J=7.6 Hz, 1H), 7.65 (d, J=8.0 Hz, 2H), 7.51 (t, J=7.1 Hz, 2H), 7.45 (t, J=7.3 Hz, 1H).

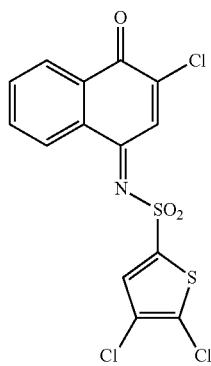
12c 5.2.32 4,5-dichloro-N-(3-chloro-4-oxonaphthalen-1(4H)-ylidene)thiophene-2-sulfonamide (12c) was prepared according to the procedure for 12a except using 4, 5-dichlorobenzenesulfonamide, which afforded the title compound 260 mg (35%) as a yellow solid, m.p.: ° C.

¹H NMR (400 MHz, CDCl₃), δ (ppm): 8.49 (s, 1H), 8.22 (dt, J=6.0, 1.6 Hz, 2H), 7.82-7.74 (m, 2H), 7.64 (s, 1H).

the procedure for (12a) except using naphthalene-2-sulfonamide, TiCl₄.2THF and THF as solvent which afforded the title compound 594.8 mg (77.9%) as a yellow solid, m.p.: 200-202° C.

¹H-NMR, 400 MHz, CDCl₃, δ (ppm): 8.73 (s, 1H), 8.64 (s, 1H), 8.20 (d, 7.7 Hz, 1H), 8.14 (d, J=7.9 Hz, 1H), 8.05 (m, 3H), 7.97 (d, 8.0 Hz, 1H), 7.72 (q, J=7.4 Hz, 2H), 7.66 (t, J=7.1 Hz, 2H).

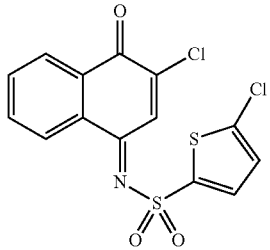

12d

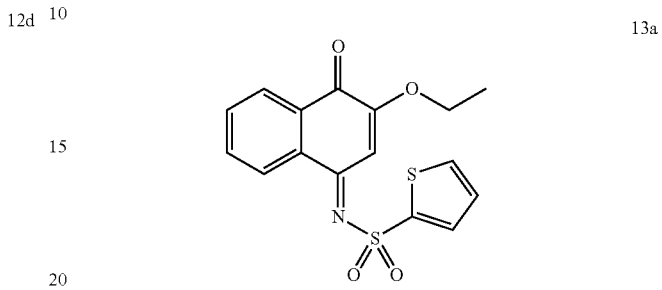

13a 5.2.33 5-chloro-N-(3-chloro-4-oxonaphthalen-1(4H)-ylidene)thiophene-2-sulfonamide (12d) was prepared according to the procedure for 12a except using 5-chlorothiophene-2-sulfonamide, which afforded the title compound 320.1 mg (43.0%) as a yellow solid, m.p.: 149-151° C.

¹H-NMR, 400 MHz, CDCl₃, δ (ppm): 8.55 (s, 1H), 8.22 (m, 2H), 7.76 (m, 2H), 7.64 (d, J=4.1 Hz, 1H), 7.01 (d, J=4.1 Hz, 1H).

5.2.36 N-(3-ethoxy-4-oxonaphthalen-1(4H)-ylidene)thiophene-2-sulfonamide (13a): 33.8 mg (E)-N-(3-chloro-4-oxonaphthalen-1(4H)-ylidene)thiophene-2-sulfonamide was suspended in 2 ml ethanol, to which was added 0.5 ml sodium ethoxide in ethanol solution (0.2 M). The suspension disappeared and in 5 min it turned cloudy with yellow precipitate. The resulting reaction mixture was concentrated and the crude product was purified by flash column (EtOAc/Hex) affording the title compound 10 mg (28.8%) as a bright yellow solid.

¹H-NMR, 400 MHz, CDCl₃, δ (ppm): 8.24 (m, 1H), 8.16 (m, 1H), 7.82 (d, J=2.5 Hz, 1H), 7.69 (m, 3H), 7.44 (s, 1H), 7.14 (dd, J=3.8 Hz, 4.9 Hz, 1H), 4.26 (q, J=7.0 Hz, 2H), 1.57 (t, J=7.0 Hz, 3H)

HRMS (ESI+ve) m/z calculated for $C_{16}H_{13}NO_4S_2$ (M+H)⁺ 348.0359, found 348.0371.

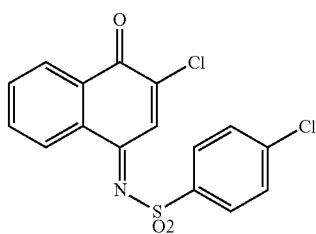

12e 5.2.34 4-chloro-N-(3-chloro-4-oxonaphthalen-1(4H)-ylidene)benzenesulfonamide (12e) was prepared according to the procedure for 12a except using 4-chlorobenzenesulfonamide, TiCL₄.2THF and THF as solvent which afforded the title compound 452.2 mg (61.8%) as a yellow solid, m.p.: 138-140° C.

¹H-NMR, 400 MHz, CDCl₃, δ (ppm): 8.62 (s, 1H), 8.21 (dd, J=1.1 Hz, 7.7 Hz, 1H), 8.12 (dd, J=0.9 Hz, 7.6 Hz, 1H), 8.02 (d, J=8.7 Hz, 2H), 7.75 (td, J=1.3 Hz, 7.5 Hz, 1H), 7.70 (td, J=1.5 Hz, 7.6 Hz, 1H), 7.59 (d, J=8.8 Hz, 2H).

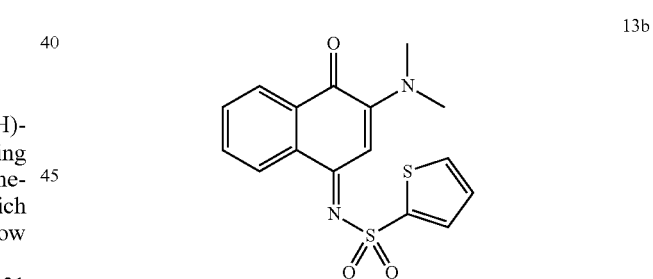

13b 5.2.37 N-(3-(dimethylamino)-4-oxonaphthalen-1(4H)-ylidene)thiophene-2-sulfonamide (13b): 33.5 mg (E)-N-(3-chloro-4-oxonaphthalen-1(4H)-ylidene)thiophene-2-sulfonamide was dissolved in 2 ml THF, to which was added 0.4 ml dimethylamine in THF solution (2 M). The wine-red solution was stirred at r.t. for 10 min and concentrated. The residue was suspended in 50 ml ethyl acetate and washed with water and brine. Dried over Na₂SO₄, the organic phase was filtered and the filtrate was concentrated to dryness affording the title compound 36 mg (100%) as a wine-red solid, m.p.: 183-185° C.

¹H-NMR, 400 MHz, CDCl₃, δ (ppm): 8.25 (d, J=7.7 Hz, 1H), 8.01 (d, J=7.6 Hz, 1H), 7.75 (d, J=3.7 Hz, 1H), 7.65 (t, J=7.3 Hz, 1H), 7.58 (m, 2H), 7.08 (t, J=5.0 Hz, 1H), 6.91 (s, 1H), 3.40 (s, 6H).

HRMS (ESI+ve) m/z calculated for $C_{16}H_{14}N_2O_3S_2$ (M+H)⁺ 347.0519, found 347.0522.

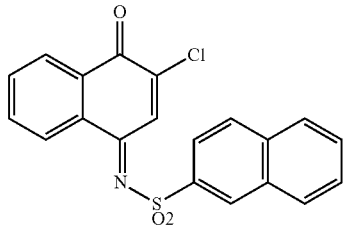

12f 5.2.35 N-(3-chloro-4-oxonaphthalen-1(4H)-ylidene)naphthalene-2-sulfonamide (12f) was prepared according to

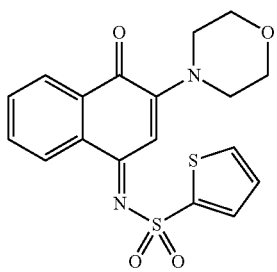

5.2.38 N-(3-morpholino-4-oxonaphthalen-1(4H)-ylidene)thiophene-2-sulfonamide (13c) was prepared according to the procedure for 13b except using 0.2 eq. morpholine, which afforded the title compound 36.3 mg (93.6%) as a wine-red solid, m.p.: 195° C. (dec.).

$^1$H-NMR, 400 MHz, CDCl$_3$, δ (ppm): 8.21 (d, J=7.4 Hz, 1H), 8.01 (d, J=7.4 Hz, 1H), 7.77 (d, J=3.6 Hz, 1H), 7.63 (m, 3H), 7.13 (s, 1H), 7.10 (t, J=4.9 Hz, 1H), 3.88 (t, J=4.5 Hz, 4H), 3.77 (t, J=4.3 Hz, 4H).

HRMS (ESI+ve) m/z calculated for C$_{18}$H$_{16}$N$_2$O$_4$S$_2$ (M+H)$^+$ 389.0624, found 389.0628.

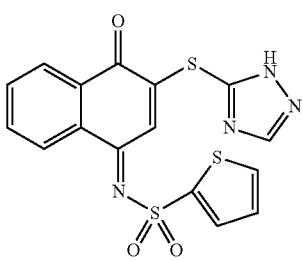

5.2.39 N-(3-(1-methyl-1H-tetrazol-5-ylthio)-4-oxonaphthalen-1(4H)-ylidene)thiophene-2-sulfonamide (13d): 36 mg (E)-N-(3-chloro-4-oxonaphthalen-1(4H)-ylidene)-thiophene-2-sulfonamide (12a) was dissolved in 3 ml THF, to which was added 11.7 mg 1-methyl-tetrazole-5-thiol. The reaction mixture was stirred at r.t. for 2 hrs and concentrated via rotavap. The residue was dissolved in dichloromethylene and triturated with hexane. The precipitate was filtered and washed with dichloromethylene/hexane (1:1) affording the title compound 28.8 mg (68.9%) as an orange-red solid, m.p.: 172° C. (dec.).

$^1$H-NMR, 400 MHz, CDCl$_3$, δ (ppm): 8.25 (m, 1H), 8.16 (m, 1H), 8.01 (s, 1H), 7.78 (d, J=3.8 Hz, 1H), 7.74 (m, 3H), 7.15 (dd, J=4.0 Hz, 4.9 Hz, 1H), 4.21 (s, 3H).

HRMS (ESI+ve) m/z calculated for C$_{16}$H$_{11}$N$_5$O$_3$S$_3$ (M+H)$^+$ 418.0097, found 418.0099.

5.2.40 N-(3-(1H-1,2,4-triazol-5-ylthio)-4-oxonaphthalen-1(4H)-ylidene)thiophene-2-sulfonamide (13e) was prepared according to the procedure for 13d except using 3-mercapto-1,2,4-triazole, which afforded the title compound 38.8 mg (96.5%) as an orange-red solid, m.p.: 197° C. (dec.).

$^1$H-NMR, 400 MHz, CD$_3$CN, δ (ppm): 8.63 (s, 1H), 8.18 (m, 1H), 8.15 (m, 1H), 7.89 (dd, J=1.3 Hz, 5.0 Hz, 1H), 7.81 (m, 3H), 7.55 (dd, J=1.3 Hz, 3.8 Hz, 1H), 7.21 (dd, J=3.0 Hz, 5.8 Hz, 1H).

HRMS (ESI+ve) m/z calculated for C$_{16}$H$_{10}$N$_4$O$_3$S$_3$ (M+H)$^+$ 402.9988, found 402.9989.

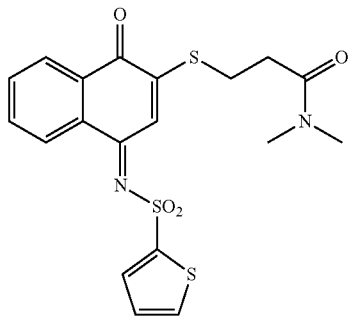

5.2.41 N,N-dimethyl-3-(1-oxo-4-(thiophen-2-ylsulfonylimino)-1,4-dihydronaphthalen-2-ylthio)propanamide (13f) was prepared according to the procedure for 13d except using 4,5-dichloro-N-(3-chloro-4-oxonaphthalen-1(4H)-ylidene)thiophenesulfonamide (12c) and 3-mercapto-N,N-dimethylpropanamide( ) which afforded the title compound 16.1 mg (48%) as a white solid, m.p.: ° C.

$^1$H NMR (400 MHz, CDCl$_3$) δ 8.18-8.16 (m, 1H), 8.07-8.06 (m, 1H), 7.83 (s, 1H), 7.75 (dd, J=3.6, 1.2 Hz, 1H), 7.65-7.61 (m, 3H), 7.08 (dd, J=5.2, 4.0 Hz, 1H); 3.28 (t, J=6.8 Hz, 2H), 2.95 (s, 6H), 2.80 (t, J=6.8 Hz, 2H).

HRMS (ESI+ve) m/z calculated for C$_{19}$H$_{19}$N$_2$O$_4$S$_3$ (M+H)$^+$ 435.0502, found 435.0508.

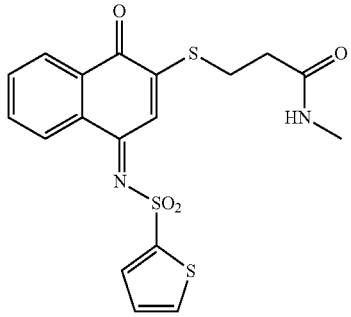

5.2.42 (N-methyl-3-(1-oxo-4-(thiophen-2-ylsulfonylimino)-1,4-dihydronaphthalen-2-ylthio)propanamide (13g) was prepared according to the procedure for 13d except using 4, 5-dichloro-N-(3-chloro-4-oxonaphthalen-1(4H)-ylidene)thiophenesulfonamide (12c) and 3-mercapto-N-methylpropanamide( ) which afforded the title compound 21 mg (32%) as a yellow solid, m.p.: ° C.

$^1$H NMR (400 MHz, CDCl$_3$) δ 8.23 (dd, J=5.6, 3.6 Hz, 1H), 8.15 (dd, J=5.6, 3.6 Hz, 1H), 7.85 (s, 1H), 7.83 (dd, J=3.6, 1.2 Hz, 1H), 7.74 (dd, J=5.2, 1.6 Hz, 1H), 7.71 (dd, J=6.0, 3.2 Hz,

1H); 7.17 (dd, J=6.0, 5.2, 2H), 6.19 (bs, 1H), 3.32 (t, J=8.0 Hz, 2H), 2.85 (d, J=4.8 Hz, 3H), 2.65 (t, J=8.0 Hz, 2H).

HRMS (ESI+ve) m/z calculated for $C_{18}H_{17}N_2O_4S_3$ (M+H)$^+$ 421.0345, found 421.0344.

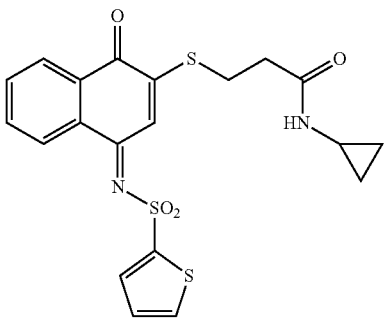

13h 5.2.43 N-cyclopropyl-3-(1-oxo-4-(thiophen-2-ylsulfonylimino)-1,4-dihydronaphthalen-2-ylthio)propanamide (13h) was prepared according to the procedure for 13d except using 4,5-dichloro-N-(3-chloro-4-oxonaphthalen-1(4H)-ylidene)thiophenesulfonamide (12c) and 3-mercapto-N-cyclopropylpropanamide which afforded the title compound 20 mg (37%) as a yellow solid, m.p.: ° C.

$^1$H NMR (400 MHz, CDCl$_3$) δ 8.23 (dd, J=5.6, 3.2 Hz, 1H), 8.16 (dd, J=5.6, 3.2 Hz, 1H), 7.83 (dd, J=4.0, 1.6 Hz, 1H), 7.82 (s, 1H), 7.73 (dd, J=5.2, 1.6 Hz, 1H), 7.70 (dd, J=6.0, 3.6 Hz, 2H); 7.19 (dd, J=4.8, 4.0, 1H), 6.42 (bs, 1H), 3.31 (t, J=8.4 Hz, 2H), 2.82-2.78 (m, 1H), 2.60 (t, J=8.4 Hz, 2H), 0.78 (q, J=5.6 Hz, 2H), 0.60 (q, J=5.6 Hz, 2H).

HRMS (ESI+ve) m/z calculated for $C_{20}H_{19}N_2O_4S_3$ (M+H)$^+$ 447.0512, found 447.0505.

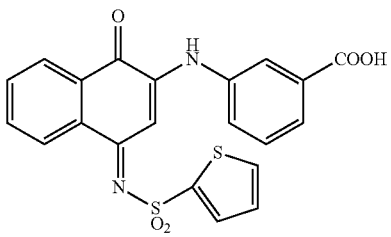

13i 5.2.44 3-(1-oxo-4-(thiophen-2-ylsulfonylimino)-1,4-dihydronaphthalen-2-ylamino)-benzoic acid (13i): 33.8 mg (E)-N-(3-(1-methyl-1H-tetrazol-5-ylthio)-4-oxonaphthalen-1(4H)-ylidene)thiophene-2-sulfonamide (12a) was dissolved in 3 ml THF, to which was added 13.7 mg 3-aminobenzoic acid. The resulting orange solution was stirred at r.t. for 30 min and 0.2 ml THF solution containing 1 eq. pyridine was added. The reaction was continued for 30 min. The mixture was diluted to 50 ml with ethyl acetate and washed with 0.5 N NaHSO$_4$ solution, water and brine. Dried over Na$_2$SO$_4$, the organic phase was filtered and the filtrate was concentrated. The residue was washed with dichloromethylene/hexane (1:1) affording the title compound 32.5 mg (74.2%) as a red solid, m.p.: 230° C. (dec.).

$^1$H-NMR, 400 MHz, CD$_3$CN, δ (ppm): 9.23 (br, 1H), 8.25 (d, J=7.8 Hz, 1H), 8.16 (d, J=7.2 Hz, 1H), 8.03 (s, 1H), 7.99 (d, J=7.5 Hz, 1H), 7.78 (m, 3H), 7.66 (t, J=8.0 Hz, 1H), 7.60 (m, 2H), 7.19 (d, J=2.7 Hz, 1H), 4.3 Hz, 1H).

HRMS (ESI-ve) m/z calculated for $C_{21}H_{14}N_2O_5S_2$ (M-H)$^-$ 437.0271, found 437.0276.

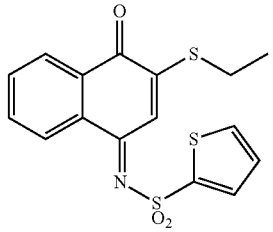

13j 5.2.45 N-(3-(ethylthio)-4-oxonaphthalen-1(4H)-ylidene)thiophene-2-sulfonamide (13j) was prepared according to the procedure for 13d except using ethanethiol, which, after purification via flash chromatography (Hex/EtOAc), afforded the title compound 25 mg (34.4%) as an orange-red solid, m.p.: ° C.

1H-NMR, 400 MHz, CDCl$_3$, δ (ppm): 8.23 (m, 1H), 8.15 (m, 1H), 7.90 (s, 1H), 7.82 (dd, J=1.3 Hz, 3.8 Hz, 1H), 7.69 (m, 3H), 7.15 (dd, J=3.8 Hz, 5.0 Hz, 1H), 3.02 (q, J=7.4 Hz, 2H), 1.50 (t, J=7.4 Hz, 3H).

HRMS (ESI-ve) m/z calculated for $C_{16}H_{13}NO_3S_3$ (M+H)$^+$ 364.0130, found 364.0136.

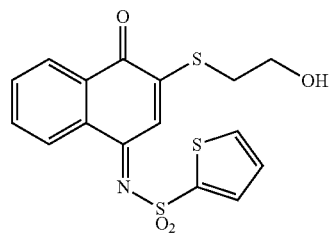

13k 5.2.46 N-(3-(2-hydroxyethylthio)-4-oxonaphthalen-1(4H)-ylidene)thiophene-2-sulfonamide (13k) was prepared according to the procedure for 13d except using 2-mercaptoethanol, which, after purification via flash chromatography (Hex/EtOAc), afforded the title compound 43 mg (56.7%) as an orange-red oil.

$^1$H-NMR, 400 MHz, CDCl$_3$, δ (ppm): 8.23 (m, 1H), 8.15 (m, 1H), 7.99 (s, 1H), 7.83 (dd, J=1.3 Hz, 3.8 Hz, 1H), 7.70 (m, 3H), 7.15 (dd, J=3.8 Hz, 5.0 Hz, 1H), 4.03 (t, J=6.1 Hz, 2H), 3.23 (t, J=6.1 Hz, 2H).

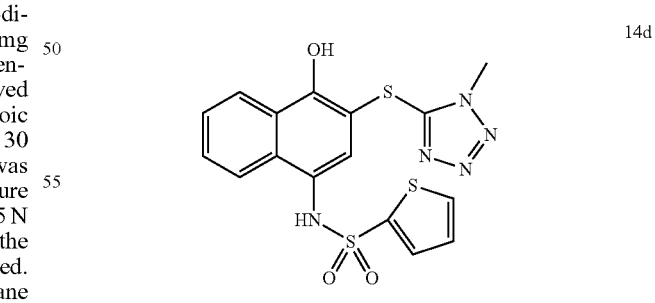

14d 5.2.47 N-(4-hydroxy-3-(1-methyl-1H-tetrazol-5-ylthio)naphthalen-1-yl)thiophene-2-sulfonamide (14d): 13 mg (E)-N-(3-(1-methyl-1H-tetrazol-5-ylthio)-4-oxonaphthalen-1(4H)-ylidene)thiophene-2-sulfonamide (13d) was dissolved in 50 ml ethyl acetate, to which was added 27 mg sodium hydrosulfite solid followed by 10 ml water. The mixture was shaken in a separation funnel until the yellow organic phase turned colorless. The organic phase was separated and washed with water and brine. Dried over Na₂SO₄, the organic phase was filtered and the filtrate was concentrated to dryness. The residue was dissolved in dichloromethylene and triturated with hexane. The precipitate was washed with dichloromethylene/hexane (1:1) affording the title compound 13 mg (99%) as a white solid, m.p.: 130° C. (dec.).

¹H-NMR, 400 MHz, CD₃CN, δ (ppm): 8.28 (dd, J=3.0 Hz, 6.7 Hz, 1H), 8.14 (s, 1H), 7.98 (dd, J=3.5 Hz, 6.2 Hz, 1H), 7.94 (br, 1H), 7.65 (dd, J=1.2 Hz, 5.0 Hz, 1H), 7.61 (dd, J=3.4 Hz, 6.5 Hz, 2H), 7.38 (dd, J=1.2 Hz, 3.7 Hz, 1H), 7.16 (s, 1H), 6.99 (ss, J=3.8 Hz, 4.9 Hz, 1H), 4.00 (s, 3H).

HRMS (ESI+ve) m/z calculated for C₁₆H₁₃N₅O₃S₃ (M+H)⁺ 420.0253, found 420.0240.

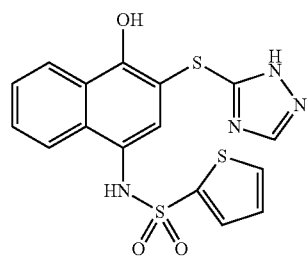
14e 5.2.48 N-(3-(1H-1,2,4-triazol-5-ylthio)-4-hydroxynaphthalen-1-yl)thiophene-2-sulfonamide (14e) was prepared according to the procedure for 14d except using (E)-N-(3-(1H-1,2,4-triazol-5-ylthio)-4-oxonaphthalen-1(4H)-ylidene)thiophene-2-sulfonamide (13e), which afforded the title compound 20 mg (100%) as a white solid, m.p.: 180° C. (dec.).

¹H-NMR, 400 MHz, d⁶-DMSO, δ (ppm): 10.19 (br, 1H), 10.05 (s, 1H), 8.61 (br, 1H), 8.16 (d, J=7.6 Hz, 1H), 7.89 (d, J=7.4 Hz, 1H), 7.81 (d, J=4.2 Hz, 1H), 7.48 (t, J=7.9 Hz, 2H), 7.28 (d, J=2.5 Hz, 1H), 6.99 (t, J=4.2 Hz, 1H), 6.91 (br, 1H).

HRMS (ESI−ve) m/z calculated for C₁₆H₁₂N₄O₃S₃ (M−H)⁻ 402.9999, found 402.9989.

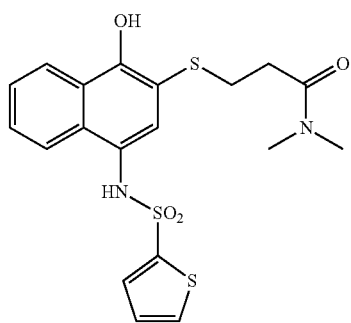
14f 5.2.49 3-(1-hydroxy-4-(thiophene-2-sulfonamido)naphthalen-2-ylthio)-N,N-dimethylpropanamide (14f) was prepared according to the procedure for 9a except using 13f affording 9.8 mg (98%) title compound, m.p.: ° C.

¹H NMR (400 MHz, CD₃CN) δ 8.32-8.29 (m, 1H), 7.97-7.95 (m, 1H), 7.83 (s, 1H), 7.71 (dd, J=5.2, 1.2 Hz, 1H), 7.54-7.52 (m, 2H), 7.40 (dd, J=3.6, 1.2 Hz, 1H); 7.08-7.06 (m, 2H), 2.30 (s, 3H), 2.98 (s, 3H), 2.93 (t, J=6.4 Hz, 2H), 2.57 (t, J=6.4 Hz, 2H).

HRMS (ESI+ve) m/z calculated for C₁₉H₂₁N₂O₄S₃ (M+H)⁺ 437.0658, found 447.0606.

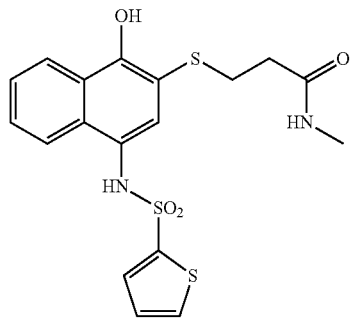
14g 5.2.50 3-(1-hydroxy-4-(thiophene-2-sulfonamido)naphthalen-2-ylthio)-N-methylpropanamide (14g) was prepared according to the procedure for 9a except using 13g affording 7.8 mg (80%) title compound, m.p.: ° C.

¹H NMR (400 MHz, CD₃CN) δ 9.67 (s, 1H), 8.30-8.28 (m, 1H), 7.99-7.97 (m, 1H), 7.86 (s, 1H), 7.71 (dd, J=5.2, 1.6 Hz, 1H), 7.54 (dd, J=6.8, 3.6 Hz, 2H), 7.41 (dd, J=5.2, 1.6 Hz, 1H); 7.08-7.06 (m, 2H), 6.56 (bs, 1H), 3.81 (t, J=8.0 Hz, 2H), 2.75 (d, J=4.8 Hz, 3H), 2.30 (t, J=8.0 Hz, 2H).

HRMS (ESI+ve) m/z calculated for C₁₈H₁₉N₂O₄S₃ (M+H)⁺ 423.0502, found 423.0478.

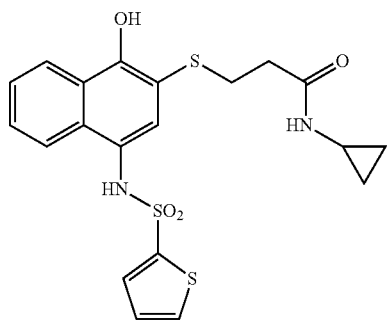
14h 5.2.51 N-cyclopropyl-3-(1-hydroxy-4-(thiophene-2-sulfonamido)naphthalen-2-ylthio)propanamide (14h) was prepared according to the procedure for 9a except using 13h affording 8.8 mg (89%) title compound, m.p.: ° C.

¹H NMR (400 MHz, CD₃CN) δ 9.50 (s, 1H), 8.29 (dd, J=5.6, 3.2 Hz, 1H), 7.99 (dd, J=5.6, 3.2 Hz, 1H), 7.85 (s, 1H), 7.70 (dd, J=3.6, 1.2 Hz, 1H), 7.55-7.53 (m, 2H), 7.41 (dd, J=3.6, 1.2 Hz, 1H), 7.08-7.05 (m, 2H), 6.75 (bs, 1H), 2.92 (t, J=8.4 Hz, 2H), 2.74-2.68 (m, 1H), 2.46 (t, J=8.4 Hz, 2H), 0.68 (q, J=5.6 Hz, 2H), 0.47 (q, J=5.6 Hz, 2H).

HRMS (ESI+ve) m/z calculated for C₂₀H₂₁N₂O₄S₃ (M+H)⁺ 449.0658, found 449.0639.

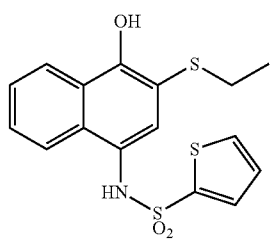
14j

5.2.52 N-(3-(ethylthio)-4-hydroxynaphthalen-1-yl)thiophene-2-sulfonamide (14j)

was prepared according to the procedure for 14d except using (E)-N-(3-ethylthio-4-oxonaphthalen-1(4H)-ylidene)thiophene-2-sulfonamide (13j), which afforded the title compound 14 mg (100%) as a grey solid, m.p.: ° C.

$^1$H-NMR, 400 MHz, CD$_2$Cl$_2$, δ (ppm): 8.24 (m, 1H), 7.90 (m, 1H), 7.58 (dd, J=1.2 Hz, 5.0 Hz, 1H), 7.53 (m, 2H), 7.46 (s, 1H), 7.39 (dd, J=1.3 Hz, 3.8 Hz, 1H), 7.28 (s, 1H), 7.00 (dd, J=3.8 Hz, 4.9 Hz, 1H), 6.71 (br, 1H), 2.71 (q, J=7.3 Hz, 2H), 1.17 (t, J=7.3 Hz, 3H).

HRMS (ESI+ve) m/z calculated for C$_{16}$H$_{15}$NO$_3$S$_3$(M+Na)$^+$388.0106, found 388.0107.

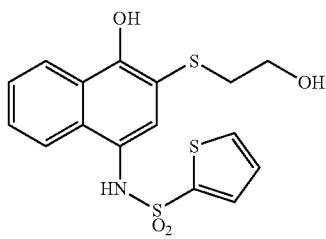

14k

5.2.53 N-(4-hydroxy-3-(2-hydroxyethylthio)naphthalen-1-yl)thiophene-2-sulfonamide (14k)

was prepared according to the procedure for 14d except using N-(3-(2-hydroxyethylthio)-4-oxonaphthalen-1(4H)-ylidene)thiophene-2-sulfonamide (13k), which, after purification via flash chromatography (Hex/EtOAc), afforded the title compound 20.3 mg (53.1%) as a grey solid, m.p.: ° C.

$^1$H-NMR, 400 MHz, d$^6$-DMSO, δ (ppm): 10.06 (s, 1H), 9.70 (s, 1H), 8.12 (d, J=7.7 Hz, 1H), 7.88 (m, 2H), 7.45 (m, 2H), 7.35 (dd, J=1.3 Hz, 3.7 Hz, 1H), 7.07 (dd, J=3.8 Hz, 5.0 Hz, 1H), 6.99 (s, 1H), 5.10 (t, J=5.1 Hz, 1H), 2.75 (t, J=6.7 Hz, 2H).

$^1$H-NMR, 400 MHz, CD$_2$Cl$_2$+CD$_3$CN, δ (ppm): 8.24 (m, 1H), 8.10 (br, 1H), 7.90 (m, 1H), 7.58 (dd, J=1.3 Hz, 5.0 Hz, 1H), 7.51 (m, 2H), 7.37 (dd, J=1.3 Hz, 17 Hz, 1H), 7.23 (s, 1H), 7.11 (br, 1H), 7.00 (dd, J=3.8 Hz, 5.0 Hz, 1H), 3.60 (t, J=5.9 Hz, 2H), 2.83 (t, J=5.8 Hz, 2H), 2.02 (br, 1H).

HRMS (ESI+ve) m/z calculated for C$_{16}$H$_{15}$NO$_4$S$_3$(M+Na)$^+$404.0055, found 404.0049.

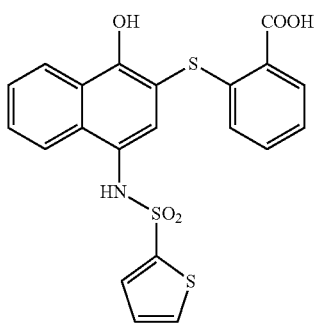

14l

5.2.54 2-(1-hydroxy-4-(thiophene-2-sulfonamido)naphthalen-2-ylthio)benzoic acid (14l)

was prepared according to the procedure of procedure B for 10a except using thiosalicylic acid, which afforded the title compound 19 mg (99%) as a white solid, m.p.: 215° C. (dec.).

$^1$H-NMR, 400 MHz, d$^6$-DMSO, δ (ppm): 13.13 (br, 1H), 10.09 (s, 1H), 8.20 (d, J=8.3 Hz, 1H), 8.01 (d, J=7.7 Hz, 1H), 7.93 (d, J=8.1 Hz, 1H), 7.76 (d, J=5.0 Hz, 1H), 7.54 (m, 2H), 7.33 (m, 2H), 7.18 (t, 7.5 Hz, 1H), 6.91 (m, 2H), 6.47 (d, J=8.5 Hz, 1H).

HRMS (ESI-ve) m/z calculated for C$_{21}$H$_{15}$NO$_5$S$_3$ (M-H)$^-$ 456.0040, found 456.0025.

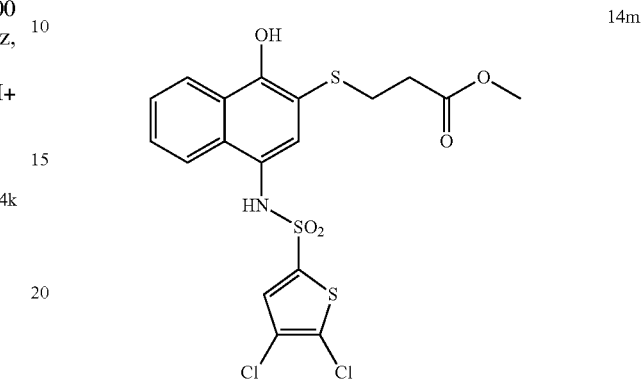

14m

5.2.55 Methyl-3-(4-(4,5-dichlorothiophene-2-sulfonamido)-1-hydroxynaphthalen-2-ylthio)propanoate (14m)

was prepared according to the procedure of procedure B for 10a except using 4,5-dichloro-N-(3-chloro-4-oxonaphthalen-1(4H)-ylidene)thiophenesulfonamide (12c) and ethyl mercaptoacetate, which afforded the title compound 16.1 mg (33%) as a grey solid after flash chromatography (Hex/EtOAc), m.p.: ° C.

$^1$H NMR (400 MHz, CD$_3$CN) δ 8.24 (s, 1H), 8.22 (d, J=8.4 Hz, 1H), 7.87 (d, J=8.4 Hz, 1H), 7.65 (s, 1H), 7.60-7.51 (m, 2H), 7.29 (s, 2H); 3.66 (s, 3H), 2.94 (t, J=6.8 Hz, 2H), 2.73 (t, J=6.8 Hz, 2H).

HRMS (ESI-ve) m/z calculated for C$_{18}$H$_{14}$Cl$_2$NO$_5$S$_3$ (M-H)$^-$ 489.9417, found 489.9454.

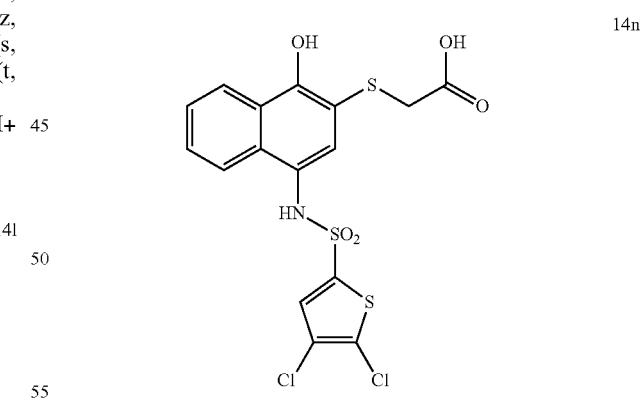

14n

5.2.56 2-(4-(4,5-dichlorothiophene-2-sulfonamido)-1-hydroxynaphthalen-2-ylthio)acetic acid (14n)

was prepared according to the procedure of procedure B for 10a except using 4,5-dichloro-N-(3-chloro-4-oxonaphthalen-1(4H)-ylidene)thiophenesulfonamide (12c), which afforded the title compound 17.8 mg (39%) as a white solid, m.p.: ° C.

$^1$H NMR (400 MHz, DMSO-d$_6$) δ 10.63 (s, 1H), 10.36 (s, 1H), 8.18 (d, J=8.4 Hz, 1H), 7.81 (d, J=8.4 Hz, 1H), 7.53 (t, J=7.6 Hz, 1H), 7.49-7.45 (m, 2H), 7.14 (s, 1H).

HRMS (ESI-ve) m/z calculated for C$_{16}$H$_{10}$Cl$_2$NO$_5$S$_3$ (M-H)$^-$ 461.9104, found 461.9083.

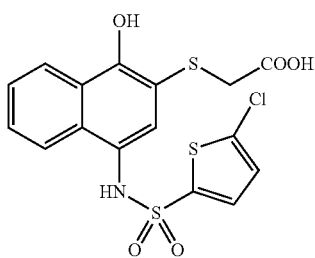

5.2.57 2-(4-(5-chlorothiophene-2-sulfonamido)-1-hydroxynaphthalen-2-ylthio)acetic acid (14o) was prepared according to the procedure of procedure B for 10a except using (E)-5-chloro-N-(3-chloro-4-oxonaphthalen-1(4H)-ylidene)thiophene-2-sulfonamide (12d), which afforded the title compound 32.4 mg (54%) as a white solid, m.p.: 143-145° C.

$^1$H-NMR, 400 MHz, d$^6$-DMSO, δ (ppm): 12.73 (br, 1H), 10.28 (s, 1H), 9.97 (br, 1H), 8.15 (d, J=7.7 Hz, 1H), 7.85 (d, J=8.6 Hz, 1H), 7.47 (m, 2H), 7.22 (d, J=4.1 Hz, 1H), 7.13 (s, 1H), 7.12 (d, J=4.1 Hz, 1H), 3.56 (s, 2H).

HRMS (ESI–ve) m/z calculated for $C_{16}H_{12}ClNO_5S_3$ (M–H)$^-$ 427.9493, found 427.9461.

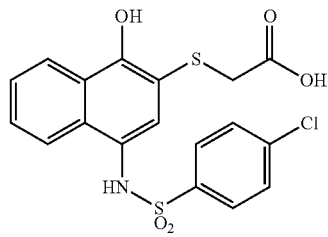

5.2.58 2-(4-(4-chlorophenylsulfonamido)-1-hydroxynaphthalen-2-ylthio)acetic acid (14p) was prepared according to the procedure of procedure B for 10a except using (E)-4-chloro-N-(3-chloro-4-oxonaphthalen-1(4H)-ylidene)-benzene sulfonamide (12e), which afforded the title compound 57.7 mg (68.4%) as a white solid, m.p.: 158-160° C.

$^1$H-NMR, 400 MHz, d$^6$-DMSO, δ (ppm): 12.76 (br, 1H), 10.03 (s, 1H), 9.85 (br, 1H), 8.12 (d, J=8.2 Hz, 1H), 7.81 (d, J=8.4 Hz, 1H), 7.60 (d, J=8.7 Hz, 2H), 7.54 (d, J=8.8 Hz, 2H), 7.46 (t, J=7.5 Hz, 1H), 7.41 (t, J=7.5 Hz, 1H), 7.01 (s, 1H), 3.5 (s, 2H).

HRMS (ESI–ve) m/z calculated for $C_{18}H_{14}ClNO_5S_2$ (M–H)$^-$ 421.9929, found 421.9955.

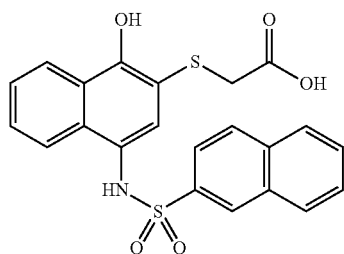

5.2.59 2-(1-hydroxy-4-(naphthalene-2-sulfonamido) naphthalen-2-ylthio)acetic acid (14q) was prepared according to the procedure of procedure B for 10a except using (E)-N-(3-chloro-4-oxonaphthalen-1(4H)-ylidene)naphthalene-2-sulfonamide (12f), which afforded the title compound 64.3 mg (73.5%) as a white solid, m.p.: 185-187° C.

$^1$H-NMR, 400 MHz, d$^6$-DMSO, δ (ppm): 12.72 (br, 1H), 10.02 (s, 1H), 9.75 (br, 1H), 8.20 (s, 1H), 8.07 (t, J=8.3 Hz, 2H), 8.01 (d, J=8.3 Hz, 1H), 7.98 (d, J=8.4 Hz, 1H), 7.90 (d, J=8.2 Hz, 1H), 7.75 (d, J=8.7 Hz, 1H), 7.65 (t, J=7.5 Hz, 1H), 7.58 (t, J=7.6 Hz, 1H), 7.40 (t, J=7.2 Hz, 1H), 7.35 (t, J=7.3 Hz, 1H), 6.97 (s, 1H).

$^1$H-NMR, 400 MHz, CD$_3$CN, δ (ppm): 8.22 (m, 1H), 8.19 (s, 1H), 8.02 (m, 3H), 7.93 (d, J=7.9 Hz, 1H), 7.81 (s, 1H), 7.78 (d, J=8.9 Hz, 1H), 7.69 (t, J=7.5 Hz, 1H), 7.62 (t, J=7.2 Hz, 1H), 7.49 (m, 2H), 6.99 (s, 1H), 3.28 (s, 2H).

HRMS (ESI–ve) m/z calculated for $C_{22}H_{17}NO_5S_2$ (M–H)$^-$ 438.0475, found 438.0500.

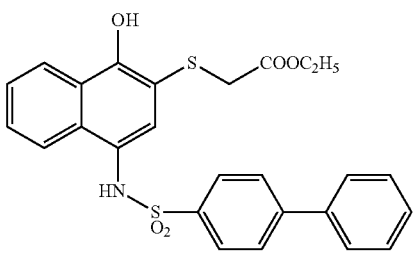

5.2.60 Ethyl 2-(4-(biphenyl-4-ylsulfonamido)-1-hydroxynaphthalen-2-ylthio)acetate (14r) was prepared according to the procedure of procedure B for 10a except using (E)-N-(3-chloro-4-oxonaphthalen-1(4H)-ylidene)biphenyl-4-sulfonamide (12b) and ethyl mercapto-acetate, which afforded the title compound 71.5 mg (85.5%) as an off-white solid, m.p.: 166-168° C.

$^1$H-NMR, 400 MHz, CDCl$_3$, δ (ppm): 8.40 (s, 1H), 8.27 (m, 1H), 7.85 (m, 1H), 7.76 (d, J=8.4 Hz, 2H), 7.59 (d, J=8.4 Hz, 2H), 7.55 (d, J=6.9 Hz, 2H), 7.46 (m, 4H), 7.41 (t, J=7.1 Hz, 1H), 7.28 (s, 1H), 6.83 (s, 1H), 4.15 (q, J=7.1 Hz, 2H), 3.41 (s, 2H), 1.20 (t, J=7.1 Hz, 3H).

HRMS (ESI–ve) m/z calculated for $C_{26}H_{23}NO_5S_2$ (M+Na)$^+$ 516.0910, found 516.0903.

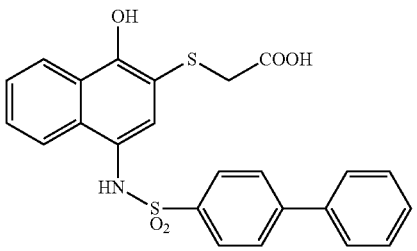

5.2.61 2-(4-(biphenyl-4-ylsulfonamido)-1-hydroxynaphthalen-2-ylthio)acetic acid (14s) was prepared according to the procedure of procedure B for 10a except using ethyl 2-(4-(biphenyl-4-ylsulfonamido)-1-hydroxynaphthalen-2-ylthio)acetate (14r) and applying r.t. overnight to the reaction, which afforded the title compound 19.2 mg (40.7%) as a grey solid, m.p.: 170° C. (dec.).

$^1$H-NMR, 400 MHz, d$^6$-DMSO, δ (ppm): 12.76 (br, 1H), 9.96 (s, 1H), 9.81 (br, 1H), 8.11 (d, J=7.7 Hz, 1H), 7.89 (d, J=7.6 Hz, 1H), 7.77 (d, J=8.2 Hz, 2H), 7.67 (m, 4H), 7.45 (m, 5H), 7.01 (s, 1H), 3.47 (s, 2H).

HRMS (ESI–ve) m/z calculated for $C_{24}H_{19}NO_5S_2$ (M–H)$^-$ 464.0632, found 464.0638.

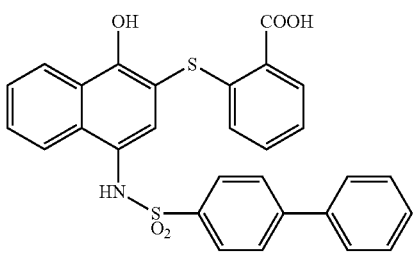

5.2.62 2-(4-(biphenyl-4-ylsulfonamido)-1-hydroxynaphthalen-2-ylthio)benzoic acid (14t) was prepared according to the procedure of procedure B for 10a except using 2-thiosalicylic acid and (E)-N-(3-chloro-4-oxonaphthalen-1(4H)-ylidene)biphenyl-4-sulfonamide (12b), which afforded the title compound 17.4 mg (65.9%) as an off-white solid, m.p.: 205° C. (dec.).

$^1$H-NMR, 400 MHz, d$^6$-DMSO, δ (ppm): 13.12 (br, 1H), 10.07 (br, 1H), 9.90 (s, 1H), 8.20 (d, J=8.8 Hz, 1H), 8.12 (d, J=8.2 Hz, 1H), 7.92 (d, J=7.9 Hz, 1H), 7.65 (d, J=8.5 Hz, 2H), 7.60 (d, J=8.3 Hz, 2H), 7.54 (m, 2H), 7.40 (m, 6H), 7.13 (t, 7.8 Hz, 1H), 6.72 (s, 1H), 6.42 (d, J=8.1 Hz, 1H).

HRMS (ESI–ve) m/z calculated for $C_{29}H_{21}NO_5S_2$ (M–H)$^-$ 526.0788, found 526.0788.

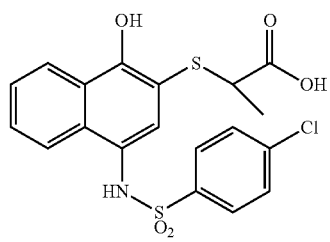

5.2.63 2-(4-(4-chlorophenylsulfonamido)-1-hydroxynaphthalen-2-ylthio)propanoic acid (14u) was prepared according to the procedure of procedure B for 10a except using thiolactic acid and (E)-4-chloro-N-(3-chloro-4-oxonaphthalen-1(4H)-ylidene)-benzenesulfonamide (12e), which afforded the title compound 41.3 mg (49%) as a white solid, m.p.: 177-179° C.

$^1$H-NMR, 400 MHz, CD$_3$CN, δ (ppm): 8.22 (m, 1H), 7.93 (m, 1H), 7.84 (s, 1H), 7.64 (d, J=8.6 Hz, 2H), 7.55 (m, 2H), 7.47 (d, J=8.5 Hz, 2H), 7.10 (s, 1H), 3.64 (q, J=7.2 Hz, 1H), 1.35 (d, J=7.2 Hz, 3H).

HRMS (ESI–ve) m/z calculated for $C_{19}H_{16}ClNO_5S_2$ (M–H)$^-$ 436.0086, found 436.0106.

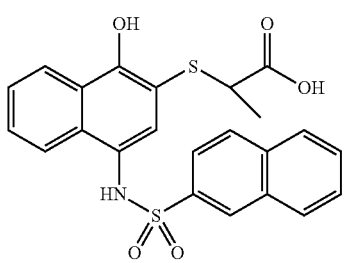

5.2.64 2-(1-hydroxy-4-(naphthalene-2-sulfonamido)naphthalen-2-ylthio)propanoic acid (14v) was prepared according to the procedure of procedure B for 10a except using thiolactic acid and (E)-N-(3-chloro-4-oxonaphthalen-1(4H)-ylidene)naphthalene-2-sulfonamide (12f), which afforded the title compound 51.3 mg (58.6%) as an off-white solid, m.p.: 176-178° C.

$^1$H-NMR, 400 MHz, d$^6$-DMSO, δ (ppm): 12.70 (br, 1H), 10.01 (s, 1H), 9.74 (br, 1H), 8.18 (s, 1H), 8.10 (m, 2H), 7.99 (m, 3H), 7.80 (dd, J=1.6 Hz, 8.7 Hz, 1H), 7.65 (t, J=7.5 Hz, 1H), 7.58 (t, J=7.6 Hz, 1H), 7.43 (m, 2H), 6.88 (s, 1H), 0.87 (d, J=7.1 Hz, 3H).

$^1$H-NMR, 400 MHz, CD$_3$CN, δ (ppm): 8.19 (m, 2H), 8.04 (m, 2H), 7.99 (d, J=8.2 Hz, 1H), 7.92 (d, J=8.2 Hz, 1H), 7.85 (s, 1H), 7.81 (dd, J=1.6 Hz, 8.7 Hz, 1H), 7.68 (t, J=7.6 Hz, 1H), 7.61 (t, J=7.5 Hz, 1H), 7.50 (m, 2H), 7.00 (s, 1H), 3.36 (q, J=7.2 Hz, 1H), 1.09 (d, J=7.2 Hz, 3H).

HRMS (ESI–ve) m/z calculated for $C_{23}H_{19}NO_5S_2$ (M–H)$^-$ 452.0632, found 452.0621.

5.3 Proteasome Inhibition Assay

The assay was conducted by using a fluorogenic peptide as substrate to test synthesized compounds for inhibitory activity against the chymotrypsin-like activity of the purified rabbit 20S proteasome. Briefly, 70 ng of purified 20S proteasome was incubated with 20 µM Suc-Leu-Leu-Val-Tyr-AMC for 1 hour at 37° C. in 100 µl of assay buffer (50 mM Tris-HCl, pH 7.6) with or without inhibitors. After incubation, production of hydrolyzed 7-amido-4-methyl-coumarin (AMC) was measured using a WALLAC Victor2 1420 Multilabel Counter with an excitation filter of 355 nm and an emission filter of 460 nm (Perkin Elmer Life Sciences, Turku, Finland). The inhibitory activity of the compounds was calculated based on vehicle control.

REFERENCES

1. Adams, J., *Cancer Cell*, 2004, 5, 417-421
2. Yamasaki, L.; Pagano, M. *Curr. Opin. Cell Biol.*, 2004, 16, 623-628.
3. Ciechanover, A.; Orian, A.; Schwartz, A. L. *J Cell Biochem Suppl*, 2000, 34, 40-51.
4. Ciechanover, A. *Cell*, 1994, 79, 13-21.
5. Hochstrasser, M. *Curr. Opin. Cell Biol.* 1995, 7, 215-223.
6. Coux, O.; Tanaka, K.; Goldberg, A. L. *Annu Rev Biochem*, 1996, 65, 801-847.
7. Baumeister, W.; Walz, J.; Zuhl, F.; Seemuller, E. *Cell*, 1998, 92, 367-380.
8. Murata, S.; Yashiroda, H.; Tanaka, K. *Nat. Rev. Mol.*, 2009, 10, 104-115.
9. Yamasaki, L.; Pagano, M. *Curr. Opin. Cell Biol.*, 2004, 16, 623-628.
10. Ostrowska, H. *Cell. Mol. Biol. Lett.*, 2008, 13, 353-365.
11. Bennett, M. K.; Kirk, C. *J. Curr. Opin. Drug Discovery Dev.*, 2008, 11, 616-625.
12. Adams, *J. Nat. Rev. Cancer*, 2004, 4, 349-360.
13. Voorhees, P. M.; Dees, E. C.; O'Neil, B.; Orlowski, R. Z. *Clin. Cancer Res.* 2003, 9, 6316-6325.
14. Nalepa, G.; Rolfe, M.; Harper, J. W. *Nat. Rev. Drug Discovery* 2006, 5, 596-613.
15. Zavrski, I.; Jakob, C.; Schmid, P.; Krebbel, H.; Kaiser, M.; Fleissner, C.; Rosche, M.; Possinger, K.; Sezer, O. *Anti-Cancer Drugs*, 2005, 16, 475-481.
16. Jung, L.; Holle, L.; Dalton William, S. *Oncology*, 2004, 18, 4-13.
17. Lara, P. N., Jr.; Davies, A. M.; Mack, P. C.; Mortenson, M. M.; Bold, R. J.; Gumerlock, P. H.; Gandara, D. R. *Semin. Oncol.*, 2004, 31, 40-46.

18. Adams, J. *Semin. Oncol.,* 2001, 28, 613-619.
19. Sterz, J.; von Metzler, I.; Hahne, J.-C.; Lamottke, B.; Rademacher, J.; Heider, U.; Terpos, E.; Sezer, O. *Expert Opin. Invest. Drugs,* 2008, 17, 879-895.
20. Kuhn, D. J.; Chen, Q.; Voorhees, P. M.; Strader, J. S.; Shenk, K. D.; Sun, C. M.; Demo, S. D.; Bennett, M. K.; van Leeuwen, F. W. B.; Chanan-Khan, A. A.; Orlowski, R. Z. *Blood,* 2007, 110, 3281-3290.
21. Chauhan, D.; Hideshima, T.; Anderson, K. C. *Br. J. Cancer,* 2006, 95, 961-965.
22. McConkey, D. J. and Zhu, K., *Drug Resistance Updates,* 2008, 11, 164-179.
23. Chauhan, D., Catley, L., Li, G., et al., *Cancer Cell,* 2005, 8, 407-419.
24. Chauhan, D., Singh, A., Brahmandam, M., et al., *Blood,* 2008, 111, 1654-1664.
25. Miller, C. P.; Ban, K.; Dujka, M. E.; McConkey, D. J.; Munsell, M.; Palladino, M.; Chandra, J.; *Blood,* 2007, 110, 267-277.
26. PI-008183 to be published.
27. Altland, H. W. and Briffa, Jr., B. F., *J. Org. Chem.,* 1985, 50, 433-437.
28. U.S.S.R patent 1558901, 1990
29. Lien, J. C.; Huang, L. J.; Teng, C. M; et al, *Chem. Pharm. Bull.,* 2002, 50, 672-674.
30. Obafemi, C. A., *Phosphorus and Sulfur and the Related Elements,* 1980, 8, 197-199
31. Adams, R. and Whitaker, L., *J. Am. Chem. Soc.,* 1956, 78, 658-663.
32. Travis, B. R., Cimaramitaro, B. P. and Borhan, B., *European Journal of Organic Chemistry,* 2002, 20, 3429-3434.
33. Adams, R. and Wankel, R. A., *J. Am. Chem. Soc.,* 1951, 73, 131-134
34. Matsubara, R.; Doko, T.; Uetake, R. and Kobayashi, S., *Angew. Chem. Int. Ed,* 2007, 46, 3047-3050.
35. Esquivias, J.; Arrayas, R. G. and Carretero, J. C., *J. Am. Chem. Soc.,* 2007, 129, 1480-1481
36. Amone, A., *Synth. Commun.,* 2007, 37, 2569-2577
37. Bennett, M. K., Kirk, C. J., *Current Opinion in Drug Discovery & Development,* 2008, 11, 616-625.
38. Fenteany, G. and Schreiber, S. L., *Chemistry & Biology,* 1996, 3, 905-912.

It should be understood that the examples and embodiments described herein are for illustrative purposes only and that various modifications or changes in light thereof will be suggested to persons skilled in the art and are to be included within the spirit and purview of this application and the scope of the appended claims. In addition, any elements or limitations of any invention or embodiment thereof disclosed herein can be combined with any and/or all other elements or limitations (individually or in any combination) or any other invention or embodiment thereof disclosed herein, and all such combinations are contemplated with the scope of the invention without limitation thereto.

REFERENCES

U.S. Pat. No. 4,559,157
U.S. Pat. No. 4,608,392
U.S. Pat. No. 4,820,508
U.S. Pat. No. 4,938,949
U.S. Pat. No. 4,992,478
U.S. Pat. No. 5,167,649
U.S. Pat. No. 6,960,648
U.S. Published Patent Application No. 20020035243
U.S. Published Patent Application No. 20020120100
U.S. Published Patent Application No. 20030032594

Adams J and Kauffman M (2004) "Development of the proteasome inhibitor Velcade (Bortezomib)" *Cancer Invest,* 22:304-11
Adams J, Palombella V J, Sausville E A, et al. (1999) "Proteasome Inhibitors: A Novel Class of Potent and Effective Antitumor Agents" *Cancer Res,* 59:2615-22
Adams J (2004a) "The development of proteasome inhibitors as anticancer drugs" *Cancer Cell,* 5:417-2
Adams J (2004b) "The proteasome: A suitable antineoplastic target" *Nat Rev Cancer,* 4:349-60
Aghajanian C, Soignet S, Dizon D S, et al. (2002) "A phase I trial of the novel proteasome inhibitor PS341 in advanced solid tumor malignancies" *Clin Cancer Res,* 8:2505-11
Arrigo A P, Tanaka K, Goldberg A L, Welch W J (1988) "Identity of the 19S 'prosome' particle with the large multifunctional protease complex of mammalian cells (the proteasome)" *Nature,* 331:192-4
Bang S M, Lee J H, Yoon S S, et al. (2006) "A multicenter retrospective analysis of adverse events in Korean patients using bortezomib for multiple myeloma" *Int J Hematol,* 83:309-13
Bazzaro M, Lee M K, Zoso A, et al. (2006) "Ubiquitin-proteasome system stress sensitizes ovarian cancer to proteasome inhibitor-induced apoptosis" *Cancer Res,* 66:3754-63
Blackburn C (2005) *Tetrahedron Lett.,* 46:1405
Bold R J, Virudachalam S, McConkey D J (2001) "Chemosensitization of pancreatic cancer by inhibition of the 26S proteasome" *J Surg. Res.,* 100:11-17
Burger A M and Seth A K (2004) "The ubiquitin-mediated protein degradation pathway in cancer: Therapeutic implications" *Eur J Cancer,* 40:2217-29
Calandra J C, Adams E C, Jr. (1950) *J. Am. Chem. Soc.,* 72:4804
Ciechanover A (1994) "The ubiquitin-proteasome proteolytic pathway" *Cell,* 79:13-21
Codony-Servat J, Tapia M A, Bosch M, et al. (2006) "Differential cellular and molecular efffects of bortezomib, a proteasome inhibitor, in human breast cancer cells" *Mol Cancer Ther,* 5:665-75
Coux O, Tanaka K, Goldberg A L (1996) "Structure and functions of the 20S and 26S proteasomes" *Annu Rev Biochem,* 65:801-47
Davies A M, Ho C, Metzger A S, et al. (2007) "Phase I study of two different schedules of bortezomib and pemetrexed in advanced solid tumors with emphasis on non-small cell lung cancer" *J Thorac Oncol,* 2:1112-6
Davis N B, Taber D A, Ansari R H, et al. (2004) "Phase II trial of PS-341 in patients with renal cell cancer: A University of Chicago phase II consortium study" *J Clin Oncol,* 22:115-9
Downward J (2003) "Targeting ras signalling pathways in cancer therapy" Nat Rev *Cancer,* 3:11-22
Esquivias, J., R. G. Arrayas and J. C. Carretero (2007) *J. Am. Chem. Soc.,* 129:1480-1481
Groll M, Berkers C R, Ploegh H L, Ovaa H (2006) "Crystal structure of the boronic acid-based proteasome inhibitor bortezomib in complex with the yeast 20S proteasome" *Structure,* 14:451-6
Groll M, Ditzel L, Löwe J, et al. (1997) "Structure of the 20S proteasome from yeast at 2.4 A resolution" *Nature,* 386: 463-71
Groll M, Koguchi Y, Huber R, Kohno J (2001) "Crystal structure of the 20S proteasome:TMC-95A complex: A non-covalent proteasome inhibitor" *J Mol Biol,* 311:543-8
Hahn W C and Weinberg R A (2002) "Modelling the molecular circuitry of cancer" *Nat Rev Cancer,* 2:331-41

Hershko A, Heller H, Elias S, Ciechanover A (1983) "Components of the ubiquitin-protein ligase system" *J Biol Chem,* 258:8206-14

Hideshima T, Richardson P, Chauhan D, et al. (2001) "The proteasome inhibitor PS-341 inhibits growth, induces apoptosis, and overcomes drug resistance in human multiple myeloma cells" *Cancer Res,* 61:3071-6

Hochstrasser M (1995) "Ubiquitin, proteasomes, and the regulation of intracellular protein degradation" *Curr Opin Cell Biol,* 7:215-23

Ikezoe T, Yang Y, Saito T, Koeffler H P, Taguchi H (2004) "Proteasome inhibitor PS-341 down-regulates prostate-specific antigen (PSA) and induces growth arrest and apoptosis of androgen-dependent human prostate cancer LNCaP cells" *Cancer Sci,* 95:271-5

Jagannath S, Durie B G, Wolf J, et al. (2005) "Bortezomib therapy alone and in combination with dexamethasone for previously untreated symptomatic multiple myeloma" *Br J Haematol,* 129:776-83

Kazi A, Wang Z, Kumar N, Falsetti S C, Chan T H, Dou Q P (2004) "Structure-activity relationships of synthetic analogs of (−)-epigallocatechin-3-gallate as proteasome inhibitors" *Anticancer Res,* 24:943-54

Kisselev A F and Goldberg A L (2001) "Proteasome inhibitors: From research tools to drug candidates" *Chem & Biol,* 8:739-58

Kondagunta G V, Drucker B, Schwartz L, et al. (2004) "Phase II trial of bortezomib for patients with advanced renal cell carcinoma" *J Clin Oncol,* 22:3720-5

Ling Y-h, Liebes L, Zou Y, Perez-Soler R. (2003) "Reactive Oxygen Species Generation and Mitochondrial Dysfunction in the Apoptotic Response to Bortezomib, a Novel Proteasome Inhibitor, in Human H460 Non-small Cell Lung Cancer Cells" *J Biol Chem,* 278:33714-23

Liu J, Yang G, Thompson-Lanza J A, et al. (2004) "A genetically defined model for human ovarian cancer" *Cancer Res,* 64:1655-63

Mani A and Gelmann E P (2005) "The ubiquitin-proteasome pathway and its role in cancer" *J Clin Oncol,* 23:4776-89

Matsubara, R., T. Doko, R. Uetake and S. Kobayashi (2007) *Angew. Chem. Int. Ed,* 46:3047-3050

Mortenson M M, Schlieman M G, Virudachalam S, Bold R J (2004) "Effects of the proteasome inhibitor bortezomib alone and in combination with chemotherapy in the A549 non-small-cell lung cancer cell line" *Cancer Chemother Pharmacol,* 54:343-53

Nagy H K, Tomson A J, Horwitz J P (1960) *J. Am. Chem. Soc.,* 82:1609-1613

Nalepa G, Rolfe M, Harper J W (2006) "Drug discovery in the ubiquitin-proteasome system" *Nat Rev Cancer,* 5:596-612

Oakervee H E, Popat R, Curry N, et al. (2005) "PAD combination therapy (PS-341/bortezomib, doxorubicin and dexamethasone) for previously untreated patients with multiple myeloma" *Br J Haematol,* 129:755-62

Papandreou C N, Daliani D D, Nix D, et al. (2004) "Phase I trial of the proteasome inhibitor bortezomib in patients with advanced solid tumors with observations in androgen-independent prostate cancer" *J Clin Oncol,* 22:2108-21

Papandreou C N and Logothetis C J (2004) "Bortezomib as a potential treatment for prostate cancer" *Cancer Res,* 64:5036-43

Prescott B (1969) "Potential antimalarial agents. Derivatives of 2-chloro-1,4-naphthoquinone" *J. Med Chem,* 12:181-2

Qian J, Niu J, Li M, Chiao P J, et al. (2005) "In vitro modeling of human pancreatic duct epithelial cell transformation defines gene expression changes induced by K-ras oncogenic activation in pancreatic carcinogenesis" *Cancer Res,* 65:5045-53

Raff M C (1992) "Social controls on cell survival and cell death" *Nature,* 356:397-400

Rangarajan A, Hong S J, Gifford A, Weinberg R A (2004) "Species- and cell type-specific requirements for cellular transformation" *Cancer Cell,* 6:171-83

Richardson P G, Hideshima T, Anderson K C (2003) "Bortezomib (PS-341): a novel, first-in-class proteasome inhibitor for the treatment of multiple myeloma and other cancers" *Cancer Control,* 10:361-9

Richardson P G, Mitsiades C, Hideshima T, Anderson K C (2005) "Proteasome inhibition in the treatment of cancer" *Cell Cycle,* 4:290-6

Scagliotti G (2006) "Proteasome inhibitors in lung cancer" *Crit. Rev Oncol Hematol,* 58:177-89

Sunwoo J B, Chen Z, Dong G, et al. (2001) "Novel proteasome inhibitor PS-341 inhibits activation of nuclear factor-kappa B, cell survival, tumor growth, and angiogenesis in squamous cell carcinoma" *Clin Cancer Res,* 7:1419-28

Toyoizumi T, Mick R, Abbas A E, Kang E H, Kaiser L R, Molnar-Kimber K L (1999) "Combined therapy with chemotherapeutic agents and herpes simplex virus type IICP34.5 mutant (HSV-1716) in human non-small cell lung cancer" *Human Gene Therapy,* 10(18):17

Voges D, Zwickl P, Baumeister W (1999) "The 26S proteasome: a molecular machine designed for controlled proteolysis" *Annu Rev Biochem,* 68:1015-68

Walz A J, Sundberg R J (2000) *J Org Chem,* 65:8001.

Williams S, Pettaway C, Song R, Papandreou C, Logothetis C, MCConkey D J (2003) "Differential effects of the proteasome inhibitor bortezomib on apoptosis and angiogenesis in human prostate tumor xenografts" *Mol Cancer Ther,* 2:835-43

We claim:

1. A method of treating an oncological disorder in a person or animal, said method comprising administering to the person or animal an effective amount of a proteasome inhibitor compound having the chemical structure shown in formula I:

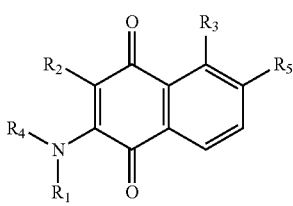

wherein
  $R_1$ is an organic cyclic ring structure bonded to a sulfonamide structure;
  $R_2$ is H, halogen, alkyl, —$NR_6R_7$, or heteroalkyl;
  $R_3$ is H, halogen, —OH, —O-alkyl, alkyl, cycloalkyl, heterocycloalkyl, aryl, heteroaryl, —$NO_2$, —$NH_2$ or substituted amines;
  $R_4$ is H, alkyl, heteroalkyl, aryl, or heteroaryl, any of which can be optionally substituted with one or more of —$NO_2$, alkyl, heteroalkyl, aryl, or heteroaryl, or halogen;
  $R_5$ is H, —OH, halogen, alkyl, aryl, heteroaryl, cycloalkyl, heterocycloalkyl, —O-alkyl, —O-aryl, heteroalkyl, —$NO_2$, —$NH_2$, or substituted amine; and $R_6$ and $R_7$ are independently H, O, alkyl, aryl, heterocycloalkyl, or heteroaryl, or together can form a heterocycloalkyl or a heteroaryl, any of which can be optionally substituted with one or more of —$NO_2$, alkyl, heteroalkyl, aryl, or halogen;

or a pharmaceutically acceptable salt thereof, wherein the oncological disorder is selected from among ovarian cancer, pancreatic cancer, breast cancer, lung cancer, prostate cancer, and multiple myeloma.

2. A method of inducing apoptosis in a cell or inhibiting chymotrypsin-like enzymatic activity in a cell, said method comprising contacting a cell in vivo with an effective amount of a proteasome inhibitor compound having the chemical structure shown in formula I:

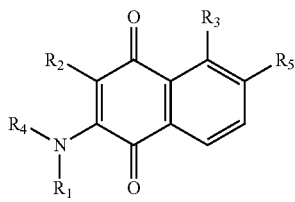

wherein
- $R_1$ is an organic cyclic ring structure bonded to a sulfonamide structure;
- $R_2$ is H, halogen, alkyl, —$NR_6R_7$, or heteroalkyl;
- $R_3$ is H, halogen, —OH, —O-alkyl, alkyl, cycloalkyl, heterocycloalkyl, aryl, heteroaryl, —$NO_2$, —$NH_2$ or substituted amines;
- $R_4$ is H, alkyl, heteroalkyl, aryl, or heteroaryl, any of which can be optionally substituted with one or more of —$NO_2$, alkyl, heteroalkyl, aryl, or heteroaryl, or halogen;
- $R_5$ is H, —OH, halogen, alkyl, aryl, heteroaryl, cycloalkyl, heterocycloalkyl, —O-alkyl, —O-aryl, heteroalkyl, —$NO_2$, —$NH_2$, or substituted amine; and
- $R_6$ and $R_7$ are independently H, O, alkyl, aryl, heterocycloalkyl, or heteroaryl, or together can form a heterocycloalkyl or a heteroaryl, any of which can be optionally substituted with one or more of —$NO_2$, alkyl, heteroalkyl, aryl, or halogen;

or a pharmaceutically acceptable salt thereof.

3. The method of claim 2, wherein $R_2$ is $NR_6R_7$ and has a chemical structure of:

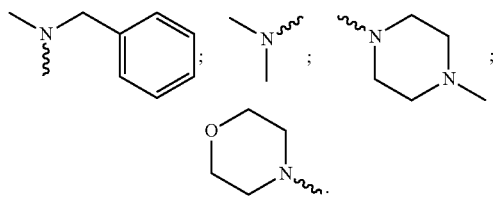

4. The method of claim 2, wherein $R_2$ is Cl or F.

5. The method of claim 2, wherein $R_4$ is ethyl, methyl, butyl, —$CH_2$-phenyl, —$CH_2$-naphthyl, —$CH_2$-4-nitro-phenyl, —$CH_2$-4-methyl-phenyl, or —$CH_2$-4-trifluoromethyl-phenyl.

6. The method of claim 2, wherein $R_1$ has the chemical structure

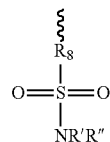

wherein $R_8$ is cycloalkyl, aryl, heterocycloalkyl, or heteroaryl, wherein $R_8$ can be substituted at any position with R'";

wherein R' and R" are independently selected from H, alkyl, aryl, heterocycloalkyl, heteroaryl, alkylcarbonyl, heterocycloalkylcarbonyl, arylcarbonyl or heteroarylcarbonyl, any of which can optionally be substituted with one or more halogen, alkyl, or alkoxy; and R'" is —$NO_2$, —OH, alkyl, cycloalkyl, heterocycloalkyl, aryl, heteroaryl, —O-alkyl, —O-aryl, —O-heteroaryl, —O-heterocycloalkyl, or an amine (primary, secondary, or tertiary).

7. The method of claim 2, wherein $R_1$ has the chemical structure

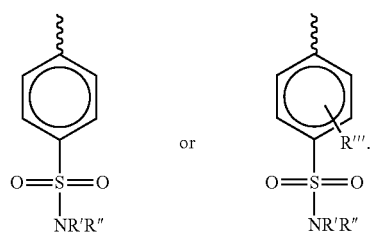

8. The method of claim 6, wherein R' and R" are independently selected from H and the following:

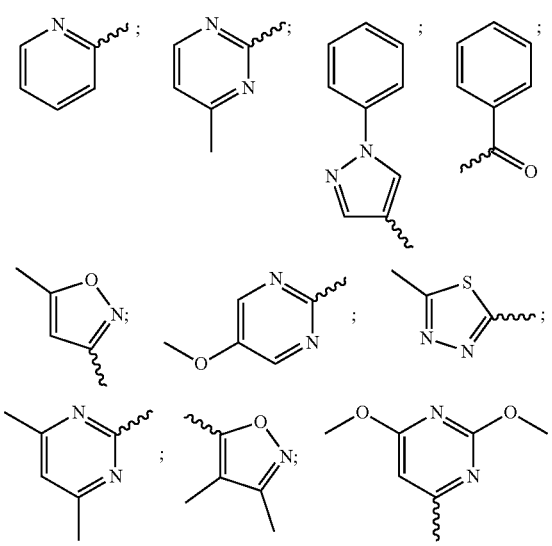

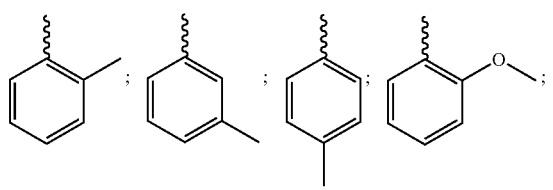
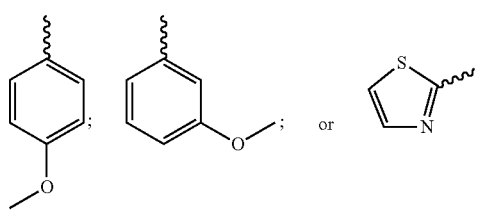
wherein ⸹ indicates the point of attachment.
9. The method of claim 2, wherein the compound is
PI-083
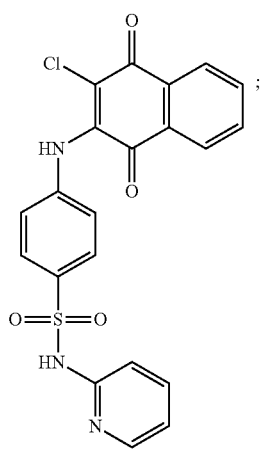
1
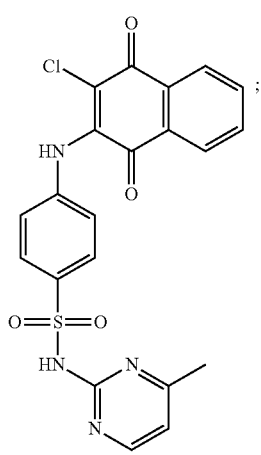
2
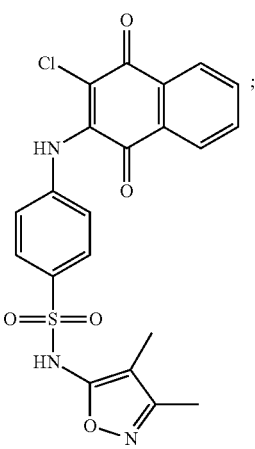
3
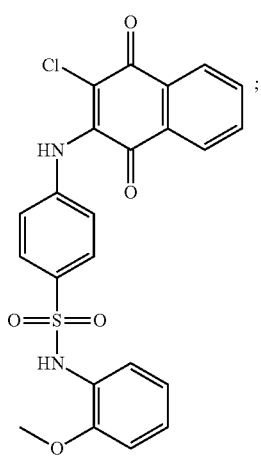
4
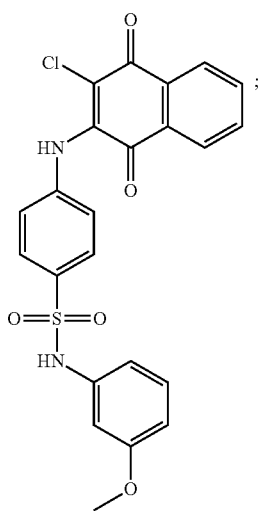

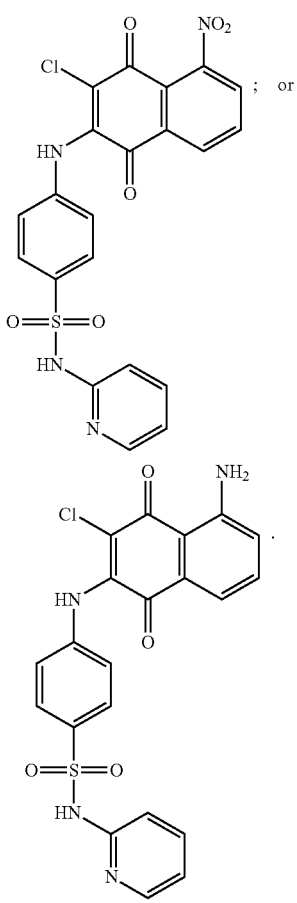

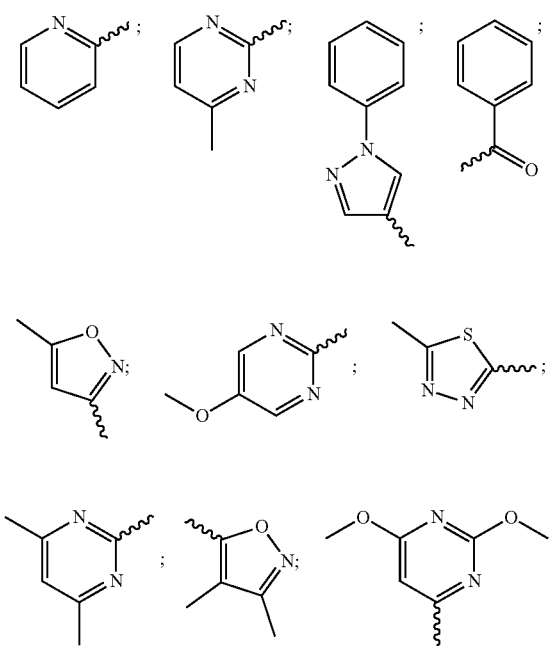

10. The method of claim 7, wherein R' and R" are independently selected from H and the following:

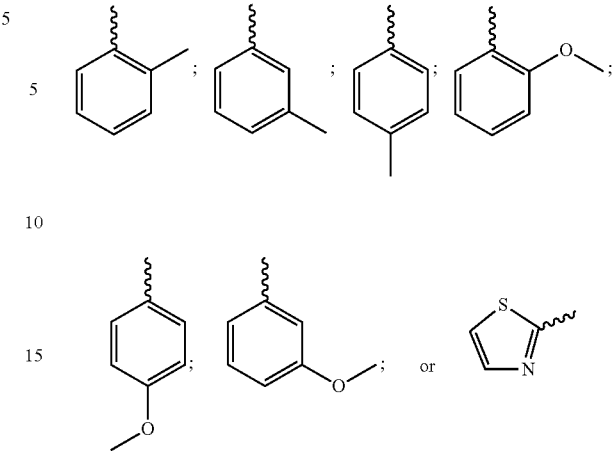

wherein ⦃ indicates the point of attachment.

11. The method of claim 2, wherein the compound is

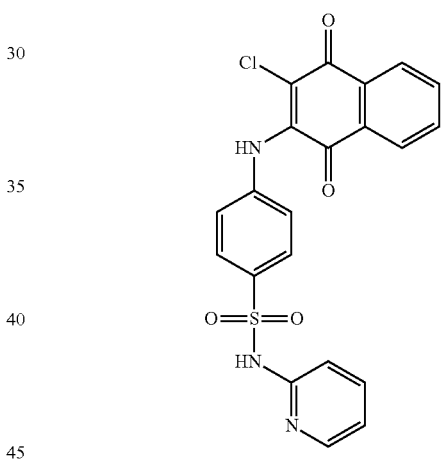

PI-083

12. The method of claim 1, wherein $R_2$ is $NR_6R_7$ and has a chemical structure of:

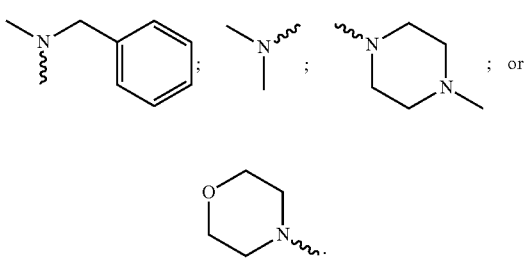

13. The method of claim 1, wherein $R_2$ is Cl or F.

14. The method of claim 1, wherein $R_4$ is ethyl, methyl, butyl, —$CH_2$-phenyl, —$CH_2$-naphthyl, —$CH_2$-4-nitro-phenyl, —$CH_2$-4-methyl-phenyl, or —$CH_2$-4-trifluoromethyl-phenyl.

15. The method of claim 1, wherein $R_1$ has the chemical structure

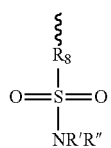

wherein $R_8$ is cycloalkyl, aryl, heterocycloalkyl, or heteroaryl, wherein $R_8$ can be substituted at any position with R'";

wherein R' and R" are independently selected from H, alkyl, aryl, heterocycloalkyl, heteroaryl, alkylcarbonyl, heterocycloalkylcarbonyl, arylcarbonyl or heteroarylcarbonyl, any of which can optionally be substituted with one or more halogen, alkyl, or alkoxy; and R'" is —$NO_2$, —OH, alkyl, cycloalkyl, heterocycloalkyl, aryl, heteroaryl, —O-alkyl, —O-aryl, —O-heteroaryl, —O-heterocycloalkyl, or an amine (primary, secondary, or tertiary).

16. The method of claim 1, wherein $R_1$ has the chemical structure

 or 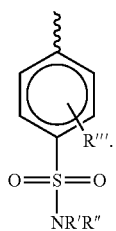

17. The method of claim 8, wherein R' and R" are independently selected from H and the following:

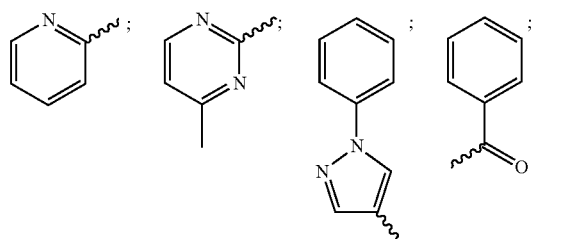

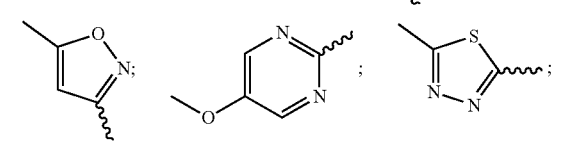

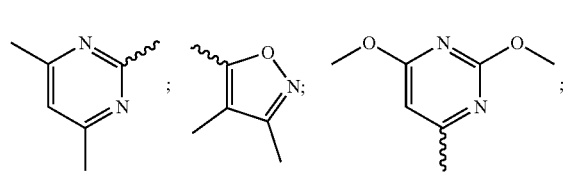

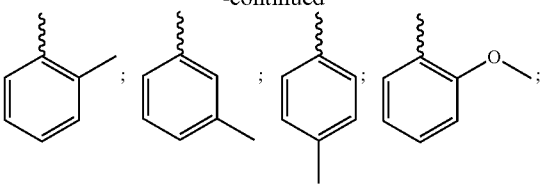

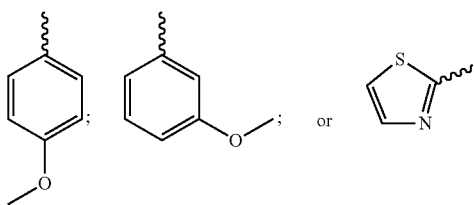

wherein ξ indicates the point of attachment.

18. The method of claim 1, wherein the compound is

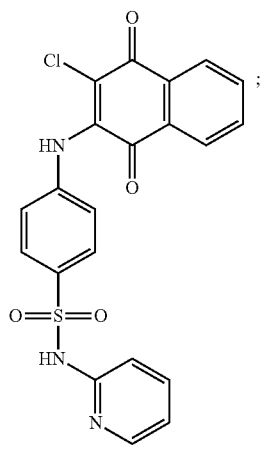

PI-083

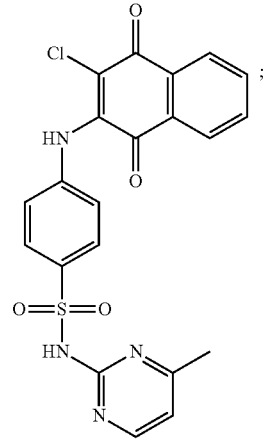

1

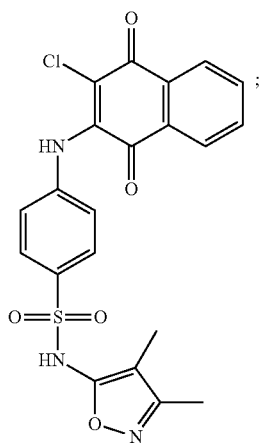
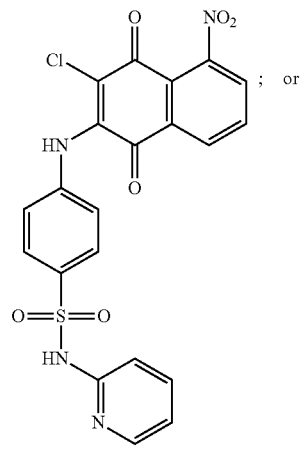
19. The method of claim 10, wherein R' and R" are independently selected from H and the following:
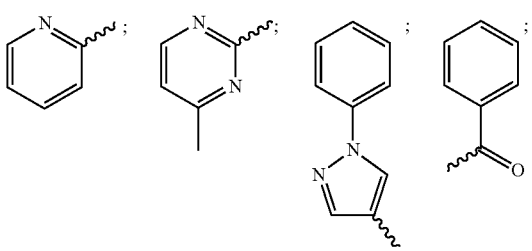
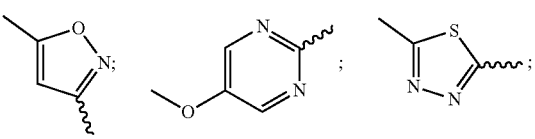

wherein ⸺ indicates the point of attachment.

20. The method of claim 1, wherein the compound is

PI-083

21. The method of claim 2, wherein the cell is an ovarian cancer cell, pancreatic cancer cell, breast cancer cell, lung cancer cell, prostate cancer cell, or multiple myeloma cell.

* * * * *

UNITED STATES PATENT AND TRADEMARK OFFICE
CERTIFICATE OF CORRECTION

| | |
|---|---|
| PATENT NO. | : 8,673,910 B2 |
| APPLICATION NO. | : 12/997192 |
| DATED | : March 18, 2014 |
| INVENTOR(S) | : Harshani Rithma Lawrence et al. |

It is certified that error appears in the above-identified patent and that said Letters Patent is hereby corrected as shown below:

In the Specification

Column 1,
Line 20, "Nation" should read --National--

Column 2,
Line 60, "-D-aryl" should read -- -O-aryl--

Column 32,
Line 48, "135 subunit" should read --β5 subunit--

Column 42,
Line 55, "30 mM at 4°C" should read --30 min at 4°C--

Column 45,
Line 5, "12-14 h" should read --12-24 h--

Column 47,
Line 38, "DIPEA, μw" should read --DIPEA, DMF, μw--

Column 51,
Line 46, "11g: $R^1$=H, $R^2$=$R^3$=H, Cl;=OMe" should read --11g: $R^1$=H, $R^2$=$R^3$=H, $R^4$=OMe--

Column 53,
Line 24, "$R_1$ groups" should read --$R^1$ groups--

Column 69,
Lines 28-29, "N-(3-methoxy-phenyl)-4-nitro-benzenesulfonamide (RK1-1-27D)"

Signed and Sealed this
Twenty-third Day of September, 2014

Michelle K. Lee
*Deputy Director of the United States Patent and Trademark Office*

CERTIFICATE OF CORRECTION (continued)
U.S. Pat. No. 8,673,910 B2 should read

--N-(3-methoxy-phenyl)-4-nitro-benzenesulfonamide (11f). (RK1-1-27D)--

Column 72,
Line 53, "(121)" should read --(12f)--

Column 74,
Line 67, "$C_{23}H_8ClN_2O_4S$" should read --$C_{23}H_{18}ClN_2O_4S$--

Column 75,
Line 32, "$C_{22}H_6ClN_2O_4S$" should read --$C_{22}H_{16}ClN_2O_4S$--

Column 83,
Lines 26-33,

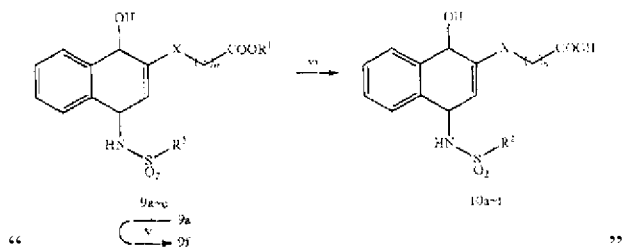

"    "    ""

should read

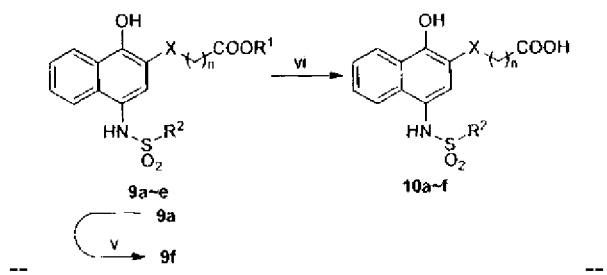

--                                                          --

Column 83,
Line 60, "8f X=S, n=1, R¹=C₂H₅, R²= —⟨phenyl⟩—CH₂" should read --8f X=S, n=1, R¹=C₂H₅, R²= —⟨phenyl⟩—CH₃--

Column 109,
Line 8, "7.85 (t, Hz, 2H)" should read --7.85 (t, $J$=8.0 Hz, 2H)--
Line 58, "(81)" should read --(8f)--

Column 110,
Line 53, "(M+Na)$^{+b\ 446.0161}$" should read --(M+Na)$^+$ 446.0161--

CERTIFICATE OF CORRECTION (continued)
U.S. Pat. No. 8,673,910 B2

Column 112,
Line 45, "(M-H)." should read --(M-H)⁻--

Column 123,
Line 42, "7.23 (dd, J=1.3 Hz, 17 Hz, 1H)" should read --7.23 (dd, J = 1.3 Hz, 3.7 Hz, 1H)--

Column 129,
Line 30, "Cimaramitaro, B.P." should read --Ciaramitaro, B.P.--
Line 38, "36. Amone, A.," should read --36. Arnone, A.,--